(12) United States Patent
Igarashi et al.

(10) Patent No.: US 11,445,289 B2
(45) Date of Patent: Sep. 13, 2022

(54) AUDIO PROCESSING DEVICE AND AUDIO PROCESSING METHOD

(71) Applicant: SONY CORPORATION, Tokyo (JP)

(72) Inventors: Go Igarashi, Tokyo (JP); Shigetoshi Hayashi, Tokyo (JP); Naoki Shinmen, Tokyo (JP); Kohei Asada, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/644,287

(22) PCT Filed: Jun. 22, 2018

(86) PCT No.: PCT/JP2018/023774
§ 371 (c)(1),
(2) Date: Mar. 4, 2020

(87) PCT Pub. No.: WO2019/053993
PCT Pub. Date: Mar. 21, 2019

(65) Prior Publication Data
US 2020/0245057 A1    Jul. 30, 2020

(30) Foreign Application Priority Data
Sep. 13, 2017  (JP) .............................. JP2017-175747

(51) Int. Cl.
*H04R 1/10* (2006.01)
*G10L 21/0208* (2013.01)
(Continued)

(52) U.S. Cl.
CPC ........ *H04R 1/1083* (2013.01); *G10L 21/0208* (2013.01); *G10L 21/0272* (2013.01);
(Continued)

(58) Field of Classification Search
CPC .............................. H04R 1/1083; H04R 1/105
See application file for complete search history.

(56) References Cited

U.S. PATENT DOCUMENTS

| 4,809,708 A | 3/1989 | Geisler et al. |
|---|---|---|
| 2006/0064037 A1 | 3/2006 | Shalon et al. |

(Continued)

FOREIGN PATENT DOCUMENTS

| CN | 101217828 A | 7/2008 |
|---|---|---|
| CN | 104871559 A | 8/2015 |

(Continued)

OTHER PUBLICATIONS

International Search Report and Written Opinion of PCT Application No. PCT/JP2018/023774, dated Sep. 25, 2018, 07 pages of ISRWO.

(Continued)

*Primary Examiner* — Ping Lee
(74) *Attorney, Agent, or Firm* — Chip Law Group

(57) ABSTRACT

[Problem] To propose a mechanism capable of performing a noise cancellation process in an ear hole opening type audio processing device. [Solution] An audio processing device including: an audio information acquisition unit that acquires audio information; a holding unit that abuts on a cavum concha or an inner wall of an ear canal and holds the audio information acquisition unit in a space closer to an eardrum side than a tragus, in a state of being worn by a user; an opening portion that opens an ear hole to an outside; and a signal processing unit that generates a noise cancellation signal based on the audio information acquired by the audio information acquisition unit.

14 Claims, 84 Drawing Sheets

(51) Int. Cl.
*G10L 21/0272* (2013.01)
*H04R 3/04* (2006.01)
*H04R 5/033* (2006.01)
*H04R 5/04* (2006.01)

(52) U.S. Cl.
CPC ........... *H04R 1/105* (2013.01); *H04R 1/1008* (2013.01); *H04R 3/04* (2013.01); *H04R 5/033* (2013.01); *H04R 5/04* (2013.01); *H04R 2420/07* (2013.01); *H04R 2460/01* (2013.01)

(56) References Cited

U.S. PATENT DOCUMENTS

| | | |
|---|---|---|
| 2009/0097681 A1 | 4/2009 | Puria et al. |
| 2011/0125063 A1 | 5/2011 | Shalon et al. |
| 2014/0003640 A1 | 1/2014 | Puria et al. |
| 2014/0126756 A1 | 5/2014 | Gauger, Jr. |
| 2016/0277854 A1 | 9/2016 | Puria et al. |
| 2018/0063652 A1 | 3/2018 | Perkins et al. |
| 2018/0308466 A1* | 10/2018 | Zhou ............... G10K 11/178 |
| 2019/0012444 A1* | 1/2019 | Lesso ............... G06F 21/32 |
| 2019/0069097 A1 | 2/2019 | Perkins et al. |
| 2020/0084553 A1 | 3/2020 | Perkins et al. |

FOREIGN PATENT DOCUMENTS

| | | |
|---|---|---|
| EP | 2915341 A1 | 9/2015 |
| JP | 2008-116782 A | 5/2008 |
| JP | 2008-124792 A | 5/2008 |
| JP | 2016-500994 A | 1/2016 |
| JP | 2017-011383 A | 1/2017 |
| JP | 2017-028718 A | 2/2017 |
| WO | 89/01315 A1 | 2/1989 |
| WO | 2006/033104 A1 | 3/2006 |
| WO | 2009/049320 A1 | 4/2009 |
| WO | 2014/071013 A1 | 5/2014 |
| WO | 2017/134973 A1 | 8/2017 |

OTHER PUBLICATIONS

Office Action for CN Patent Application No. 201880055636.2, dated Jun. 4, 2021, 07 pages of Office Action and 06 pages of English Translation.

Partial European Search Report of EP Application No. 18856161.1 dated Oct. 8, 2020, 12 pages.

* cited by examiner

AUDIO PROCESSING DEVICE AND AUDIO PROCESSING METHOD

FIELD

The present disclosure relates to an audio processing device and an audio processing method.

BACKGROUND

In recent years, noise cancellation (NC) techniques have been widely developed. According to the noise cancellation technique, it is possible to cancel noise by outputting audio to reduce (that is, cancel) an external sound (noise) from a speaker.

Noise cancellation systems are often mounted on devices worn on an ear such as headphones and an earphone. The noise cancellation system mounted in these devices are roughly divided into a type that performs feed forward (FF) noise cancellation (hereinafter referred to as FF-NC) and a type that performs feedback (FB) noise cancellation (hereinafter referred to as FB-NC), or a combination type of FF-NC and FB-NC. When the FF-NC type noise cancellation system is mounted, an FF-NC microphone is provided on an outer side (outside) of the device. When the FB-NC type noise cancellation system is mounted, an FB-NC microphone is provided on an inner side (space side formed by the device, user's head, and the like) of the device. In the combination type, both the microphones are provided. In particular, the combination type has high noise canceling performance obtained by utilizing each characteristic of FF-NC and FB-NC, and basically, each control can be designed independently. Therefore, the combination type noise cancellation system is mounted on a high-end device in recent years. For example, the combination type noise cancellation system is disclosed in the following Patent Literature 1.

In addition, there is a demand for further improvement in the noise canceling performance regardless of the FF-NC type, the FB-NC type, or the combination type. For example, the following Patent Literature 2 proposes a technique for suppressing influence of a digital delay while considering a merit of digitization in a filter circuit for FB-NC.

CITATION LIST

Patent Literature

Patent Literature 1: JP 2008-116782 A
Patent Literature 2: JP 2008-124792 A

SUMMARY

Technical Problem

However, the techniques disclosed in the above patent literatures have room for further performance improvement. For example, the techniques disclosed in the above Patent Literatures 1 and 2 target a so-called sealed audio processing device. Therefore, an application of the techniques disclosed in Patent Literatures 1 and 2 is not assumed in an audio processing device that has recently appeared and opens an ear hole to the outside in a worn state.

Therefore, the present disclosure proposes a mechanism capable of performing a noise cancellation process in an ear hole opening type audio processing device.

Solution to Problem

According to the present disclosure, an audio processing device is provided that includes: an audio information acquisition unit that acquires audio information; a holding unit that abuts on a cavum concha or an inner wall of an ear canal and holds the audio information acquisition unit in a space closer to an eardrum side than a tragus, in a state of being worn by a user; an opening portion that opens an ear hole to an outside; and a signal processing unit that generates a noise cancellation signal based on the audio information acquired by the audio information acquisition unit.

Moreover, according to the present disclosure, an audio processing method is provided that includes: acquiring audio information using an audio information acquisition device that abuts on a cavum concha or an inner wall of an ear canal and is held in a space closer to an eardrum side than a tragus while opening an ear hole to an outside in a state of being worn by a user; and generating a noise cancellation signal based on the acquired audio information.

Advantageous Effects of Invention

As described above, the mechanism capable of performing the noise cancellation process in the ear hole opening type audio processing device is provided according to the present disclosure. Note that the above-described effect is not necessarily limited, and any effect illustrated in the present specification or other effects that can be grasped from the present specification may be exhibited in addition to the above-described effect or instead of the above-described effect.

DESCRIPTION OF EMBODIMENTS

Hereinafter, preferred embodiments of the present disclosure will be described in detail with reference to the accompanying drawings. Note that constituent elements having substantially the same functional configuration in the present specification and the drawings will be denoted by the same reference sign, and the redundant description thereof will be omitted.

Note that a description will be given in the following order.
1. First Embodiment
2. Second Embodiment
3. Third Embodiment
4. Hardware Configuration Example
5. Summary 1. First Embodiment The present embodiment relates to a noise cancellation process using an audio processing device (ear hole opening device) having an audio information acquisition unit arranged near an entrance of an ear canal.

<1.1. Technical Problem>

In recent years, various wearable devices that are assumed to be constantly worn have been developed. For example, an ear hole opening device that does not seal an ear hole (an entrance of the ear canal) in a worn state has appeared in recent years. The ear hole opening device is a kind of so-called earphone device, and is used by being worn by a user similarly to the earphone device. However, the ear hole opening device does not seal the ear hole in the worn state, and thus, achieves listening characteristics of ambient sounds equivalent to that in a non-wearing state. However, an ear is not sealed with an ear pad or the like in the ear hole opening device, and thus, it is difficult to expect noise cancellation due to passive sound insulation. Therefore, it is desirable to add a noise cancellation function by active processing to the ear hole opening device. However, the above-described Patent Literatures 1 and 2 only disclose a noise cancellation process in sealed earphones/headphones.

Therefore, the present embodiment discloses a no-noise cancellation process based on active processing suitable for an ear hole opening type device.

<1.2. Exterior Configuration of Ear Hole Opening Device>

Figure 1:
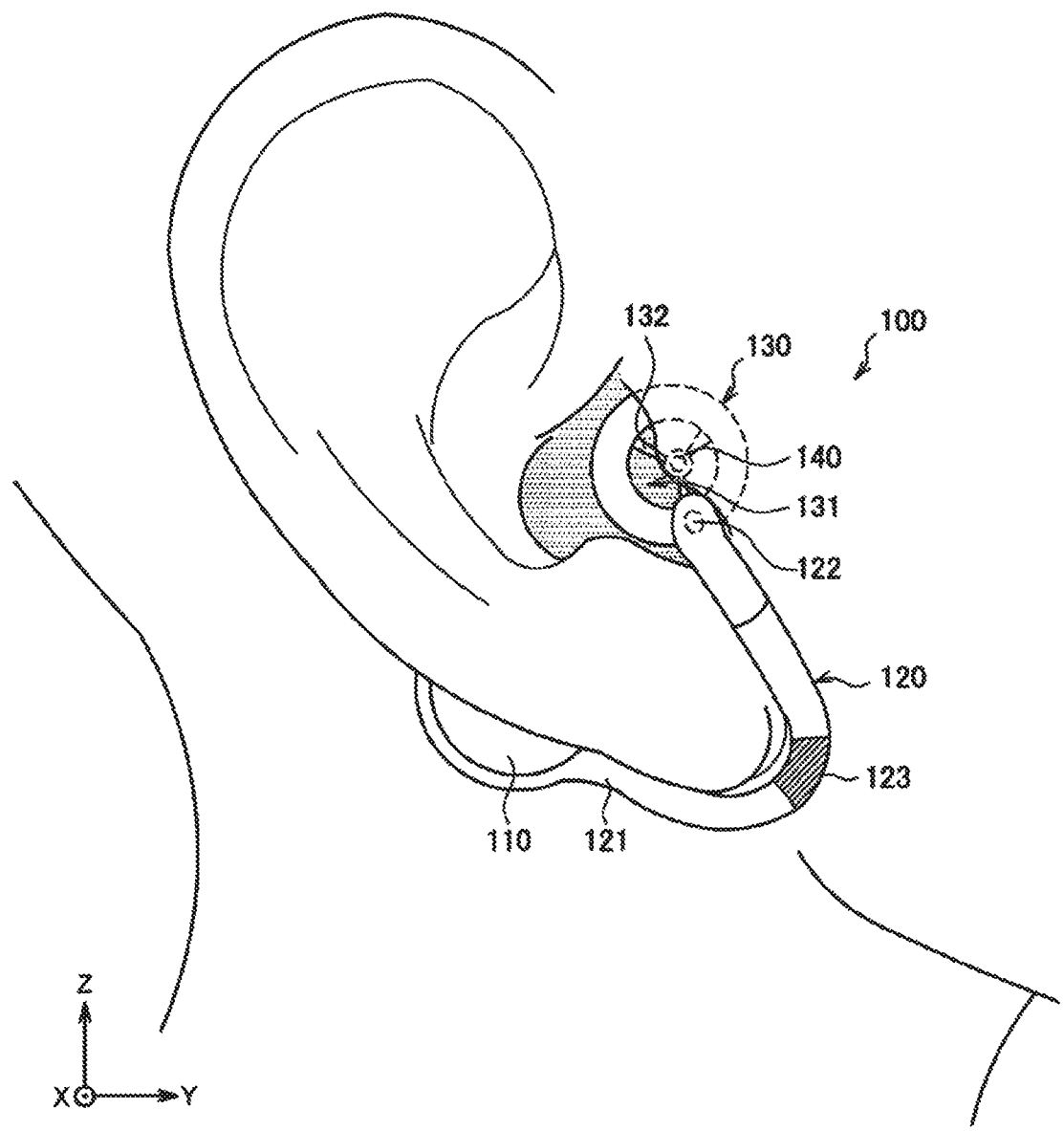
FIG. 1 is a view for describing an example of an exterior configuration of an ear hole opening device according to a first embodiment.

FIG. 1 is a view for describing an example of an exterior configuration of the ear hole opening device according to the present embodiment. As illustrated in FIG. 1, an ear hole opening device 100 is used by being worn on one ear of a listener (that is, a user). FIG. 1 illustrates the exterior of the ear hole opening device 100 worn on a right ear as an example. The Y axis is a coordinate axis with the front in the horizontal direction (eye direction) as positive, the X axis is a coordinate axis with the left side of a person in the horizontal direction as positive, and the Z axis is a coordinate axis with the vertical direction as negative. These coordinate axes are also used in the subsequent drawings.

As illustrated in FIG. 1, the ear hole opening device 100 includes: an audio output unit 110 that outputs (generates) audio; a sound guide unit 120 that takes audio generated by the audio output unit 110 from one end 121; and a holding unit 130 that holds the sound guide unit 120 near another end 122. The sound guide unit 120 is made of a hollow tube material, and both ends thereof are open ends. The one end 121 of the sound guide unit 120 is an audio input hole for a sound generated from the audio output unit 110, and the other end 122 is an audio output hole. Therefore, the sound guide unit 120 is in the state of being open on one side as the one end 121 is attached to the audio output unit 110.

The holding unit 130 is engaged with the vicinity of the entrance of the ear canal (for example, an intertragic notch) to support the sound guide unit 120 near the other end 122 such that the audio output hole of the other end 122 of the sound guide unit 120 faces the interior side of the ear canal. An outer diameter of the sound guide unit 120 at least near the other end 122 is formed to be smaller than an inner diameter of the ear hole (entrance of an ear canal 5). Therefore, the ear hole of the listener is not blocked even in a state where the other end 122 of the sound guide unit 120 is held near the entrance of the ear canal by the holding unit 130. That is, the ear hole is open. It is possible to say that the ear hole opening device 100 is different from a typical earphone and is an ear hole opening type earphone.

In addition, the holding unit 130 includes an opening portion 131 that opens the ear hole to the outside even in the state of holding the sound guide unit 120. In the example illustrated in FIG. 1, the holding unit 130 is a ring-shaped structure, an audio information acquisition unit 140 is provided in a part where rod-shaped support members 132 provided in a ring inner direction are combined near the ring center, and all the other parts of the ring-shaped structure are the opening portions 131. Note that the holding unit 130 is not limited to the ring-shaped structure but may have an arbitrary shape that supports the other end 122 of the sound guide unit 120 and is provided with the audio information acquisition unit 140 as long as a hollow structure is provided.

When taking the audio generated by the audio output unit 110 into the tube from the one end 121 thereof, the tubular sound guide unit 120 propagates the air vibration thereof to be radiated from the other end 122 held near the entrance of the ear canal by the holding unit 130 toward the ear canal and transmitted to an eardrum.

As described above, the holding unit 130 holding the vicinity of the other end 122 of the sound guide unit 120 includes the opening portion 131 that opens the entrance (ear hole) of the ear canal to the outside. Therefore, the ear hole of the listener is not blocked even in the state where the ear hole opening device 100 is worn. The listener can sufficiently listen to ambient sounds through the opening portion 131 in the middle of wearing the ear hole opening device 100 and listening to the audio output from the audio output unit 110.

In addition, although the ear hole opening device 100 according to the present embodiment opens the ear hole, the leakage of the sound generated from the audio output unit 110 (that is, the reproduced sound) to the outside can be reduced. This is because the other end 122 of the sound guide unit 120 is attached so as to face the interior of the ear canal near the entrance of the ear canal and sufficient sound quality can be obtained even if the output of the audio output unit 110 is small. In addition, the directivity of the air vibration radiated from the other end 122 of the sound guide unit 120 can also contribute to prevention of the sound leakage.

The sound guide unit 120 has a bent shape that is folded back from the back side of a pinna to the front side at a middle part. This bent part forms a pinch portion 123 having an opening and closing structure, and can maintain the ear hole opening device 100 worn by the listener by generating a pinching force to pinch an earlobe.

The audio information acquisition unit 140 provided near the ring center of the ring-shaped holding unit 130 is provided to face the opposite side of the eardrum. The audio information acquisition unit 140 typically includes an audio input unit (that is, a microphone) and mainly detects (that is, collects) ambient sounds. That is, the audio input unit is provided in the opposite direction to the other end 122 arranged to face the interior side of the ear canal. Therefore, the influence of the sound generated from the audio output unit 110 output from the other end 122 on a sound collection result by the audio input unit is mitigated.

The audio information acquisition unit 140 functions as a so-called error microphone for noise cancellation, and a detection result by the audio information acquisition unit 140 is treated as an error signal. Since the audio information acquisition unit 140 is arranged near the ear hole, that is, near the eardrum, high noise canceling performance is expected.

Note that the ear hole opening device 100 illustrated in FIG. 1 is configured assuming wearing on the right ear, but the ear hole opening device 100 for wearing on the left ear is configured to be laterally symmetric with respect to this configuration. In addition, the ear hole opening device 100 may be configured for both ears including both the right ear and the left ear. In the case of being configured for both ears, the ear hole opening device 100 for the right ear and the ear hole opening device 100 for the left ear may be configured separately to be independent from each other and communicate with each other.

<1.3. Internal Configuration of Ear Hole Opening Device>

Figure 2:
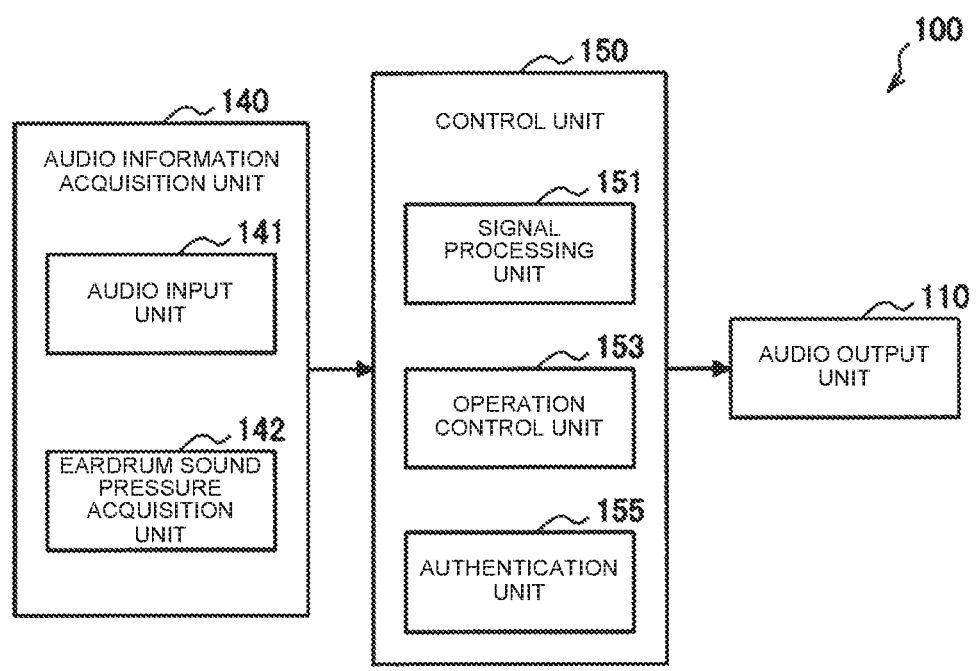
FIG. 2 is a diagram illustrating an example of an internal configuration of an ear hole opening device according to the embodiment.

FIG. 2 is a diagram illustrating an example of an internal configuration of the ear hole opening device 100 according to the present embodiment. As illustrated in FIG. 2, the ear hole opening device 100 includes the audio output unit 110, the audio information acquisition unit 140, and a control unit 150.

Audio Output Unit 110

The audio output unit 110 has a function of outputting audio based on an audio signal. The audio output unit 110 can also be referred to as a driver. The driver 110 outputs audio to a space based on an output signal output from a signal processing unit 151.

Audio Information Acquisition Unit 140

The audio information acquisition unit 140 has a function of acquiring audio information. The audio information acquisition unit 140 includes an audio input unit 141 and an eardrum sound pressure acquisition unit 142.

The audio input unit 141 includes a microphone (hereinafter also simply referred to as a microphone) that detects ambient sounds and generates an audio signal indicating the sound collection result by the microphone. That is, the audio information may be the audio signal indicating the sound collection result by the microphone. The eardrum sound pressure acquisition unit 142 estimates a sound pressure of the eardrum and generates sound pressure information of the eardrum. That is, the audio information may be the eardrum sound pressure information. The eardrum sound pressure acquisition unit 142 directly estimates the eardrum sound pressure, for example, by measuring a vibration of the eardrum. A configuration of the eardrum sound pressure acquisition unit 142 will be described in detail later.

Note that the eardrum sound pressure does not need to be measured directly. For example, the eardrum sound pressure may be approximated with a sound pressure near the entrance of the ear canal. Since the audio input unit 141 (audio information acquisition unit 140) is held near the entrance of the ear canal as illustrated in FIG. 1, the audio signal generated by the audio input unit 141 can also be grasped as information indicating the eardrum sound pressure.

Control Unit 150

The control unit 150 functions as an arithmetic processing device and a control device, and controls the entire processing performed by the ear hole opening device 100 according to various programs. The control unit 150 is realized by an electronic circuit, for example, a central processing unit (CPU), a micro-processing unit (MPU), a demand-side platform (DSP), or the like. Note that the control unit 150 may include a read-only memory (ROM) that stores programs to be used, calculation parameters, and the like, and a random-access memory (RAM) that temporarily stores parameters that change as appropriate.

As illustrated in FIG. 2, the control unit 150 includes the signal processing unit 151, an operation control unit 153, and an authentication unit 155.

The signal processing unit 151 has a function of generating a noise cancellation signal for noise based on the audio information (audio signal or eardrum sound pressure information) acquired by the audio information acquisition unit 140. For example, the signal processing unit 151 performs a noise cancellation process of a FB scheme or a FF scheme using the audio information as an error signal to generate the noise cancellation signal. The signal processing unit 151 generates an audio signal (hereinafter also referred to as an output signal) based on the noise cancellation signal, and outputs the audio signal to the audio output unit 110 as an output. The output signal may be the noise cancellation signal itself or may be a synthesized signal obtained by synthesizing another audio signal such as a music signal acquired from a sound source and the noise cancellation signal. The signal processing unit 151 includes various constituent elements for noise cancellation processes which will be described with reference to FIGS. 8 to 13 and the like. For example, the signal processing unit 151 includes: various filter circuits configured to generate a noise cancellation signal; an adaptive control unit configured to adaptively control the filter circuits; an adder configured to synthesize signals; an own voice extraction unit to be described later; an internal model; and the like. In addition, the signal processing unit 151 also includes circuits such as an amplifier, an analog-digital converter (ADC), and a digital-analog converter (DAC). The signal processing unit 151 may perform not only the noise cancellation process but also a process of emphasizing a high range of sound information included in the audio information (audio signal or eardrum sound pressure information) acquired by the audio information acquisition unit 140, adding a reverberation, or the like. As a result, it is possible to make it easy to hear ambient sounds. That is, the technique according to the present embodiment can be also applied to a noise cancellation technique in an open space or a hearing aid.

The operation control unit 153 has a function of controlling an operation mode of the ear hole opening device 100. For example, the operation control unit 153 stops or starts some or all of the functions of the ear hole opening device 100.

The authentication unit 155 has a function of identifying and authenticating a user wearing the ear hole opening device 100.

<1.4. Wearing Mode of Ear Hole Opening Device>

Figure 3:
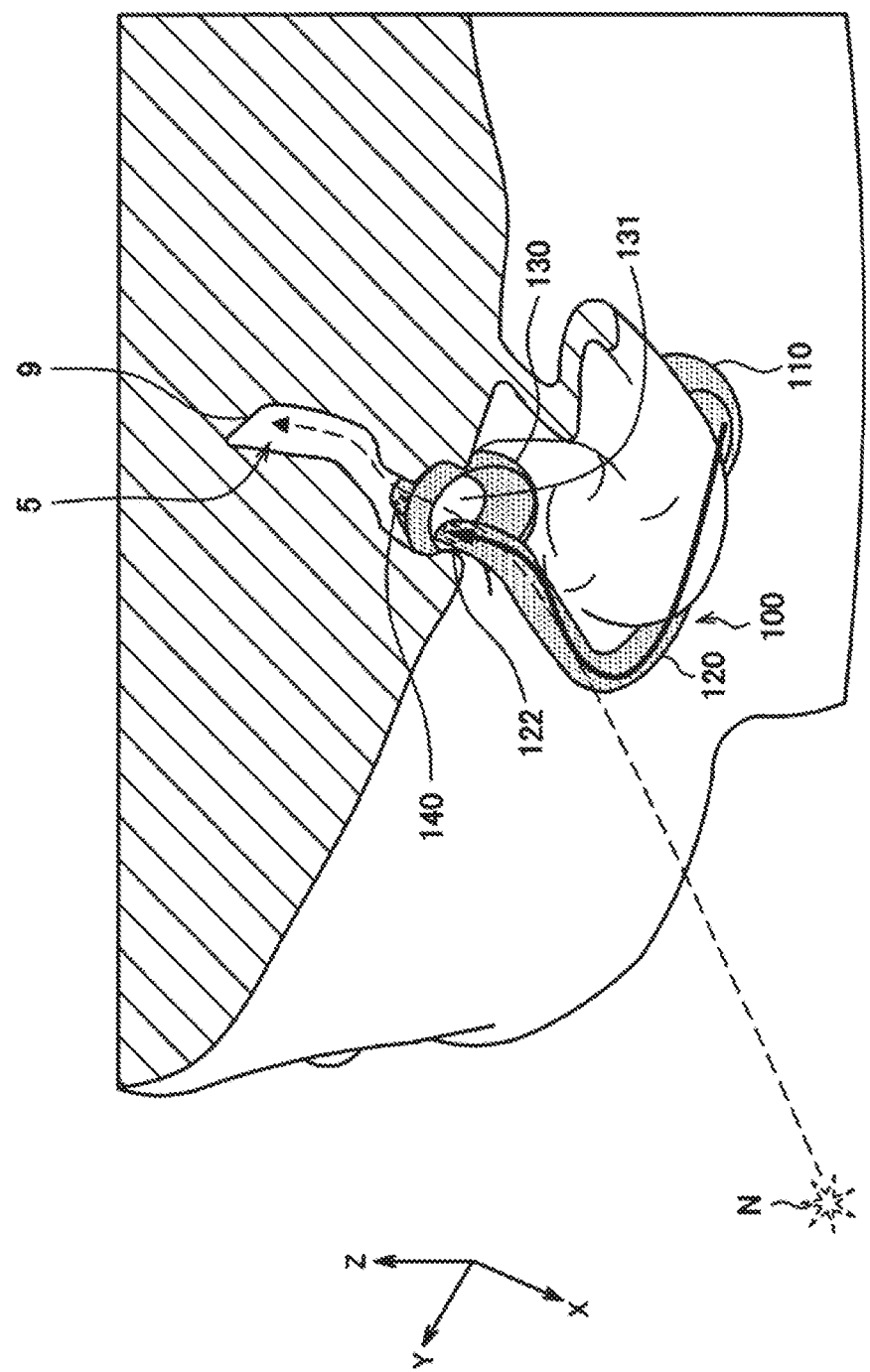
FIG. 3 is a view for describing an outline of a noise cancellation process using the ear hole opening device according to the embodiment.

FIG. 3 is a view for describing an outline of the noise cancellation process using the ear hole opening device 100 according to the present embodiment. FIG. 3 illustrates a cross-sectional view at the ear canal of the head of the user wearing the ear hole opening device 100 on the left ear. As illustrated in FIG. 3, noise N reaches the audio information acquisition unit 140, passes through the opening portion 131, and passes through the ear canal 5 to reach an eardrum 9. The ear hole opening device 100 generates a noise cancellation signal based on the noise N acquired by the audio information acquisition unit 140. The audio output unit 110 outputs audio based on an audio signal generated based on the noise cancellation signal. The audio output from the audio output unit 110 propagates through the sound guide unit 120 and is released from the other end 122 to cancel the noise N.

As illustrated in FIG. 3, a position of the audio information acquisition unit 140 is near the entrance of the ear canal 5, that is, near the eardrum 9. For this reason, the microphone 141 can collect the audio near the eardrum 9. When a noise cancellation process is performed using the microphone 141 as a cancellation point, high noise canceling performance is realized. In addition, the eardrum sound pressure acquisition unit 142 can acquire sound pressure information of the eardrum 9 from the vicinity of the eardrum 9. As a result, the precision of sound pressure information increases, which can contribute to the improvement of noise canceling performance.

The holding unit 130 maintains a relative positional relationship between the audio information acquisition unit 140 and the other end 122 that is the output hole of the audio output from the audio output unit 110. That is, a characteristic (characteristic $H_1$ to be described later) of a space between the audio output unit 110 and the audio information acquisition unit 140 is fixed. As a result, the noise canceling performance can be stabilized. Note that the relative positional relationship is maintained by the holding unit 130 holding both the sound guide unit 120 and the audio information acquisition unit 140 together.

Next, a wearing position of the ear hole opening device will be described with reference to FIGS. 4 to 7. Hereinafter, a description will be given assuming that the ear hole opening device 100 is equipped with the microphone 141 as the audio information acquisition unit 140.

Figure 4:
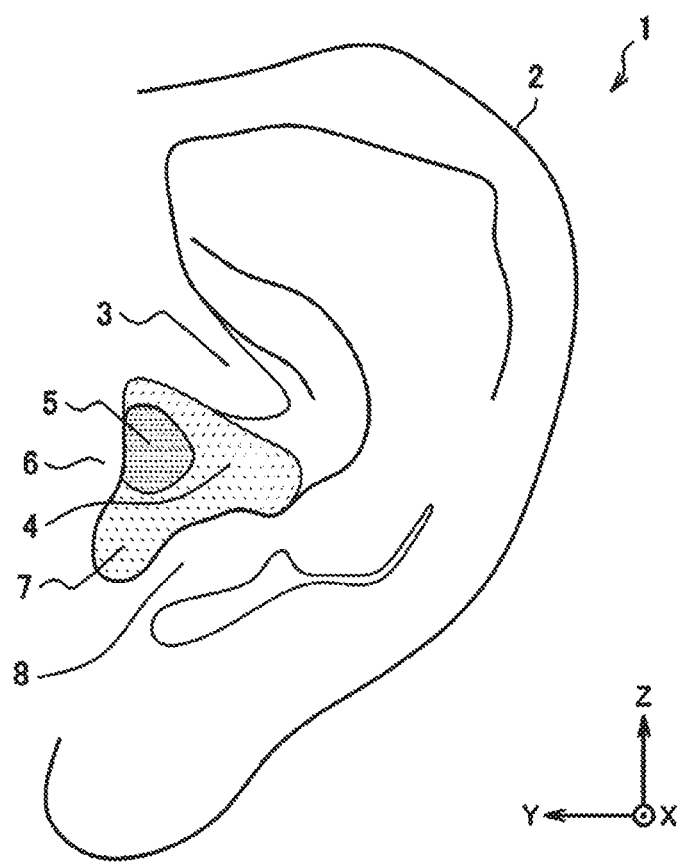
FIG. 4 is a view for describing a typical human ear structure.

FIG. 4 is a view for describing a typical human ear structure. As illustrated in FIG. 4, a pinna 2 forms specific unevenness in a human ear 1 and reflects audio from various directions to guide the reflected audio to the ear canal 5. The ear canal 5 is a passage of audio, and the audio that has passed through the ear canal 5 reaches the eardrum at the interior of the ear canal 5. Around the ear canal 5, there are a crus of helix 3, a cavum concha 4, a tragus 6, an intertragic notch 7, and an antitragus 8.

Figure 5:
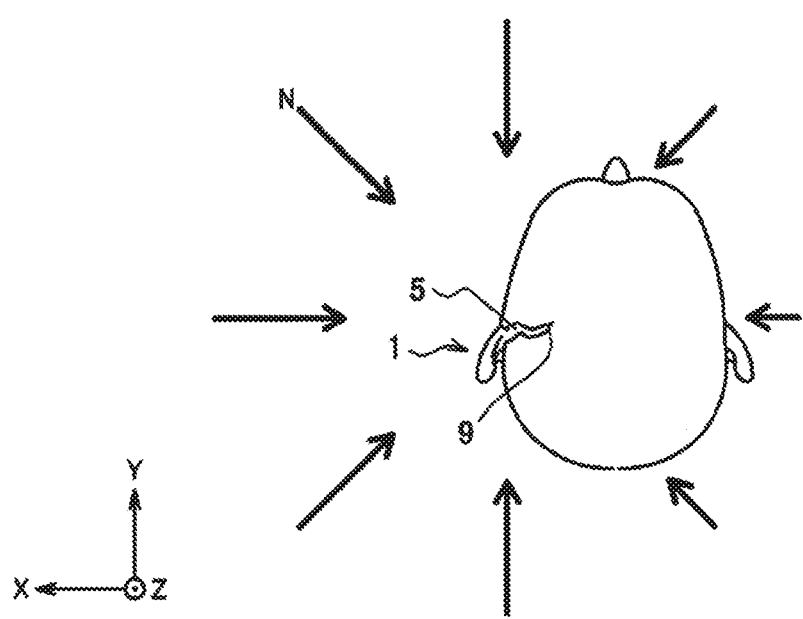
FIG. 5 is a view for describing noise N arriving at a human ear.

FIG. 5 is a view for describing the noise N arriving at the human ear. As illustrated in FIG. 5, the noise N arrives at the human ear 1 from all directions in a horizontal direction. Although FIG. 5 illustrates the left ear, the same applies to the right ear. Noise collected by the microphone 141 has a frequency characteristic that depends on an arrival direction of the noise depending on the arrangement of the microphone 141. For example, the influence of reflection received from the pinna 2 differs between noise coming from the front of the user (that is, the Y-axis positive side) and noise coming from the back (that is, the Y-axis negative side). Therefore, even if noise from a specific direction can be canceled sufficiently, there may occur an event where it is difficult to sufficiently noise from another direction depending on the arrangement of the microphone 141 This is not limited to the horizontal direction, and the same applies to an elevation direction.

Figure 6:
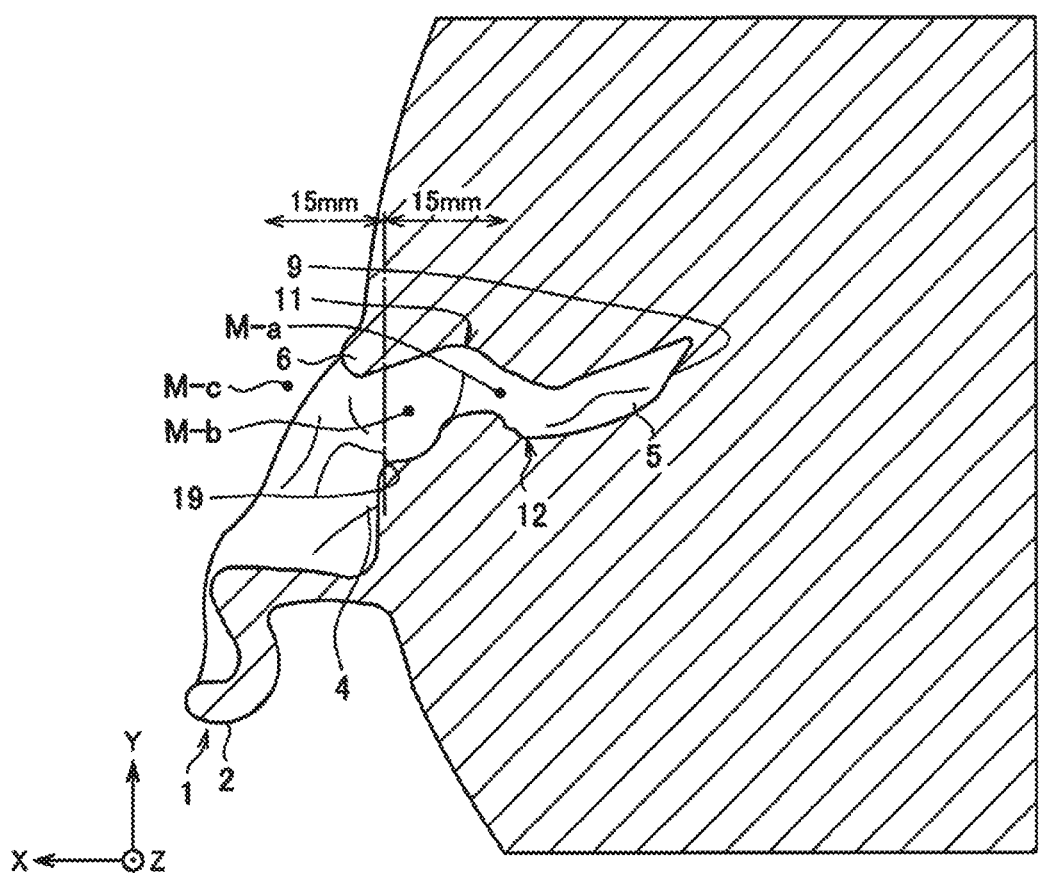
FIG. 6 is a view for describing an arrangement of a microphone in the ear hole opening device according to the embodiment.

FIG. 6 is a view for describing the arrangement of the microphone 141 of the ear hole opening device 100 according to the present embodiment. FIG. 6 illustrates a cross-sectional view illustrating a state of the ear canal. As illustrated in FIG. 6, the ear canal 5 has an S-shape bending at each of a first curve 11 and a second curve 12, and the eardrum 9 is located at the interior of the ear canal 5. It is considered that the dependence of the frequency characteristic on the noise arrival direction described above with reference to FIG. 5 is relatively small if a space closer to the eardrum 9 than the tragus 6. Therefore, it is desirable that the microphone 141 be arranged in the space closer to the eardrum 9 than the tragus 6. More specifically, it is desirable that the microphone 141 be arranged inside the ear canal 5, that is, in the space closer to the eardrum 9 than a boundary 19 between the cavum concha 4 and the ear canal 5. As a result, the particularly high noise canceling performance can be realized.

It is desirable that the microphone 141 be arranged in a space 15 mm away from the boundary 19 of the cavum concha 4 and the ear canal 5 to the eardrum 9 side or arranged in a space 15 mm away from the boundary 19 of the cavum concha 4 and the ear canal 5 on the opposite side of the eardrum 9. In other words, it is desirable that the holding unit 130 hold the microphone 141 in the space 15 mm away from the boundary 19 of the cavum concha 4 and the ear canal 5 to the eardrum 9 side or in the space 15 mm away from the boundary 19 of the cavum concha 4 and the ear canal 5 on the opposite side of the eardrum 9 in a state where the ear hole opening device 100 is worn by the user. Here, a difference between the frequency characteristic at the position of the microphone 141 and the frequency characteristic at the position of the eardrum 9 decreases as the microphone 141 approaches the eardrum 9. Therefore, it is more desirable if the position of the microphone 141 is closer to the eardrum 9. In this regard, the above difference between the frequency characteristics can fall within an allowable range if the space 15 mm away from the boundary 19 to the opposite side of the eardrum 9, and the predetermined noise canceling performance can be ensured. In addition, in the case where the microphone 141 is arranged in the range within 15 mm away from the boundary 19 to the eardrum 9 side, the position of the microphone 141 can be made closer to the eardrum 9 as compared with the case where the microphone 141 is arranged in the space away from the boundary 19 on the opposite side of the eardrum 9. Further, at least the microphone 141 can be prevented from coming into contact with the eardrum 9 and damaging the eardrum 9, and the safety can be ensured.

Microphone positions M-a and M-b are in the space 15 mm away from the boundary 19 to the eardrum 9 side. Specifically, the microphone position M-a is between the first curve 11 and the second curve 12 of the ear canal 5. The microphone position M-b is between the boundary 19 and the first curve 11 of the ear canal 5. In addition, a microphone position M-c is in the space 15 mm away from the boundary 19 on the opposite side of the eardrum 9. The predetermined noise canceling performance can be ensured at any of these microphone positions. In particular, the microphone position M-a is most desirable in terms that the dependence of the frequency characteristics on the arrival direction can be minimized.

Figure 7:
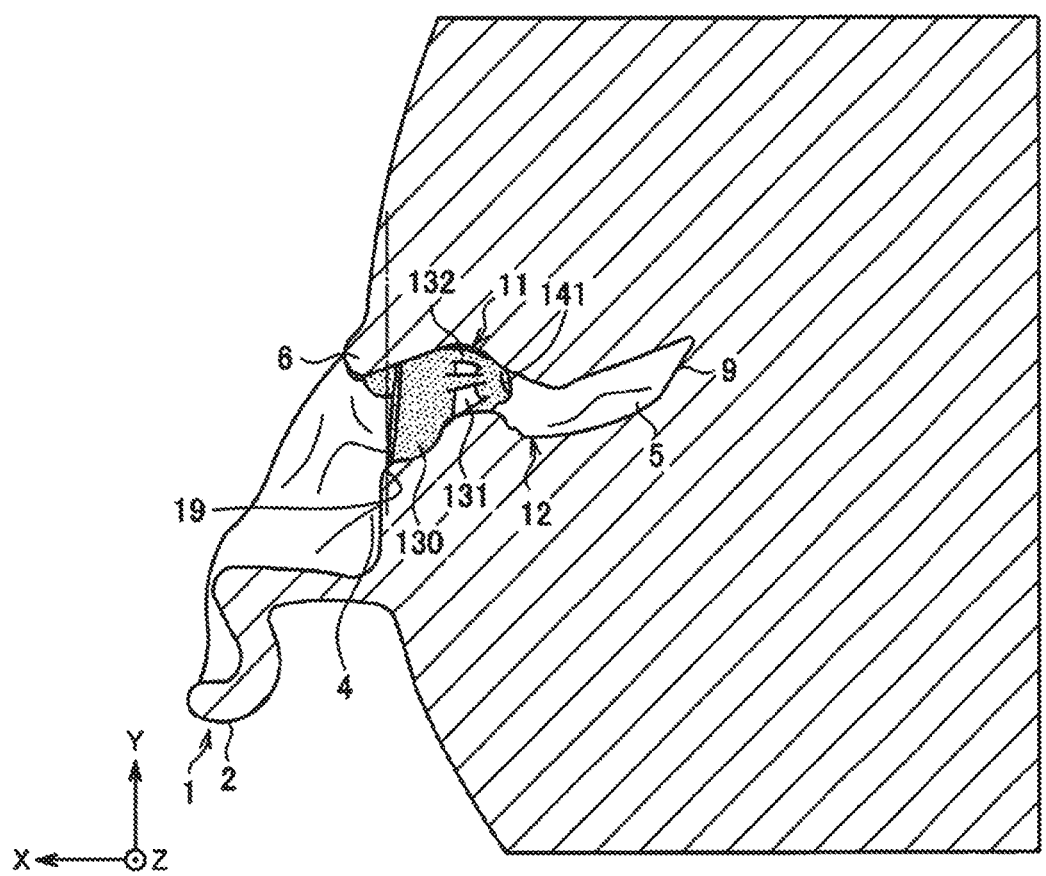
FIG. 7 is a view illustrating a state where the ear hole opening device according to the embodiment is attached to a user.

FIG. 7 is a view illustrating a state where the ear hole opening device 100 according to the present embodiment is worn by the user. As illustrated in FIG. 7, the holding unit 130 abuts on an inner wall of the ear canal 5 of one ear in the state where the ear hole opening device 100 is worn by the user. Then, the holding unit 130 holds the microphone 141 in the space closer to the eardrum 9 than the tragus 6, the space 15 mm away from the boundary 19 between the cavum concha 4 and the ear canal 5 to the eardrum 9 side. More specifically, the holding unit 130 holds the microphone 141 at the microphone position M-a illustrated in FIG. 6. With such an arrangement, the position of the microphone 141 (that is, the cancellation point) can be set to a position where the difference in frequency characteristics from the position of the eardrum 9 is small, and the high noise canceling performance can be realized. Note that a place where the holding unit 130 abuts is not limited to the inner wall of the ear canal 5. The holding unit 130 may abut on the cavum concha 4, for example.

<1.5. Details of Noise Cancellation Process>

Hereinafter, the noise cancellation process using the ear hole opening device 100 according to the present embodiment will be described.

(1) Classical Control FB Scheme

First, a classical control FB scheme will be described with reference to FIGS. 8 and 9.

Figure 8:
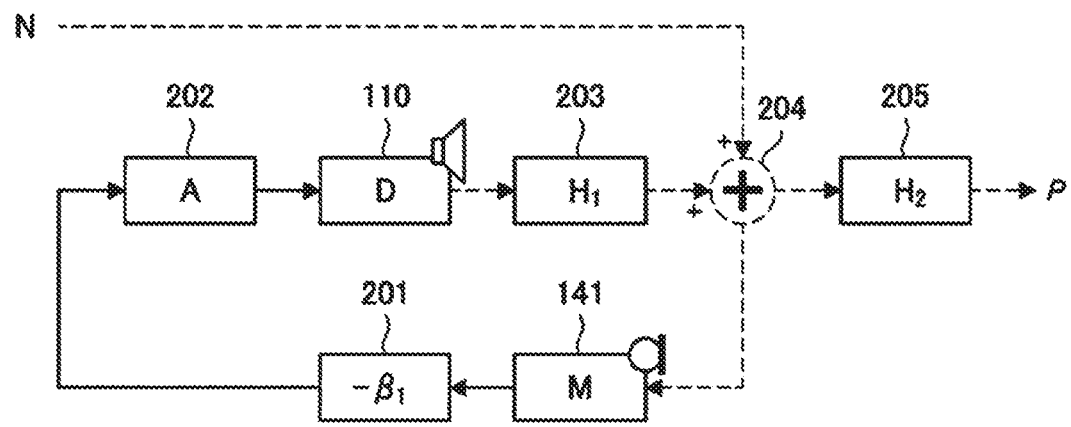
FIG. 8 is a diagram illustrating a model configuration example of a noise cancellation process of a classical control FB scheme using the ear hole opening device according to the embodiment.

FIG. 8 is a diagram illustrating a model configuration example of the noise cancellation process of the classical control FB scheme using the ear hole opening device 100 according to the present embodiment. Symbols of blocks illustrated in the model configuration example as illustrated in FIG. 8 indicate characteristics (that is, transfer functions) corresponding to specific circuit parts, circuit systems in a noise cancellation system, or the like. Each time an audio signal (or audio) passes through each block, the characteristic illustrated in the corresponding block is applied. The symbols in the blocks illustrated in FIGS. 8 to 13 have meanings as follows.

$H_1$: Characteristic of space 203 from driver 110 to microphone 141
$H_2$: Characteristic of space 205 from microphone 141 to eardrum (spatial characteristic of ear canal)
M: Characteristic of microphone 141
A: Characteristic of amplifier 202
D: Characteristic of driver 110
F: Characteristic of passive sound insulation element 220
M': Simulated characteristic of M of microphone 141
A': Simulated characteristic of amplifier 202
D': Simulated characteristic of driver 110
H': Simulated characteristic of space 203
A'D'$H_1$'M': Characteristic of internal model 208
$-\beta_1$: Characteristic of first FB filter 201
$\beta_2$: Characteristic of second FB filter 207
E: Characteristic of equalizer 213

In addition, N represents noise, M represents a music signal, P represents a sound pressure at an eardrum position, and V represents user's voice (own voice).

The microphone 141 collects audio and generates an audio signal. The audio signal generated by the microphone 141 is input to the first FB filter 201.

The first FB filter 201 is a filter circuit that performs the noise cancellation process of the FB scheme. The first FB filter 201 performs the noise cancellation process using the microphone 141 as the cancellation point based on the audio signal input from the microphone 141, and generates a noise cancellation signal. The audio signal that has passed through the first FB filter 201 is input to the amplifier 202.

The amplifier 202 is a power amplifier that amplifies and outputs the input audio signal. The amplifier 202 amplifies and outputs the audio signal input from the first FB filter 201. The audio signal that has passed through the amplifier 202 is input to the driver 110.

The driver 110 outputs audio inside a space based on the input audio signal.

The audio output from the driver 110 first passes through the space 203 and then interferes with the noise N in a space 204 to cancel the noise N. The noise N that has not been canceled is collected by the microphone 141. Further, the noise N that has not been canceled passes through the opening portion 131, passes through the space 205, and reaches the eardrum position as the eardrum sound pressure P.

The microphone 141 is a point that minimizes noise (that is, the cancellation point). Therefore, it is desirable if the arrangement position of the microphone 141 is closer to the eardrum.

Here, as a comparative example, a noise cancellation process in a case where the ear hole opening device 100 is configured as an earphone (sealed noise canceling earphone) that does not have the opening portion 131 will be described with reference to FIG. 9.

Figure 9:
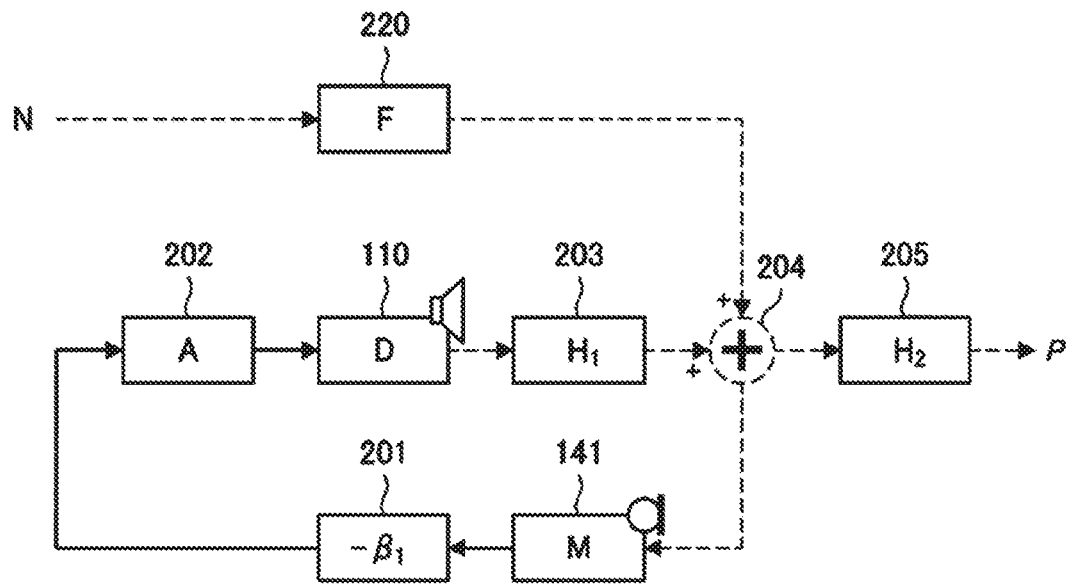
FIG. 9 is a diagram illustrating a model configuration example of a noise cancellation process of the classical control FB scheme using a sealed noise canceling earphone according to a comparative example.

FIG. 9 is a diagram illustrating a model configuration example of the noise cancellation process of the classical control FB scheme using the sealed noise canceling earphone according to the comparative example. The model configuration example illustrated in FIG. 9 is the same as the model configuration example illustrated in FIG. 8 except that the passive sound insulation element 220 is provided. In the sealed noise canceling earphone, the passive sound insulation element 220, such as a sealed housing and an earpiece, is present between the noise N and the microphone 141. For this reason, the noise N is attenuated by the influence of the passive sound insulation element 220 and then collected by the microphone 141. In other words, relatively large noise is collected in the ear hole opening device 100 as compared with the sealed noise canceling earphone. Therefore, it is desirable that the ear hole opening device 100 according to the present embodiment use an amplifier and a driver that have a larger output than the sealed noise canceling earphone.

Here, the noise cancellation process of the classical control FB scheme using the ear hole opening device 100, which has been described with reference to FIG. 8, will be considered.

First, the audio signal input to the driver 110 is defined as y. Then, the sound pressure P at the position of the microphone 141 is defined by the following Formula (A1).

$$P(N+yDH_1)H_2 \quad (A1)$$

The audio signal y is defined by the following Formula (A2).

$$\{-\beta_1 M(yDH_1 + N)\}A = y \quad (A2)$$
$$-\beta_1 AMDH_1 y - \beta_1 AMN = y$$
$$\{1 + \beta_1 AMDH_1\}y = -\beta_1 AMN$$
$$y = \frac{-\beta_1 AM}{\{1 + \beta_1 AMDH_1\}}N$$

The sound pressure P is derived by the following Formula (A3) from the Formulas (A1) and (A2).

$$P = (N + yDH_1)H_2 \quad (A3)$$
$$P = NH_2 + \frac{-\beta_1 MA}{(\beta_1 MADH_1 + 1)}DH_1 H_2 N$$
$$= \left\{H_2 + \frac{-\beta_1 MA}{(\beta_1 MADH_1 + 1)}DH_1 H_2\right\}N$$
$$= \left\{\frac{H_2 \beta_1 MADH_1 + H_2 - \beta_1 MADH_1 H_2}{(\beta_1 MADH_1 + 1)}\right\}N$$
$$= \left\{\frac{1 + \beta_1(MADH_1 - MADH_1)}{\beta_1 MADH_1 + 1}\right\}H_2 N$$
$$= \left(\frac{H_2}{\beta_1 MADH_1 + 1}\right)N$$

Here, a coefficient relating to the noise N in Formula (A3) will be also referred to as a sensitivity function. A characteristic pi of the first FB filter 201 is a designable parameter. As pi is maximized, the denominator of the sensitivity coefficient is maximized, the sensitivity coefficient is minimized, so that the sound pressure P is minimized. That is, as pi is maximized, the sound pressure at the eardrum position decreases, and noise is canceled more greatly.

(2) Internal Model Control FB Scheme

Next, an internal model control FB scheme (inter model control (IMC) scheme) will be described with reference to FIG. 10.

Figure 10:
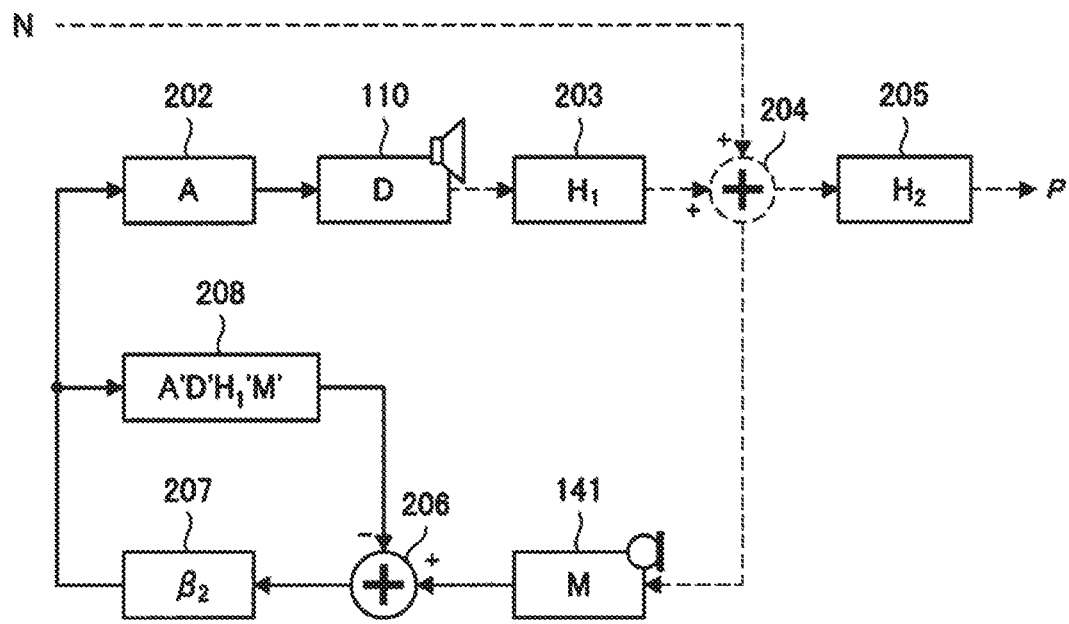
FIG. 10 is a diagram illustrating a model configuration example of a noise cancellation process of an internal model control FB scheme using the ear hole opening device according to the embodiment.

FIG. 10 is a diagram illustrating a model configuration example of a noise cancellation process of the internal model control FB scheme using the ear hole opening device 100 according to the present embodiment. The model configuration example illustrated in FIG. 10 is different from the model configuration example illustrated in FIG. 8 in terms that the second FB filter 207 is provided instead of the first FB filter 201 and the internal model 208 and an adder 206 are provided. Hereinafter, differences from the model configuration example illustrated in FIG. 8 will be mainly described.

The second FB filter 207 is a filter circuit that performs the noise cancellation process of the FB scheme. The second FB filter 207 performs the noise cancellation process using the microphone 141 as the cancellation point based on the input audio signal, and generates a noise cancellation signal. The audio signal that has passed through the second FB filter 207 is input to the amplifier 202 and also input to the internal model 208.

The internal model 208 corresponds to the internal model of the ear hole opening device 100. The internal model is a signal processing internal path, and is a model having a characteristic simulating a secondary path. Note that the secondary path is a physical space transfer characteristic from a secondary sound source to an error microphone. The internal model 208 herein has characteristics simulating characteristics until the noise cancellation signal output from the second FB filter 207 is output from the driver 110 and collected by the microphone 141 and returns to the second FB filter. The internal model 208 in the model configuration example illustrated in FIG. 10 has a characteristic of A'D'H$_1$'M'. The audio signal that has passed through the internal model 208 is input to the adder 206. The adder 206 subtracts the audio signal that has passed through the internal model 208 from the audio signal generated by the microphone 141 to perform synthesis. The synthesized signal is input to the second FB filter 207.

(3) Combination of Classical Control FB Scheme and Internal Model Control FB Scheme Next, a case where the classical control FB scheme and the internal model control FB scheme are used in combination will be described with reference to FIG. 11.

Figure 11:
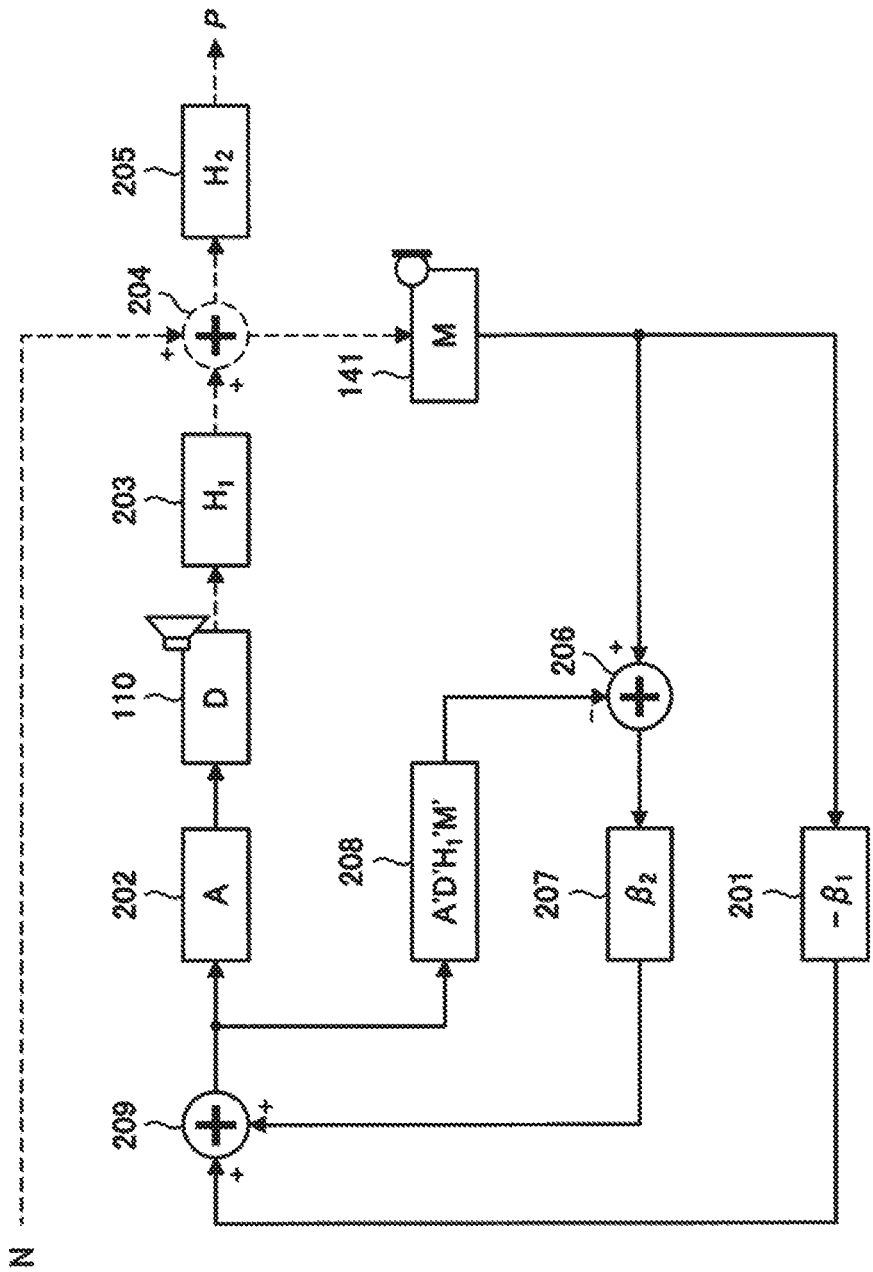
FIG. 11 is a diagram illustrating a model configuration example of a noise cancellation process using both the classical control FB scheme and the internal model control FB scheme using the ear hole opening device according to the embodiment.

FIG. 11 is a diagram illustrating a model configuration example of a noise cancellation process using both the classical control FB scheme and the internal model control FB scheme using the ear hole opening device 100 according to the present embodiment. The model configuration example illustrated in FIG. 11 is obtained by adding a first FB filter (characteristic: −V and an adder 209 to the model configuration example illustrated in FIG. 10. Hereinafter, constituent elements newly added to the model configuration example illustrated in FIG. 10 will be mainly described.

The audio signal input from the microphone 141 is input to the adder 206 and also input to the first FB filter 201. As described above, the first FB filter 201 generates the noise cancellation signal based on the input audio signal.

The audio signals that have passed through each of the first FB filter 201 and the second FB filter 207 are input to the adder 209 to be synthesized. The synthesized signal is input to the internal model 208 and output from the driver 110 via the amplifier 202.

Although the noise cancellation process of the FB scheme has been described as above, the present technique is not limited to this example. The ear hole opening device 100 may perform noise cancellation process of the FF scheme together with or instead of the noise cancellation process of the FB scheme. In such a case, it is desirable that the ear hole opening device 100 measure audio characteristics when being worn by the user in advance and sets the characteristics of the FF filter.

(4) Processing in Music Reproduction

Figure 12:
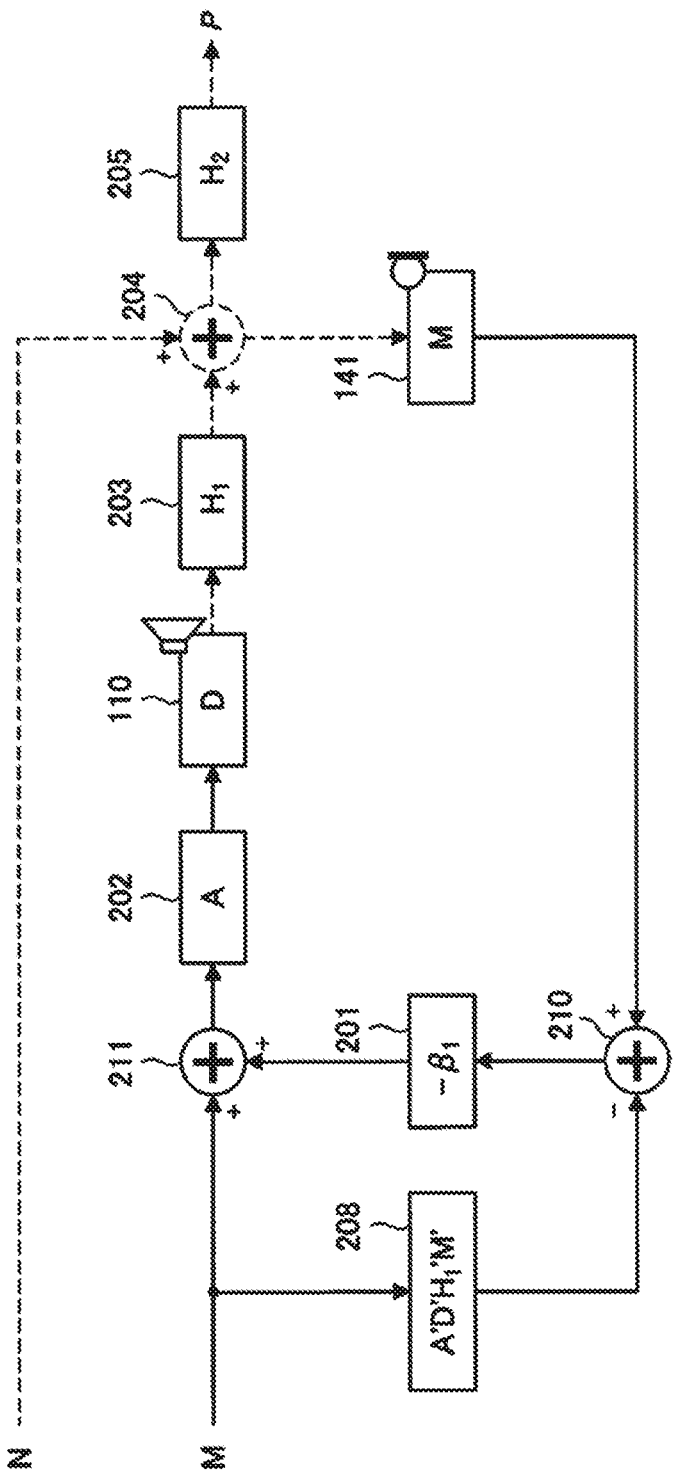
FIG. 12 is a diagram illustrating a model configuration example of a noise cancellation process of the classical control FB scheme during music reproduction using the ear hole opening device according to the embodiment.

FIG. 12 is a diagram illustrating a model configuration example of a noise cancellation process of the classical control FB scheme during music reproduction using the ear hole opening device 100 according to the present embodiment. In the model configuration example illustrated in FIG. 12, an internal model 208, an adder 210, and an adder 211 are added to the model configuration example illustrated in FIG. 8, and an audio signal M is additionally input. Hereinafter, constituent elements newly added to the model configuration example illustrated in FIG. 8 will be mainly described.

The music signal M is input to the internal model 208 and the adder 211. The music signal that has passed through the internal model 208 is input to the adder 210. In addition, the audio signal generated by the microphone 141 is input to the adder 210. The adder 210 subtracts the music signal that has passed through the internal model 208 from the audio signal generated by the microphone 141 to perform synthesis. Then, the synthesized signal is input to the first FB filter 201. The audio signal that has passed through the first FB filter 201 is input to the adder 211. The adder 211 synthesizes the audio signal that has passed through the first FB filter 201 and the music signal M. The synthesized signal is output from the driver 110 via the amplifier 202.

In this manner, the FB filter is applied after subtracting the music signal component from the noise-containing audio signal output from the microphone 141 in this noise cancellation process. As a result, it is possible to prevent music that needs to be reproduced from being reduced together with noise.

(5) Processing in Own Voice Extraction

The signal processing unit 151 extracts user's own voice based on the audio information acquired by each of the pair of audio information acquisition units 140 for both ears, and synthesizes the extracted user's voice with the noise cancellation signal. When noise is collected including the user's own voice, the noise cancellation signal includes a component that cancels the user's own voice. In this regard, the user's own voice is output at the ear as the user's own voice is synthesized with the noise cancellation signal. Accordingly, it is possible to prevent the user from feeling uncomfortable as if his/her voice is canceled as noise and his/her voice becomes distant. Hereinafter, a process of extracting the own voice and synthesizing the extracted voice with the noise cancellation signal will be described in detail with reference to FIG. 13.

Figure 13:
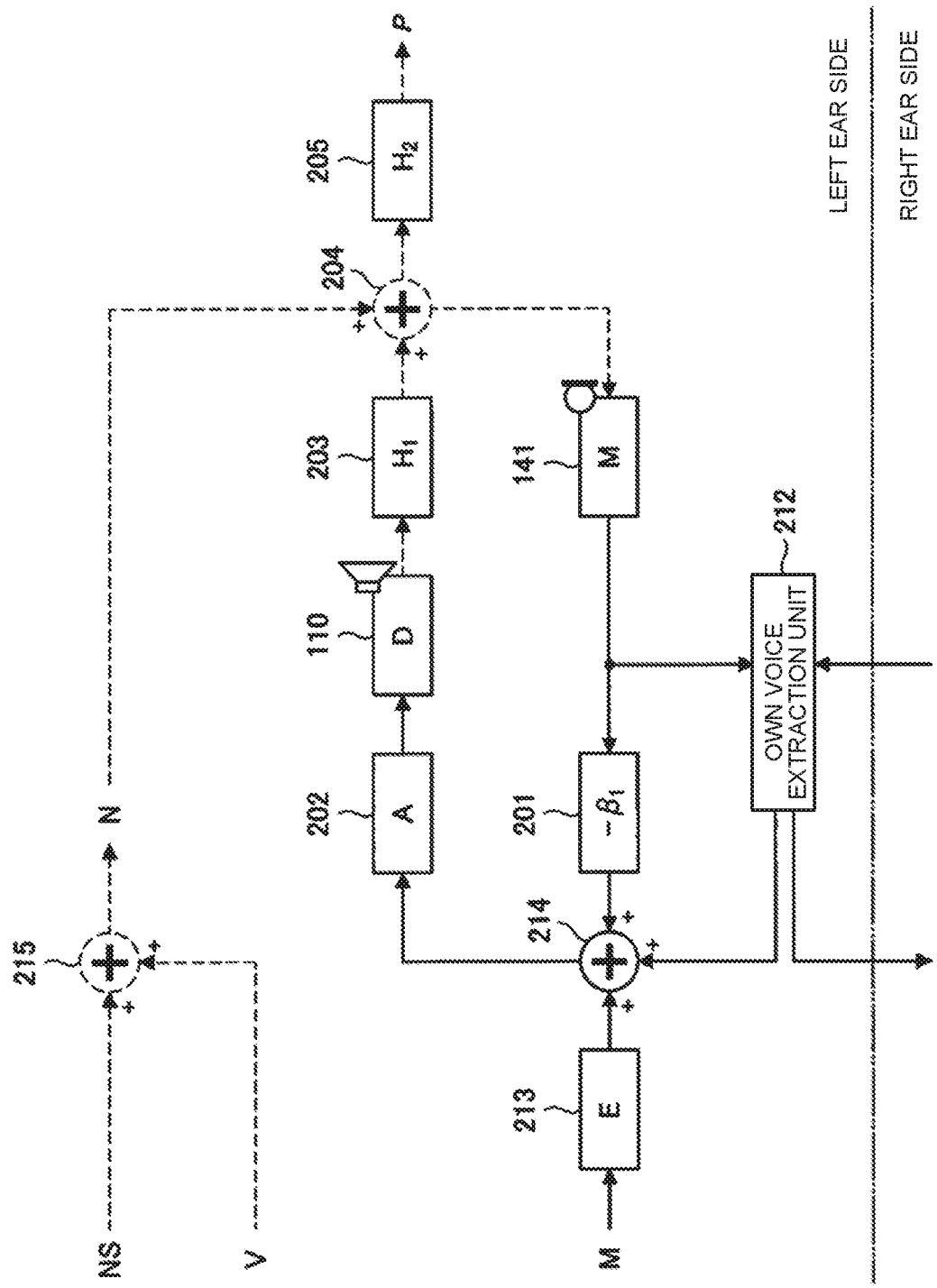
FIG. 13 is a diagram illustrating a model configuration example of a noise cancellation process of the classical control FB scheme including own voice extraction using the ear hole opening device according to the embodiment.

FIG. 13 is a diagram illustrating a model configuration example of a noise cancellation process of the classical control FB scheme including own voice extraction using the ear hole opening device 100 according to the present embodiment. The model configuration example illustrated in FIG. 13 is obtained by adding an own voice extraction unit 212, an equalizer 213, an adder 214, and a space 215 to the model configuration example illustrated in FIG. 8. The incoming noise N is audio obtained by synthesizing a noise source NS and user's speech voice V (that is, own voice) in the space 215. However, the model configuration example illustrated in FIG. 13 illustrates the model configuration example on the left ear side, and does not illustrate the right ear side. Hereinafter, constituent elements newly added to the model configuration example illustrated in FIG. 8 will be mainly described in the model configuration example illustrated in FIG. 13.

The microphone 141 for the left ear collects the noise N having passed through the space 204 and generates an audio signal. The same applies to the right ear. The audio signals generated by the left and right microphones 141 are input to the own voice extraction unit 212. The own voice extraction unit 212 extracts the own voice V based on the input audio signals. For example, the own voice extraction unit 212 extracts the own voice V by extracting an in-phase signal component from the input audio signal. The own voice extraction unit 212 outputs an audio signal indicating the extracted own voice V to the left and right adders 214.

Meanwhile, the audio signal generated by the microphone 141 is also input to the first FB filter 201. A noise cancellation signal generated by the first FB filter 201 is input to the adder 214. In addition, the music signal M is input to the equalizer 213. The equalizer 213 adjusts the sound quality of the input music signal M based on the characteristic E. The music signal that has passed through the equalizer 213 is input to the adder 214.

The adder 214 synthesizes the audio signals input from each of the own voice extraction unit 212, the first FB filter 201, and the equalizer 213. The synthesized signal is output from the driver 110 via the amplifier 202.

As a result, even if the own voice V having passed through the opening portion 131 is canceled by the noise cancellation signal, the own voice V extracted by the own voice extraction unit 212 is output from the driver 110. As a result, it is possible to prevent the user from feeling uncomfortable as if his/her voice is canceled as noise and his/her voice becomes distant.

Note that the ear hole opening device 100 may further include a microphone configured to collect user's own voice as the audio information acquisition unit 140 in addition to the microphone 141 held by the holding unit 130. For example, the ear hole opening device 100 can include the microphone in the vicinity of the pinch portion 123 illustrated in FIG. 1. In such a case, the own voice extraction unit 212 extracts the user's voice based on an audio signal generated by the microphone. As a result, the own voice extraction unit 212 can extract the user's voice with higher accuracy.

<1.6. Noise Cancellation Process Based on Sound Pressure Information of Eardrum>

The ear hole opening device 100 may perform a noise cancellation process based on eardrum sound pressure information. In such a case, the audio information acquisition unit 140 acquires the eardrum sound pressure information as audio information. Then, the signal processing unit 151 performs the noise cancellation process based on the eardrum sound pressure information instead of the audio signal generated by the microphone 141. Of course, the signal processing unit 151 may perform the noise cancellation process using both the audio signal generated by the microphone 141 and the eardrum sound pressure information acquired by the eardrum sound pressure acquisition unit 142. Hereinafter, a description will be given assuming that the ear hole opening device 100 is equipped with the eardrum sound pressure acquisition unit 142 as the audio information acquisition unit 140.

(1) Configuration of Eardrum Sound Pressure Acquisition Unit 142

The eardrum sound pressure acquisition unit 142 has a function of acquiring vibration information of the ear canal or the eardrum and acquiring sound pressure information of a cancellation point based on the acquired vibration information.

Specifically, the eardrum sound pressure acquisition unit 142 transmits a transmission wave, acquires a reflection wave which is the reflected transmission wave, and acquires the vibration information indicating displacement or speed at a reflection point. In the reflection wave, a frequency change proportional to a movement speed of the reflection point occurs. Specifically, a frequency of the reflection wave increases when an object approaches, and the frequency decreases when the object moves away. The eardrum sound pressure acquisition unit 142 estimates the displacement or speed of the reflection point based on a frequency difference between the transmission wave and the reflection wave. The transmission wave is transmitted to the ear canal or the eardrum, and is reflected at an arbitrary reflection point in the ear canal or the eardrum. The reflection point may be the same as or different from the cancellation point.

For example, the eardrum sound pressure acquisition unit 142 may be realized by a laser distance measuring device, and the transmission wave may be a laser. In addition, the eardrum sound pressure acquisition unit 142 may be realized by an ultrasonic distance measuring device, and in this case, the transmission wave is an ultrasonic wave. However, the transmission wave is desirably a laser from the viewpoint of interference. In the case of using the laser, there is an advantage that collection of wind noise by the microphone 141 does not occur in principle. Note that a laser light source may emit light intermittently instead of emitting light continuously. In addition, the light emission frequency may be equal to a sampling rate relating to reflection wave acquisition. As a result, power consumption can be reduced. Hereinafter, a description will be given assuming that the eardrum sound pressure acquisition unit 142 is realized by the laser distance measuring device.

The eardrum sound pressure acquisition unit 142 can also measure a distance between the eardrum sound pressure acquisition unit 142 and the reflection point. For example, the laser distance measuring device measures a distance between the laser distance measuring device and the reflection point based on a time from transmission of a laser to reception of the laser reflected from the reflection point. Such a measurement method will be also referred to as a time of flight (ToF) scheme. Note that it is sufficient that at least a device that transmits a transmission wave and receives a reception wave is held by the holding unit 130 in the eardrum sound pressure acquisition unit 142, and an arrangement of a device that estimates and acquires an eardrum sound pressure based on vibration information is not particularly limited.

The cancellation point is one point on the eardrum. That is, the eardrum sound pressure acquisition unit 142 acquires the eardrum sound pressure information. Since the eardrum sound pressure information is used for the noise cancellation process, the high noise canceling performance can be realized.

The reflection point is also desirably one point on the eardrum. In this case, the eardrum vibration information is directly acquired, and thus, the eardrum sound pressure acquisition unit 142 can acquire the eardrum sound pressure information based on the eardrum vibration information. Accordingly, the eardrum sound pressure information can be estimated with high accuracy.

On the other hand, the reflection point may be on the inner wall of the ear canal. In this case, the eardrum sound pressure acquisition unit 142 estimates the eardrum sound pressure information based on vibration information of two or more points on the inner wall of the ear canal. For example, the eardrum sound pressure acquisition unit 142 refers to a model having a correlation between a vibration of the inner wall of the ear canal and a vibration of the eardrum to estimate the eardrum vibration information based on the vibration information of two or more points on the inner wall of the ear canal. Then, the eardrum sound pressure information is estimated based on the estimation result of the vibration information of the eardrum. As a result, even when the eardrum is not directly irradiated with a laser, it is possible to execute the noise cancellation process using the eardrum sound pressure information. In addition, the eardrum sound pressure acquisition unit 142 may measure the eardrum vibration information and the vibration information of the inner wall of the ear canal and estimate the sound pressure information of the eardrum position based on these measurement results. In this case, the sound pressure information of the eardrum position can be estimated with higher accuracy.

In addition, the eardrum sound pressure acquisition unit 142 can measure a self-generated sound (for example, own voice) due to body conduction based on vibration information of the inner wall of the ear canal. The eardrum sound pressure acquisition unit 142 can measure the self-generated sound based on left and right air propagation sound wave information in addition to the vibration information of the inner wall of the ear canal.

Note that whether the reflection point is the eardrum or the inner wall of the ear canal can be determined based on, for example, information indicating a three-dimensional shape to be described later.

Hereinafter, a state of distance measurement using the eardrum sound pressure acquisition unit 142 realized as the laser distance measuring device will be described in detail with reference to FIGS. 14 to 17.

Figure 14:
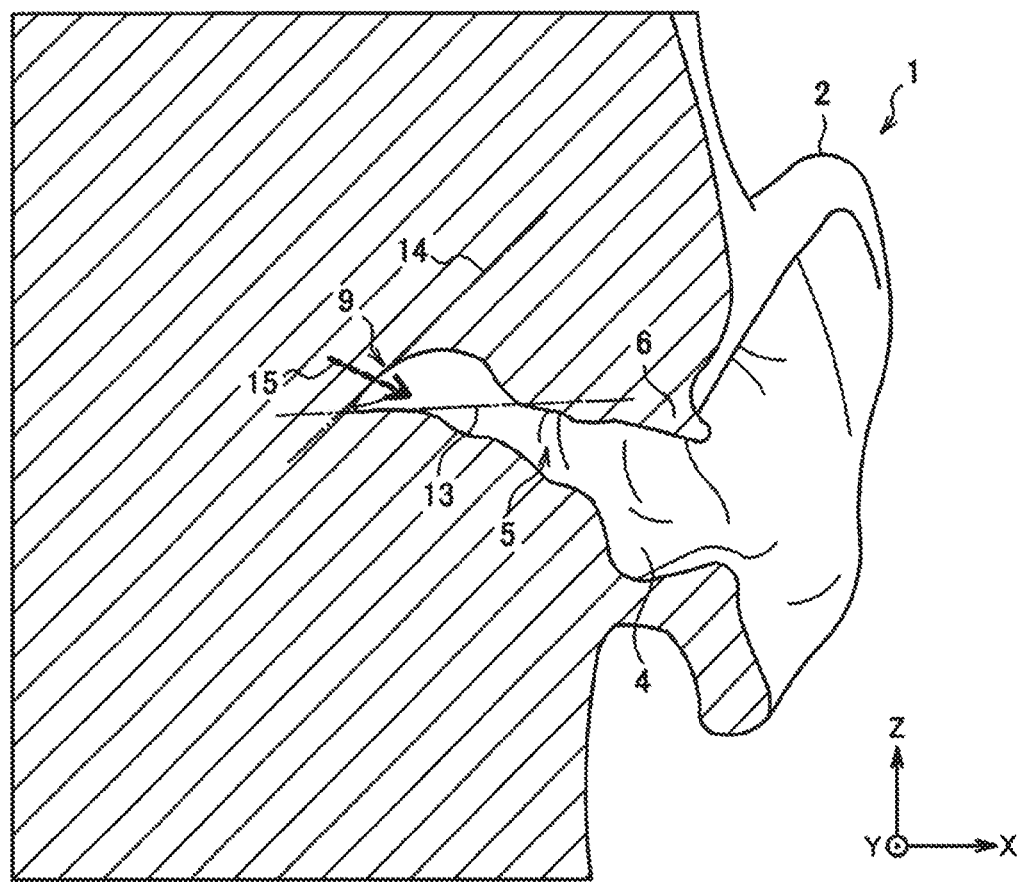
FIG. 14 is a cross-sectional view illustrating a state of the inside of an ear canal of user's left ear.

FIG. 14 is a cross-sectional view illustrating a state of the inside of the ear canal of the user's left ear. As illustrated in FIG. 14, an eardrum vibrating surface 14 forms a predetermined angle with respect to a lower wall 13 of the ear canal. In the case of an adult, the eardrum vibrating surface 14 forms an angle of about 50 degrees with respect to the lower wall 13 of the ear canal.

Figure 15:
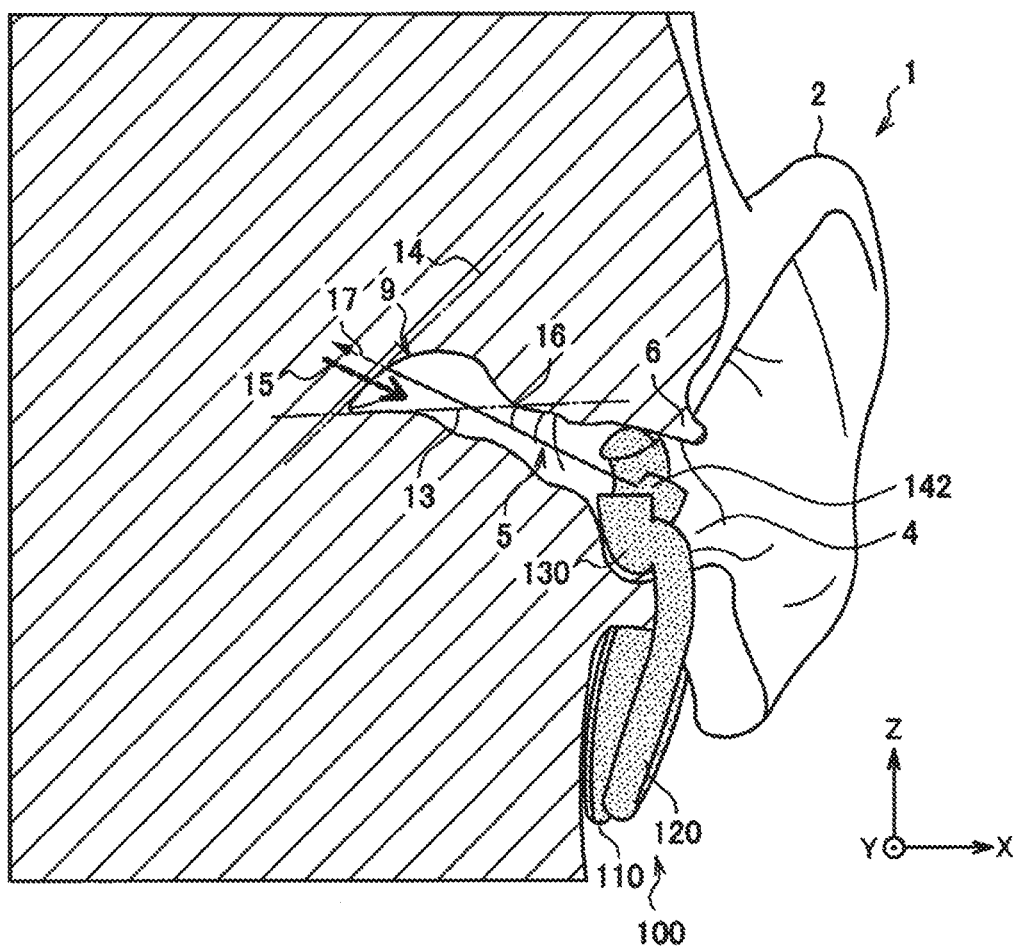
FIG. 15 is a view illustrating a state where the inside of the ear canal of user's left ear illustrated in FIG. 14 is irradiated with a laser by the ear hole opening device.
Figure 16:
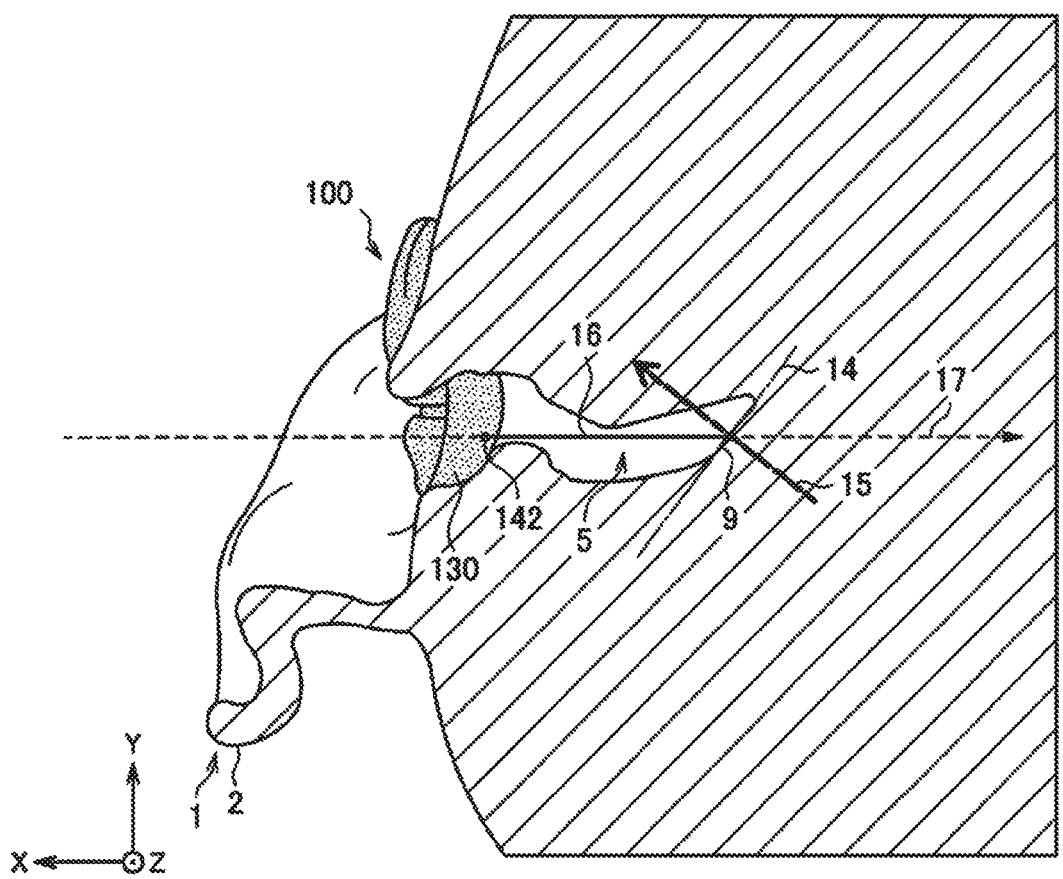
FIG. 16 is a view illustrating a state where the inside of the ear canal of user's left ear illustrated in FIG. 14 is irradiated with a laser by the ear hole opening device.
Figure 17:
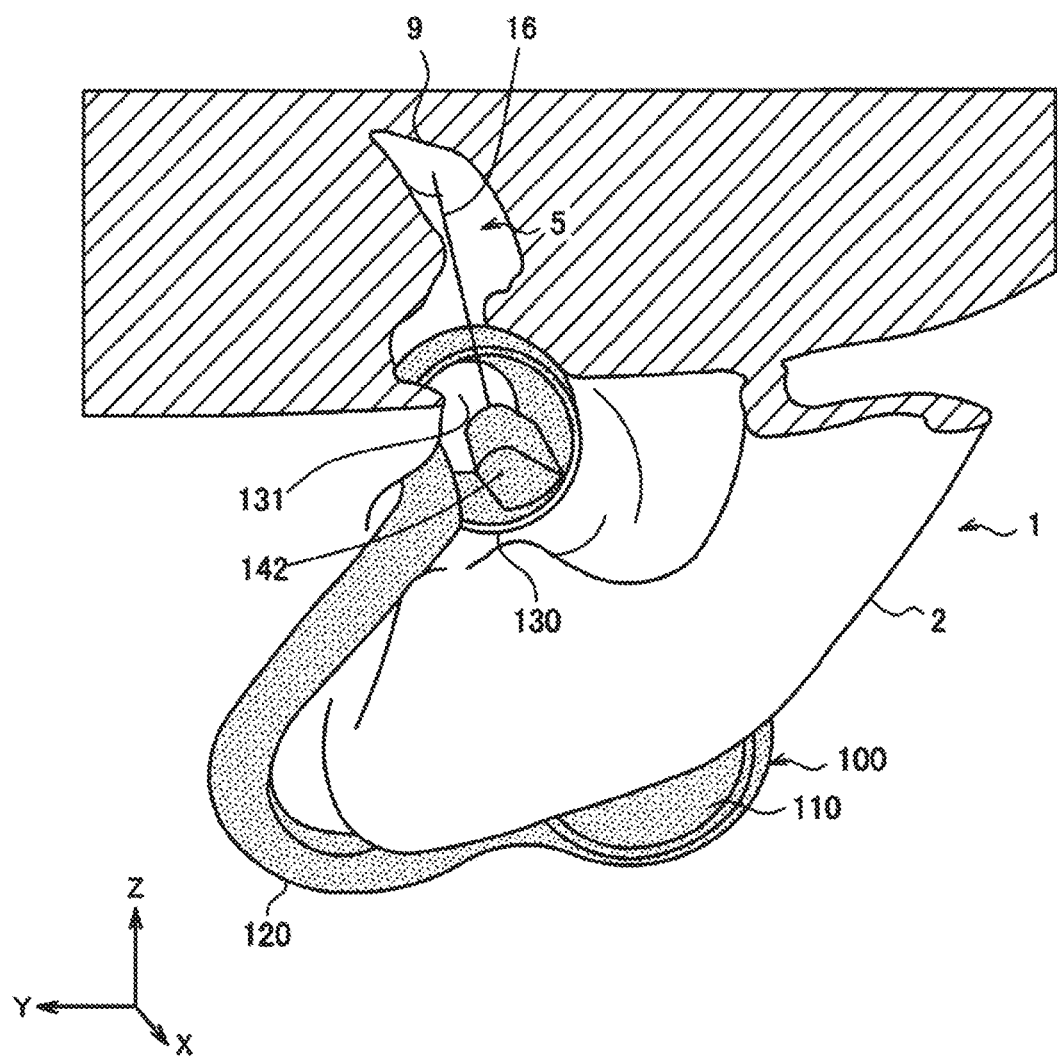
FIG. 17 is a view illustrating a state where the inside of the ear canal of user's left ear illustrated in FIG. 14 is irradiated with a laser by the ear hole opening device.

FIGS. 15 to 17 are views illustrating a state where the inside of the ear canal of user's left ear illustrated in FIG. 14 is irradiated with a laser by the ear hole opening device 100. FIG. 15 is a view from the same viewpoint as FIG. 14, FIG. 16 is a view of the viewpoint looking down from the Z-axis positive direction to the Z-axis negative direction, and FIG. 17 is a view of the viewpoint from the vicinity of the middle between the X-axis positive direction and the Z-axis positive direction toward the origin. As illustrated in FIGS. 15 to 17, the eardrum 9 is irradiated with a laser 16 by the eardrum sound pressure acquisition unit 142 (laser distance measuring device). As illustrated in FIGS. 15 and 16, an irradiation direction 17 of the laser 16 and a vibration direction 15 of the eardrum 9 can intersect each other with a specific angle. It is desirable to correct this angular difference in order to accurately estimate the sound pressure information of the eardrum 9. The correction of the angular difference may be performed by logical calculation or may be performed by physical control of the laser irradiation direction to be described later.

As illustrated in FIGS. 15 and 16, it is desirable that the holding unit 130 hold the eardrum sound pressure acquisition unit 142 at a position where the inner wall of the ear canal 5 is not present on a straight line between the eardrum sound pressure acquisition unit 142 and the eardrum 9. In other words, it is desirable that the eardrum sound pressure acquisition unit 142 be held at a position where there is no obstacle between the eardrum sound pressure acquisition unit 142 and the eardrum 9. As a result, it is possible to directly reflect the laser emitted from the eardrum sound pressure acquisition unit 142 to one point on the eardrum 9.

(2) Eardrum Sound Pressure Acquisition Process

Hereinafter, an eardrum sound pressure acquisition process will be described with reference to FIGS. 18 to 20.

First Example

Figure 18:
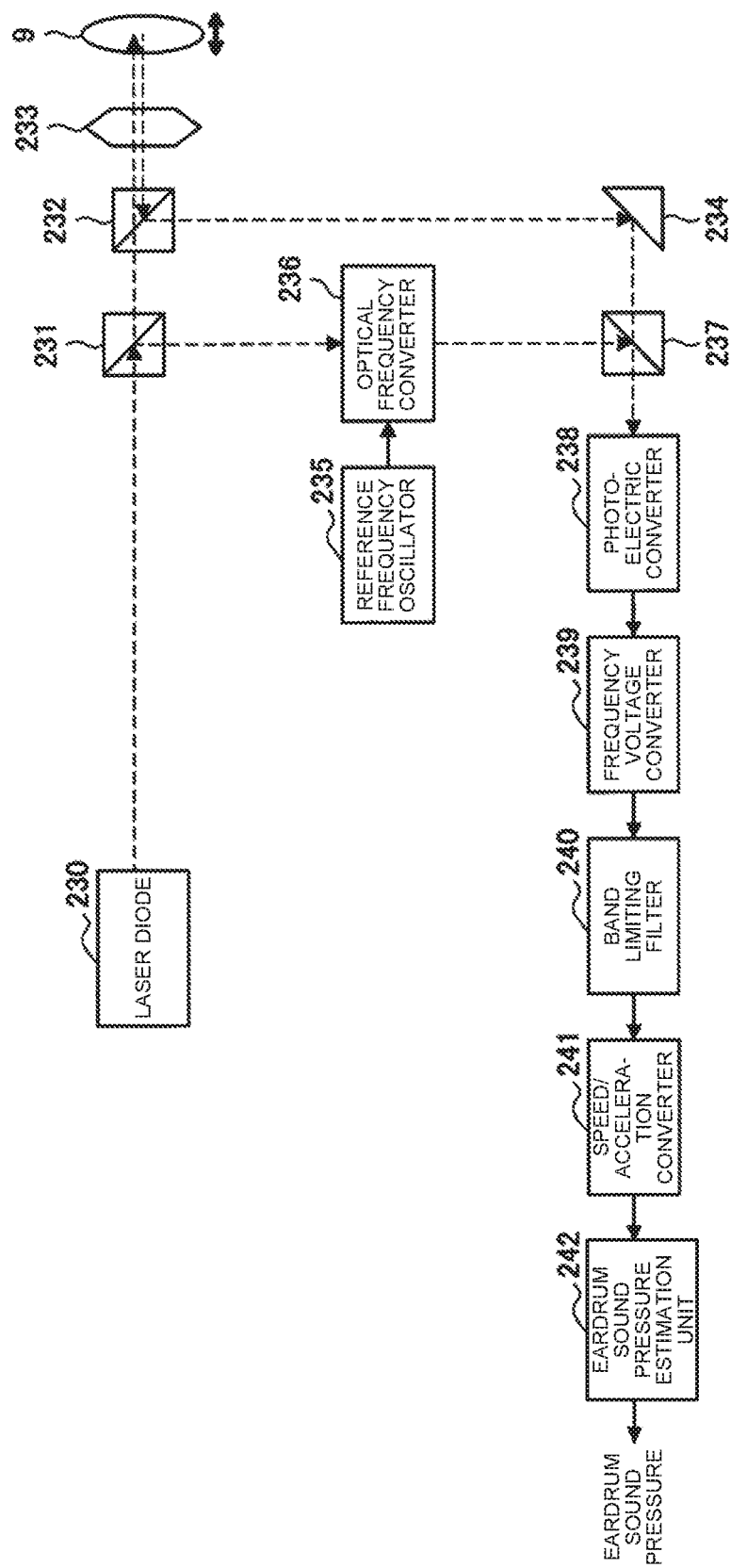
FIG. 18 is a diagram for describing a model configuration example of an eardrum sound pressure estimation process according to the embodiment.

FIG. 18 is a diagram for describing a model configuration example of an eardrum sound pressure estimation process according to the present embodiment.

A laser diode 230 generates and emits a laser. The laser emitted from the laser diode 230 is separated into two directions by a beam splitter 231, and one beam thereof passes through the beam splitter 232 and a focus lens 233 and reaches the eardrum 9. The laser reflected by the eardrum 9 passes through the focus lens 233, is reflected by the beam splitter 232 and a mirror 234, passes through the beam splitter 237, and is input to a photoelectric converter 238.

On the other hand, the other beam of the laser emitted from the laser diode 230 and separated by the beam splitter 231 is input to an optical frequency converter 236. A signal oscillated at a reference frequency by a reference frequency oscillator 235 is also input to the optical frequency converter 236. The optical frequency converter 236 modulates a frequency of the laser emitted from the laser diode 230 to the reference frequency and outputs the reference frequency. The laser output from the optical frequency converter 236 is reflected by the beam splitter 237 and input to the photoelectric converter 238.

The laser that has passed through the beam splitter 237 is converted into a light intensity signal by the photoelectric converter 238. The light intensity signal indicates an eardrum vibration frequency that is frequency-modulated with the reference frequency. The light intensity signal is converted into a signal of a frequency domain by a frequency voltage converter 239, the converted signal is subjected to a band-limiting filter 240 and is input to a speed/acceleration converter 241. The signal after having been subjected to band-limiting filter processing by the band-limiting filter 240 is an eardrum vibration speed signal. The speed/acceleration converter 241 converts an eardrum speed into an eardrum acceleration based on the eardrum speed signal, and outputs a signal indicating the eardrum acceleration to the eardrum sound pressure estimation unit 242. The eardrum sound pressure estimation unit 242 estimates an eardrum sound pressure (sound pressure information of the eardrum 9) based on the eardrum acceleration. Note that the eardrum sound pressure is estimated by the following formula.

$$\text{Eardrum sound pressure } P_D = K \cdot a$$

Here, a [m/s²] is an acceleration signal obtained by the speed/acceleration converter 241. K [kg/m²] is a constant composed of the area, the mass, and the tension of the eardrum, a correction coefficient based on an entry angle of a laser into the eardrum, and the like. Note that at least a part of the eardrum sound pressure acquisition process may be performed by a digital circuit. For example, the processing of the speed/acceleration converter 241 and the eardrum sound pressure estimation unit 242 may be performed by the digital circuit. In addition, the eardrum sound pressure estimation unit 242 may include the function as the speed/acceleration converter 241.

Second Example

A shape of an ear, particularly a shape of an ear canal and an arrangement of an eardrum vary from person to person. Therefore, a laser irradiation point (that is, a reflection point) is not necessarily located at the center of the eardrum in a state where the ear hole opening device 100 is worn by a user.

Therefore, the eardrum sound pressure acquisition unit 142 may estimate sound pressure information of the eardrum additionally based on information indicating a three-dimensional shape of user's ear canal. For example, the eardrum sound pressure acquisition unit 142 controls a laser irradiation direction based on the information indicating the three-dimensional shape of the ear canal and uses the eardrum as the reflection point. As a result, the eardrum sound pressure can be estimated directly, and thus, the accuracy can be improved.

The eardrum sound pressure acquisition unit 142 acquires the information indicating the three-dimensional shape of the ear canal by scanning the ear canal while changing a transmission direction of a transmission wave. Specifically, the eardrum sound pressure acquisition unit 142 measures a distance while sequentially changing the laser irradiation direction, thereby acquiring a map of the distance between the eardrum sound pressure acquisition unit 142 and the reflection point as a scanning result. This distance map is the information indicating the three-dimensional shape of the ear canal with reference to the eardrum sound pressure acquisition unit 142.

Figure 19:
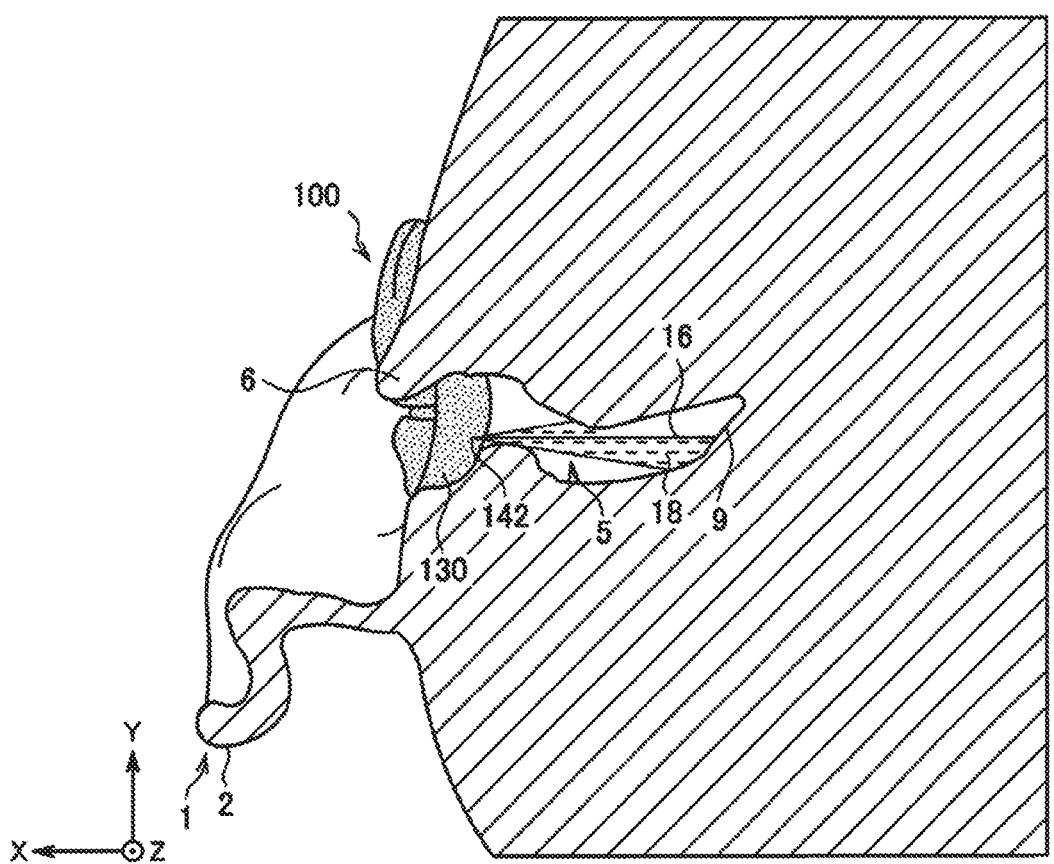
FIG. 19 is a view illustrating a state of scanning of the ear canal using the ear hole opening device according to the embodiment.

FIG. 19 is a view illustrating a state of scanning of the ear canal using the ear hole opening device 100 according to the present embodiment. As illustrated in FIG. 19, the laser 16 is emitted from the eardrum sound pressure acquisition unit 142 while changing the irradiation direction. The ear hole opening device 100 acquires information indicating a three-dimensional shape of a range 18 irradiated with the laser. Accordingly, for example, the eardrum sound pressure acquisition unit 142 can search for a direction in which the eardrum 9 can be directly irradiated with the laser.

A mechanism for acquiring the information indicating the three-dimensional shape of the ear canal can be realized as, for example, a MEMS (micro electro mechanical systems) scanner. Hereinafter, a process of estimating the eardrum sound pressure using the MEMS scanner will be described with reference to FIG. 20.

Figure 20:
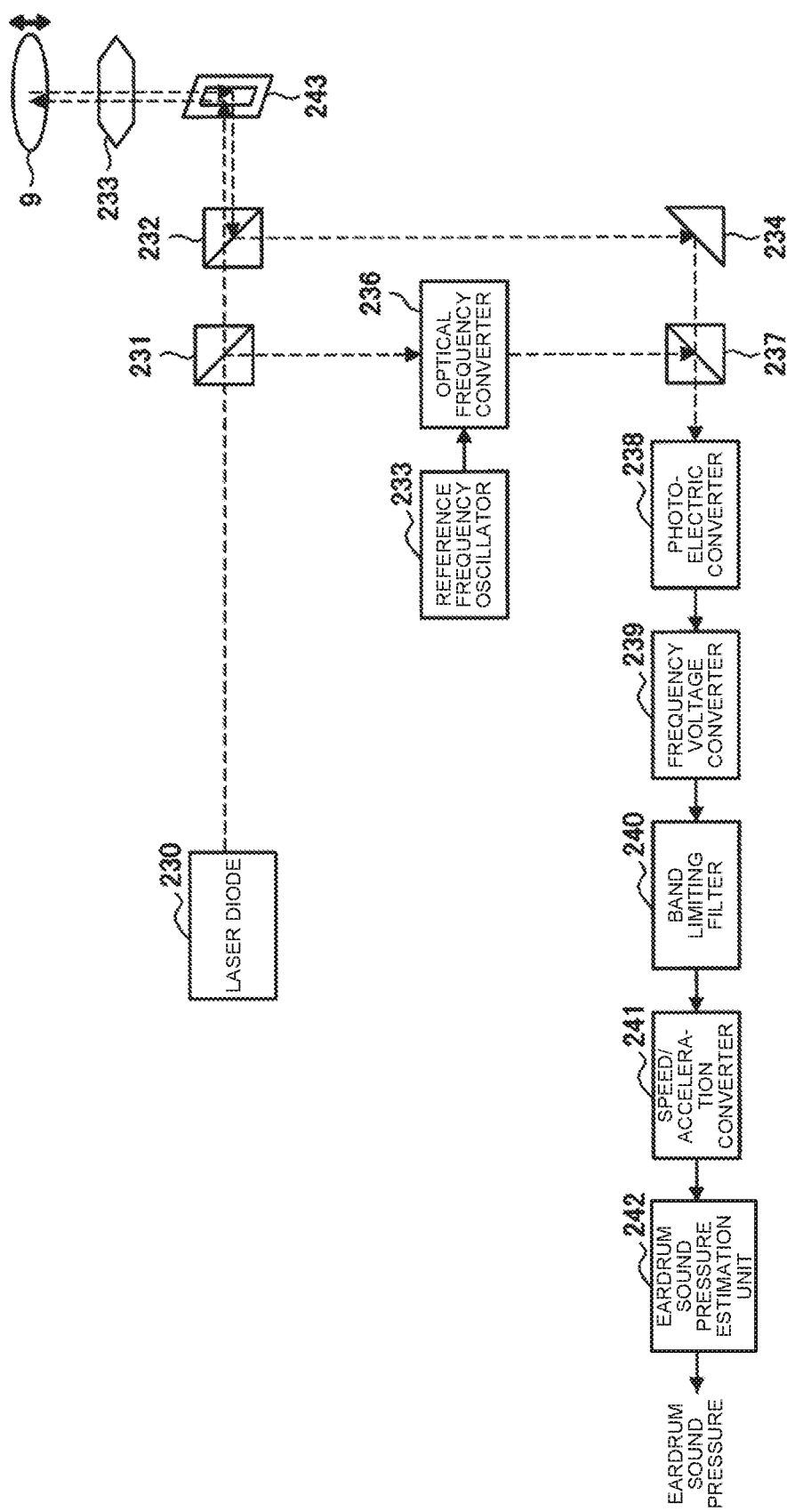
FIG. 20 is a diagram for describing a model configuration example of the eardrum sound pressure estimation process according to the embodiment.

FIG. 20 is a diagram for describing a model configuration example of the eardrum sound pressure estimation process according to the present embodiment. The model configuration example illustrated in FIG. 20 includes a MEMS scanner 243 between the beam splitter 232 and the focus lens 233 in the model configuration example illustrated in FIG. 18. The MEMS scanner 243 functions as an irradiation angle correction unit that corrects and outputs an irradiation angle of an input laser. The MEMS scanner 243 can change the irradiation direction of the laser input from the beam splitter 232. The eardrum sound pressure acquisition unit 142 acquires the information indicating the three-dimensional shape of the ear canal by controlling the MEMS scanner 243 so as to sequentially change the laser irradiation direction. Then, the eardrum sound pressure acquisition unit 142 controls the MEMS scanner 243 such that a laser is emitted in a direction in which the eardrum becomes the reflection point based on the information indicating the three-dimensional shape of the ear canal.

(3) Utilization of Information Indicating Three-Dimensional Shape

Personal Authentication

The authentication unit 155 may authenticate a user based on the information indicating the three-dimensional shape of the ear canal acquired by the eardrum sound pressure acquisition unit 142. For example, the authentication unit 155 compares a feature amount of information indicating a three-dimensional shape of user's ear canal stored in advance and a feature amount of the information indicating the three-dimensional shape of the ear canal acquired by the eardrum sound pressure acquisition unit 142. The authentication unit 155 determines whether the wearing user matches a user registered in advance based on the comparison result. Since the shape of the ear canal varies from person to person, the authentication is possible. Since even one person has different left and right ear shapes regarding human ears, the authentication unit 155 can further improve the authentication accuracy by performing the above comparison for the left and right ears. The signal processing unit 151 may perform signal processing based on the authentication result. For example, the signal processing unit 151 may perform a noise cancellation process using a filter characteristic set in advance for each user.

Hereinafter, a personal authentication process using information indicating the three-dimensional shape of the ear canal will be described with reference to FIG. 21.

Figure 21:
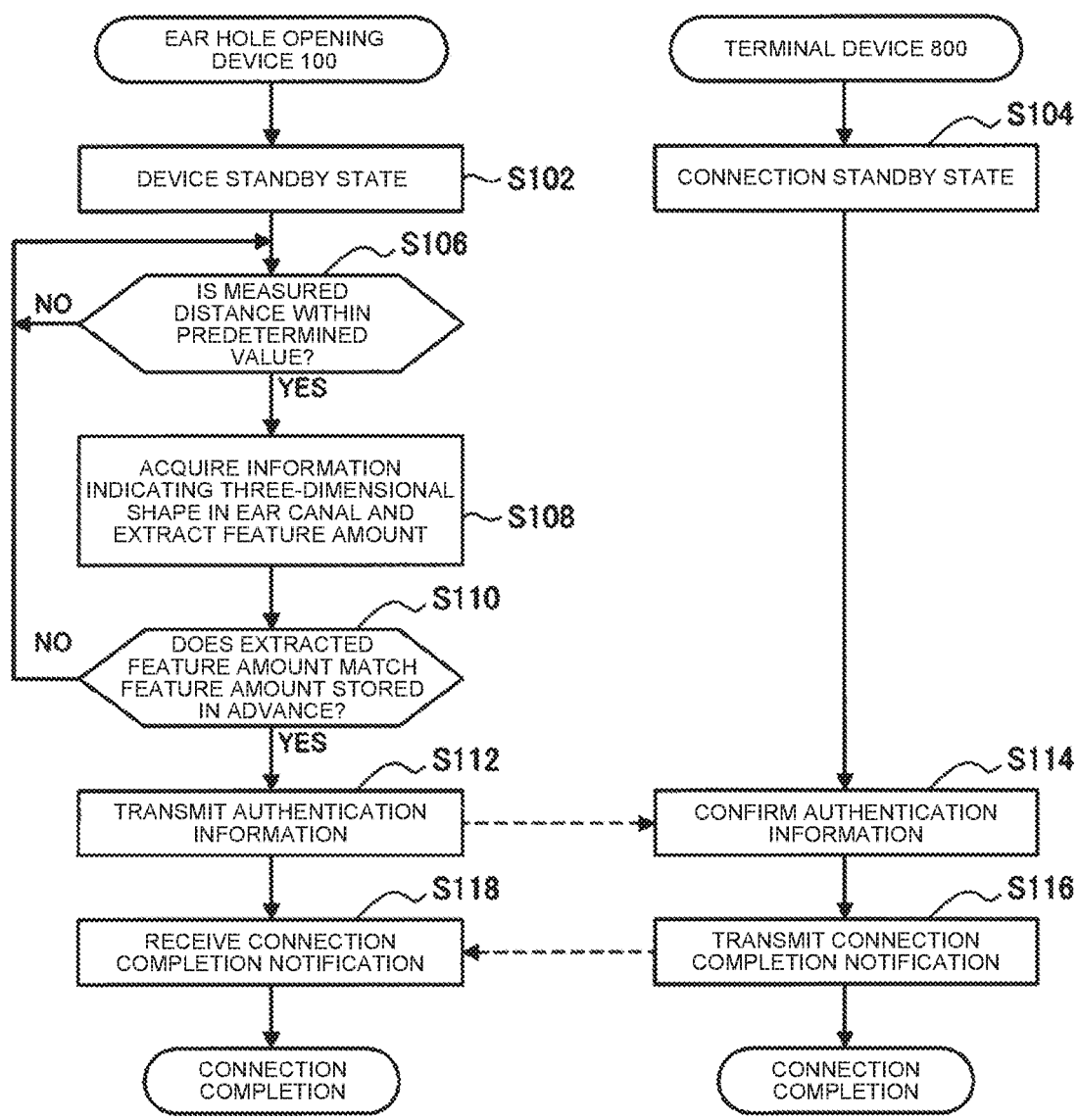
FIG. 21 is a sequence diagram illustrating an example of flow of a personal authentication process executed by the ear hole opening device and an external device according to the embodiment.

FIG. 21 is a sequence diagram illustrating an example of flow of the personal authentication process executed by the ear hole opening device 100 and a terminal device according to the present embodiment. As illustrated in FIG. 21, the ear hole opening device 100 and a terminal device 800 are involved in this sequence. The terminal device 800 is an arbitrary device such as a smartphone, a tablet terminal, and an agent device.

As illustrated in FIG. 21, the ear hole opening device 100 has not yet been worn by a user and is in a wearing standby state (Step S102). In addition, the terminal device 800 is not connected to the ear hole opening device 100 and is in a connection standby state (Step S104).

As illustrated in FIG. 21, the ear hole opening device 100 first determines whether a measured distance is within a predetermined value (Step S106). The predetermined value herein is, for example, the maximum value of an ear canal length. If the measured distance is within the predetermined value, it is understood that the distance measurement is performed at least in the ear canal. When it is determined that the measured distance is not within the predetermined value (Step S106/NO), the process returns to Step S106 again, and the wearing standby state is continued.

On the other hand, when it is determined that the measured distance is within the predetermined value (Step S106/YES), the ear hole opening device 100 acquires the information indicating the three-dimensional shape in the ear canal and extracts the feature amount (Step S108).

Next, the ear hole opening device 100 compares the extracted feature amount with the feature amount stored in advance, and determines whether both the feature amounts match (S110). When it is determined that both the feature amounts do not match (Step S110/NO), the process returns to Step S106 again.

When it is determined that both the feature amounts match (Step S110/YES), the ear hole opening device 100 transmits authentication information indicating that the user authentication has been completed to the terminal device 800 (Step S112). The terminal device 800 receives and confirms the authentication information from the ear hole opening device 100 (Step S114), performs a connection process, and transmits connection completion notification to the ear hole opening device 100 (Step S116). As a result, the terminal device 800 is turned into a connection completion state. The ear hole opening device 100 receives the connection completion notification from the terminal device 800 (Step S118). As a result, the ear hole opening device 100 is turned into the connection completion state.

Wearing Detection

The operation control unit 153 determines whether the ear hole opening device 100 is worn based on the information indicating the three-dimensional shape acquired by the eardrum sound pressure acquisition unit 142. For example, the operation control unit 153 determines that the ear hole opening device 100 is worn when the measured distance obtained by the eardrum sound pressure acquisition unit 142 is within the predetermined value, and determines that the ear hole opening device 100 is not worn when the measured distance exceeds the predetermined value. The predetermined value herein is, for example, the maximum value of an ear canal length. Then, the operation control unit 153 controls an operation of the ear hole opening device 100 based on the determination result. For example, the operation control unit 153 may cause the signal processing unit 151 to start generating a noise cancellation signal when determining that the ear hole opening device 100 is worn. In addition, the operation control unit 153 may cause the driver 110 to start outputting an output signal when determining that the ear hole opening device 100 is worn. As a result, the operation of the ear hole opening device 100 is automatically started when the user wears the ear hole opening device 100, and thus, an operation burden on the user is reduced. In addition, when determining that the ear hole opening device 100 is not worn, the operation control unit 153 may stop the generation of the noise cancellation signal and the output of the output signal. As a result, the operation of the ear hole opening device 100 is stopped or partly stopped in the non-wearing state, and thus, wasteful power consumption can be prevented.

Correction of Reproduced Sound

The signal processing unit 151 may adjust the sound quality of the output signal output from the driver 110 based on the information indicating the three-dimensional shape of the ear canal. For example, the signal processing unit 151 performs a process of attenuating a sound having an excessively reverberating frequency and emphasizing a sound having an excessively reduced frequency based on the information indicating the three-dimensional shape of the ear canal. As a result, it becomes possible to provide a user with the optimum sound quality in response to the three-dimensional shape of the user's ear canal.

(4) Other

Howling Canceller

The ear hole opening device 100 may detect howling that occurs when the microphone 141 collects the audio output by the driver 110. Then, when detecting the howling, the ear hole opening device 100 may stop or temporarily stop the output from the driver 110 or the noise cancellation process and notify the wearing of the stop. In addition, the situation where the howling has occurred may be transmitted to the outside via a wireless communication unit 170 to be described later.

Calibration Signal

The ear hole opening device 100 outputs a predetermined calibration signal from the driver 110, and collects the calibration signal by the microphone 141 so that transfer characteristics from the driver 110 to the microphone 141 can be obtained. This transfer characteristics depend on an ear shape and a worn state of each wearer. Therefore, the ear hole opening device 100 can perform the more suitable output configuration of the driver 110 by actually measuring the transfer characteristics from the driver 110 to the microphone 141 in the state of being worn by the user. In addition, the ear hole opening device 100 can adaptively configure the output configuration using the output signal and the actual audio signal collected from the microphone 141.

<1.7. Summary>

The first embodiment has been described in detail above. As described above, the ear hole opening device 100 according to the first embodiment opens the ear hole to the outside through the opening portion 131 while holding the audio information acquisition unit 140 acquiring the audio information in the space closer to the eardrum than the tragus using the holding unit 130 that abuts on the cavum concha or the inner wall of the ear canal. Then, the ear hole opening device 100 generates the noise cancellation signal based on the audio information acquired by the audio information acquisition unit 140. For example, the ear hole opening device 100 performs the noise cancellation process using the position of the audio information acquisition unit 140 or the eardrum position as the cancellation point. Since the position near the eardrum or the eardrum is the cancellation point, the high noise canceling performance can be realized.

As the ear hole opening device 100 is equipped with the noise cancellation function by such active processing, various effects are exhibited. Hereinafter, the effects exhibited in the present embodiment will be described with a specific example.

For example, an office or the like is filled with noise of a lower frequency than a speech voice such as air-conditioning sound in the office and incoming running sounds of trains or cars leaking from the outside of the office. The ear hole opening device 100 cancels this noise. In this case, the user wearing the ear hole opening day bus 100 can communicate more smoothly with others, and a mental load and a physical load are reduced.

In addition, a middle frequency band such as the speech voice is not subject to noise canceling, the speech voice is not canceled, and further the speech voice reaches the eardrum as it is since the ear hole is opened. For this reason, the user wearing the ear hole opening device 100 does not need to remove the ear hole opening device 100 each time to have a conversation.

In addition, the air inside and outside the ear canal can freely move since the ear hole is open. For this reason, the ear hole opening device 100 hardly gives the user discomfort caused by the humidity and temperature in the ear canal. Accordingly, the user can wear the ear hole opening device 100 for a long time.

In addition, the ear hole opening device 100 can increase a signal-to-noise ratio by reducing ambient noise when outputting music or a voice. This means that the user can easily listen to a target sound even if the music or voice has the same volume. In other words, the volume of the music or voice that needs to be output in order to maintain the same signal-to-noise ratio is suppressed. Therefore, it is possible to reduce a sound of the music or voice output by the ear hole opening device 100 leaking to the surroundings.

Further, the user's own voice (own voice), a beating sound, a masticating sound, a sound generated at the time of swallowing, a blood-flowing sound, a breathing sound, a vibration sound transmitted through a body during walking, a rustling sound of a cable or the like, and a rubbing sound of a portion where an earpiece comes into contact with the ear canal, and the like are not emphasized since the ear hole is open.

2. Second Embodiment

A second embodiment relates to a noise cancellation process using an audio processing device (headphones) having a microphone arranged near an entrance of an ear canal.

<2.1. Technical Problem>

First, a noise cancellation process using headphones according to a comparative example will be described, and a technical problem of the present embodiment will be described with reference to FIGS. 22 to 27.

Figure 22:
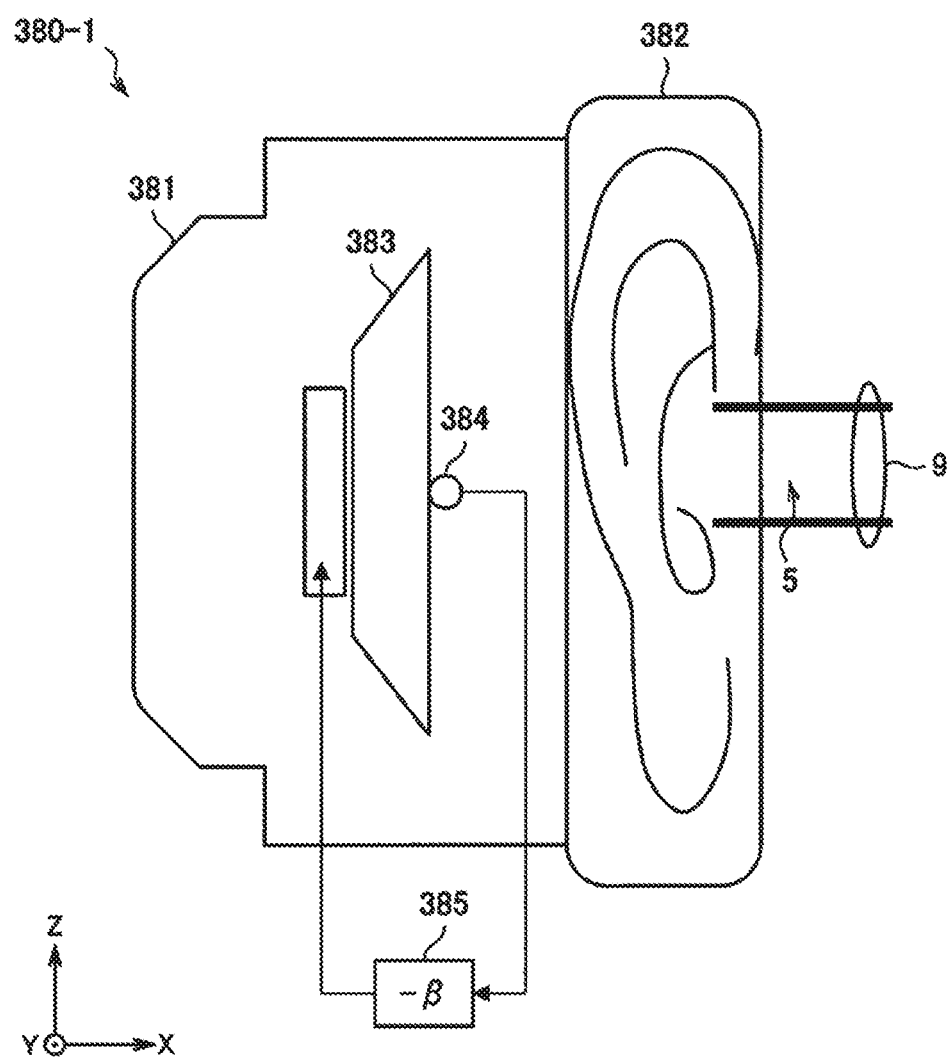
FIG. 22 is a diagram for describing a technical problem of a second embodiment.

FIG. 22 is a diagram illustrating a configuration example of headphones 380-1 equipped with an FB-NC function. As illustrated in FIG. 22, the headphones 380-1 equipped with the FB-NC function includes a housing 381 and an ear pad 382. The housing 381 and the ear pad 382 cover (typically seal) one ear of a user wearing the headphones 380-1 equipped with the FB-NC function. The housing 381 stores various devices configured for signal processing, such as a driver (speaker) 383, an FB-NC microphone 384, and an FB filter 385 (characteristic: $-\beta$).

The FB-NC microphone 384 collects ambient sounds and generates an audio signal. The FB filter 385 generates a noise cancellation signal by a noise cancellation process of the FB scheme based on the audio signal generated by the FB-NC microphone 384. The driver 383 outputs audio based on the noise cancellation signal generated by the FB filter 385. As a result, it is possible to cancel noise after passive sound insulation using passive sound insulation elements such as the housing 381, the ear pad 382, and user's head. This noise cancellation process will be described in detail with reference to FIG. 23.

Figure 23:
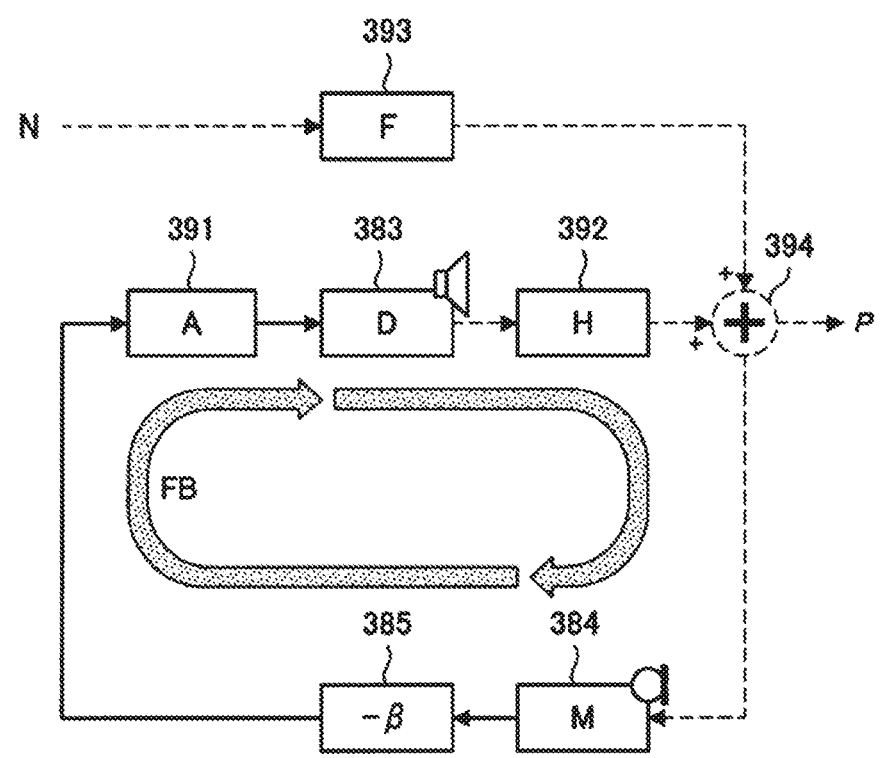
FIG. 23 is a diagram for describing a technical problem of the embodiment.

FIG. 23 is a diagram illustrating a model configuration example of the noise cancellation process using the headphones 380-1 equipped with the FB-NC function illustrated in FIG. 22. Symbols of blocks illustrated in the model configuration example as illustrated in FIG. 23 indicate characteristics (that is, transfer functions) corresponding to specific circuit parts, circuit systems in a noise cancellation system, or the like. The respective symbols have meanings as follows.

H: Spatial characteristic of space 392 from driver 383 to FB-NC microphone 384
M: Characteristic of FB-NC microphone 384
A: Characteristic of amplifier 391
D: Characteristic of driver 383
F: Characteristic of passive sound insulation element 393
$-\beta$: Characteristic of FB filter 385

In addition, N represents noise, and P represents a sound pressure at an eardrum position.

As illustrated in FIG. 23, the audio signal generated by the FB-NC microphone 384 is input to the FB filter 385. The FB filter 385 generates the noise cancellation signal based on the input audio signal. The noise cancellation signal generated by the FB filter 385 is amplified by the amplifier 391 and output from the driver 383. The audio output from the driver 383 passes through the space 392, and then, interferes with the noise N that has passed through the passive sound insulation element 393 in the space 394 to cancel the noise N. The noise N that has not been canceled is collected by the FB-NC microphone 384 and transmitted to the eardrum as the eardrum position sound pressure P.

A cancellation point is a position of the FB-NC microphone 384. When a sensitivity function is calculated for a residual signal r (residual noise) at the position of the FB-NC microphone 384, the following formula is obtained.

$$r = \frac{1}{1 + \beta ADHM} NF_1 \qquad (B1)$$

As illustrated in Formula (B1), the sensitivity function is minimized by increasing an NC filter $\beta$.

Here, the FB filter 385 includes an ADC and a DAC. The performance of FB-NC is improved by suppressing the influence caused by a system delay such as a digital processing delay due to the ADC and DAC. Meanwhile, as a parameter contributing to the delay, there is a distance delay in an audio space in addition to the system delay. This distance delay also affects the performance of FB-NC.

Figure 24:
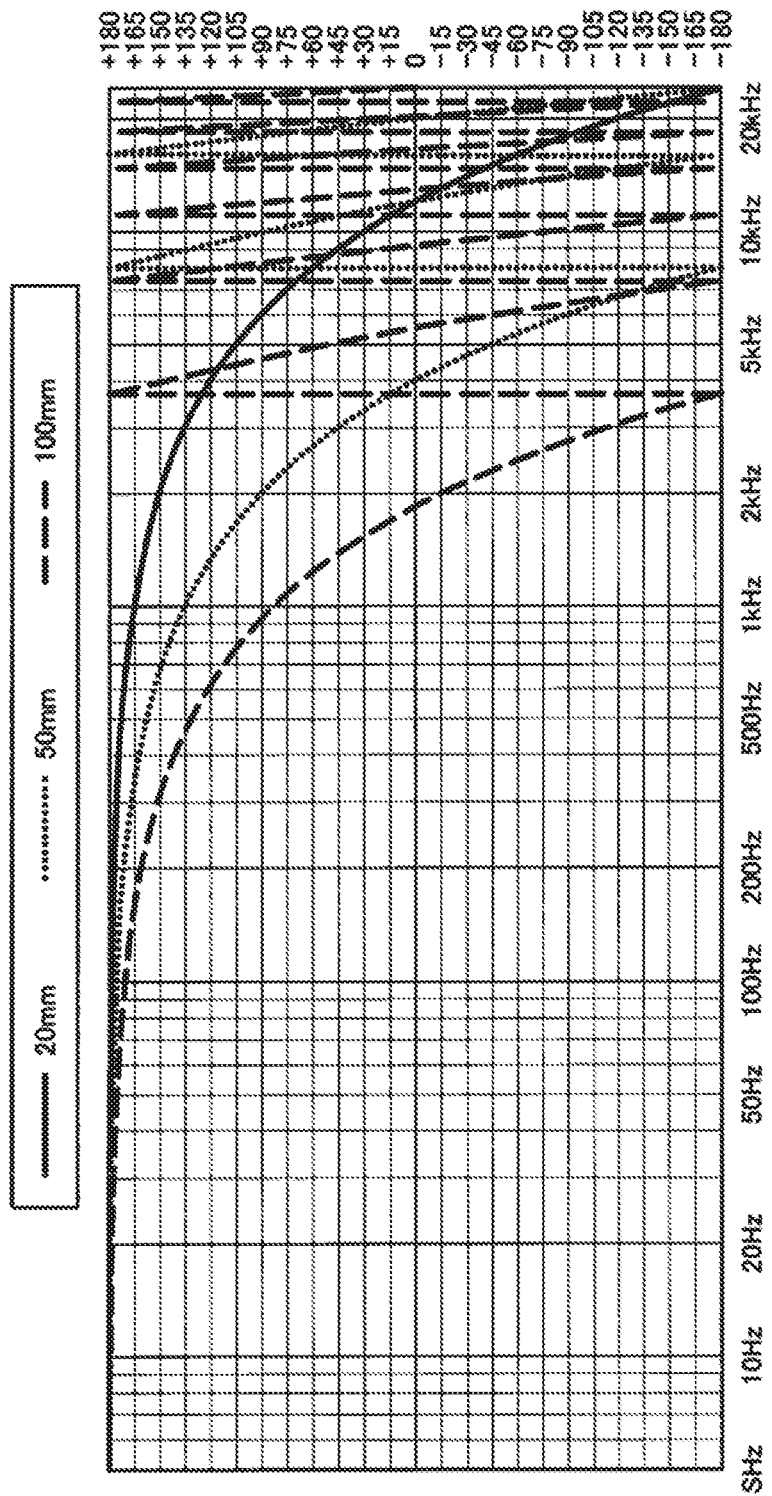
FIG. 24 is a graph for describing a technical problem of the embodiment.

FIG. 24 is a graph illustrating an example of a phase characteristic corresponding to a distance from the headphone driver to the FB-NC microphone. FIG. 24 illustrates the phase characteristics when the distance from the headphone driver to the FB-NC is 20 mm, 50 mm, or 100 mm. As illustrated in FIG. 24, a phase rotation increases as the distance from the headphone driver to the FB-NC increases. Then, the limit performance of FB-NC deteriorates as the phase rotation increases. From the above, it can be said that it is desirable to reduce the distance between the driver and the FB-NC in order to prevent the performance deterioration of FB-NC caused by the distance delay.

In the headphones 380-1 equipped with the FB-NC function illustrated in FIG. 22, the FB-NC microphone 384 is arranged at a position close to the driver 383 inside the housing 381. Accordingly, the above-described distance delay is small. However, the position of the FB-NC microphone 384 is far from a position of the eardrum 9 which is a point where a sound pressure (sound pressure caused by noise) is desirably minimized. For this reason, the minimization of the sound pressure at the position of the FB-NC microphone 384 does not necessarily lead to the minimization of the sound pressure at the position of the eardrum 9. That is, there is a risk that the performance of FB-NC may deteriorate.

Ideally, it is considered that the above-described distance delay can be eliminated by arranging the FB-NC microphone at the position of the eardrum 9. Such headphones equipped with the FB-NC function will be described with reference to FIG. 25.

Figure 25:
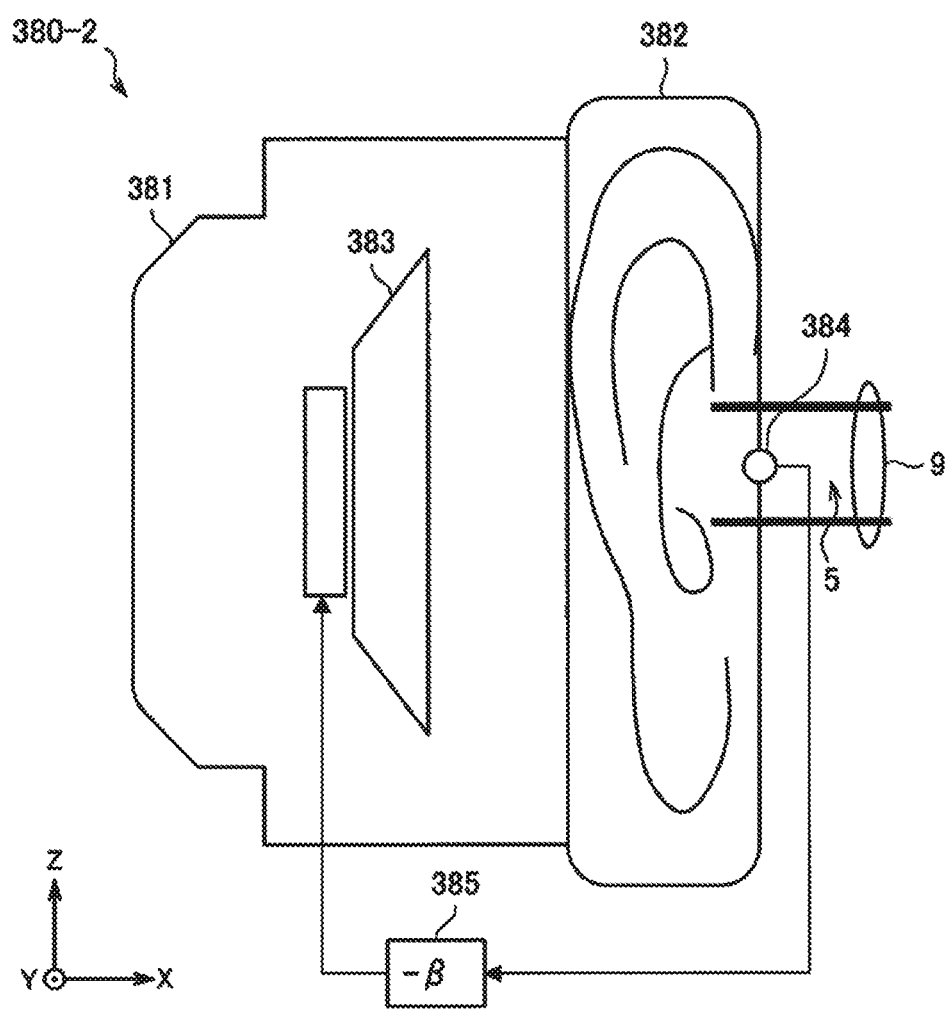
FIG. 25 is a diagram for describing a technical problem of the embodiment.

FIG. 25 is a diagram illustrating an example of headphones 380-2 equipped with the FB-NC function. As illustrated in FIG. 25, the headphones 380-2 equipped with the FB-NC function have the FB-NC microphone 384 arranged near the eardrum 9. For this reason, the minimization of the sound pressure at the position of the FB-NC microphone 384 easily leads to the minimization of the sound pressure at the position of the eardrum 9, and the deterioration of the performance of FB-NC can be suppressed. However, there is a risk that the performance of FB-NC may deteriorate due to the influence of the above-described distance delay since the distance between the driver 383 and the FB-NC microphone 384 is large.

In summary, the phase delay derived from the distance is small, but the sound pressure at the eardrum position is not always minimized according to the arrangement of the FB-NC microphone 384 illustrated in FIG. 22. On the other hand, the sound pressure at the eardrum position is fed back, but the phase delay derived from the distance is large according to the arrangement of the FB-NC microphone 384 illustrated in FIG. 25.

The following two guidelines can be considered in order to improve the performance of FB-NC in the headphones as described above, but these guidelines contradict each other on the assumption that the position of the driver is fixed.

First guideline: Reduce the distance delay: Arrange the FB-NC microphone close to the driver Second guideline: Set the cancellation point close to the eardrum: Arrange the FB-NC microphone far from the driver Therefore, a mechanism for a noise cancellation process that eliminates the contradiction is proposed in the present embodiment. Specifically, the mechanism for the noise cancellation process that uses an error microphone installed near the eardrum position in addition to the FB-NC microphone installed near the driver is proposed in the present embodiment. According to this mechanism, it is possible to minimize the sound pressure at the cancellation point close to the eardrum position using the error microphone while suppressing the distance delay using the FB-NC microphone.

Headphones equipped with the NC function include not only the above-described FB type but also the FF type and a combination type of FB and FF. In general, it is said that the headphones with the NC function of the combination type has the highest NC performance among these types. For reference, the headphones equipped with the NC function of the combination type will be described with reference to FIGS. 26 and 27.

Figure 26:
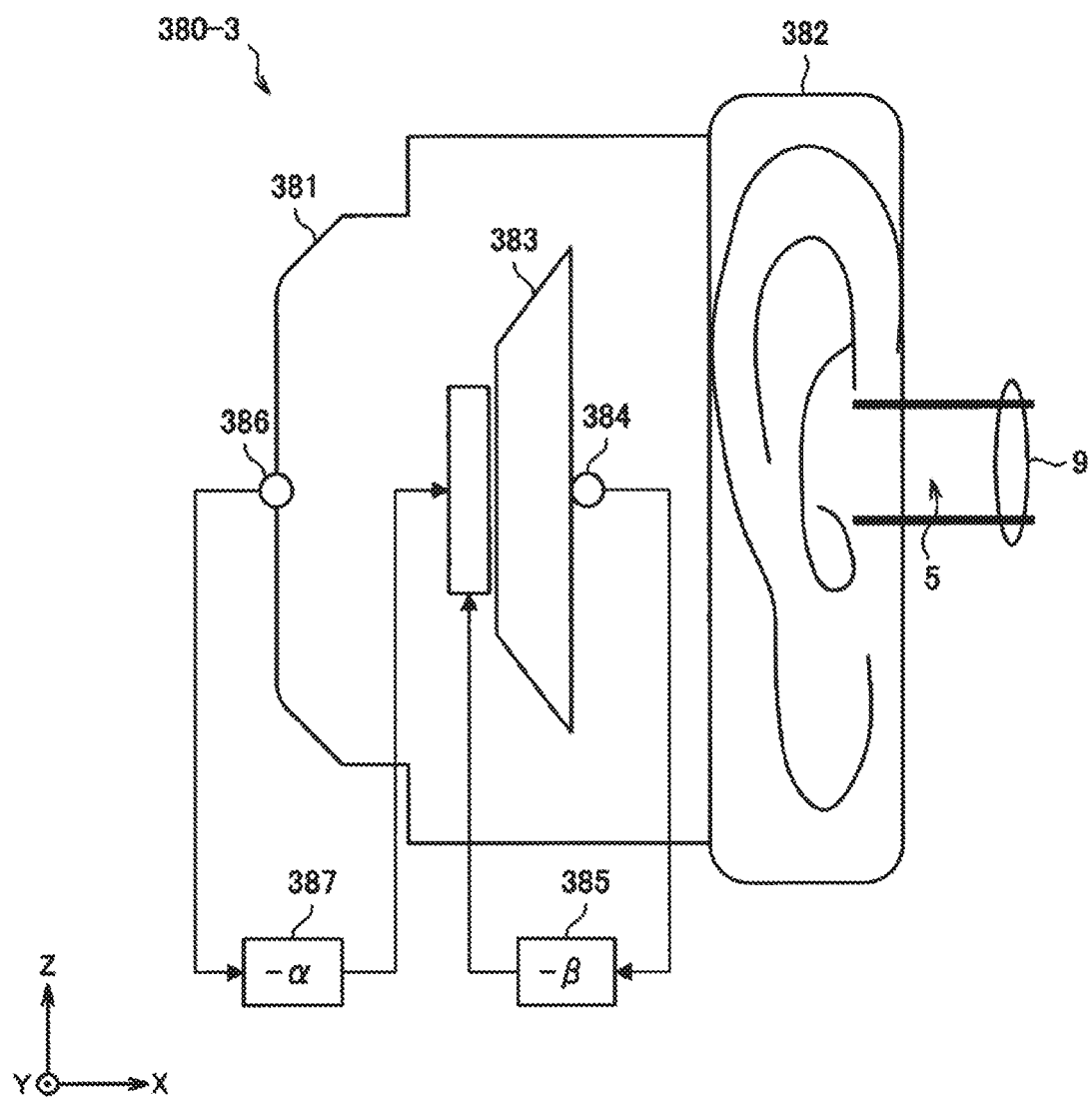
FIG. 26 is a diagram for describing a technical problem of the embodiment.

FIG. 26 is a diagram illustrating a configuration example of headphones 380-3 equipped with the combination type NC function. As illustrated in FIG. 26, the headphones 380-3 equipped with the combination type NC function includes an FF-NC microphone 386 and an FF filter 387 having a characteristic $-\alpha$, for the FF-NC, in addition to the configuration of the headphones 380-1 illustrated in FIG. 22.

Figure 27:
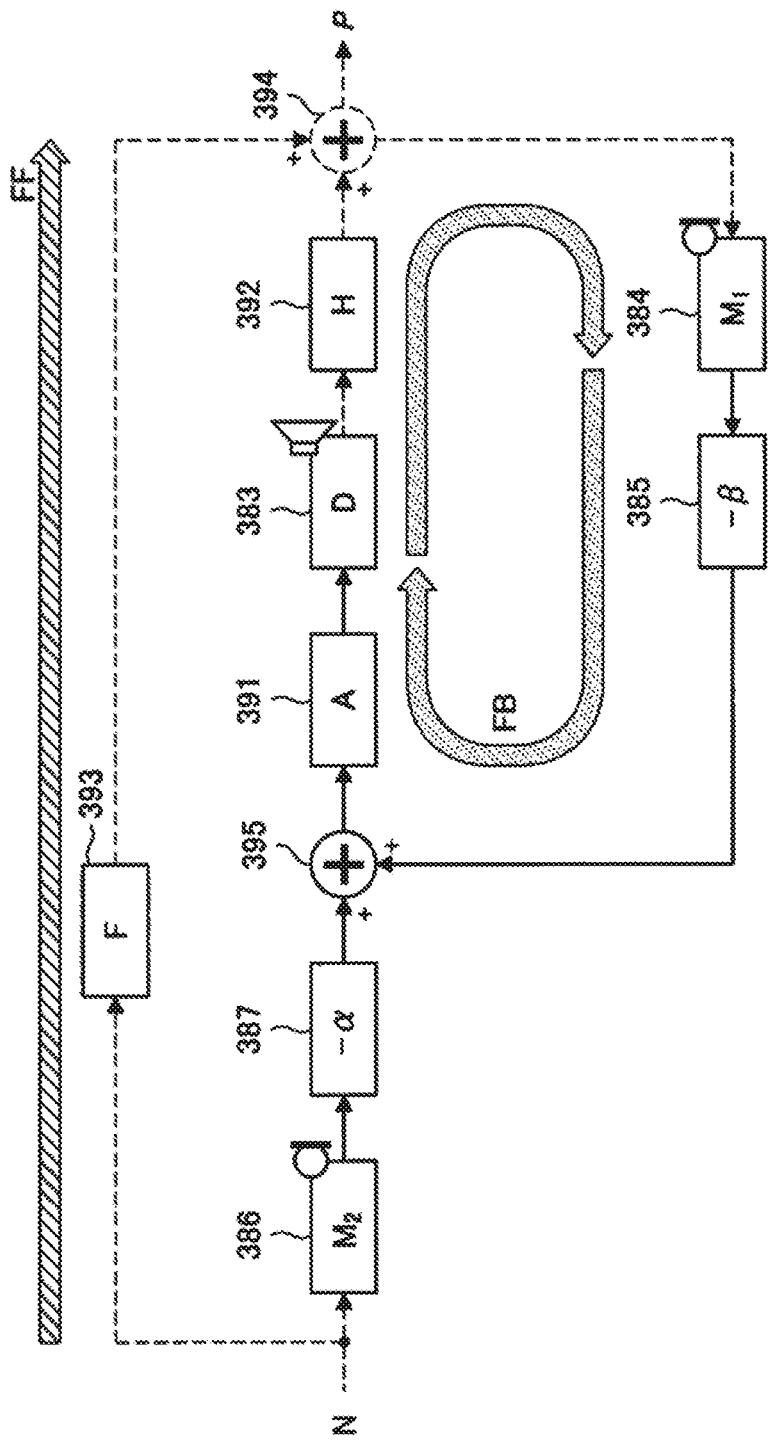
FIG. 27 is a diagram for describing a technical problem of the embodiment.

FIG. 27 is a diagram illustrating a model configuration example of a noise cancellation process using the headphones 380-3 equipped with the combination type NC function illustrated in FIG. 26. In the model configuration example illustrated in FIG. 27, constituent elements for the FF-NC are added to the model configuration example illustrated in FIG. 23. Hereinafter, such added blocks will be described. Symbols in the added blocks have meanings as follows.

$M_1$: Characteristic of FB-NC microphone 384
$M_2$: Characteristic of FF-NC microphone 386
$-\alpha$: Characteristic of FF filter 387

As illustrated in FIG. 27, an audio signal generated based on noise N collected by the FF-NC microphone 386 is input to the FF filter 387. The FF filter 387 generates a noise cancellation signal by the noise cancellation process of the FF scheme based on the input audio signal. An adder 395 synthesizes the noise cancellation signal generated by the FF filter 387 and the noise cancellation signal generated by the FB filter 385 to generate a synthesized signal. The synthesized signal is output from the driver 383 via the amplifier 391. The audio output from the driver 383 passes through the space 392, and then, interferes with the noise N that has passed through the passive sound insulation element 393 in the space 394 to cancel the noise N. The noise N that has not been canceled is collected by the FB-NC microphone 384 and transmitted to the eardrum as the eardrum position sound pressure P.

<2.2. Exterior Configuration of Headphones>

Hereinafter, an example of an exterior configuration of the audio processing device (headphones) according to the present embodiment will be described with reference to FIGS. 28 to 30.

Figure 28:
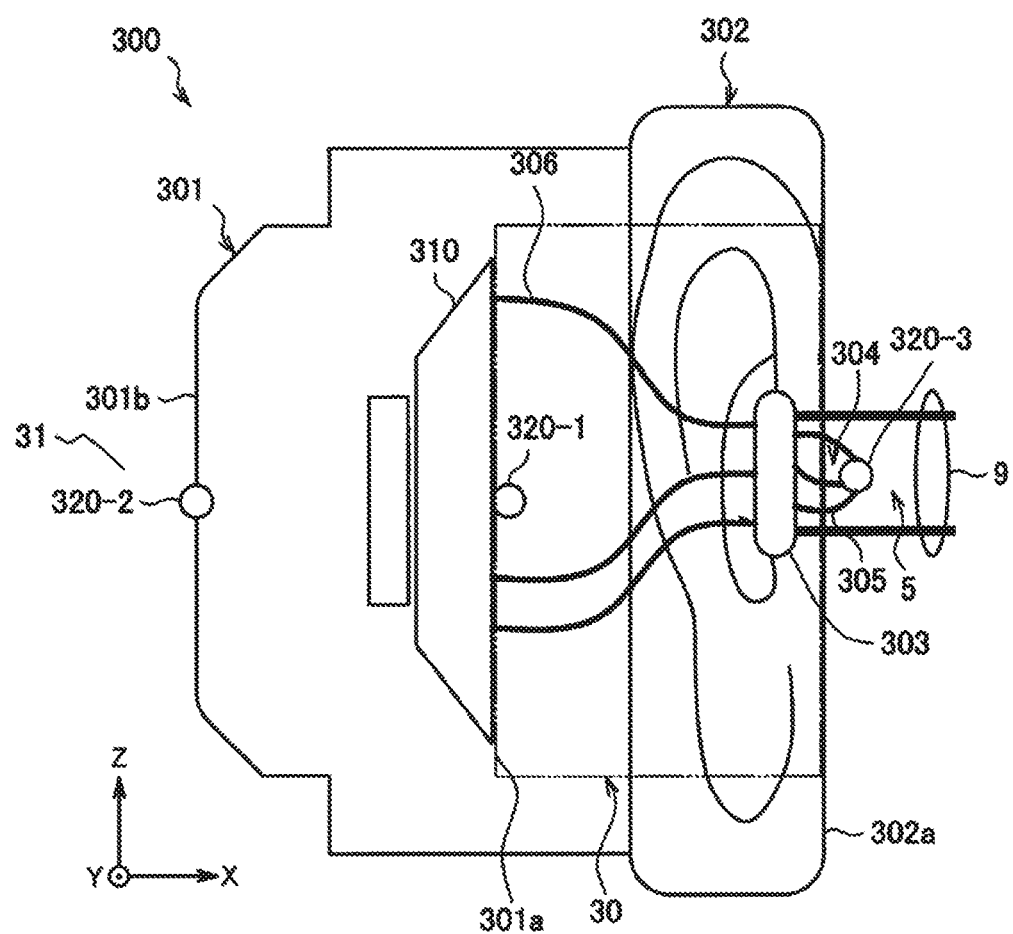
FIG. 28 is a diagram for describing an example of an exterior configuration of headphones according to the embodiment.
Figure 29:
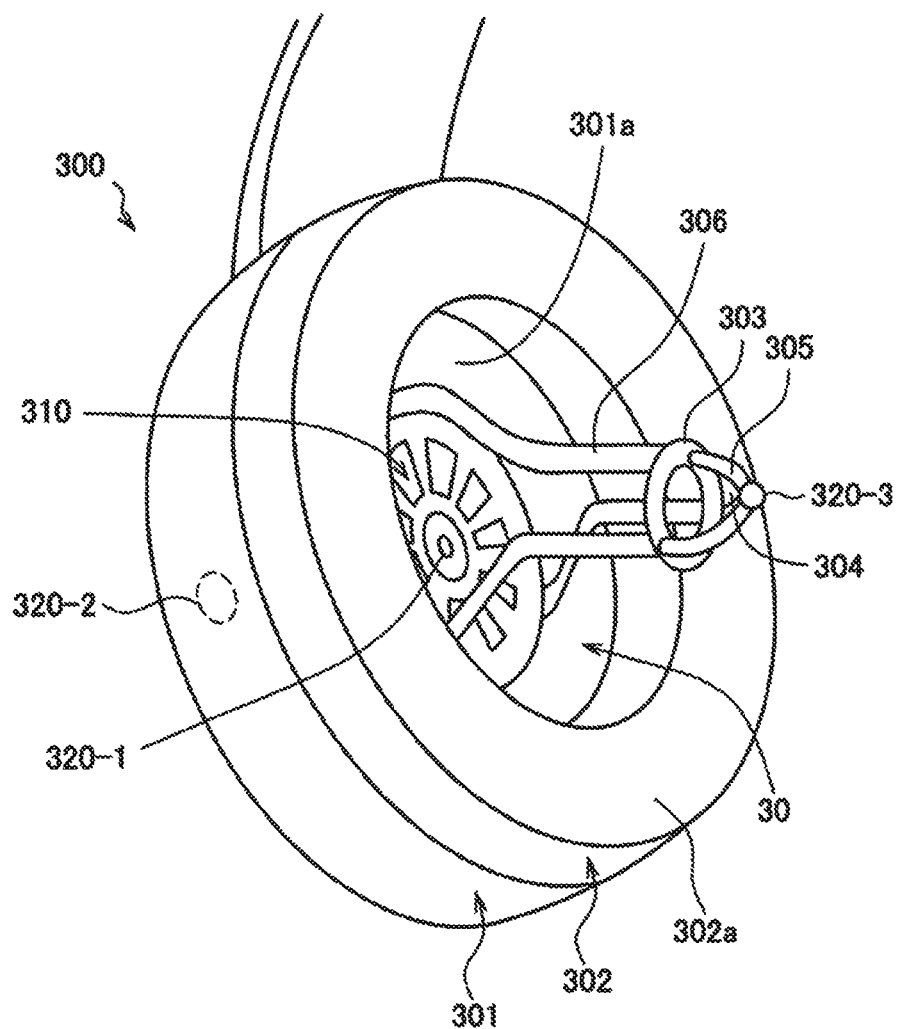
FIG. 29 is a view for describing an example of an exterior configuration of the headphones according to the embodiment.
Figure 30:
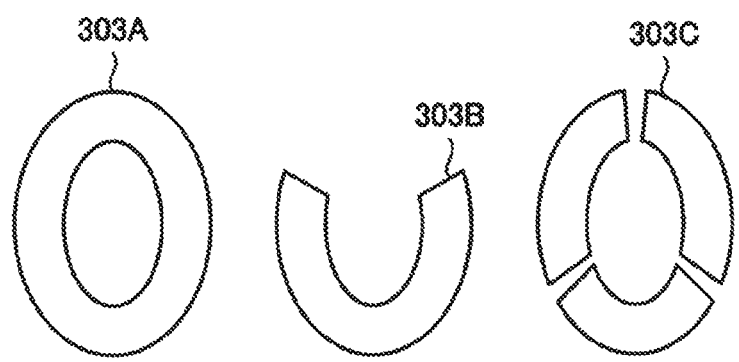
FIG. 30 is a view illustrating an example of a shape of a holding unit of the headphones according to the embodiment.

FIGS. 28 and 29 are diagrams for describing an example of the exterior configuration of headphones 300 according to the present embodiment. FIG. 28 illustrates the exterior configuration in a state where the headphones 300 are worn by a user. FIG. 29 illustrates the exterior configuration of the headphones 300 illustrated in FIG. 28 as viewed from an inner space 30 illustrated in FIG. 28. Hereinafter, the exterior configuration of the headphones 300 will be described mainly with reference to FIG. 28.

As illustrated in FIG. 28, the headphones 300 include a housing 301 and an ear pad 302. One ear of the user wearing the headphones 300 is covered (typically sealed) by the housing 301 and the ear pad 302. The housing 301 stores various devices configured for signal processing such as an audio output unit 310, audio input units 320-1 and 320-2, and a filter circuit. The ear pad 302 comes into contact with user's head at a contact surface 302a. The ear pad 302 is formed using an elastic body such as sponge, and is in close contact with the user's head while being deformed in accordance with the user's head, and forms the inner space 30. The inner space 30 is a space formed by the housing 301, the ear pad 302, and the user's head. The inner space 30 may be a sealed space isolated from an outer space 31 that is a space on the outside or may be connected to the outer space 31. Noise after passive sound insulation by passive sound insulation elements, such as the housing 301, the ear pad 302, and the user's head, arrives at the inner space 30. A wall portion 301a of the housing 301 is in contact with the inner space 30, and an outer wall portion 301b of the housing 301 is in contact with the outer space 31.

The audio output unit 310 outputs audio to a space based on the audio signal. The audio output unit 310 can also be referred to as a driver. The driver 310 is provided in the housing 301. Then, the driver 310 outputs audio toward the inner space 30 that is a space closer to the eardrum than the housing 301. For example, the driver 310 outputs the audio to the space based on the noise cancellation signal generated based on sound collection results obtained by the audio input units 320-1 to 320-3. As a result, the noise that has arrived at the inner space 30 can be canceled.

The audio input units 320 (320-1 to 320-3) collect ambient sounds and generate audio signals. As illustrated in FIG. 28, the three audio input units 320 are arranged on one ear side of the user in the state of being worn by the user.

The audio input unit 320-1 is a microphone that performs sound collection for FB-NC (that is, the FB-NC microphone). The FB-NC microphone 320-1 is arranged at a position where a distance from the eardrum 9 of the user is shorter than the audio input unit 320-2 and longer than the audio input unit 320-3 in a state where the headphones 300 are worn by the user. More specifically, the FB-NC microphone 320-1 is arranged at a position where noise is collected through shielding objects, that is, after being subjected to passive sound insulation in the state where the headphones 300 are worn by the user. Further, it is desirable that the FB-NC microphone 320-1 be arranged between the eardrum 9 of the user and the driver 310. The shielding objects herein are passive sound insulation elements and correspond to the housing 301, the ear pad 302, and the user's head. As illustrated in FIG. 28, the FB-NC microphone 320-1 is provided on the wall portion 301a of the housing 301 on the inner space 30 side. Then, the FB-NC microphone 320-1 collects audio of the inner space 30 and generates an audio signal. The audio collected at this time contains noise after passive sound insulation by the passive sound insulation elements. The FB-NC microphone 320-1 corresponds to a first audio input unit, and the audio signal generated by the FB-NC microphone 320-1 can also be referred to as a first audio signal. The audio signal generated by the FB-NC microphone 320-1 is input to the FB filter and used to generate the noise cancellation signal.

The audio input unit 320-2 is a microphone that performs sound collection for FF-NC (that is, the FF-NC microphone). In addition, the FF-NC microphone 320-2 is arranged at a position where the distance from the eardrum 9 of the user is the longest in the state where the headphones 300 are worn by the user. More specifically, the FF-NC microphone 320-2 is arranged at a position where noise is collected without passing through shielding objects, that is, without being subjected to passive sound insulation in the state where the headphones 300 are worn by the user. As illustrated in FIG. 28, the FF-NC microphone 320-2 is provided on the wall portion 301b of the housing 301 on the outer space 31 side. Then, the FF-NC microphone 320-2 collects audio of the outer space 31 and generates an audio signal. The audio collected at this time contains noise that has arrived at the outer space 31. The FF microphone 320-2 corresponds to a second audio input unit, and the audio signal generated by the FF microphone 320-2 can also be referred to as a second audio signal. Here, the FF-NC microphone 320-2 may be exposed to the outer space 31 or is not necessarily exposed. For example, the FF-NC microphone 320-2 may be embedded in the housing 301 and may collect a wrap-around sound or a sound transmitted through a cover such as a cloth. The audio signal generated by the FF-NC microphone 320-2 is input to the FF filter and used to generate the noise cancellation signal.

The audio input unit 320-3 is an audio input unit that is arranged to be spaced apart from the housing 301, and is a microphone (hereinafter also referred to as an ear canal microphone) that is arranged near the entrance of the ear canal 5 in the state where the headphones 300 are worn by the user. The ear canal microphone 320-3 is arranged at a position where the distance from the eardrum 9 of the user is the shortest in the state where the headphones 300 are worn by the user. The ear canal microphone 320-3 is arranged at a position where noise is collected through the shielding objects in the state where the headphones 300 are worn by the user. As illustrated in FIG. 28, the ear canal microphone 320-3 is arranged in the inner space 30. Here, the ear canal microphone 320-3 is held near the entrance of the ear canal 5 of the user by a holding unit 303. Then, the ear canal microphone 320-3 collects noise after passive sound insulation by the passive sound insulation elements, and generates an audio signal. The ear canal microphone 320-3 corresponds to a third audio input unit, and the audio signal generated by the ear canal microphone 320-3 can also be referred to as a third audio signal. The audio signal generated by the ear canal microphone 320-3 is used to generate the noise cancellation signal.

The holding unit 303 engages with the vicinity of the entrance of the ear canal 5 (for example, the intertragic notch), and holds the ear canal microphone 320-3 at the vicinity of the entrance of the ear canal 5. An outer diameter of the ear canal microphone 320-3 is formed so as to be much smaller than an inner diameter of the ear hole. Therefore, the ear hole of the listener is not blocked even in the state where the ear canal microphone 320-3 is held at the vicinity of the entrance of the ear canal 5 by the holding unit 303.

In addition, the holding unit 303 includes opening portions 304 that open the entrance (ear hole) of the ear canal 5 to the outside even in the state of holding the ear canal microphone 320-3. The outside is a space where noise is passively sound-insulated, and is the inner space 30. In the example illustrated in FIG. 28, the holding unit 303 is a ring-shaped structure, the ear canal microphone 320-3 is provided in a part where rod-shaped first support members 305 provided in a ring inner direction are combined near the ring center, and all the other parts of the ring-shaped structure are opening portions 304. The rod-shaped first support member 305 is gently curved, and the plurality of first support members 305 and the holding unit 303 form a hemispherical shape having the holding unit 303 as a split plane. The holding unit 303 abuts on an inner wall of the cavum concha 4 or the ear canal 5 of user's one ear in the state where the headphones 300 are worn by the user. Then, the holding unit 303 holds the ear canal microphone 320-3 in the space closer to the eardrum 9 than the tragus 6. Such a configuration of the holding unit 303 is the same as the configuration of the holding unit 130 according to the first embodiment. Note that the holding unit 303 is not limited to the ring-shaped structure, and may have an arbitrary shape that can provide the ear canal microphone 320-3 as long as a hollow structure is provided. Examples of the shape of the holding unit 303 are illustrated in FIG. 30. FIG. 30 is a view illustrating examples of the shape of the holding unit 303 of the headphones 300 according to the present embodiment. As illustrated in FIG. 30, a holding unit 303A has a ring-shaped structure, a holding unit 303B has a ring-shaped structure from which a part has been cut and removed, and a holding unit 303C has a ring-shaped structure divided into three parts. In this manner, the shape of the holding unit 303 may be a ring-shaped structure or a similar type thereof.

A second support member 306 is a structure in which one end is connected to the housing 301 and the other end is connected to the holding unit 303. As illustrated in FIG. 28, the second support member 306 may be a rod-shaped structure curved in an S shape. In addition, a plurality of the second support members 306 may be provided.

Note that FIGS. 28 and 29 illustrate an exterior configuration on the right ear side of the headphones 300, an exterior configuration on the left ear side is bilaterally symmetric with the exterior configuration on the right ear side. The headphones 300 may be configured to be separated and independent from each other between the right ear side and the left ear side, or may be integrally configured. In addition, the headphones 300 can have an arbitrary structure such as a sealed type, an open type, an overhead type, a neckband type, and an ear hook type.

<2.3. Internal Configuration of Headphones>

Figure 31:
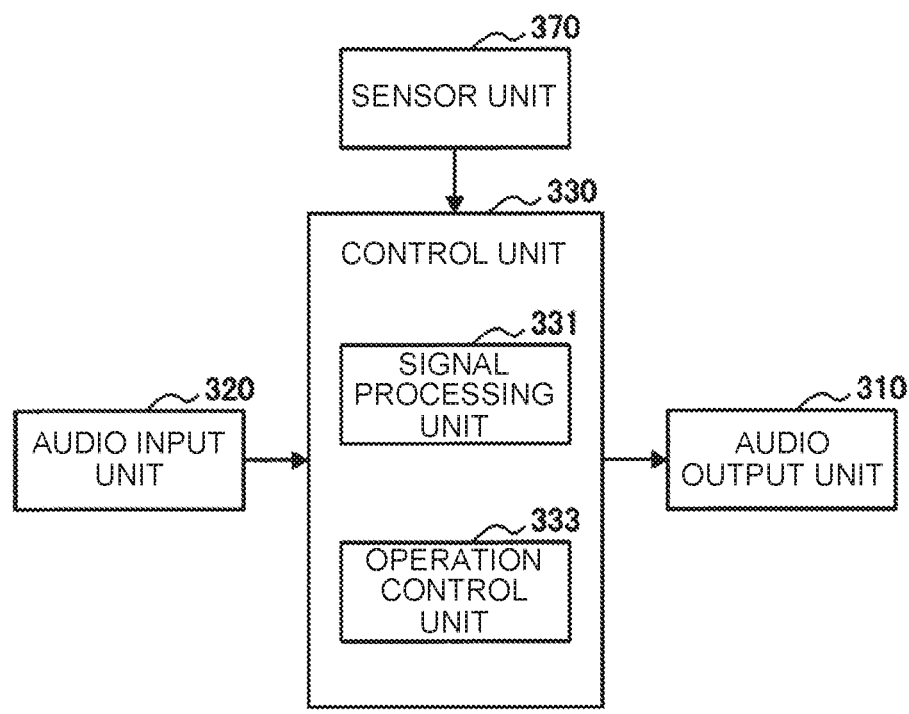
FIG. 31 is a diagram illustrating an example of an internal configuration of the headphones according to the embodiment.

FIG. 31 is a diagram illustrating an example of an internal configuration of the headphones 300 according to the present embodiment. As illustrated in FIG. 31, the headphones 300 include the audio output unit 310, the audio input unit 320, a control unit 330, and a sensor unit 370.

Audio Output Unit 310

The audio output unit 310 (driver) has a function of outputting audio based on an audio signal. The driver 310 outputs audio to a space based on an output signal output from a signal processing unit 331.

Audio Input Unit 320

The audio input unit 320 includes a microphone (hereinafter also simply referred to as a microphone) that detects ambient sounds and generates an audio signal indicating the detection result by the microphone.

Control Unit 330

The control unit 330 functions as an arithmetic processing device and a control device, and controls the entire processing performed by the headphones 300 according to various programs. The control unit 330 is realized by an electronic circuit, for example, a central processing unit (CPU), a micro-processing unit (MPU), a demand-side platform (DSP), or the like. Note that the control unit 330 may include a read-only memory (ROM) that stores programs to be used, calculation parameters, and the like, and a random-access memory (RAM) that temporarily stores parameters that change as appropriate. Typically, the control unit 330 is stored in the housing 301.

As illustrated in FIG. 31, the control unit 330 includes a signal processing unit 331 and an operation control unit 333. The signal processing unit 331 has a function of generating a noise cancellation signal for noise based on the audio signal generated by the audio input unit 320. The signal processing unit 331 generates a plurality of noise cancellation signals based on the three audio signals generated by the three audio input units 320-1 to 320-3. For example, the signal processing unit 331 performs at least one of the noise cancellation process of the FB scheme and the noise cancellation process of the FF scheme to generate the plurality of noise cancellation signals. The signal processing unit 331 generates an audio signal (hereinafter also referred to as an output signal) based on the plurality of generated noise cancellation signals, and outputs the audio signal to the driver 110. For example, the output signal may be a signal obtained by synthesizing the plurality of noise cancellation signals, or may be a synthesized signal obtained by synthesizing another audio signal such as a music signal acquired from a sound source and the noise cancellation signal. The signal processing unit 331 includes various constituent elements for noise cancellation processes which will be described with reference to FIGS. 32 to 37 and the like. For example, the signal processing unit 331 includes: various filter circuits configured to generate a noise cancellation signal; an adaptive control unit configured to adaptively control the filter circuits; an adder configured to synthesize signals; an internal model; a device configured to generate and analyze a measurement signal to be described later; and the like. In addition, the signal processing unit 331 also includes circuits such as an amplifier, an ADC, and a DAC.

Operation Control Unit 333

The operation control unit 333 has a function of controlling an operation mode of the headphones 300. The operation control unit 333 stops or activates some or all of functions of the headphones 300. For example, the operation control unit 333 controls the stop/activation of the function of the headphones 300 based on a detection result obtained by the sensor unit 370.

Sensor Unit 370

The sensor unit 370 is a device that detects information on the headphones 300 or information on a user wearing the headphones 300. The sensor unit 370 can include various sensor devices such as a pressure-sensitive sensor, a gyro sensor, an acceleration sensor, and a body temperature sensor. For example, the sensor unit 370 detects deformation of a member constituting the headphones 300, such as the ear pad 302, by the pressure-sensitive sensor. As a result, it is possible to determine wearing/non-wearing of the headphones 300.

<2.4. Details of Noise Cancellation Process>

(1) First Noise Cancellation Process

A first noise cancellation process includes processing using the ear canal microphone 320-3 as an error microphone of the FB-NC. Specifically, the signal processing unit 331 generates a third noise cancellation signal by FB-NC using the ear canal microphone 320-3 as a cancellation point based on the third audio signal generated by the ear canal microphone 320-3. Since the ear canal microphone 320-3 is arranged near the eardrum 9, the cancellation point of FB-NC can be set to be close to the eardrum 9. That is, the above second guideline is satisfied.

Further, the first noise cancellation process includes processing using the FB-NC microphone 320-1 as an error microphone of FB-NC. Specifically, the signal processing unit 331 generates a first noise cancellation signal by FB-NC using the FB-NC microphone 320-1 as a cancellation point based on the first audio signal generated by the FB-NC microphone 320-1. Since the FB-NC microphone 320-1 is arranged to be close to the driver 310, the above-described phase rotation due to the distance decreases. That is, the above first guideline is satisfied.

In this manner, it is possible to satisfy both the first guideline and the second guideline according to the first noise cancellation process. Therefore, it is possible to minimize the sound pressure at the cancellation point, which is close to the eardrum position, while suppressing the distance delay according to the first noise cancellation process. Hereinafter, details of the first noise cancellation process will be described with reference to FIG. 32.

Figure 32:
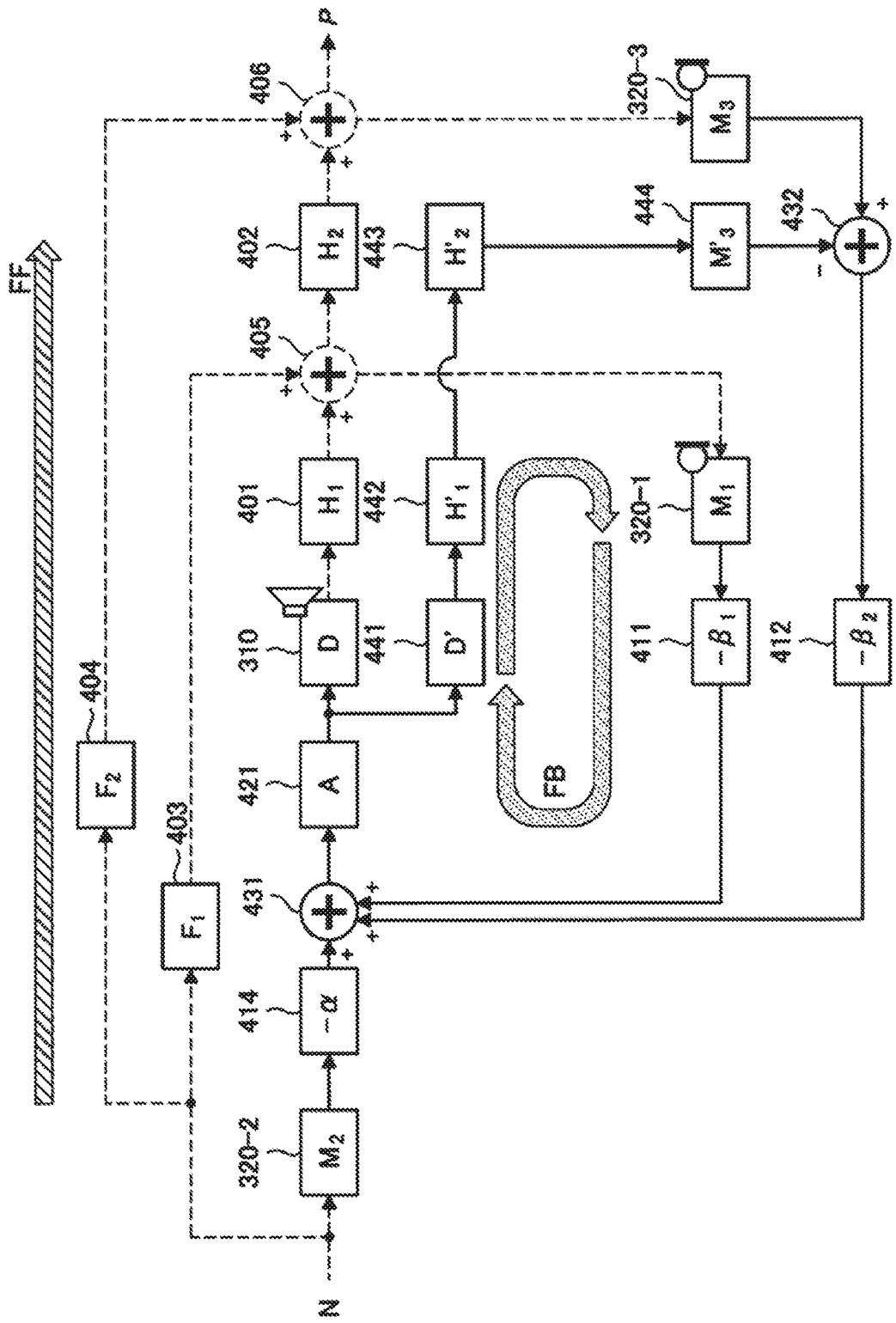
FIG. 32 is a diagram illustrating a model configuration example of a first noise cancellation process using the headphones according to the embodiment.

FIG. 32 is a diagram illustrating a model configuration example of the first noise cancellation process using the headphones 300 according to the present embodiment. Symbols in the blocks illustrated in FIGS. 32 to 37 have meanings as follows.

$H_1$: Characteristic of space 401 from driver 310 to FB-NC microphone 320-1

$H_2$: Characteristic of space 402 from FB-NC microphone 320-1 to ear canal microphone 320-3 (more precisely, difference characteristic between space from driver 310 to FB-NC microphone 320-1 and space from driver 310 to ear canal microphone 320-3)

$F_1$: Characteristic of space 403 from noise source to FB-NC microphone 320-1

$F_2$: Characteristic of space 404 from noise source to ear canal microphone 320-3

$M_1$: Characteristic of FB-NC microphone 320-1

$M_2$: Characteristic of FF-NC microphone 320-2

$M_3$: Characteristic of ear canal microphone 320-3

A: Characteristic of amplifier 421

D: Characteristic of driver 310

$-\alpha$: Characteristic of FF filter 414

$-\beta_1$: Characteristic of first FB filter 411

$-\beta_2$: Characteristic of second FB filter 412

$-\beta_3$: Characteristic of third FB filter 413

$H_1'$: Simulated characteristic of space 401

$H_2'$: Simulated characteristic of space 402

$M_1'$: Simulated characteristic of FB-NC microphone 320-1

$M_3'$: Simulated characteristic of ear canal microphone 320-3

In addition, N represents noise, and P represents a sound pressure at an eardrum position.

First, a noise cancellation process relating to the first FB filter 411 will be described. An audio signal generated based on audio collected by the FB-NC microphone 320-1 is input to the first FB filter 411. The first FB filter 411 performs the noise cancellation process of the FB scheme using the FB-NC microphone 320-1 as a cancellation point based on the input audio signal and generates a noise cancellation signal (first noise cancellation signal). The noise cancellation signal generated by the first FB filter 411 is synthesized with noise cancellation signals generated by the second FB filter 412 and the FF filter 414 by an adder 431. The synthesized signal is amplified by the amplifier 421 and output from the driver 310.

Next, a noise cancellation process relating to the FF filter 414 will be described. An audio signal generated based on audio collected by the FF-NC microphone 320-2 is input to the FF filter 414. The FF filter 414 generates the noise cancellation signal (second noise cancellation signal) by the noise cancellation process of the FF scheme based on the input audio signal. The noise cancellation signal generated by the FF filter 414 is synthesized with the noise cancellation signals generated by the first FB filter 411 and the second FB filter 412 by the adder 431. The synthesized signal is amplified by the amplifier 421 and output from the driver 310.

Finally, a noise cancellation process relating to the second FB filter 412 will be described. The ear canal microphone 320-3 collects audio and generates an audio signal. An adder 432 subtracts a signal, obtained by applying internal models (characteristics: D', $H_1$', $H_2$', and $M_3$') illustrated in blocks 441, 442, 443, and 444 to the output signal input to the driver 310, from the audio signal generated by the ear canal microphone 320-3 to perform the synthesis. The internal models herein have characteristics that simulate characteristics from the input of the output signal to the driver 310 to the generation of the third audio signal. The synthesized signal is input to the second FB filter 412. The second FB filter 412 performs the noise cancellation process of the FB scheme using the ear canal microphone 320-3 as a cancellation point based on the input audio signal, and generates the noise cancellation signal (third noise cancellation signal). The noise cancellation signal generated by the second FB filter 412 is synthesized with noise cancellation signals generated by the first FB filter 411 and the FF filter 414 by an adder 431. The synthesized signal is amplified by the amplifier 421 and output from the driver 310.

The audio output from the driver 310 first passes through the space 401 and then interferes with noise N that has passed through the space 403 in a space 405 to cancel the noise N. The noise N that has not been canceled is collected by the FB-NC microphone 320-1. In addition, the audio output from the driver 310 further passes through the space 402 and then interferes with noise N that has passed through the space 404 in a space 406 to cancel the noise N. The noise N that has not been canceled is collected by the ear canal microphone 320-3 and transmitted to the eardrum as the eardrum position sound pressure P.

The details of the first noise cancellation process have been described above. According to the first noise cancellation process, the internal model is introduced. Hereinafter, a description will be given in detail regarding a fact that noise canceling performance can be improved by introducing the internal model.

First, the output signal input to the driver 310 is defined as y. Then, the sound pressure P at the position of the ear canal microphone 320-3 is expressed by the following formula.

$$P = NF_2 + yDH_1H_2 \tag{B2}$$

Subsequently, a formula to calculate the output signal y is obtained as follows.

$$\{-\beta_1 M_1(yDH_1 + NF_1) - \beta_2(yM_3DH_1H_2 - yD'M'_3H_1'H_2' + NM_3F_2) - NM_2\alpha\}A = y \tag{B3}$$

$$-\beta_1 AM_1DH_1 y - \beta_1 AM_1 F_1 N - \beta_2 A(M_3DH_1H_2 - M'_3D'H'_1H'_2)y - \beta_2 AM_3 F_2 N - \alpha AM_2 N = y \tag{B4}$$

$$\{1 + \beta_1 AM_1DH_1 + \beta_2 A(M_3DH_1H_2 - M'_3D'H'_1H'_2)\}y = -\alpha AM_2 N - \beta_1 AM_1 F_1 N - \beta_2 AM_3 F^2 N \tag{B5}$$

As described above, the output signal y is expressed as the following formula.

$$y = \frac{-\alpha AM_2 - \beta_1 AM_1 F_1 - \beta_2 AM_3 F_2}{1 + \beta_1 AM_1 DH_1 + \beta_2 A(M_3 DH_1 H_2 - M'_3 D' H'_1 H'_2)} N \tag{B6}$$

With Formulas (B2) and (B6), a sensitivity function P at the position of the ear canal microphone 320-3 is expressed by the following formula.

$$P = \left(\frac{\begin{array}{c}-\alpha AM_2 DH_1H_2 - \beta_1 AM_1 F_1 DH_1 H_2 - \\ \beta_2 AM_3 F_2 DH_1 H_2 - \beta_2 AM'_3 F_2 D'^{H'_1 H'_2} + \\ F_2 + \beta_1 AM_1 F_2 DH_1 + \beta_2 AM_3 F_2 DH_1 H_2\end{array}}{1 + \beta_1 AM_1 DH_1 + \beta_2 A(M_3 DH_1 H_2 - M'_3 D' H'_1 H'_2)}\right)N$$

$$= \frac{AD\{-\alpha H_1 H_2 M_2 - \beta_1 M_1(H_1 H_2 F_1 - H_1 F_2) + \beta_2 M'_3 D' H'_1 H'_2\} + F_2}{1 + \beta_1 AM_1 DH_1 + \beta_2 A(M_3 DH_1 H_2 - M'_3 D' H'_1 H'_2)} N \tag{B7}$$

The term illustrated in the following Formula (B8) in the sensitivity function P illustrated in Formula (B7) can be omitted if the respective simulated characteristics included in the internal models match, that is, if $M_3 = M_3'$, $D = D'$, $H_1 = H_1'$, and $H_2 = H_2'$.

$$\beta_2 A(M_3 DH_1 H_2 - M'_3 D' H'_1 H'_2) \tag{B8}$$

On the other hand, the term illustrated in the following Formula (B9) in the sensitivity function P illustrated in Formula (B7) can be omitted by designing $\beta_2$, which is a designable parameter, according to the following Formula (B10).

$$-\beta_1 M_1 (H_1 H_2 F_1 - H_1 F_2) + \beta_2 M'_3 D' H'_1 H'_2 \tag{B9}$$

$$\beta_2 = \frac{-\beta_1 M_1 (H_1 H_2 F_1 - H_1 F_2)}{M'_3 D' H'_1 H'_2} \tag{B10}$$

When $\beta_2$ designed according to Formula (B10) is put into Formula (B9), the following formula is obtained.

$$-\beta_1 M_1(H_1 H_2 F_1 - H_1 F_2) + \beta_2 M'_3 D' H'_1 H'_2 = 0 \tag{B11}$$

As described above, when the omitted term is excluded from Formula (B7), the sensitivity function P is expressed by the following formula.

$$P = \frac{-\alpha ADH_1 H_2 M_2 + F_2}{1 + \beta_1 AM_1 DH_1} N \tag{B12}$$

From the above Formula (B12), it is understood that the sensitivity function P can be minimized by maximizing $\mu_1$. That is, it is understood that the sensitivity function at the position of the ear canal microphone 320-3 closer to the eardrum can be minimized by maximizing a gain of a system having the FB-NC microphone 320-1 with a little delay. As described above, it can be said that noise can be canceled at the position of the ear canal microphone 320-3 closer to the eardrum by introducing the internal model.

(2) Second Noise Cancellation Process

A second noise cancellation process is a process using the ear canal microphone 320-3 for FF-NC. As the second noise cancellation process, the ear canal microphone 320-3 may be used as an error microphone for adaptive FF-NC, and may be used to set a fixed FF-NC filter. Hereinafter, these will be described in order.

Case of Using Ear Canal Microphone 320-3 as Error Microphone

The ear canal microphone 320-3 may be used as an error microphone for adaptive processing in FF-NC. The adaptive processing is a method of adaptively changing a filter characteristic so as to minimize an error signal at an error microphone position. Specifically, the signal processing unit 331 generates the second noise cancellation signal by the FF-NC based on the second audio signal generated by the FF-NC microphone 320-2. The signal processing unit 331 adaptively controls the filter characteristic of the FF filter used for this FF-NC based on the third audio signal generated by the ear canal microphone 320-3. According to this method, the error microphone position of FF-NC is close to the eardrum 9, and thus, a high noise canceling effect is expected. Details of the second noise cancellation process when the ear canal microphone 320-3 is used as the error microphone will be described with reference to FIG. 33.

Figure 33:
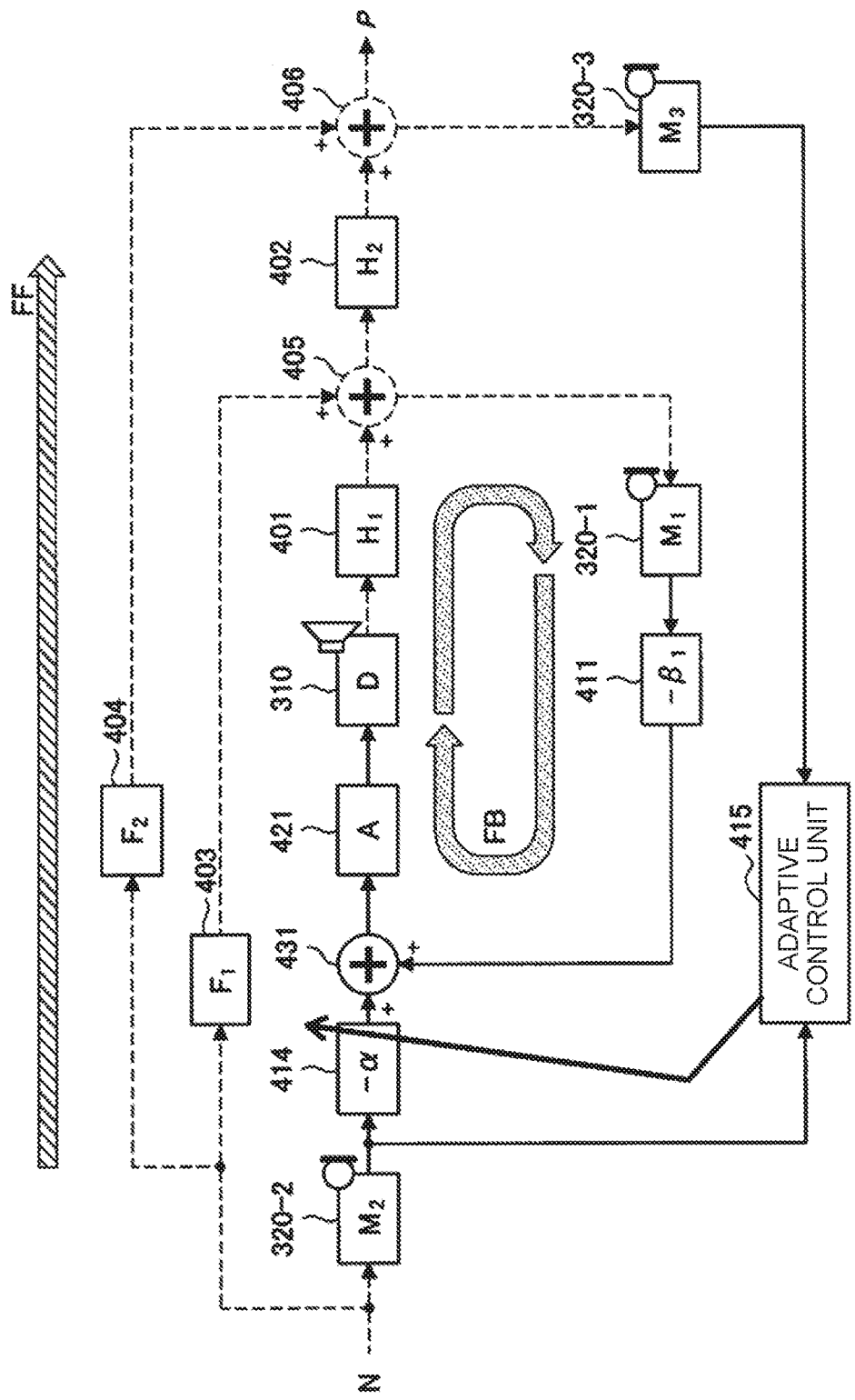
FIG. 33 is a diagram illustrating a model configuration example of a second noise cancellation process using the headphones according to the embodiment.

FIG. 33 is a diagram illustrating a model configuration example of the second noise cancellation process using the headphones 300 according to the present embodiment. Since the noise cancellation process relating to the first FB filter 411 is the same as described above with reference to FIG. 32, the description thereof is omitted here.

Hereinafter, the noise cancellation process relating to the FF filter 414 will be described. An audio signal generated based on audio collected by the FF-NC microphone 320-2 is input to the FF filter 414. The audio signal generated based on the audio collected by the FF-NC microphone 320-2 and the audio signal generated based on the audio collected by the ear canal microphone 320-3 are input to an adaptive control unit 415. Then, the adaptive control unit 415 adaptively controls the characteristic $-\alpha$ of the FF filter 414 based on these audio signals. Under the adaptive control by the adaptive control unit 415, the FF filter 414 generates the noise cancellation signal (second noise cancellation signal) by the noise cancellation process of the FF scheme based on the input audio signal. The noise cancellation signal generated by the FF filter 414 is synthesized with the noise cancellation signal generated by the first FB filter 411 by the adder 431. The synthesized signal is amplified by the amplifier 421 and output from the driver 310.

The case where the ear canal microphone 320-3 is used as the error microphone has been described in detail above. As an algorithm of the adaptive control unit 415, for example, least mean square (LMS) or filtered-X LMS can be used. There is a case where it is desirable to use a characteristic (also referred to as a secondary path or secondary path characteristic) from a secondary sound source to an error microphone for the control by the adaptive control unit 415 in order to improve the noise canceling performance. The secondary path characteristic in the model configuration example illustrated in FIG. 33 corresponds to $ADH_1H_2$, which is a characteristic from the driver 310 to the ear canal microphone 320-3.

The secondary path characteristic may be measured using a measurement signal when the user wears the headphones, or a general measurement value measured in advance may be used. Hereinafter, signal processing to measure the secondary path characteristic using the measurement signal will be described with reference to FIG. 34.

Figure 34:
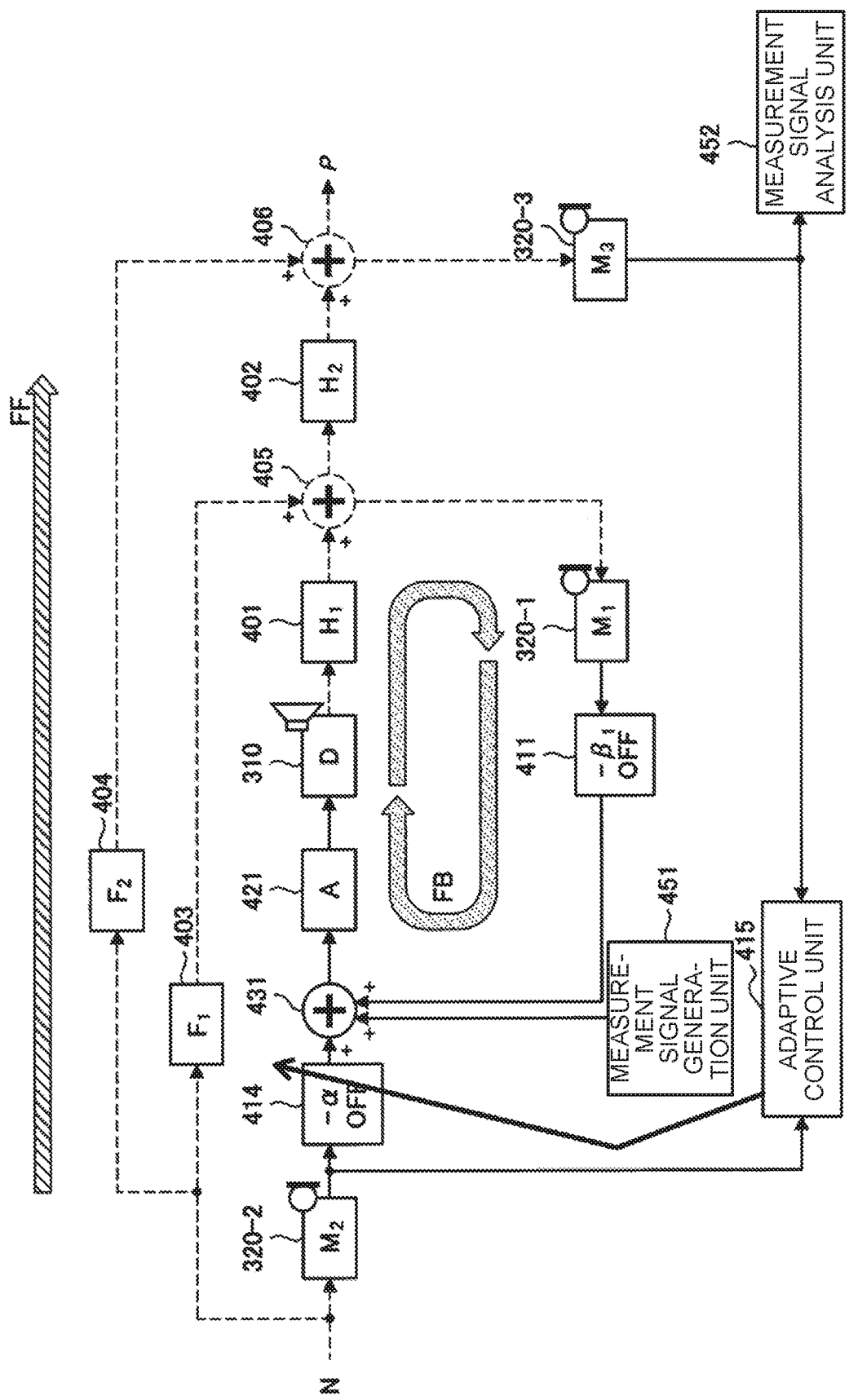
FIG. 34 is a diagram illustrating a model configuration example of a secondary path characteristic measurement process using the headphones according to the embodiment.

FIG. 34 is a diagram illustrating a model configuration example of a secondary path characteristic measurement process using the headphones 300 according to the present embodiment. In the model configuration example illustrated in FIG. 34, a measurement signal generation unit 451 and a measurement signal analysis unit 452 are added to the model configuration example illustrated in FIG. 33. In addition, both the first FB filter 411 and the FF filter 414 are turned off and stop operating. Hereinafter, the measurement signal generation unit 451 and the measurement signal analysis unit 452 will be described in detail.

The measurement signal generation unit 451 generates a measurement signal. As the measurement signal, for example, an arbitrary sequence such as a time stretched pulse (TSP) signal, white noise, and an M-sequence signal can be used. The measurement signal generated by the measurement signal generation unit 451 is amplified by the amplifier 421, input to the driver 310, and output as audio. The audio output from the driver 310 is collected by the ear canal microphone 320-3 via the spaces 401 and 402. Then, the audio signal generated by the ear canal microphone 320-3 is input to the measurement signal analysis unit 452. As described above, the audio signal input to the measurement signal analysis unit 452 is obtained by applying the characteristic $ADH_1H_2M_3$ to the measurement signal. The measurement signal analysis unit 452 calculates the secondary path characteristic $ADH_1H_2$ based on the measurement signal generated by the measurement signal generation unit 451, the audio signal obtained by the ear canal microphone 320-3, and the known $M_3$.

In this manner, the secondary path characteristic $ADH_1H_2$ can be measured. The adaptive control unit 415 can improve the noise canceling performance by controlling the characteristic $-\alpha$ of the FF filter based on the secondary path characteristic measured in advance by the above-described processing.

Here, the characteristics $H_1$ and $H_2$ differ for each user due to characteristics of the ear canal 5 and physical characteristics such as a shape of the pinna 2. Therefore, when a fixed filter is used, it is desirable to correct the filter characteristic based on the secondary path characteristic $ADH_1H_2$ of the individual user measured using the measurement signal. Hereinafter, this point will be described in detail.

Case of Correcting Fixed Filter Using Ear Canal Microphone 320-3

The ear canal microphone 320-3 may be used to correct the fixed filter of NC. Specifically, the signal processing unit 331 measures the secondary path characteristic $ADH_1H_2$ by the above-described measurement process using the measurement signal generation unit 451 and the measurement signal analysis unit 452. Then, the signal processing unit 331 corrects a characteristic (that is, a filter coefficient) of the fixed filter to generate the noise cancellation signal based on the measured secondary path characteristic $ADH_1H_2$. The fixed filter characteristic is designed based on a general secondary path characteristic, and individual differences among users can be absorbed by correcting the filter characteristic based on the secondary path characteristic measured for a user wearing the headphones 300. As a result, the noise canceling performance can be improved. The fixed filter to be corrected may be the FF filter or the FB filter. Hereinafter, an example in which the fixed filter to be corrected is the FF filter 414 illustrated in FIG. 34 will be described.

The general secondary path characteristic measured in advance is defined as $ADH_{1common}H_{2common}$. Further, the secondary path characteristic of the individual user including the influence caused by the physical characteristics such as the characteristics of the ear canal 5 and the shape of the pinna 2 is defined as $ADH_{1personal}H_{2personlal}$.

A difference characteristic between the general secondary path characteristic $ADH_{1common}H_{2common}$ and the secondary path characteristic $ADH_{1personal}H_{2personlal}$ of the individual user is defined as $\Delta H$. $\Delta H$ is defined as follows.

$$\Delta H = \frac{ADH_{1common}H_{2common}}{ADH_{1persnal}H_{2personal}}$$

FF-NC is designed so as to minimize a sound pressure at an eardrum position for a leak signal. That is, the characteristic α of the FF filter is designed such that the following expression is satisfied.

$$-NM_2 \alpha ADH_1 H_2 + NF_2 = 0 \quad (B13)$$

The fixed filter of FF-NC is designed based on a general secondary path characteristic $DH_{1common}H_{2common}$. That is, the characteristic α of the FF filter is fixedly designed as the following formula.

$$\alpha = \frac{F_2}{M_2 ADH_{1common} H_{2common}} \quad (B14)$$

When a fixed filter designed based on the general secondary path characteristics $DH_{1common}H_{2common}$ is used, the FF-NC residual caused by individual differences in physical characteristics is expressed as the following formula by putting the filter characteristic obtained by Formula (B14) into Formula (B13).

$$-NM_2 \left( \frac{F_2}{M_2 ADH_{1common} H_{2common}} \right) ADH_{1persnal} H_{2personal} + NF_2 = \quad (B15)$$
$$-NF_2 \left( \frac{H_{1persnal} H_{2personal}}{H_{1common} H_{2common}} \right) + NF_2$$

Here, the sound pressure at the eardrum position is minimized if the general secondary path characteristic and the secondary path characteristic pf the individual user are the same, that is, if $ADH_{1personal}H_{2personlal} = ADH_{1common}H_{2common}$. However, there is a difference between a general next path characteristic and the secondary path characteristic of the individual user in many cases. Therefore, the signal processing unit 331 can personalize the filter characteristic and absorb the individual difference by multiplying the filter characteristic of the fixed filter by ΔH as a correction characteristic. A filter characteristic obtained by multiplying the filter characteristic of the fixed filter by the correction characteristic ΔH is expressed by the following formula.

$$\alpha_{personal} = \alpha \times \Delta H \quad (B16)$$
$$= \frac{F_2}{M_2 ADH_{1common} H_{2common}} \times \frac{ADH_{1common} H_{2common}}{ADH_{1personal} H_{2personal}}$$

As illustrated in Formula (B16), the signal processing unit 331 can absorb the individual difference of the user by multiplying the fixed filter of FF-NC by the correction characteristic. Therefore, it is possible to improve the noise canceling performance as compared with a case where the fixed filter designed based on the general secondary path characteristic is used as it is.

(3) Third Noise Cancellation Process

A third noise cancellation process is a process in which the first noise cancellation process described above with reference to FIG. 32 and the second noise cancellation process described above with reference to FIG. 33 are combined. That is, the third noise cancellation process is a process using the ear canal microphone 320-3 as an error microphone of FB-NC by the second FB filter 412 and as an error microphone for adaptive control of FF-NC by the FF filter 414. In the third noise cancellation process, the effects of both the first noise cancellation process and the second noise cancellation process are achieved, and thus, a higher noise canceling effect than either one is expected. Hereinafter, details of the third noise cancellation process will be described with reference to FIG. 35.

Figure 35:
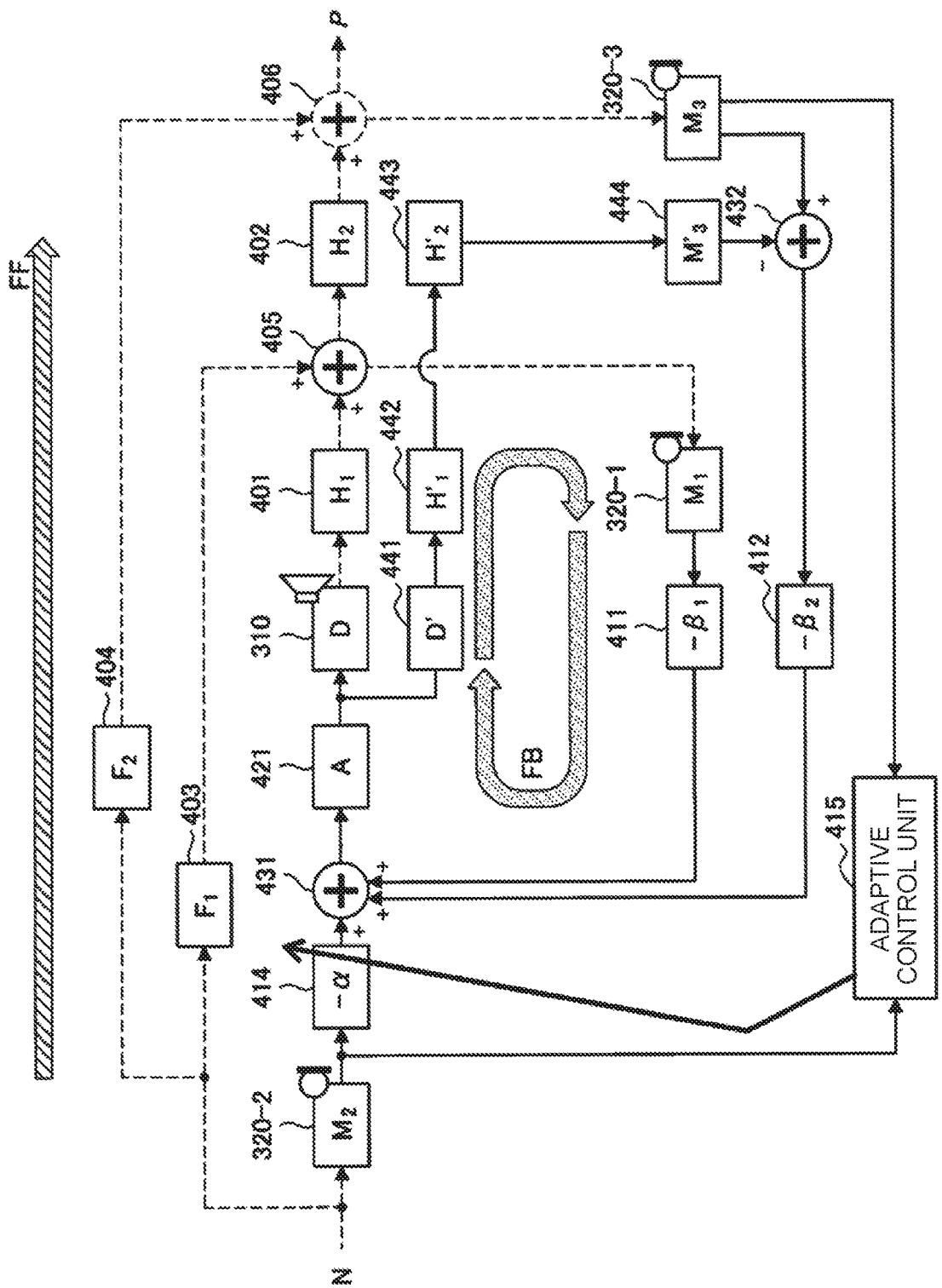
FIG. 35 is a diagram illustrating a model configuration example of a third noise cancellation process using the headphones according to the embodiment.

FIG. 35 is a diagram illustrating a model configuration example of the third noise cancellation process using the headphones 300 according to the present embodiment. As illustrated in FIG. 35, the ear canal microphone 320-3 collects audio and generates an audio signal. The audio signal is input to the second FB filter 412 via the adder 432 and is also input to the adaptive control unit 415. In this manner, the ear canal microphone 320-3 functions as the error microphone for adaptive control of FF-NC by the FF filter 414 while functioning as the error microphone of FB-NC by the second FB filter 412. Detailed signal processing is the same as described above with reference to FIGS. 32 and 33, and thus, the description thereof is omitted here.

Note that the ear canal microphone 320-3 may be used to correct a filter characteristic of a fixed filter when the FF filter 414 is designed as the fixed filter. That is, the ear canal microphone 320-3 may be used for the secondary path characteristic measurement process, and a correction characteristic based on the measurement result may be applied to the fixed filter. As a result, individual differences in the secondary path characteristics can be absorbed, and the noise canceling performance can be improved.

(4) Fourth Noise Cancellation Process

A fourth noise cancellation process is a process of performing an internal model control (IMC) type FB-NC using the ear canal microphone 320-3. Similar to the FF-NC, IMC-type FB-NC is a method of maximizing a noise canceling effect by minimizing the numerator of the sensitivity function (that is, the numerator of the coefficient relating to the noise N in the above Formula (A3)). Hereinafter, the IMC type FB-NC will be referred to as IMC-FB to be distinguished from FB-NC that maximizes the denominator of the above Formula (1) using the characteristic β. In the fourth noise cancellation process, the signal processing unit 331 generates a fourth noise cancellation signal by the IMC-FB based on the first audio signal generated by the FB-NC microphone 320-1. The signal processing unit 331 adaptively controls the filter characteristics of the FB filter 413 used for this IMC-FB based on the third audio signal generated by the ear canal microphone 320-3. According to this method, the error microphone position of IMC-FB is close to the eardrum 9, and thus, a high noise canceling effect is expected. Hereinafter, details of the fourth noise cancellation process will be described with reference to FIG. 36.

Figure 36:
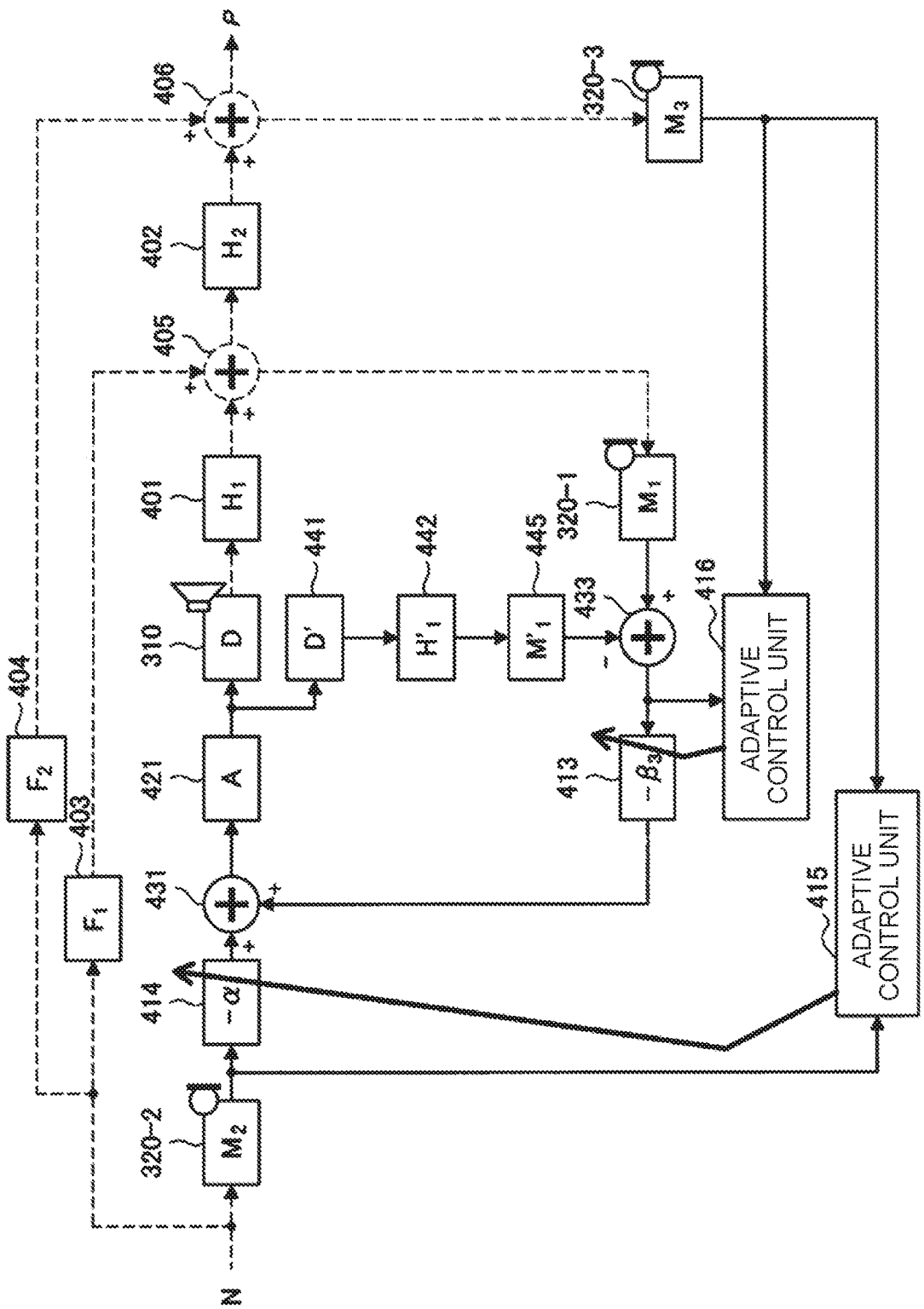
FIG. 36 is a diagram illustrating a model configuration example of a fourth noise cancellation process using the headphones according to the embodiment.

FIG. 36 is a diagram illustrating a model configuration example of the fourth noise cancellation process using the headphones 300 according to the present embodiment. The model configuration example illustrated in FIG. 36 is different from the model configuration example illustrated in FIG. 33 in terms of having the third FB filter 413 instead of the first FB filter 411 and having an adaptive control unit 416 which adaptively controls the third FB filter 413. Since the noise cancellation process relating to the FF filter 414 is the same as described above with reference to FIG. 33, the detailed description thereof is omitted here. Hereinafter, the noise cancellation process (IMC-FB) relating to the third FB filter 413 will be described in detail.

The FB-NC microphone 320-1 collects audio and generates an audio signal. An adder 433 subtracts a signal, obtained by applying internal models (:characteristics D', $H_1'$, and $M_1'$) illustrated in blocks 441, 442, and 445 to the output signal input to the driver 310, from the audio signal generated by the FB-NC microphone 320-1 to perform the synthesis. These internal models have characteristics that simulate characteristics from the input of the output signal to the driver 310 to the generation of the first audio signal. The synthesized signal is input to the third FB filter 413 and input to the adaptive control unit 416. On the other hand, the audio signal generated based on the audio collected by the ear canal microphone 320-3 is also input to the adaptive control unit 416. The adaptive control unit 416 adaptively controls the characteristic $\beta_3$ of the third FB filter 413 based on these input audio signals. Under the adaptive control by the adaptive control unit 416, the third FB filter 413 generates a noise cancellation signal by the noise cancellation process of the FB scheme based on the input audio signals. The noise cancellation signal generated by the third FB filter 413 is combined with the noise cancellation signal generated by the FF filter 414 by the adder 431. The synthesized signal is amplified by the amplifier 421 and output from the driver 310.

Note that the ear canal microphone 320-3 may be used to correct a filter characteristic of a fixed filter when the third FB filter 413 is designed as the fixed filter. That is, the ear canal microphone 320-3 may be used for the secondary path characteristic measurement process, and a correction characteristic based on the measurement result may be applied to the fixed filter. As a result, individual differences in the secondary path characteristics can be absorbed, and the noise canceling performance can be improved.

(5) Fifth Noise Cancellation Process

A fifth noise cancellation process is a process in which the first noise cancellation process described above with reference to FIG. 32 and the fourth noise cancellation process described above with reference to FIG. 36 are combined. That is, the fifth noise cancellation process is a process using the ear canal microphone 320-3 as the following three types of error microphones. Firstly, the ear canal microphone 320-3 is used as the error microphone for adaptive control of FF-NC by the adaptive control unit 415. Secondly, the ear canal microphone 320-3 is used as the error microphone of FB-NC by the second FB filter 412. Thirdly, the ear canal microphone 320-3 is used as the error microphone for adaptive control of IMC-FB by the adaptive control unit 416. In the fifth noise cancellation process, the effects of both the first noise cancellation process and the fourth noise cancellation process are achieved, and thus, a much higher noise canceling effect than either one is expected. Hereinafter, details of the fifth noise cancellation process will be described with reference to FIG. 37.

Figure 37:
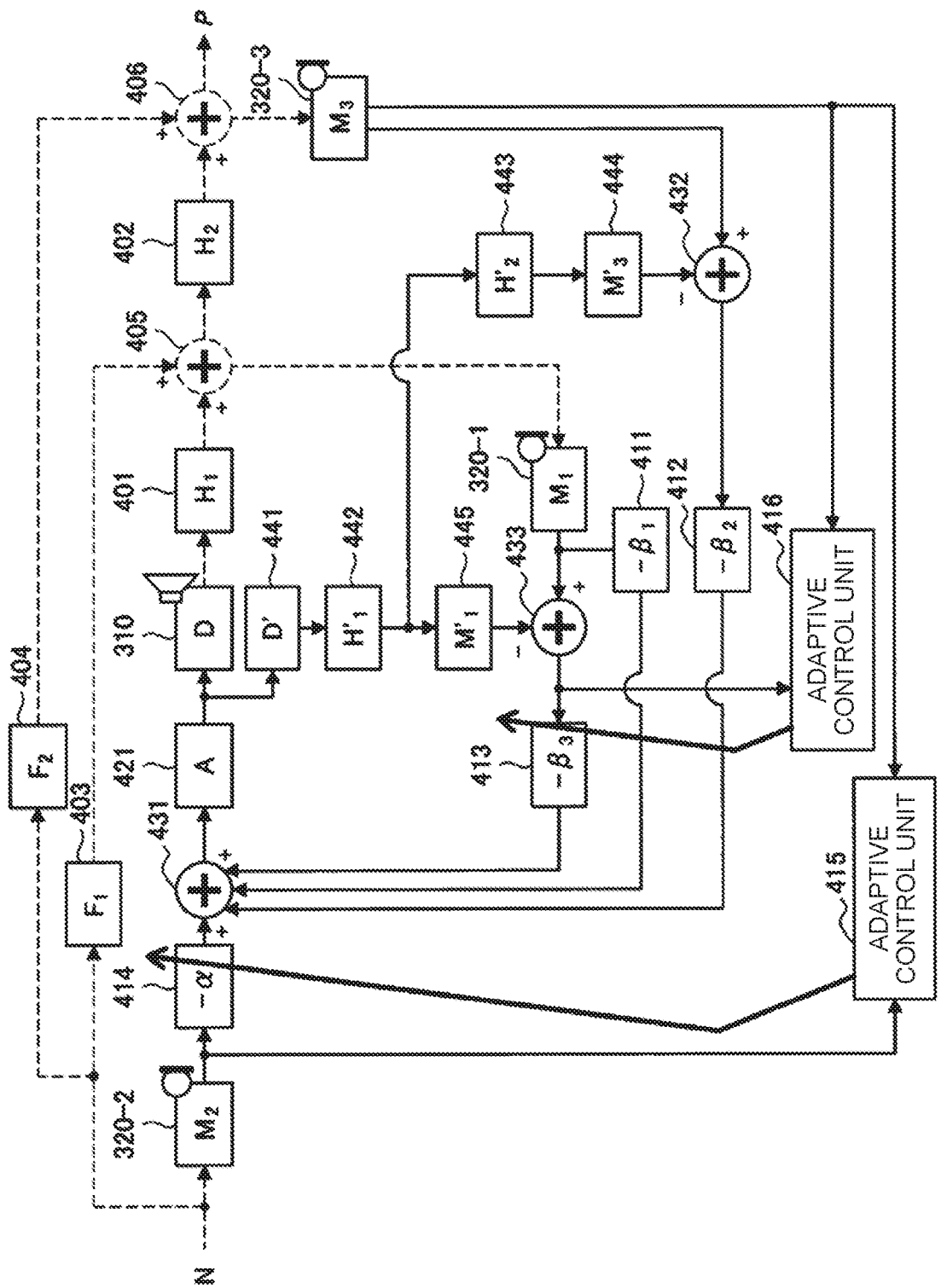
FIG. 37 is a diagram illustrating a model configuration example of a fifth noise cancellation process using the headphones according to the embodiment.

FIG. 37 is a diagram illustrating a model configuration example of the fifth noise cancellation process using the headphones 300 according to the present embodiment. As illustrated in FIG. 37, the ear canal microphone 320-3 collects audio and generates an audio signal. This audio signal is input to the second FB filter 412 via the adder 432, input to the adaptive control unit 415, and input to the adaptive control unit 416. In this manner, the ear canal microphone 320-3 functions as the three types of error microphones described above. Detailed signal processing is the same as described above with reference to FIGS. 32 and 36, and thus, the description thereof is omitted here.

(6) Supplement

Although the above description has been given based on the assumption that the headphones 300 according to the present embodiment include the three audio input units 320, the present embodiment is not limited to such an example. The headphones 300 do not necessarily have either the FB-NC microphone 320-1 or the FF-NC microphone 320-2 among the three audio input units 320. When the headphones 300 do not have the FF-NC microphone 320-2, the noise cancellation process using the FF filter 414 is omitted from the first to fifth noise cancellation processes described above. When the headphones 300 do not have the FB-NC microphone 320-1, the noise cancellation processes using the first FB filter 411 and the third FB filter 413 are omitted from the first to fifth noise cancellation processes described above. In either case, at least the position of the error microphone is close to the eardrum 9, and thus, a high noise canceling effect is expected.

<2.5. Details of Structure of Headphones 300>

Hereinafter, a structure of the headphones 300 according to the present embodiment will be described in detail.

(1) Arrangement of Audio Input Unit

First, the arrangement of the audio input unit 320 included in the headphones 300 will be described with reference to FIGS. 38 and 39

Figure 38:
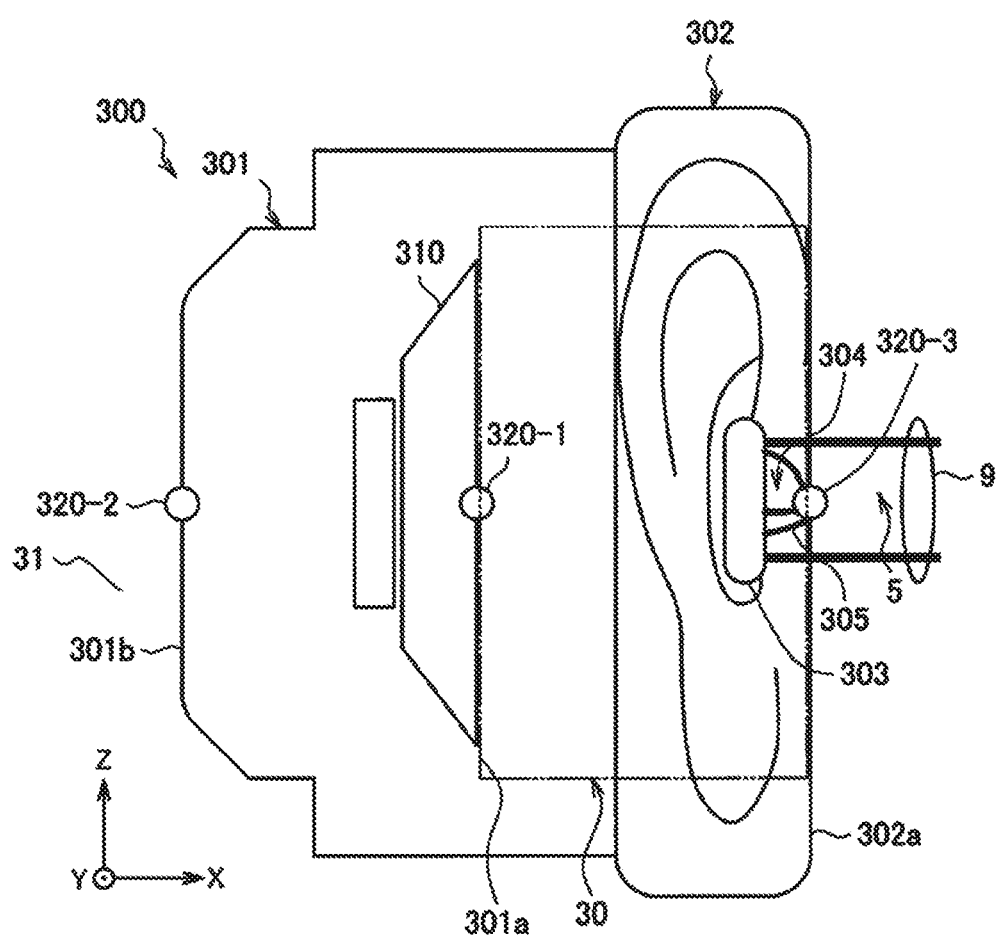
FIG. 38 is a diagram for describing an example of a configuration of the headphones according to the embodiment.
Figure 39:
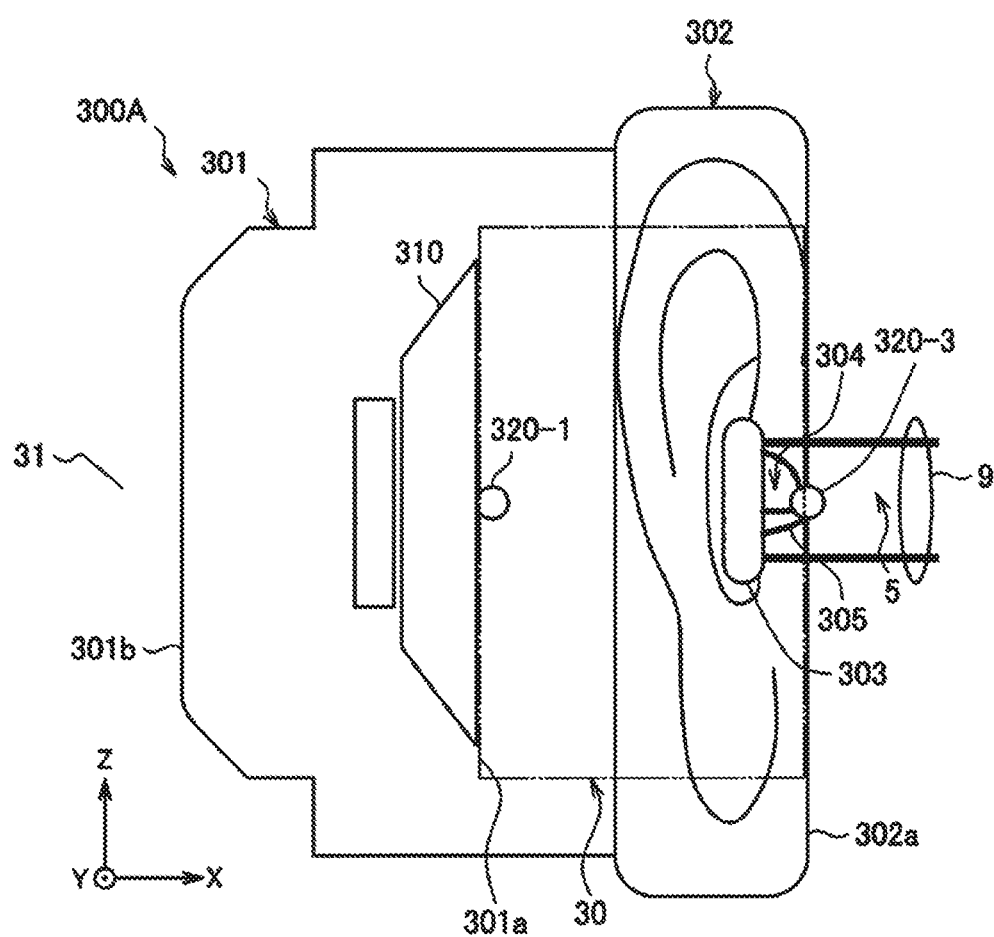
FIG. 39 is a diagram for describing an example of a configuration of the headphones according to the embodiment.

FIG. 38 is a diagram for describing an example of the configuration of the headphones 300 according to the present embodiment. FIG. 38 illustrates the configuration in the state where the headphones 300 are worn by the user. As illustrated in FIG. 38, the headphones 300 include the housing 301 and the ear pad 302. The housing 301 is provided with the driver 310, the FB-NC microphone 320-1, and the FF-NC microphone 320-2. In addition, the ear canal microphone 320-3 is arranged at a position away from the housing 301 as illustrated in FIG. 38. The configuration of each of these constituent elements is the same as described above with reference to FIG. 28 and the like.

Figure 40:
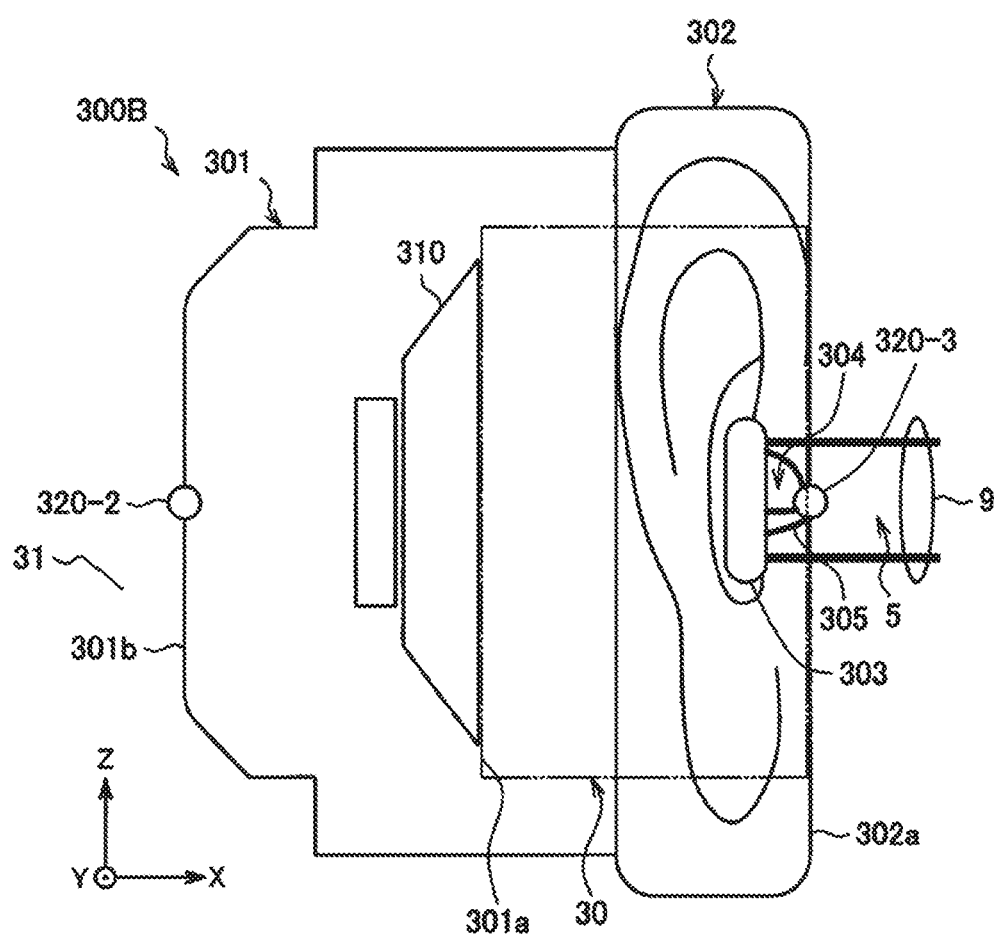
FIG. 40 is a diagram for describing an example of a configuration of the headphones according to the embodiment.

As described above, the headphones 300 do not necessarily include either the FB-NC microphone 320-1 or the FF-NC microphone 320-2. FIG. 39 illustrates an example of a configuration of headphones 300A that do not include the FF-NC microphone 320-2 but include the FB-NC microphone 320-1 and the ear canal microphone 320-3. FIG. 40 illustrates an example of a configuration of headphones 300B that do not have the FB-NC microphone 320-1 but have the FF-NC microphone 320-2 and the ear canal microphone 320-3.

(2) Shape of Holding Unit

Hereinafter, variations of the shape of the holding unit 303 will be described with reference to FIGS. 41 to 46.

Figure 41:
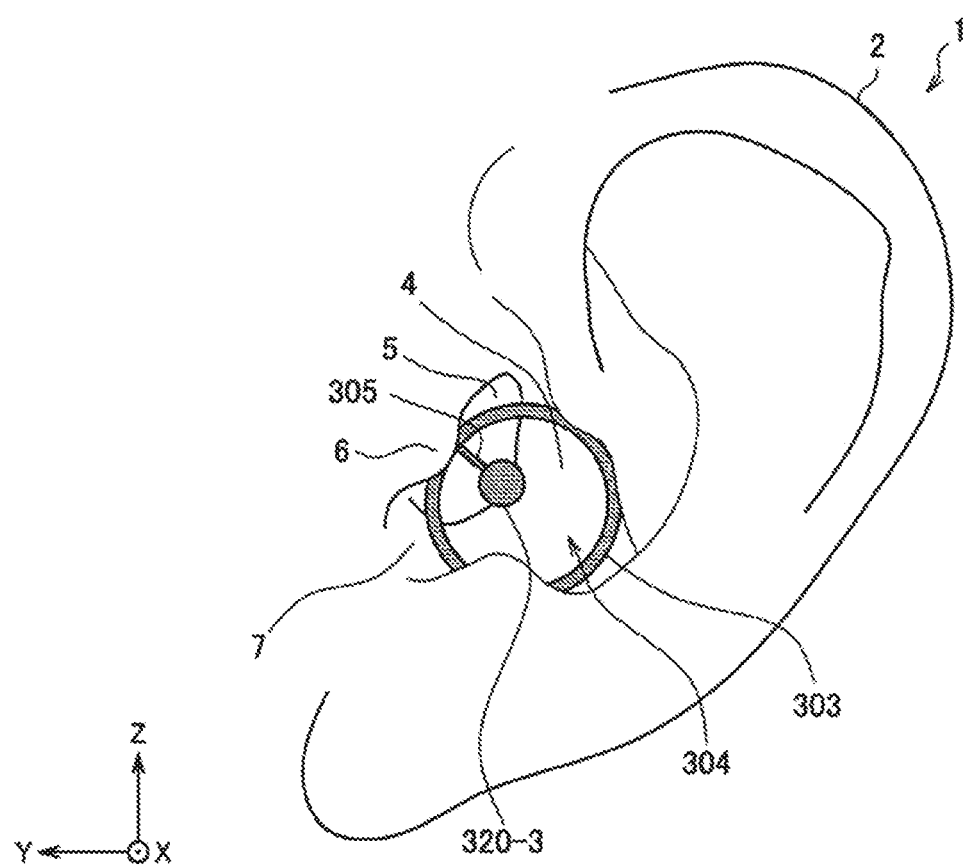
FIG. 41 is a view illustrating an example of a configuration of the holding unit of the headphones according to the embodiment.

FIG. 41 is a view illustrating an example of the configuration of the holding unit 303 of the headphones 300 according to the present embodiment. As illustrated in FIG. 41, the holding unit 303 may be a ring-shaped structure that forms a circle. The ear canal microphone 320-3 is provided at a distal end of the rod-shaped first support member 305 provided in a ring inner direction of the holding unit 303, and all the other parts of the ring-shaped structure are the opening portions 304.

Figure 42:
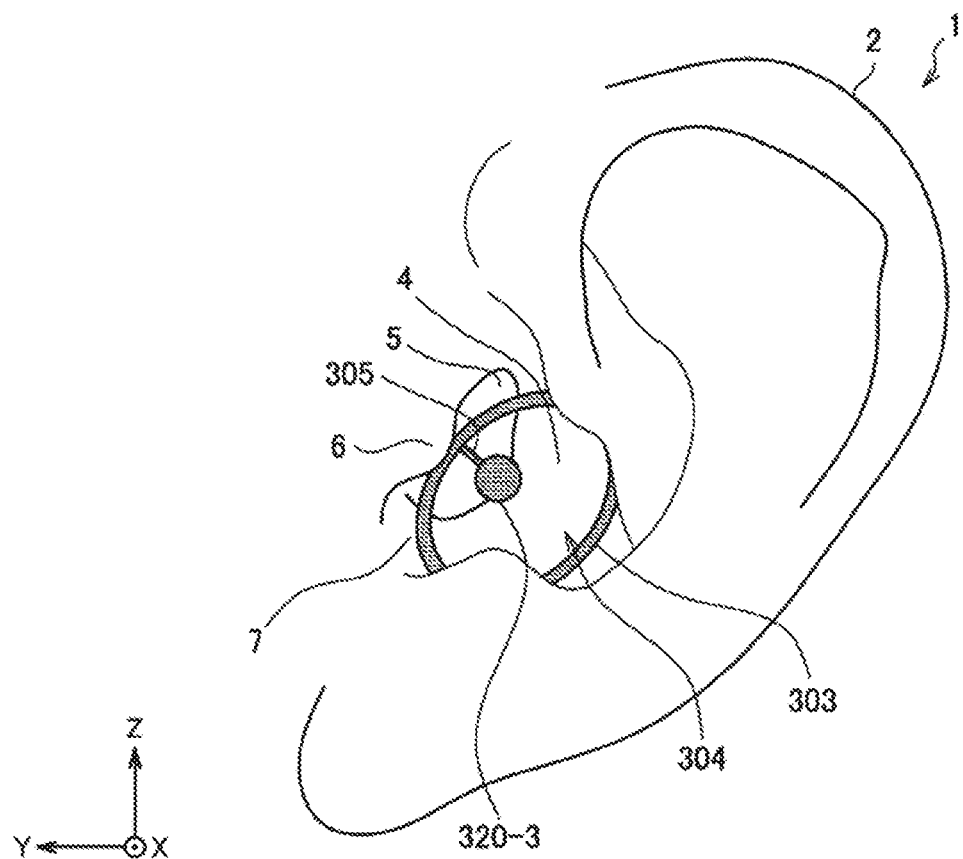
FIG. 42 is a view illustrating an example of a configuration of the holding unit of the headphones according to the embodiment.

FIG. 42 is a view illustrating an example of the configuration of the holding unit 303 of the headphones 300 according to the present embodiment. As illustrated in FIG. 42, the holding unit 303 may be a ring-shaped structure that forms an ellipse. The ear canal microphone 320-3 is provided at a distal end of the rod-shaped first support member 305 provided in a ring inner direction of the holding unit 303, and all the other parts of the ring-shaped structure are the opening portions 304.

Figure 43:
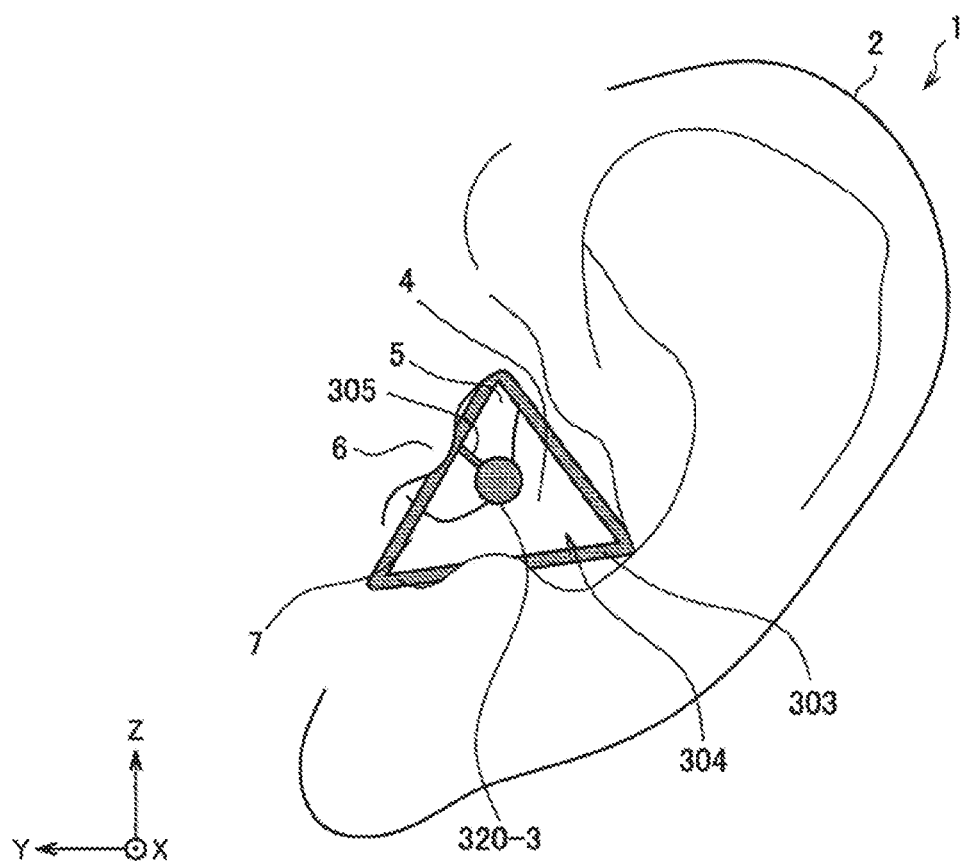
FIG. 43 is a view illustrating an example of a configuration of the holding unit of the headphones according to the embodiment.

FIG. 43 is a view illustrating an example of the configuration of the holding unit 303 of the headphones 300 according to the present embodiment. As illustrated in FIG.

43, the holding unit 303 may be a structure in which each side of a triangle is formed of a rod-shaped structure. The ear canal microphone 320-3 is provided at a distal end of the rod-shaped first support member 305 provided in a triangle inner direction of the holding unit 303, and all the other parts of the triangle-shaped structure are the opening portions 304.

Figure 44:
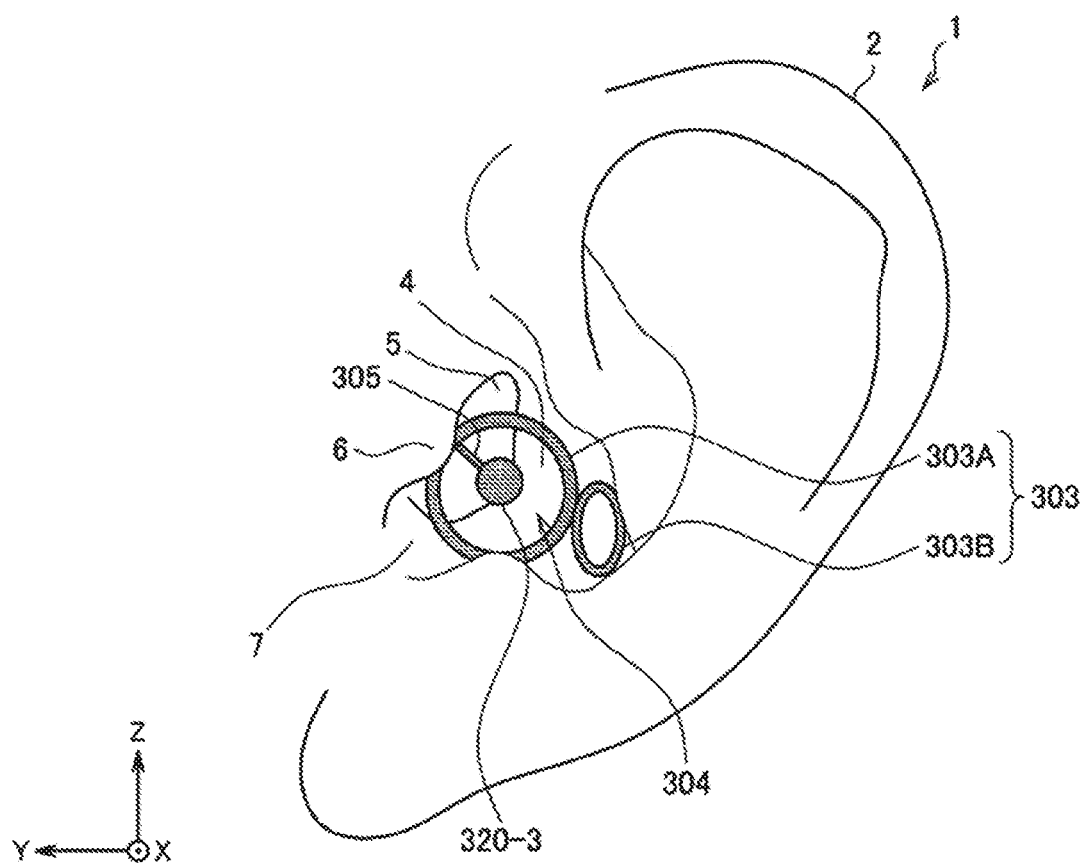
FIG. 44 is a view illustrating an example of a configuration of the holding unit of the headphones according to the embodiment.

FIG. 44 is a view illustrating an example of the configuration of the holding unit 303 of the headphones 300 according to the present embodiment. As illustrated in FIG. 44, the holding unit 303 may be a structure in which a holding unit 303A configured using a ring-shaped structure forming a circle and a holding unit 303B configured using a ring-shaped structure forming an ellipse are connected. The ear canal microphone 320-3 is provided at a distal end of the rod-shaped first support member 305 provided in a ring inner direction of the holding unit 303A, and all the other parts of the ring-shaped structure are the opening portions 304.

In the example illustrated in FIGS. 41 to 44, the holding unit 303 has the opening portion 304. On the other hand, the holding unit 303 does not necessarily have the opening portion 304 as illustrated in FIGS. 45 and 46.

Figure 45:
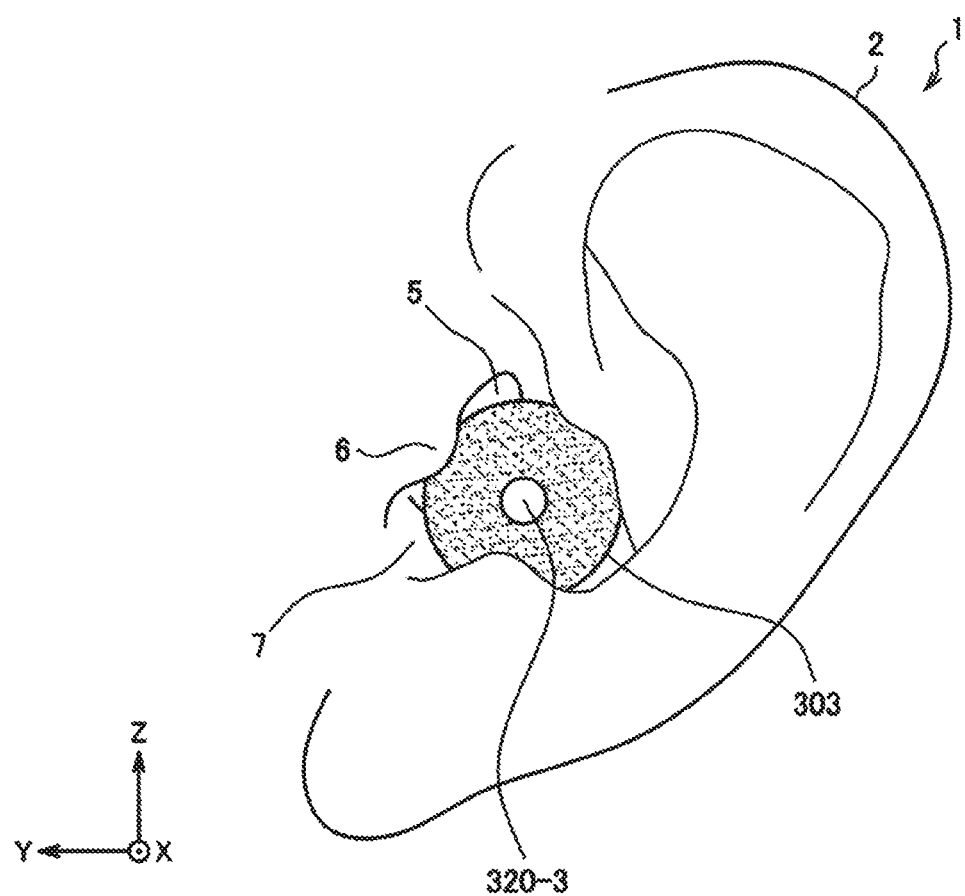
FIG. 45 is a view illustrating an example of a configuration of the holding unit of the headphones according to the embodiment.

FIG. 45 is a view illustrating an example of the configuration of the holding unit 303 of the headphones 300 according to the present embodiment. As illustrated in FIG. 45, the holding unit 303 may be a sponge-shaped structure that forms a circle. The ear canal microphone 320-3 is provided at the center of the holding unit 303.

Figure 46:
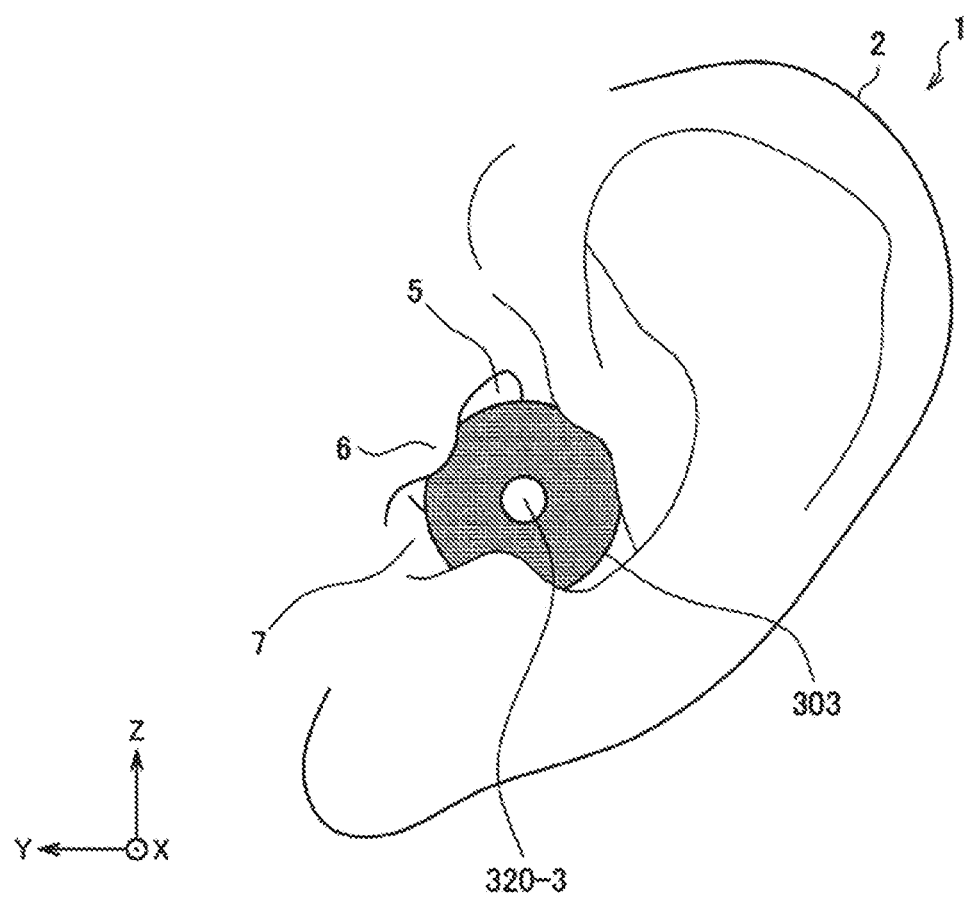
FIG. 46 is a view illustrating an example of a configuration of the holding unit of the headphones according to the embodiment.

FIG. 46 is a view illustrating an example of the configuration of the holding unit 303 of the headphones 300 according to the present embodiment. As illustrated in FIG. 46, the holding unit 303 may be an umbrella-shaped structure that has a narrow outer diameter in an insertion direction (X-axis negative direction) into the ear canal 5 and a wide outer diameter on the opposite side (X-axis positive direction). The ear canal microphone 320-3 is provided at the center of the holding unit 303.

The examples of the shape of the holding unit 303 have been described above. Note that the holding unit 303 can be formed using an elastic body such as rubber, silicon, and sponge.

It is desirable that the ear canal microphone 320-3 be arranged at the same position as the microphone 141 which has been described in the first embodiment with reference to FIG. 6 and the like. That is, it is desirable that the ear canal microphone 320-3 be arranged in a space 15 mm away from the boundary 19 of the cavum concha 4 and the ear canal 5 to the eardrum 9 side or arranged in a space 15 mm away from the boundary 19 of the cavum concha 4 and the ear canal 5 on the opposite side of the eardrum 9. In other words, it is desirable that the holding unit 303 hold the ear canal microphone 320-3 in the space 15 mm away from the boundary 19 of the cavum concha 4 and the ear canal 5 to the eardrum 9 side or in the space 15 mm away from the boundary 19 of the cavum concha 4 and the ear canal 5 on the opposite side of the eardrum 9 in a state where the headphones 300 are worn by the user. Here, a difference between the frequency characteristic at the position of the ear canal microphone 320-3 and the frequency characteristic at the position of the eardrum 9 decreases as the ear canal microphone 320-3 approaches the eardrum 9. Therefore, it is more desirable if the position of the ear canal microphone 320-3 is closer to the eardrum 9. In this regard, the above difference between the frequency characteristics can fall within an allowable range if the space 15 mm away from the boundary 19 to the opposite side of the eardrum 9, and the predetermined noise canceling performance can be ensured. In addition, when the ear canal microphone 320-3 is arranged in the range within 15 mm away from the boundary 19 to the eardrum 9 side, the position of the microphone 141 can be made closer to the eardrum 9 as compared with the case where the microphone 141 is arranged in the space on the opposite side of the eardrum 9 from the boundary 19. Further, at least the microphone 141 can be prevented from coming into contact with the eardrum 9 and damaging the eardrum 9, and the safety can be ensured.

(3) Wired Connection Unit

Next, the connection between the housing 301 and the ear canal microphone 320-3 will be described with reference to FIGS. 47 to 49.

Figure 47:
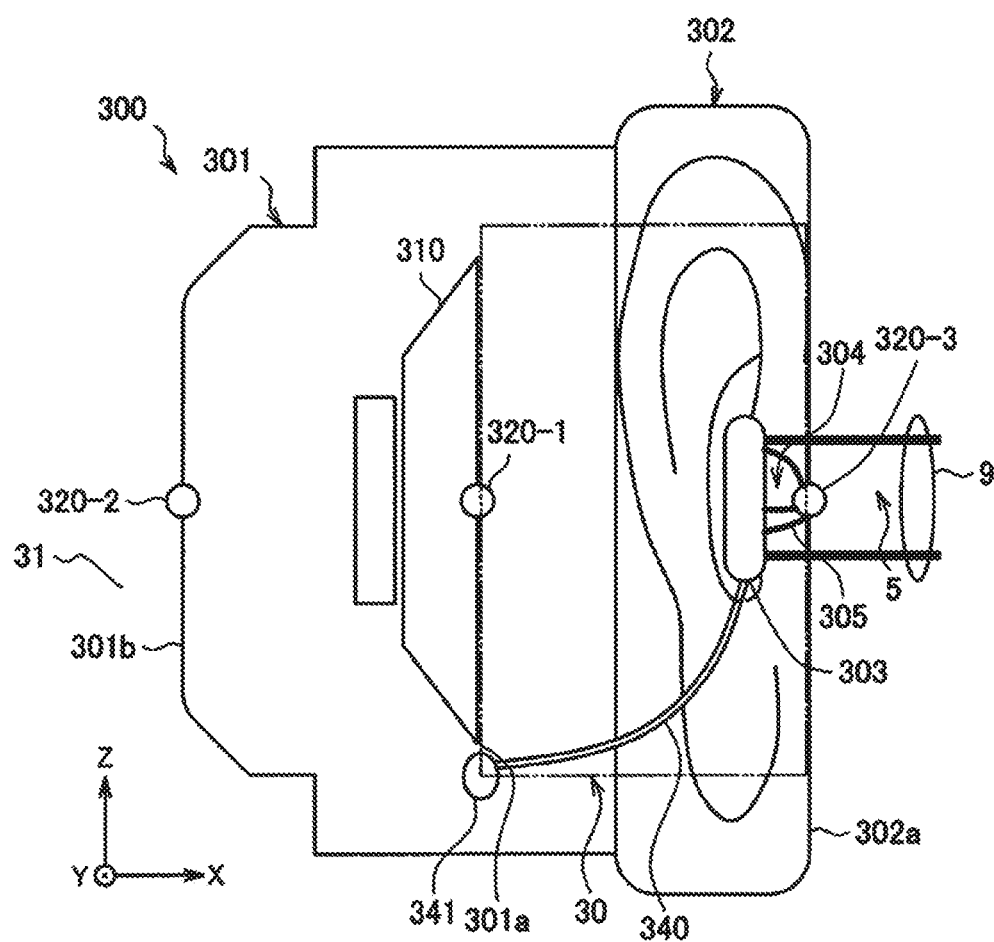
FIG. 47 is a diagram illustrating an example of a configuration of the headphones according to the embodiment.
Figure 48:
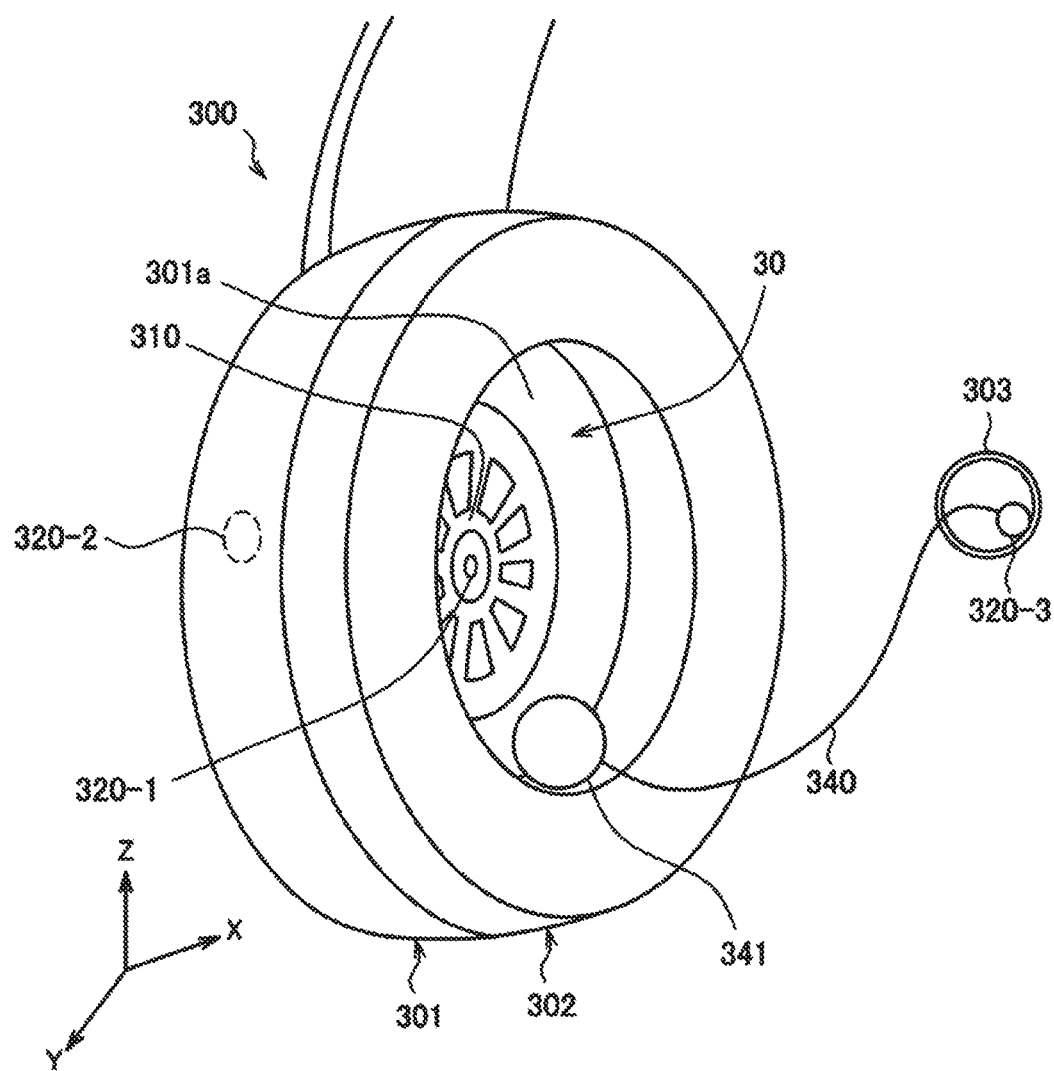
FIG. 48 is a view illustrating a configuration of the headphones illustrated in FIG. 47 as viewed from another viewpoint.

FIG. 47 is a diagram illustrating an example of the configuration of the headphones 300 according to the present embodiment. FIG. 48 is a view illustrating the configuration of the headphones 300 illustrated in FIG. 47 as viewed from another viewpoint. In the example illustrated in FIG. 47, the headphones 300 include a wired connection unit 340. The wired connection unit 340 connects the housing 301 and the ear canal microphone 320-3 in a wired manner. More specifically, the wired connection unit 340 connects the signal processing unit 331 stored in the housing 301 and the ear canal microphone 320-3 in a wired manner. The wired connection unit 340 is formed using a member capable of transmitting a signal, such as an electric wire and an optical fiber.

Further, the headphones 300 include a winding unit 341 that winds up the wired connection unit 340. For example, the winding unit 341 includes: a winding core portion around which the wired connection unit 340 is wound; a support portion which rotatably supports the winding core portion; and a drive unit that rotates the winding core portion in a direction in which the wired connection unit 340 is wound up. The drive unit includes a spring, a motor, or the like, and drives the wired connection unit 340 sent out from the winding core portion so as to be wound around the winding core portion. As a result, it is possible to prevent the wired connection unit 340 from being left in the inner space 30 excessively. Accordingly, tangling of the wired connection unit 340 is prevented. In addition, when the user wears the headphones 300, the wired connection unit 340 can be prevented from being pinched between the ear pad 302 and the user's head.

The winding unit 341 may include a stopper mechanism that changes the winding amount of the wired connection unit 340 in accordance with a user, a device that controls the rotation of the drive unit, and the like. Although the optimum winding amount can vary depending on a size of user's ear and the like, this configuration can optimize the winding amount.

The wired connection unit 340 is sent out freely from the winding unit 341. The user can wear the headphones 300 while winding the wired connection unit 340 around the winding unit 341 after wearing the holding unit 303 by pulling out the wired connection unit 340 before wearing the headphones 300.

Figure 49:
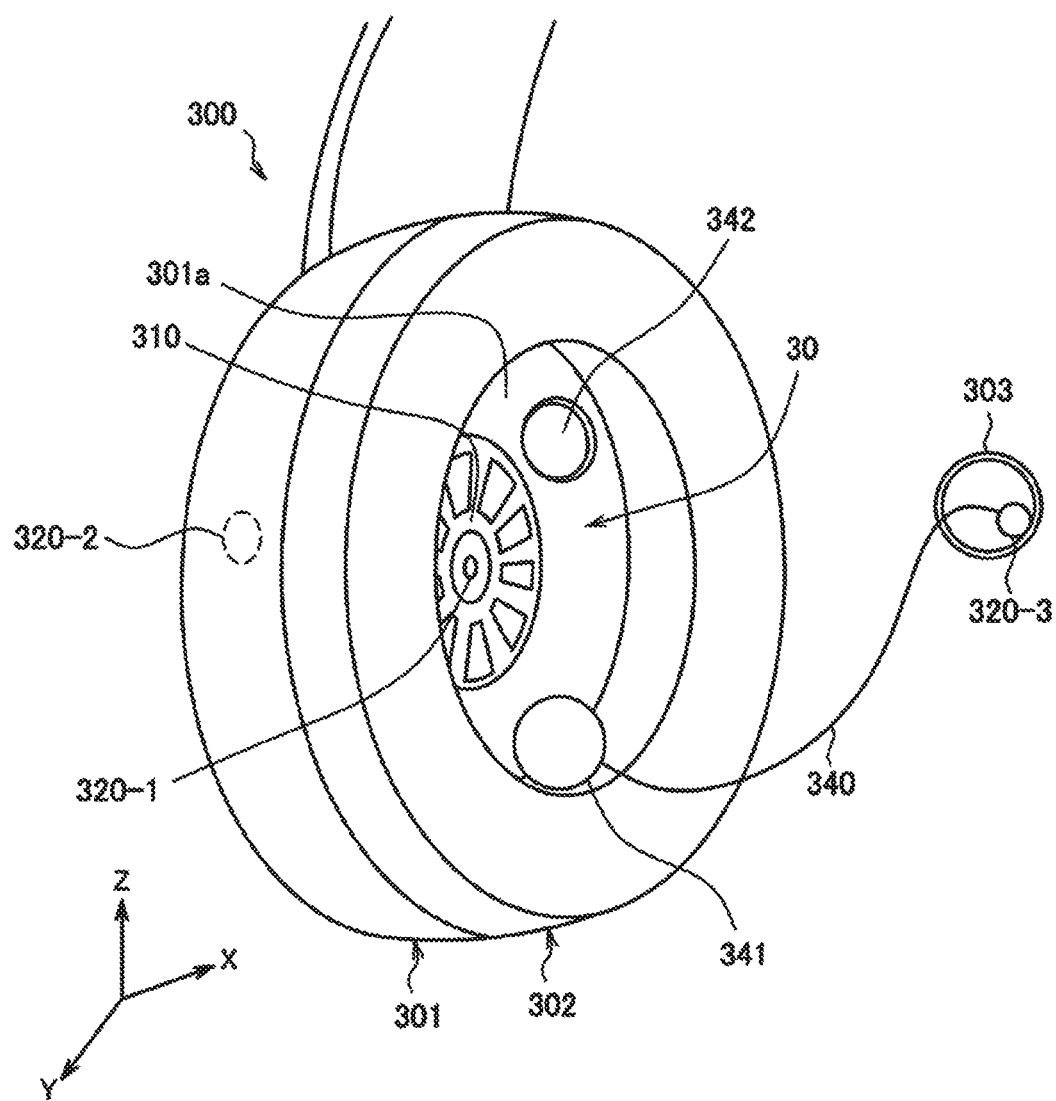
FIG. 49 is a view illustrating an example of a configuration of the headphones according to the embodiment.

FIG. 49 is a diagram illustrating an example of the configuration of the headphones 300 according to the present embodiment. As illustrated in FIG. 49, the housing 301 may include a recess 342 that can accommodate at least a part of the holding unit 303 and the ear canal microphone 320-3 on the inner space 30 side. The recess 342 is formed in the wall portion 301a on the inner space 30 side of the housing 301. For example, the recess 342 has a groove having a shape that matches the shapes of the holding unit 303 and the ear canal microphone 320-3, and the holding unit 303 and the ear canal microphone 320-3 are accommodated in the groove in the non-wearing state. Note that the recess 342 may be provided in the ear pad 302.

(4) Second Support Member

The headphones 300 can include the second support member 306 as described above with reference to FIG. 28 and the like. Hereinafter, a configuration of the second support member 306 will be described with reference to FIGS. 50 to 62.

Figure 50:
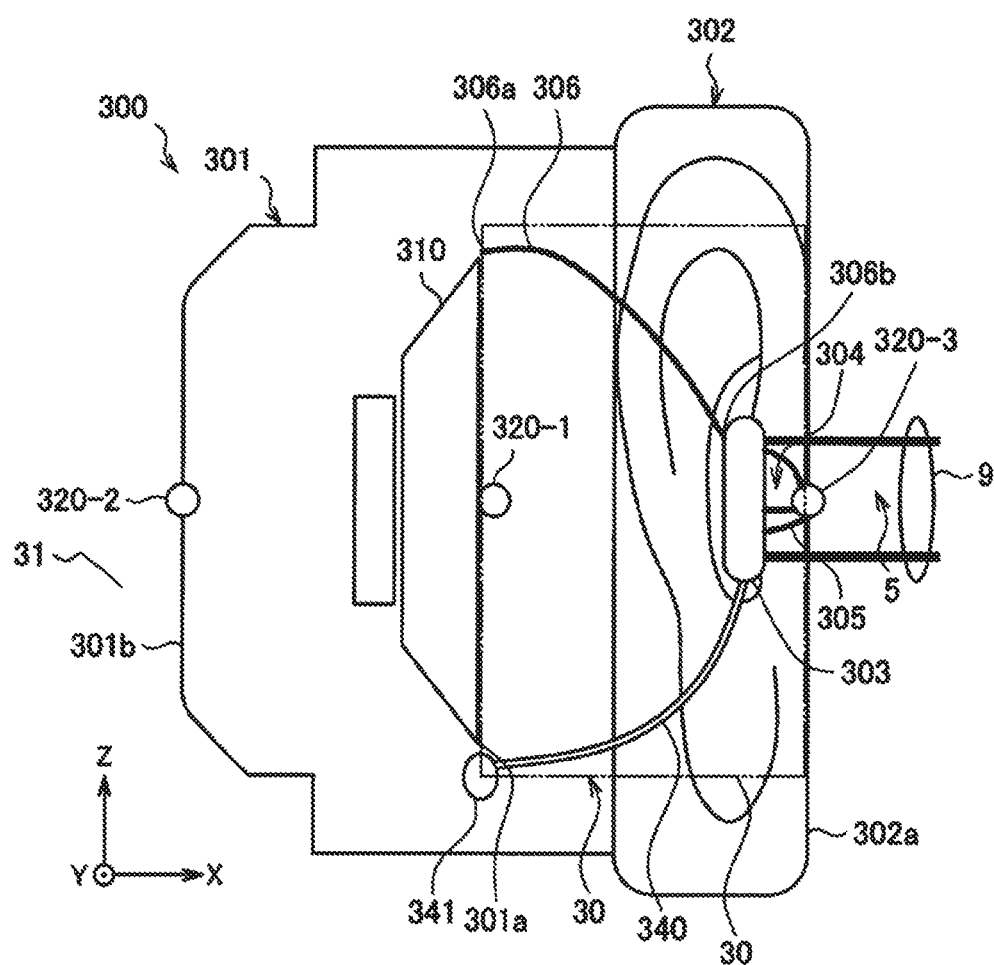
FIG. 50 is a diagram illustrating an example of a configuration of the headphones according to the embodiment.
Figure 51:
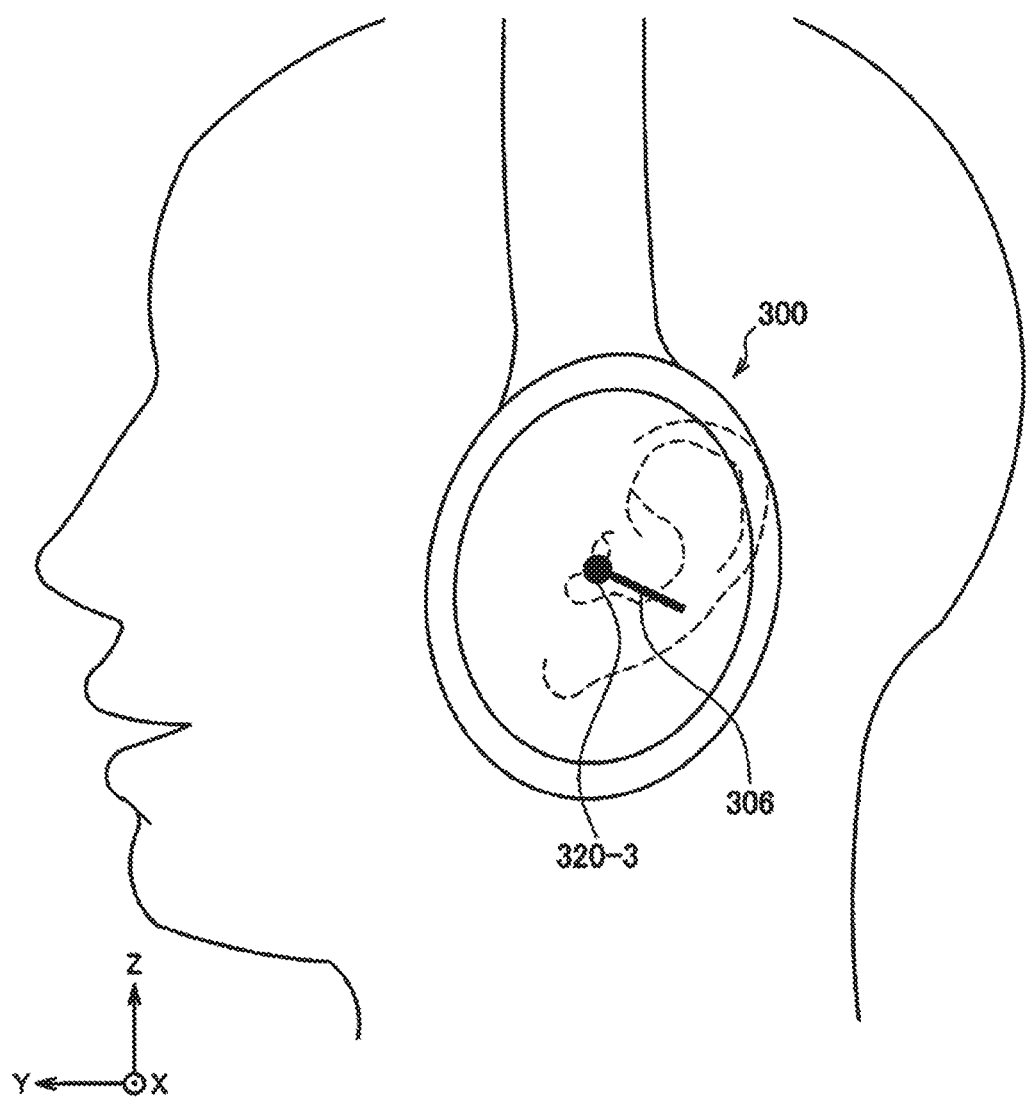
FIG. 51 is a view illustrating a configuration of the headphones illustrated in FIG. 50 as viewed from another viewpoint.
Figure 52:
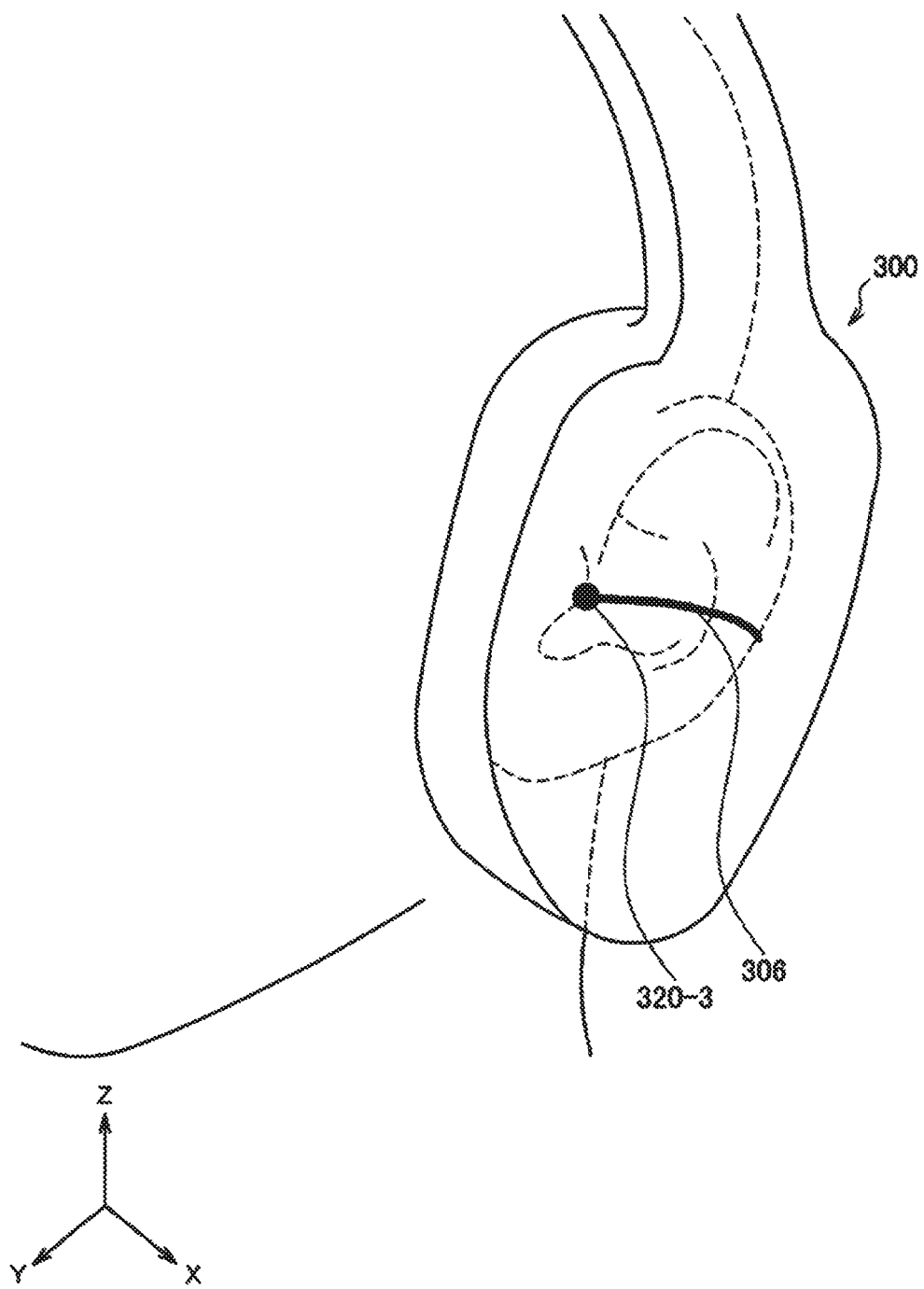
FIG. 52 is a view illustrating a configuration of the headphones illustrated in FIG. 50 as viewed from another viewpoint.
Figure 53:
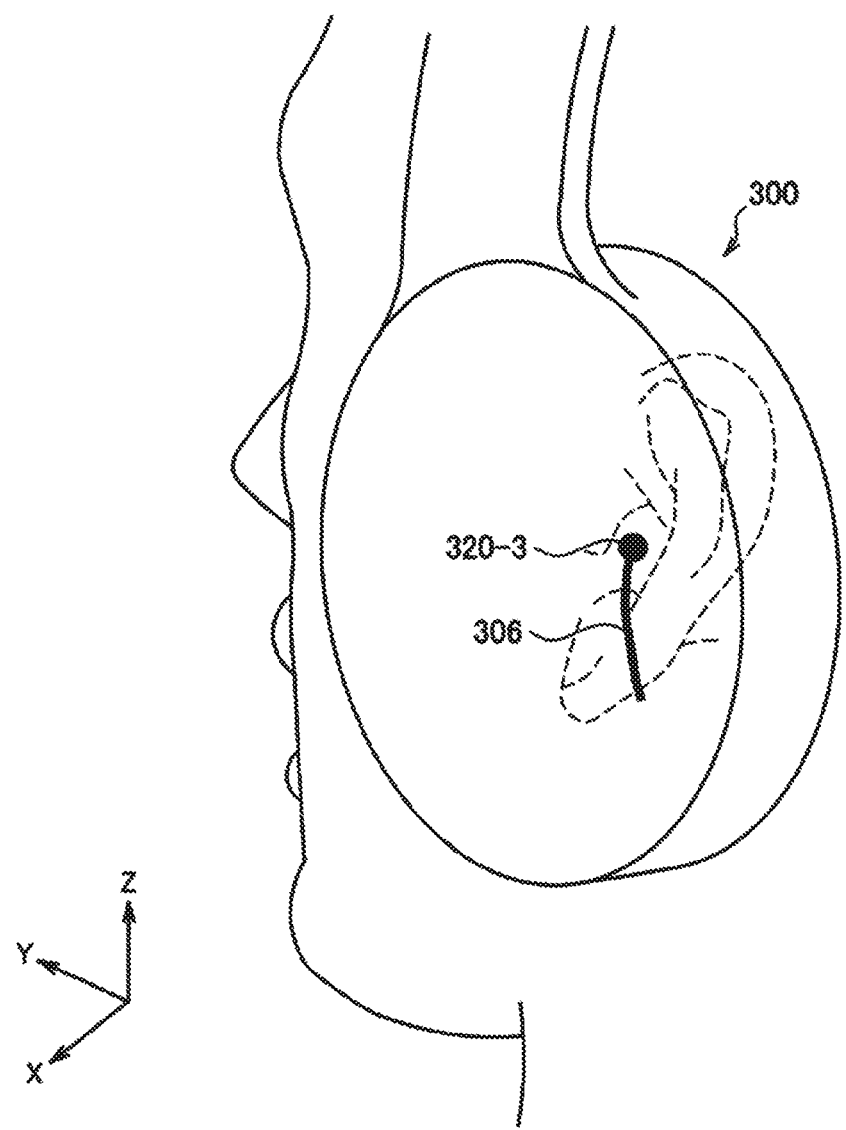
FIG. 53 is a view illustrating a configuration of the headphones illustrated in FIG. 50 as viewed from another viewpoint.

FIG. 50 is a diagram illustrating an example of the configuration of the headphones 300 according to the present embodiment. FIGS. 51 to 53 are views illustrating the configuration of the headphones 300 illustrated in FIG. 50 as viewed from other viewpoints. In the example illustrated in FIG. 50, the headphones 300 include the second support member 306 having one end 306a connected to the housing 301 and another end 306b connected to the holding unit 303. As illustrated in FIG. 50, the second support member 306 may be a rod-shaped structure curved in an S shape. The second support member 306 is formed using an elastic body such as silicon and rubber so as to protrude from the housing 301 to the user's ear side. As a result, the second support member 306 fixes the holding unit 303 to be gently pressed near the entrance of the user's ear canal 5 while following a shape and a size of the ear and a size of the head of the user when the headphones 300 are worn by the user. In addition, the second support member 306 may be formed using a thermoplastic resin, and in this case, the holding unit 303 can be prevented from being excessively pressed against the user's ear.

Figure 54:
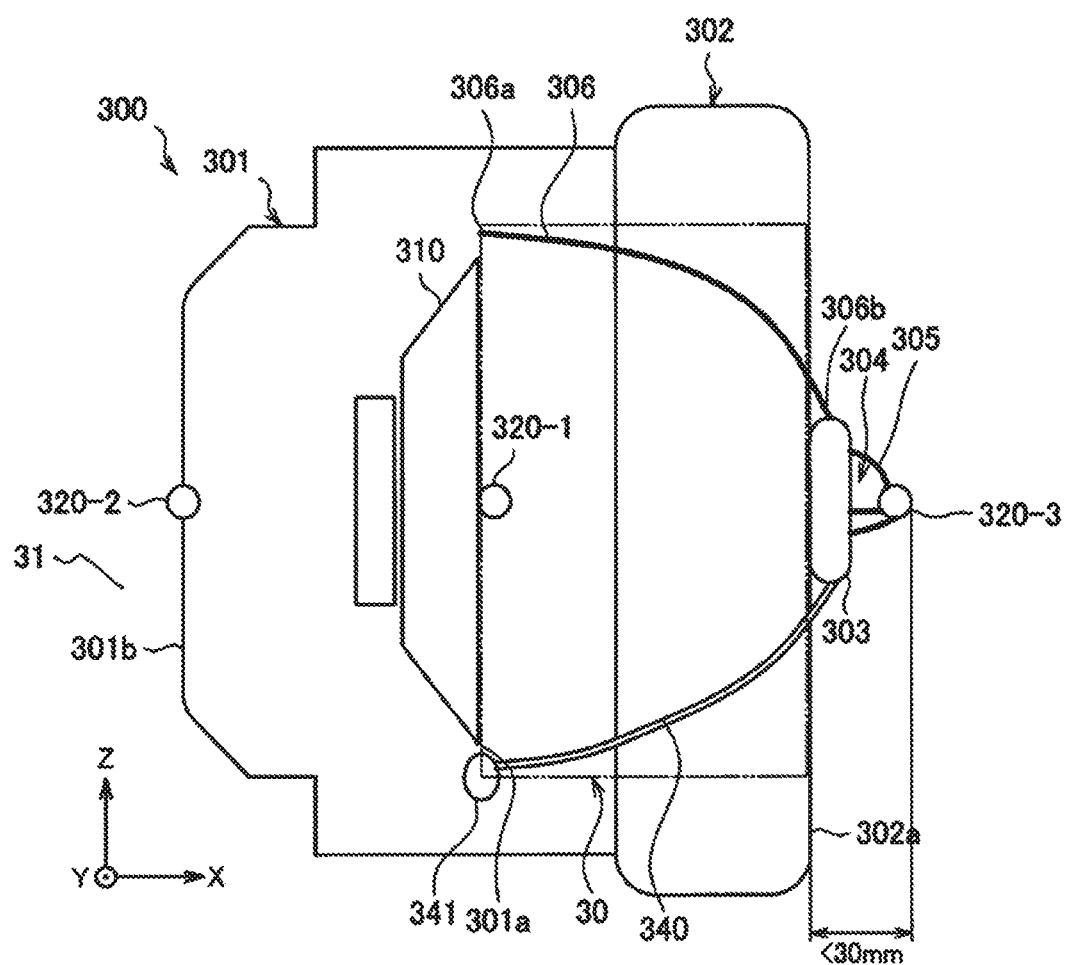
FIG. 54 is a diagram illustrating a configuration when the headphones illustrated in FIG. 50 are not worn.

FIG. 54 is a diagram illustrating a configuration when the headphones 300 illustrated in FIG. 50 are not worn. As illustrated in FIG. 54, the holding unit 303 protrudes outward beyond the contact surface 302a between the ear pad 302 and the user's head. As a result, the second support member 306 is elastically deformed, and the holding unit 303 is pressed against the user's ear by the stress caused by the elastic deformation when the headphones 300 are worn by the user. A length of the holding unit 303 protruding beyond the contact surface 302a is desirably 30 mm or less. As a result, it is possible to prevent the holding unit 303 from being excessively pressed against the user's ear. In addition, the holding unit 303 can be prevented from being excessively inserted into the user's ear canal 5.

Figure 55:
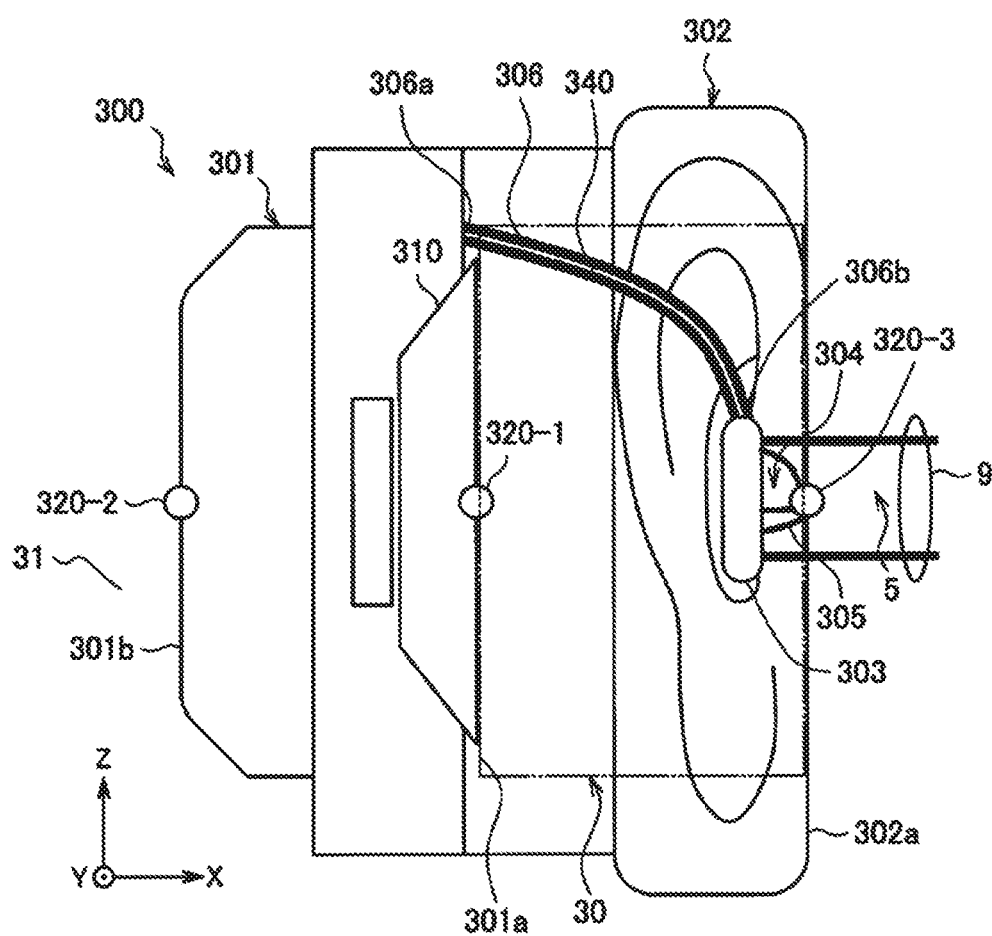
FIG. 55 is a diagram illustrating an example of a configuration of headphones according to the embodiment.

FIG. 55 is a diagram illustrating an example of the configuration of the headphones 300 according to the present embodiment. In the example illustrated in FIG. 55, the wired connection unit 340 is stored inside the second support member 306. In this case, the wired connection unit 340 is not exposed in the inner space 30, and thus, the time and effort for pulling out or winding the wired connection unit 340 from or around the winding unit 341 is omitted so that the convenience for the user is improved.

Figure 56:
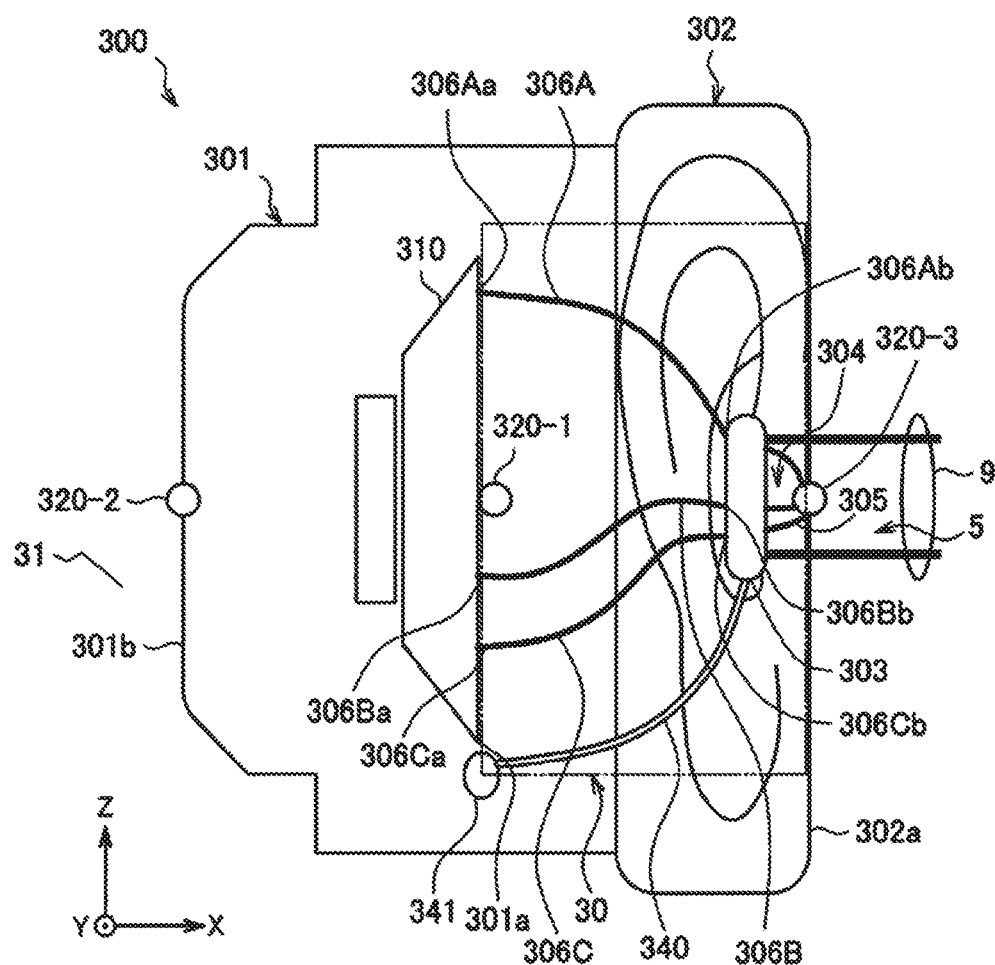
FIG. 56 is a diagram illustrating an example of a configuration of the headphones according to the embodiment.
Figure 57:
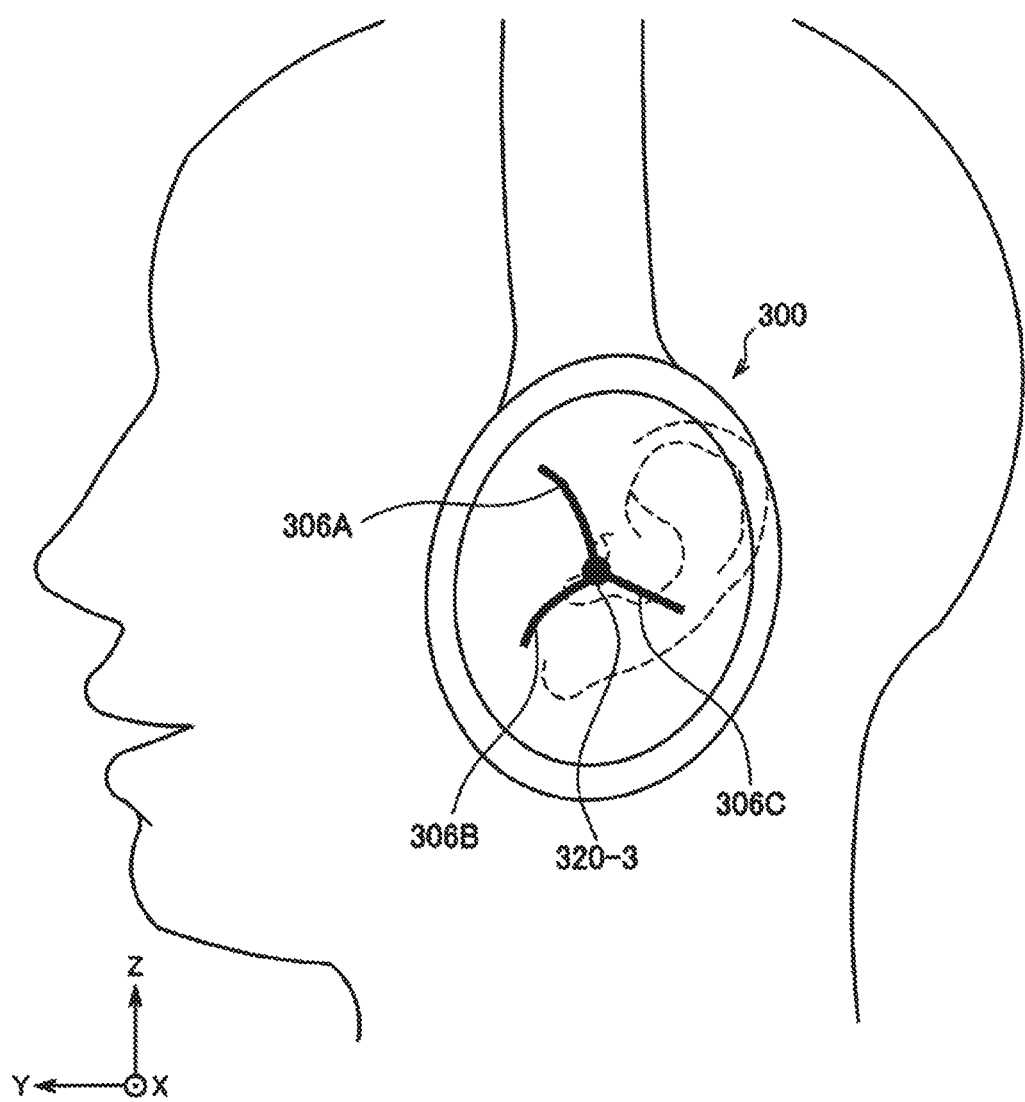
FIG. 57 is a view illustrating a configuration of the headphones illustrated in FIG. 56 as viewed from another viewpoint.
Figure 58:
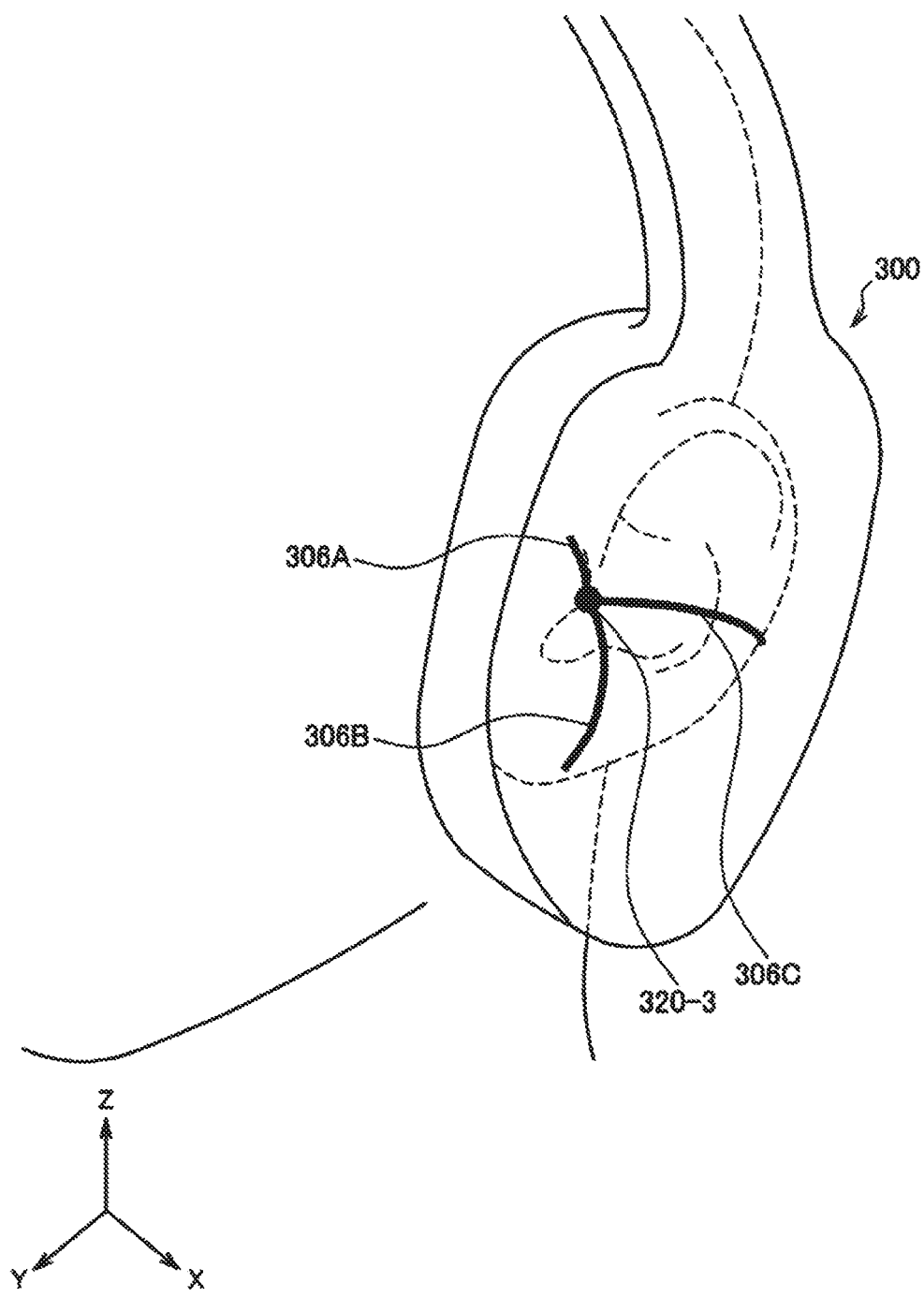
FIG. 58 is a view illustrating a configuration of the headphones illustrated in FIG. 56 as viewed from another viewpoint.
Figure 59:
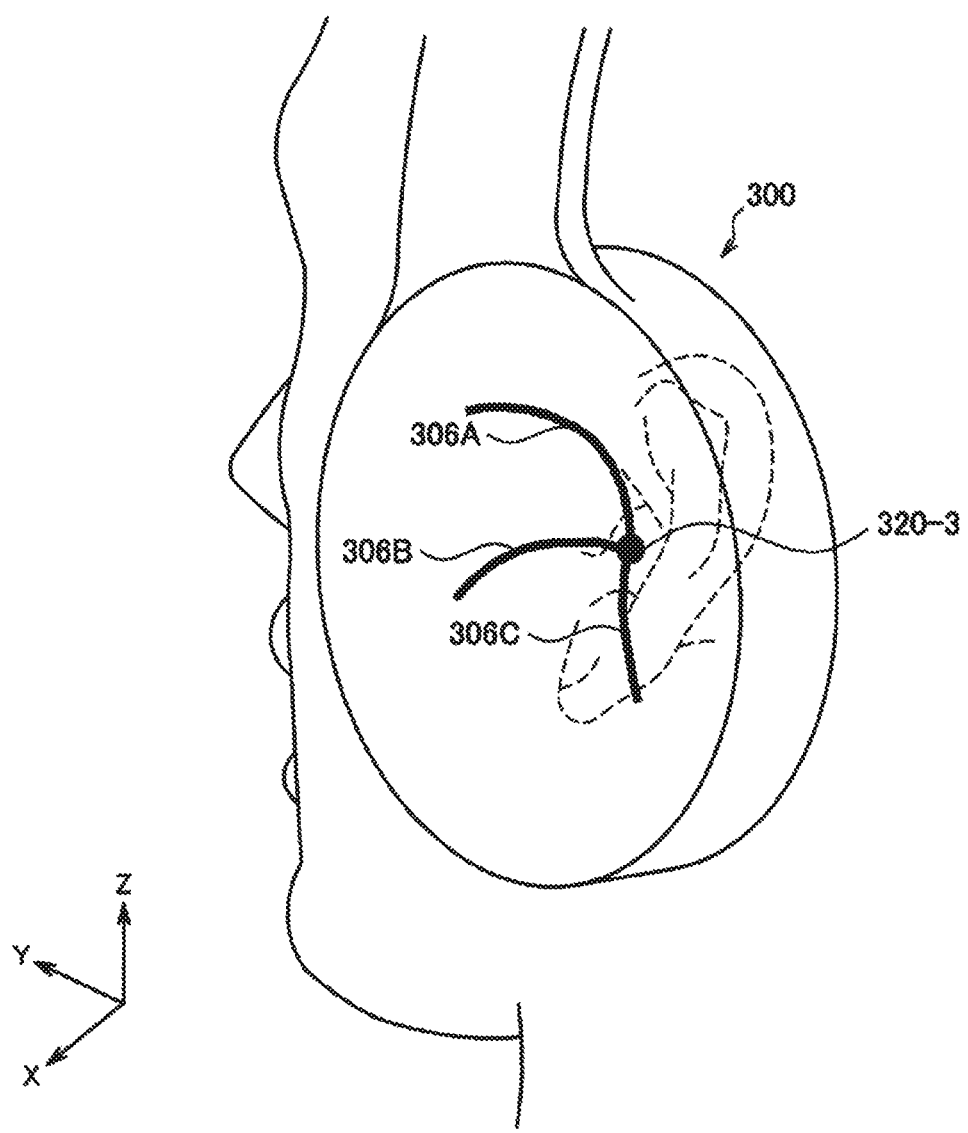
FIG. 59 is a view illustrating a configuration of the headphones illustrated in FIG. 56 as viewed from another viewpoint.

FIG. 56 is a diagram illustrating an example of the configuration of the headphones 300 according to the present embodiment. FIGS. 57 to 59 are views illustrating the configuration of the headphones 300 illustrated in FIG. 56 as viewed from other viewpoints. In the example illustrated in FIG. 56, the headphones 300 include a plurality of second support members 306A to 306C. One ends 306Aa to 306Ca of the second support members 306A to 306C are connected to the housing 301 at different positions. The other ends 306Ab to 306Cb of the second support members 306A to 306C are connected to the holding unit 303 at different positions. With this configuration, a relative positional relationship between the ear canal microphone 320-3 and the driver 310 is hardly changed every time the headphones 300 are worn. Since the relative positional relationship is constant, it is unnecessary to update a noise canceling filter every time the headphones 300 are worn, or the update amount can be suppressed. In addition, this configuration makes it difficult for the ear canal microphone 320-3 to be displaced from the ear hole during wearing of the headphones 300. As a result, the noise cancellation process during wearing of the headphones 300 can be stabilized.

Figure 60:
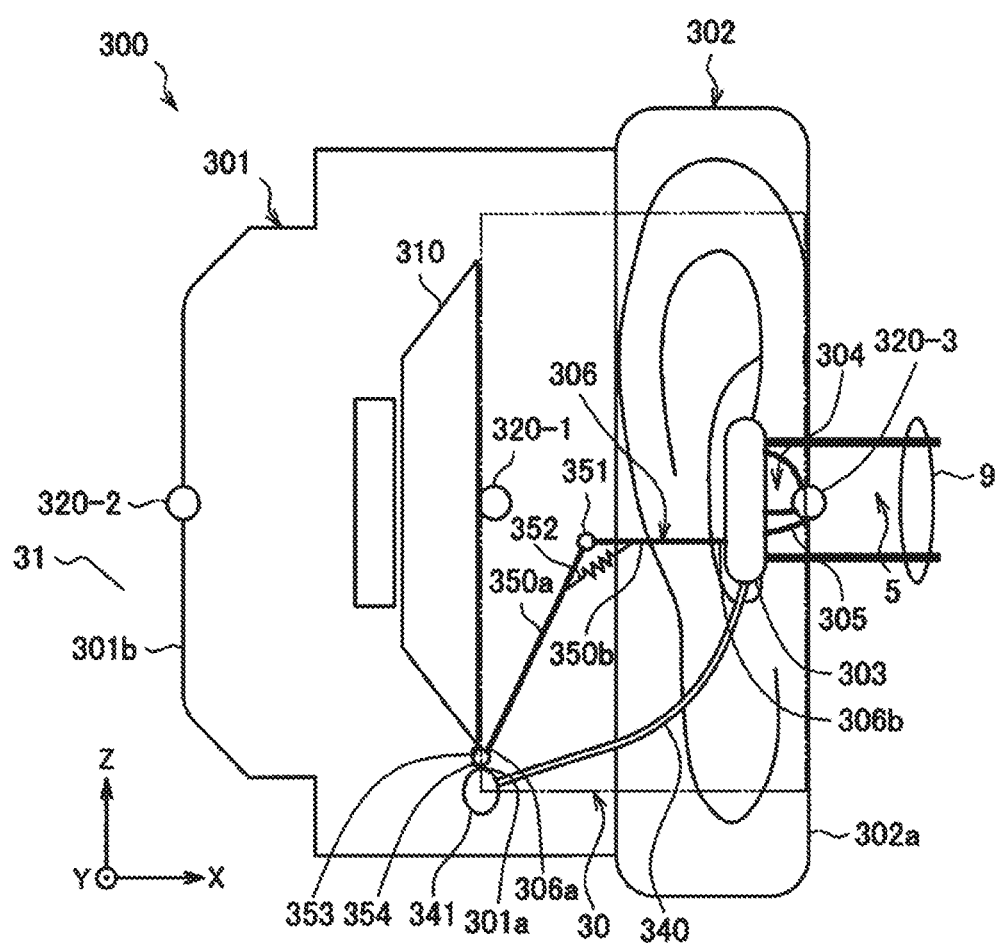
FIG. 60 is a diagram illustrating an example of a configuration of the headphones according to the embodiment.
Figure 61:
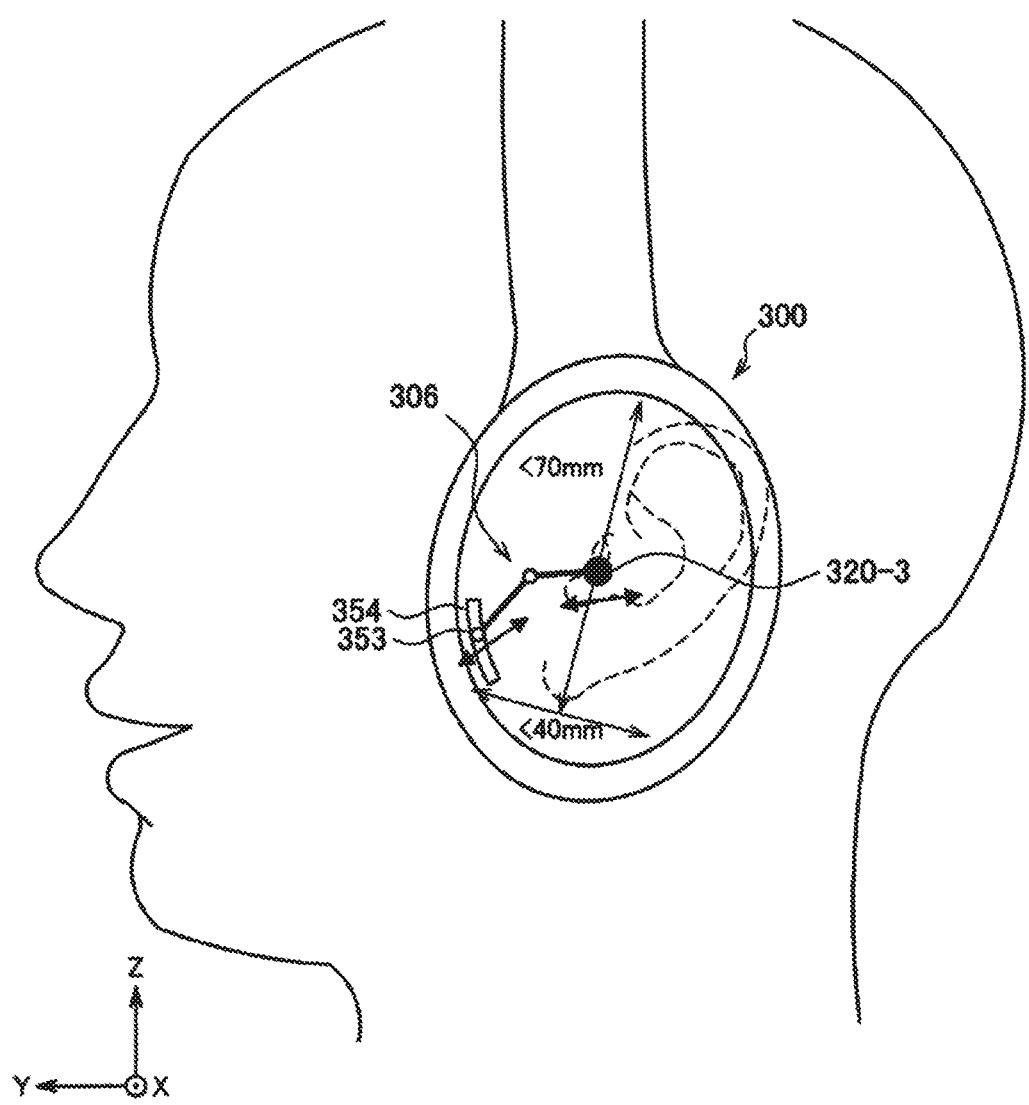
FIG. 61 is a view illustrating a configuration of the headphones illustrated in FIG. 60 as viewed from another viewpoint.

FIG. 60 is a diagram illustrating an example of the configuration of the headphones 300 according to the present embodiment. FIG. 61 is a view illustrating the configuration of the headphones 300 illustrated in FIG. 60 as viewed from another viewpoint. In the example illustrated in FIG. 60, the second support member 306 has a link structure. Specifically, the second support member 306 includes links 350a and 350b and a joint portion 351 that movably connects the links 350a and 350b. The link 350 may be formed using an elastic body or may be formed using an elastoplastic body or a plastic body such as plastic, metal, and wood. The second support member 306 may have one degree of freedom or a plurality of degrees of freedom. For example, the second support member 306 may have three or more links 350. In addition, the joint portion 351 may be a pin that connects the respective links 350 so as to be rotatable with one degree of freedom, or may be a ball and a socket that connects the respective links 350 with two or more degrees of freedom. Since the second support member 306 having the link structure with the high degree of freedom is used, the holding unit 303 can be fitted to users having various ear shapes.

In addition, each of the links 350a and 350b is connected by a restraining member 352, and a movable range is restrained within a predetermined range when referring to FIG. 60. For example, the restraining member 352 is formed using an elastic body such as rubber and a spring. The restraining member 352 can restrain a direction in which the holding unit 303 and the ear canal microphone 320-3 face to a predetermined range by restraining the movable range of the link 350 to the predetermined range. For example, the restraining member 352 can restrain the direction in which the holding unit 303 and the ear canal microphone 320-3 face to a direction of the user's ear.

In addition, the second support member 306 may have a slide mechanism. When referring to FIG. 61, the one end 306a of the second support member 306 is connected to a sliding member 353 that slides on the wall portion 301a of the housing 301. The sliding member 353 is engaged with a rail 354 provided on the wall portion 301a of the inner space 30 and slides. The rail 354 is a groove-shaped structure, for example, and is formed so as to partially surround the driver 310. Since the second support member 306 has the slide mechanism, the movable range of the holding unit 303 and the ear canal microphone 320-3 are widened, and thus, the holding unit 303 can be fitted to users having various ear shapes.

Note that the movable range of the holding unit 303 and the ear canal microphone 320-3 is desirably limited within 40 mm or less in the longitudinal direction of the user's head (substantially the Y-axis direction) and within 70 mm or less in the vertical direction of the user's head (substantially the Z-axis direction) inside a plane parallel to the contact surface 302a as illustrated in FIG. 61. This restriction is realized by, for example, the length of the link 350, the movable range of the joint portion 351, the arrangement of the rail 354, and the like. Due to the limitation of the movable range, the movable range of the holding unit 303 and the ear canal microphone 320-3 can be limited to a range that enables fitting to the user's ear.

Figure 62:
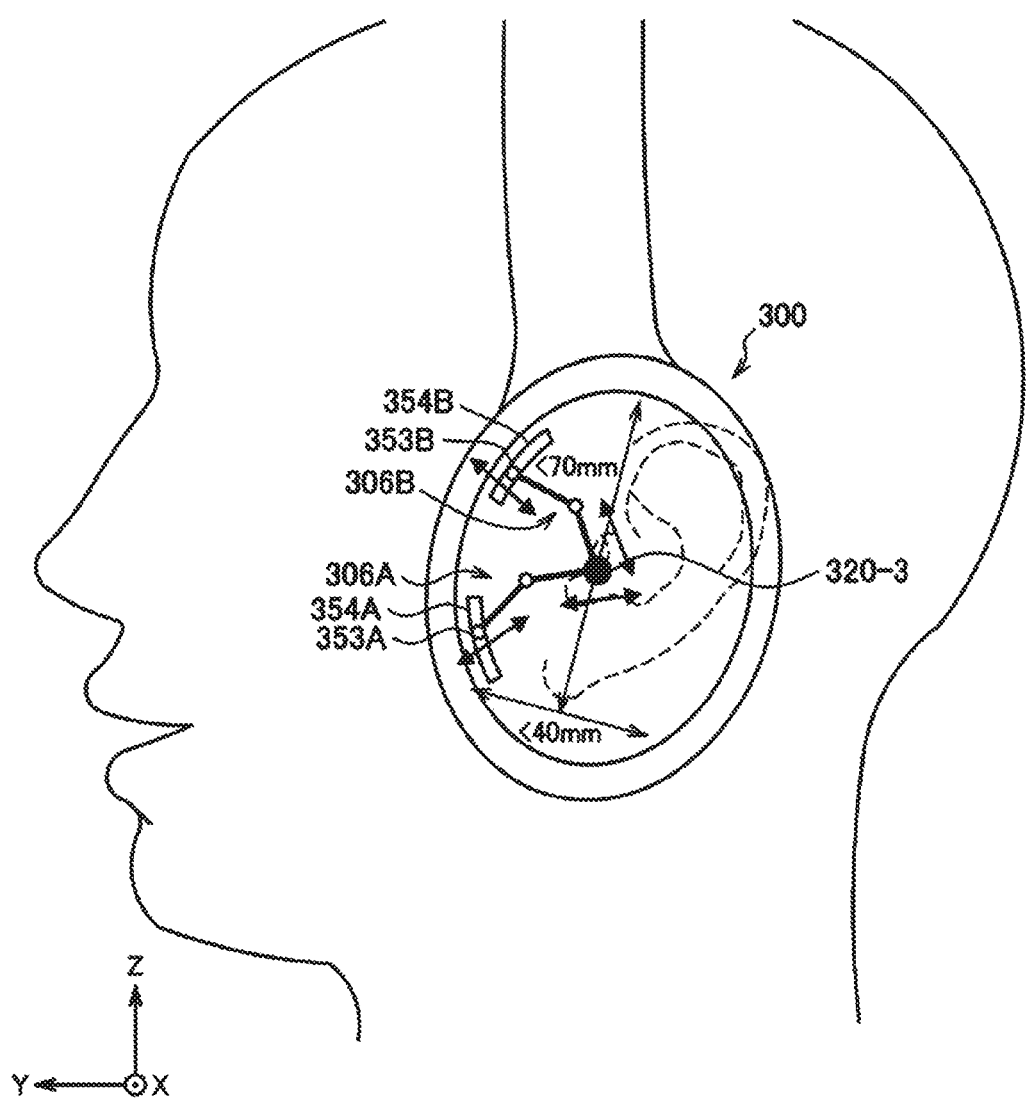
FIG. 62 is a view illustrating an example of a configuration of the headphones according to the embodiment.
Figure 63:
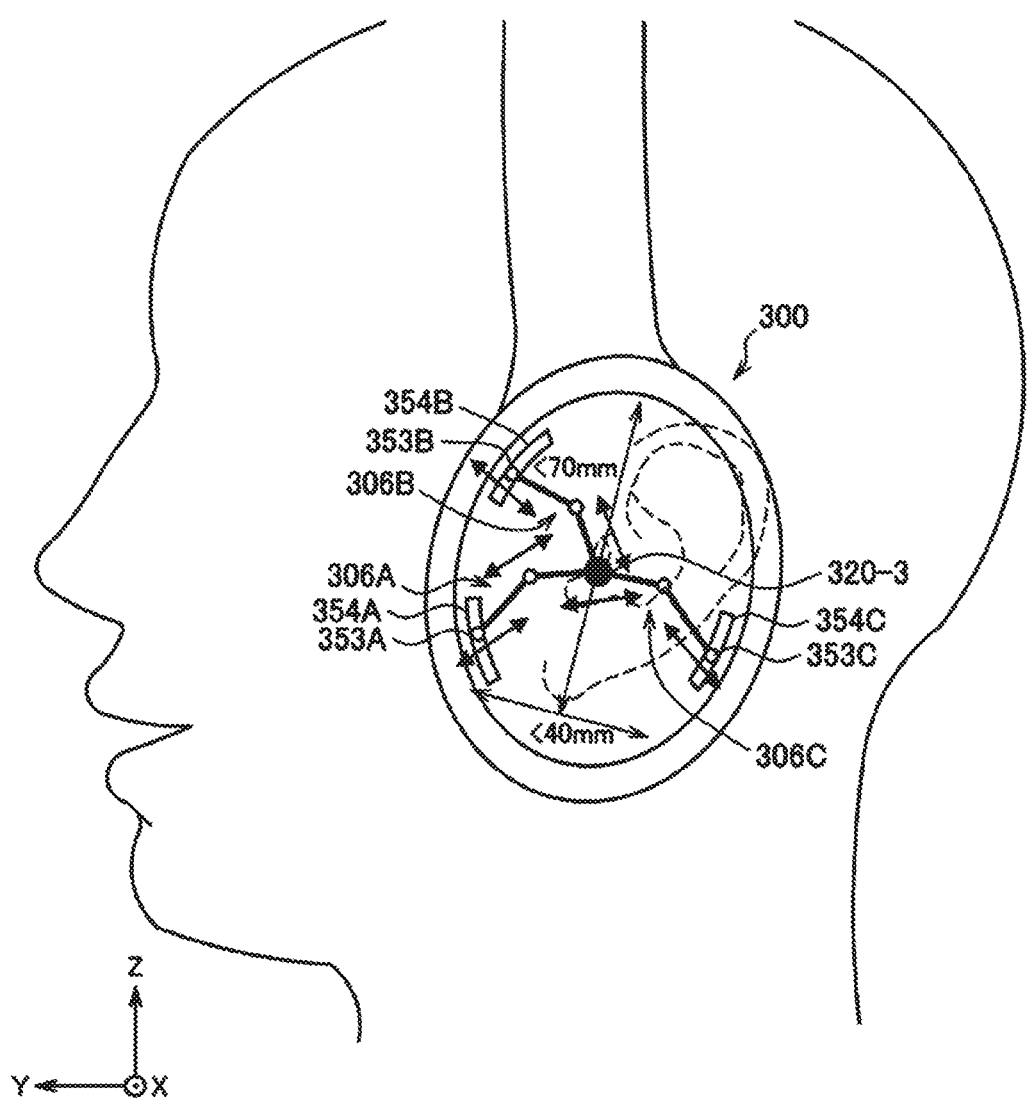
FIG. 63 is a view illustrating an example of a configuration of the headphones according to the embodiment.

FIGS. 62 and 63 are views illustrating examples of the configuration of the headphones 300 according to the present embodiment. In the example illustrated in FIG. 62, the headphones 300 include second support members 306A and 306B having a link structure. In the example illustrated in FIG. 63, the headphones 300 include second support members 306A, 306B, and 306C having a link structure. The second support member 306A is connected to a sliding member 353A that slides on a rail 354A. The second support member 306B is connected to a sliding member 353B that slides on a rail 354B. The second support member 306C is connected to a sliding member 353C that slides on a rail 354C. As described above, the headphones 300 may include the plurality of second support members 306 having the link structure. With this configuration, a relative positional relationship between the ear canal microphone 320-3 and the driver 310 is hardly changed every time the headphones 300 are worn. Since the relative positional relationship is constant, it is unnecessary to update a noise canceling filter every time the headphones 300 are worn, or the update amount can be suppressed. In addition, this configuration makes it difficult for the ear canal microphone 320-3 to be displaced from the ear hole during wearing of the headphones 300. As a result, the effect of the noise cancellation process during wearing of the headphones 300 can be stabilized.

Figure 64:
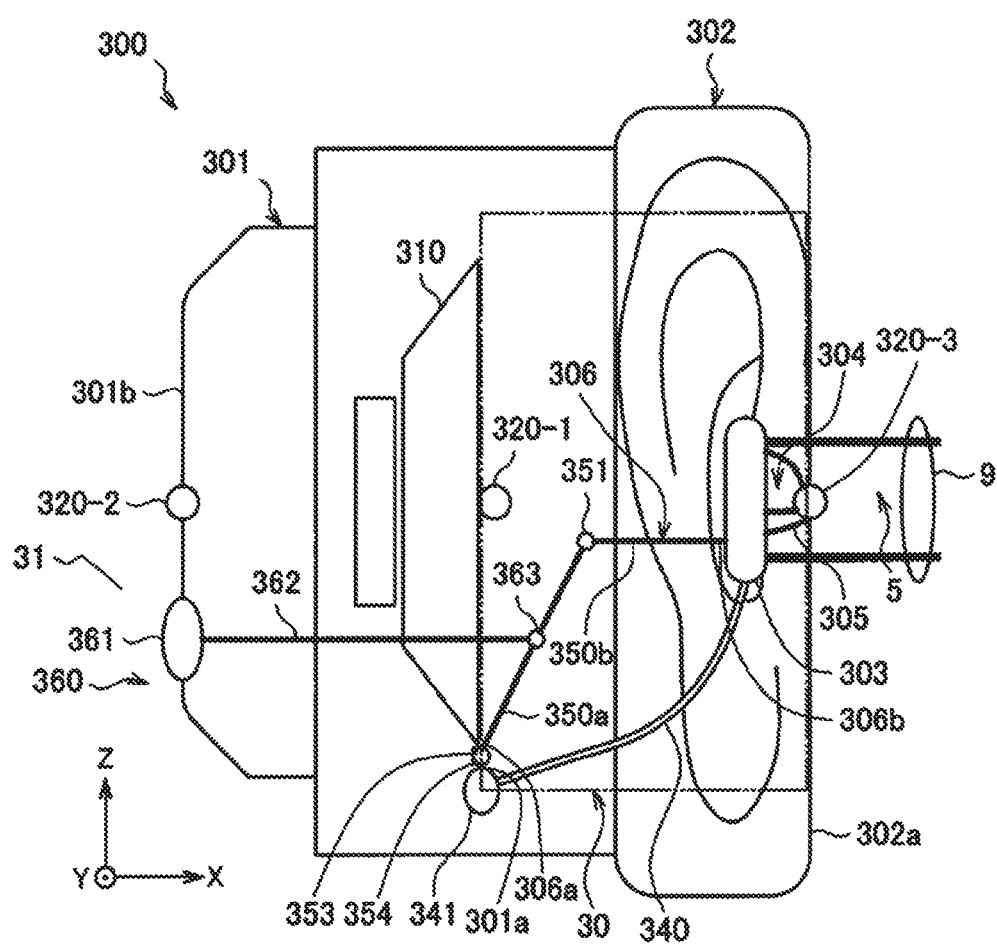
FIG. 64 is a diagram illustrating an example of a configuration of the headphones according to the embodiment.

FIG. 64 is a diagram illustrating an example of the configuration of the headphones 300 according to the present embodiment. In the example illustrated in FIG. 64, the headphones 300 include an attitude control device 360 that controls an attitude of the second support member 306. The attitude control device 360 includes an operating body 361, a link 362, and a joint portion 363. The link 362 is arranged through a through-hole that penetrates the housing 301 from the inner space 30 to the outer space 31. One end of the link 362 protruding into the inner space 30 is movably connected to the second support member 306 by the joint portion 363. The other end of the link 362 on the outer space 31 side is connected to the operating body 361. The operating body 361 is at least partially exposed to the outer space 31 and is movably arranged. When the operating body 361 is moved, the movement is transmitted to the second support member 306 via the link 362 and the joint portion 363. The user can move or deform the attitude of the second support member 306 by pinching the operating body 361 and moving the operating body 361 in three axial direction. Accordingly, the user can move the second support member 306 while wearing the headphones 300, that is, without putting the hand into the inner space 30. In addition, even if the holding unit 303, the ear canal microphone 320-3, or the second support member 306 is caught on the ear at the time of wearing or removing the headphones 300, the user can easily resolve the catching by operating the attitude control device 360. Accordingly, the member caught by the user can be prevented from being damaged or the user can be prevented from being injured. The attitude control device 360 may include power such as a motor, and may control the attitude of the second support member 306 using such power. For example, the attitude control device 360 automatically controls the attitude of the second support member 306 when detecting wearing or removal of the headphones 300.

<2.6. Control in Response to Wearing/Non-Wearing of Headphones 300>

The operation control unit 333 determines wearing/non-wearing of the headphones 300.

For example, in the example illustrated in FIG. 49, the operation control unit 333 determines the wearing/non-wearing of the headphones 300 based on whether the holding unit 303 and the ear canal microphone 320-3 are accommodated in the recess 342. For example, the operation control unit 333 determines that the headphones 300 are worn when the holding unit 303 and the ear canal microphone 320-3 are not accommodated in the recess 342. In addition, the operation control unit 333 determines that the headphones 300 are not worn when the holding unit 303 and the ear canal microphone 320-3 are accommodated in the recess 342. Note that a sensor or a switch that detects whether the holding unit 303 and the ear canal microphone 320-3 are accommodated in the recess 342 may be provided in the recess 342 or the winding unit 341.

In addition, the operation control unit 333 may determine the wearing/non-wearing of the headphones 300 based on whether the deformation of the second support member 306 has been detected in the example illustrated in FIG. 50. In addition, the operation control unit 333 may determine the wearing/non-wearing of the headphones 300 based on whether there has been user's operation input to the attitude control device 360, whether the deformation of the ear pad 302 has been detected, and the like in the example illustrated in FIG. 64.

Then, the operation control unit 333 controls the operation of the headphones 300 based on the result of the determination on the wearing/non-wearing of the headphones 300. For example, the operation control unit 333 may cause the signal processing unit 331 to start generating a noise cancellation signal when determining that the headphones 300 are worn. In addition, the operation control unit 333 may cause the driver 310 to start outputting an output signal when determining that the headphones 300 are worn. As a result, the operation of the ear hole opening device 100 is automatically started when the user wears the headphones 300, and thus, an operation burden on the user is reduced. In addition, when determining that the headphones 300 are not worn, the operation control unit 333 may stop the generation of the noise cancellation signal and the output of the output signal. As a result, the operation of the headphones 300 is automatically stopped or partly stopped in the non-wearing state, and thus, wasteful power consumption can be prevented.

<2.7. Summary>

The second embodiment has been described in detail above. As described above, the headphones 300 according to the second embodiment include the FB-NC microphone 320-1, the FF-NC microphone 320-2, and the ear canal microphone 320-3, and perform the noise cancellation process based on the audio signals generated by these microphones. When the ear canal microphone 320-3 is used as the error microphone of FB-NC, the cancellation point of FB-NC is close to the eardrum 9, and thus, the high noise canceling effect is expected. Further, when the FB-NC microphone 320-1 is used together as the error microphone of FB-NC, both the first and second guidelines can be satisfied. That is, it is possible to minimize the sound pressure at the cancellation point close to the eardrum position while suppressing the distance delay.

In addition, the ear canal microphone 320-3 may be used as the error microphone for adaptive processing in FF-NC or IMC-FB. In either case, the error microphone is arranged near the eardrum 9, and thus, the improvement of the noise canceling performance is expected.

In addition, the ear canal microphone 320-3 may be used in the measurement processing for calculation of the correction characteristic of the fixed filter. In this case, since individual differences caused by the physical characteristics of the users wearing the headphones 300 can be absorbed, the noise canceling performance can be improved as compared with the case where the noise cancellation process is performed using the fixed filter as it is.

<3. Third Embodiment>

A third embodiment is a mode of realizing the noise cancellation process described in the second embodiment by cooperation of a first audio processing device and a second audio processing device. For example, the first audio processing device may be an earphone such as the ear hole opening device 100 described in the first embodiment. In addition, the second audio processing device may be headphones 500 to be described below. Note that the two audio processing devices that cooperate with each other are not limited to the combination of the earphone and the headphones as long as devices can be worn in the state of partially or entirely overlapping each other.

<3.1. Basic Configuration of Ear Hole Opening Device>

First, a basic configuration of the ear hole opening device 100 according to the present embodiment will be described with reference to FIGS. 65 and 66.

Figure 65:
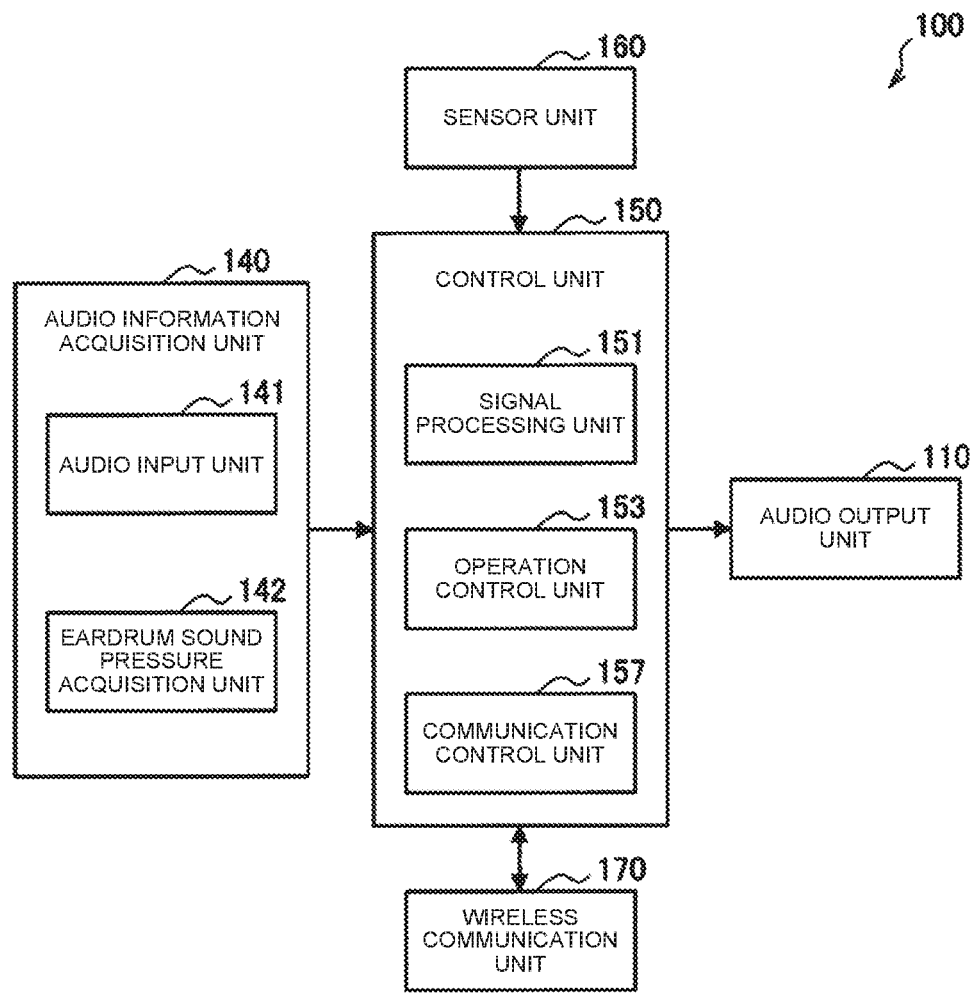
FIG. 65 is a diagram illustrating an example of an internal configuration of an ear hole opening device according to a third embodiment.

FIG. 65 is a diagram illustrating an example of an internal configuration of the ear hole opening device 100 according to the present embodiment. As illustrated in FIG. 65, the ear hole opening device 100 includes the driver 110, the audio information acquisition unit 140, the control unit 150, a sensor unit 160, and the wireless communication unit 170.

The configuration of the driver 110 is the same as described above in the first embodiment.

The configuration of the audio information acquisition unit 140 is the same as described above in the first embodiment.

The control unit 150 includes the signal processing unit 151 and the operation control unit 153 described above in the first embodiment, and includes a communication control unit 157 instead of the authentication unit 155. The configurations of the signal processing unit 151 and the operation control unit 153 are the same as described above in the first embodiment. The communication control unit 157 has a function of controlling wireless communication processing performed by the wireless communication unit 170. Specifically, the communication control unit 157 controls communication partner selection and communication data transmission/reception processing. The control unit 150 according to the present embodiment may include the authentication unit 155.

The sensor unit 160 is a device that detects information on the ear hole opening device 100, information on a user wearing the ear hole opening device 100, or information on the headphones 500 that are worn to overlap the ear hole opening device 100. The sensor unit 160 can include various sensor devices such as a pressure-sensitive sensor, a gyro sensor, an acceleration sensor, and a body temperature sensor. In addition, the sensor unit 160 may include a magnetic sensor. In addition, the sensor unit 160 may include an RFID device such as a radio frequency identifier (RFID) tag and a reader.

The wireless communication unit 170 is an interface for wireless communication between the ear hole opening device 100 and the headphones 500. The wireless communication unit 170 can perform wireless communication by an arbitrary scheme. For example, the wireless communication unit 170 may perform wireless communication by optical communication. The optical communication can realize an ultra-low delay. In addition, the wireless communication unit 170 may perform wireless communication using an analog method similar to radio broadcasting such as frequency modulation (FM) and amplitude modulation (AM). These analog methods can also realize a low delay. In addition, the wireless communication unit 170 may perform wireless communication conforming to Wi-Fi (registered trademark), Bluetooth (registered trademark), or a so-called 2.4 GHz band wireless communication standard such as BLE (Bluetooth Low Energy (registered trademark)). In addition, the wireless communication unit 170 may perform wireless communication by a method using magnetic resonance, such as near field magnetic induction (NFMI). Of course, a communication scheme, a band, and a modulation scheme are not limited to the above examples.

The internal configuration of the ear hole opening device 100 has been described above. Next, an exterior configuration and basic internal processing of the ear hole opening device 100 will be described with reference to FIG. 66.

Figure 66:
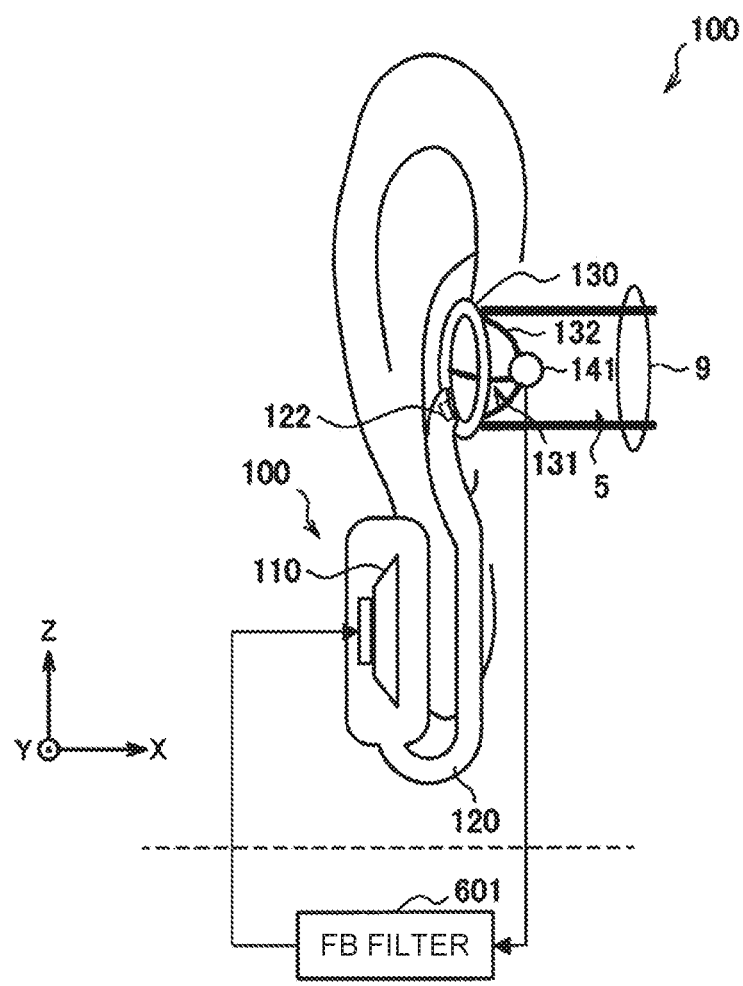
FIG. 66 is a diagram for describing an outline of the ear hole opening device according to the embodiment.

FIG. 66 is a diagram for describing an outline of the ear hole opening device 100 according to the present embodiment. The drawing in the upper part of FIG. 66 illustrates the exterior configuration of the ear hole opening device 100. As illustrated in the upper part of FIG. 66, the ear hole opening device 100 has the exterior configuration which is the same as described above in the first embodiment. The present embodiment will be described on the assumption that the microphone 141 is used as the audio information acquisition unit 140, but the eardrum sound pressure acquisition unit 142 may be used as the audio information acquisition unit 140.

The lower part of FIG. 66 illustrates the outline of the internal processing when the ear hole opening device 100 operates alone. An audio signal generated by the microphone 141 is input to a FB filter 601. The FB filter 601 performs a noise cancellation process of a FB scheme based on the input audio signal to generate a noise cancellation signal, and outputs the noise cancellation signal to the driver 110. The driver 110 outputs audio based on the input noise cancellation signal. In this manner, the noise cancellation process of the FB scheme using the microphone 141 as a cancellation point is performed.

Detailed signal processing is the same as described above with reference to FIG. 8. The FB filter 601 corresponds to the first FB filter 201. Specifically, the FB filter 601 performs the noise cancellation process of the FB scheme using the microphone 141 as the cancellation point.

<3.2. Basic Configuration of Headphones 500>

Subsequently, a basic configuration of the headphones 500 according to the present embodiment will be described with reference to FIGS. 67 and 68.

Figure 67:
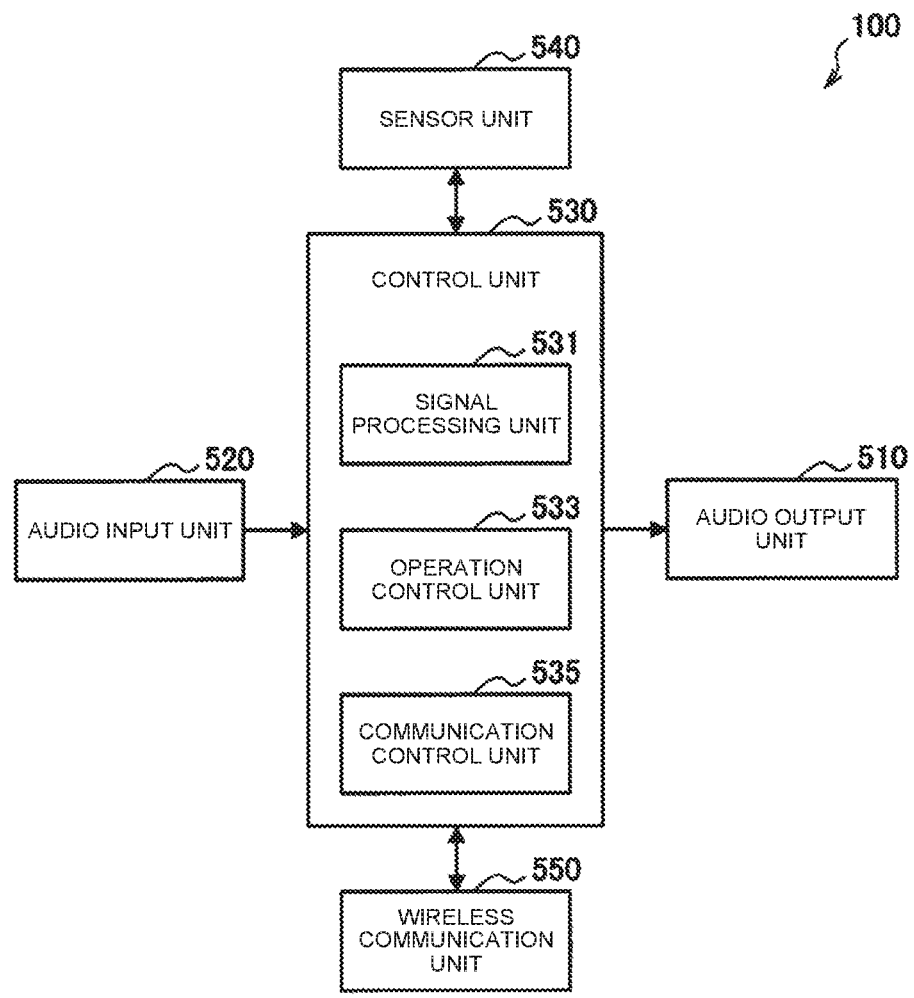
FIG. 67 is a diagram illustrating an example of the internal configuration of headphones according to the embodiment.

FIG. 67 is a diagram illustrating an example of an internal configuration of the headphones 500 according to the present embodiment. As illustrated in FIG. 67, the headphones 500 include an audio output unit 510, an audio input unit 520, a control unit 530, a sensor unit 540, and a wireless communication unit 550.

Audio Output Unit 510

The audio output unit 510 (driver) has a function of outputting audio based on an audio signal. For example, the driver 510 outputs audio to a space based on an output signal output from a signal processing unit 531.

Audio Input Unit 520

The audio input unit 520 includes a microphone (hereinafter also simply referred to as a microphone) that detects ambient sounds and generates an audio signal indicating the detection result by the microphone.

Control Unit 530

The control unit 530 functions as an arithmetic processing device and a control device, and controls the entire processing performed by the headphones 500 according to various programs. The control unit 530 is realized by an electronic circuit, for example, a central processing unit (CPU), a micro-processing unit (MPU), a demand-side platform (DSP), or the like. Note that the control unit 530 may include a read-only memory (ROM) that stores programs to be used, calculation parameters, and the like, and a random-access memory (RAM) that temporarily stores parameters that change as appropriate. Typically, the control unit 530 is stored in the housing.

As illustrated in FIG. 67, the control unit 530 includes the signal processing unit 531, an operation control unit 533, and a communication control unit 535.

The signal processing unit 531 has a function of generating a noise cancellation signal for noise based on the audio signal generated by the audio input unit 520 and the audio signal received from the ear hole opening device 100 by the wireless communication unit 550. The signal processing unit 531 can generate a plurality of noise cancellation signals. For example, the signal processing unit 531 performs at least one of the noise cancellation process of the FB scheme and the noise cancellation process of the FF scheme to generate the plurality of noise cancellation signals. The signal processing unit 531 generates an audio signal (hereinafter also referred to as an output signal) based on the plurality of generated noise cancellation signals, and outputs the audio signal to the driver 510. For example, the output signal may be a signal obtained by synthesizing the plurality of noise cancellation signals, or may be a synthesized signal obtained by synthesizing another audio signal such as a music signal acquired from a sound source and the noise cancellation signal. The signal processing unit 531 includes various constituent elements for noise cancellation processes which will be described with reference to FIGS. 68 to 74 and the like. For example, the signal processing unit 531 includes: various filter circuits configured to generate a noise cancellation signal; an adaptive control unit configured to adaptively control the filter circuits; an adder configured to synthesize signals; and the like. In addition, the signal processing unit 531 also includes circuits such as an amplifier, an ADC, and a DAC.

The operation control unit 533 has a function of controlling an operation mode of the headphones 500. The operation control unit 533 stops or activates some or all of functions of the headphones 500. For example, the operation control unit 533 controls the stop/activation of the function of the headphones 500 based on a detection result obtained by the sensor unit 540.

Sensor Unit 540

The sensor unit 540 is a device that detects information on the headphones 500, information on a user wearing the headphones 500, or information on the ear hole opening device 100 that is worn to overlap the headphones 500. The sensor unit 540 can include various sensor devices such as a pressure-sensitive sensor, a gyro sensor, an acceleration sensor, and a body temperature sensor. In addition, the sensor unit 540 may include a magnetic sensor or an RFID device such as a radio frequency identifier (RFID) tag and a reader.

Wireless Communication Unit 550

The wireless communication unit 550 is an interface for wireless communication between the headphones 500 and the ear hole opening device 100. The wireless communication unit 550 can perform wireless communication by an arbitrary scheme. For example, the wireless communication unit 550 may perform wireless communication by optical communication. The optical communication can realize an ultra-low delay. In addition, the wireless communication unit 550 may perform wireless communication using an analog method similar to radio broadcasting such as frequency modulation (FM) and amplitude modulation (AM). These analog methods can also realize a low delay. In addition, the wireless communication unit 550 may perform wireless communication conforming to Wi-Fi (registered trademark), Bluetooth (registered trademark), or a so-called 2.4 GHz band wireless communication standard such as BLE (Bluetooth Low Energy (registered trademark)). In addition, the wireless communication unit 550 may perform wireless communication by a method using magnetic resonance, such as near field magnetic induction (NFMI). Of course, a communication scheme, a band, and a modulation scheme are not limited to the above examples.

The internal configuration of the headphones 500 has been described above. Next, an exterior configuration and basic internal processing of the headphones 500 will be described with reference to FIG. 68.

Figure 68:
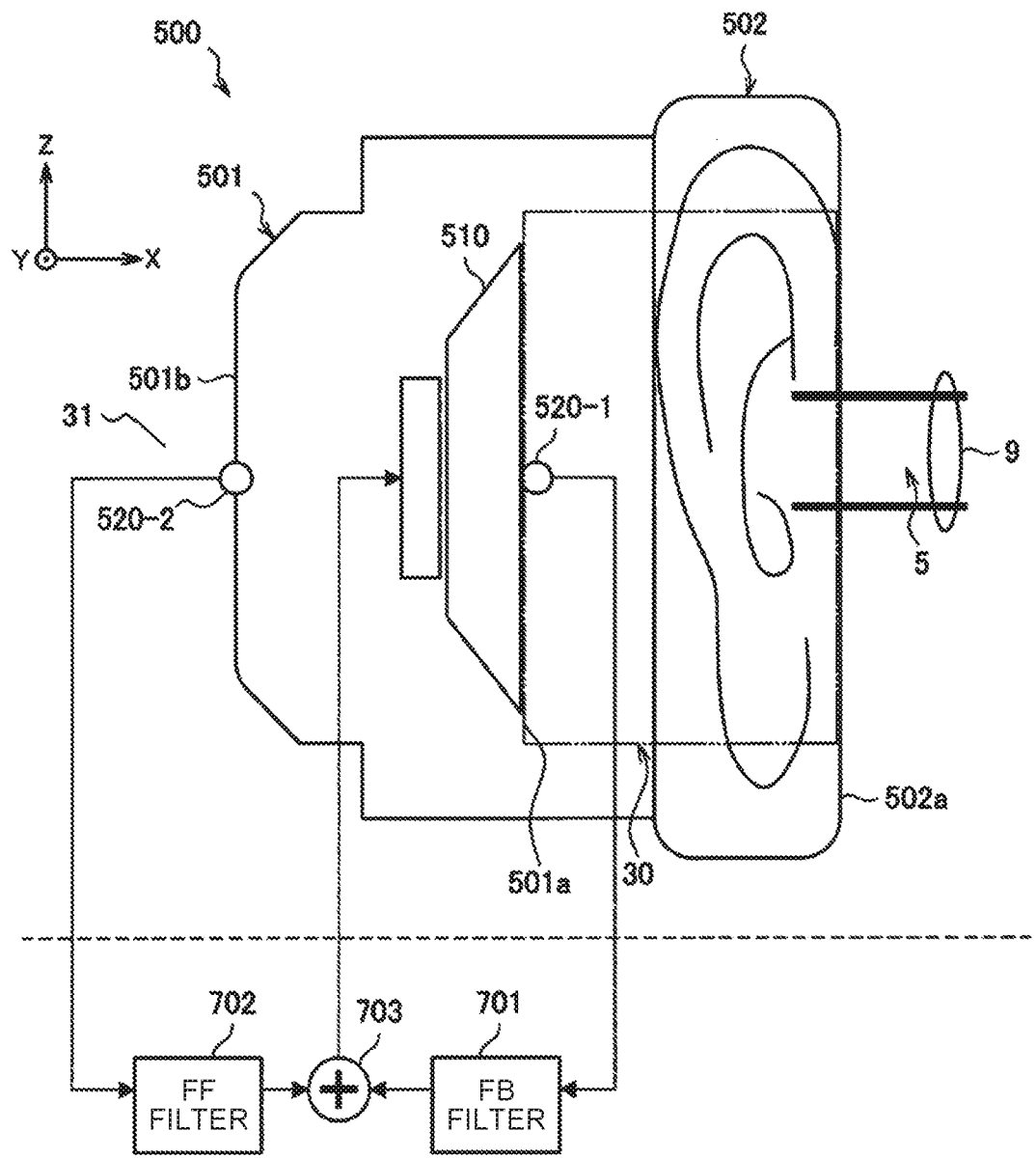
FIG. 68 is a diagram for describing the outline of the ear hole opening device according to the embodiment.

FIG. 68 is a diagram for describing an outline of the headphones 500 according to the present embodiment. The drawing in the upper part of FIG. 68 illustrates the exterior configuration of the headphones 500. As illustrated in the upper part of FIG. 68, the headphones 500 have a configuration in which the ear canal microphone 320-3 is removed from the headphones 300 described above in the second embodiment. This will be described in detail hereinafter.

As illustrated in the upper part of FIG. 68, the headphones 500 include a housing 501 and an ear pad 502. One ear of the user wearing the headphones 500 is covered (typically sealed) by the housing 501 and the ear pad 502. The housing 501 stores various devices configured for signal processing such as the driver 510, audio input units 520-1 and 520-2, and a filter circuit. The ear pad 502 comes into contact with user's head at a contact surface 502a. The ear pad 502 is formed using an elastic body such as sponge, and is in close contact with the user's head while being deformed in accordance with the user's head, and forms the inner space 30. The inner space 30 is a space formed by the housing 501, the ear pad 502, and the user's head. The inner space 30 may be a sealed space isolated from an outer space 31 that is a space on the outside or may be connected to the outer space 31. Noise after passive sound insulation by passive sound insulation elements, such as the housing 501, the ear pad 502, and the user's head, arrives at the inner space 30. A wall portion 501a of the housing 501 is in contact with the inner space 30, and an outer wall portion 501b of the housing 501 is in contact with the outer space 31.

The driver 510 outputs audio to a space based on the audio signal. The driver 510 is provided in the housing 501. Then, the driver 510 outputs audio toward the inner space 30 that is a space closer to the eardrum than the housing 501. For example, the driver 510 outputs audio to the space based on the noise cancellation signal. As a result, the noise that has arrived at the inner space 30 can be canceled.

The audio input units 520 (520-1 and 520-2) collect ambient sounds and generate audio signals. As illustrated in FIG. 68, the two audio input units 520 are arranged on one ear side of the user in the state of being worn by the user.

The audio input unit 520-1 is a microphone that performs sound collection for FB-NC (that is, the FB-NC microphone). The FB-NC microphone 520-1 is arranged at a position where a distance from the eardrum 9 of the user is shorter than the audio input unit 320-2 in a state where the headphones 500 are worn by the user. More specifically, the FB-NC microphone 520-1 is arranged at a position where noise is collected through shielding objects, that is, after being subjected to passive sound insulation in the state where the headphones 500 are worn by the user. Further, it is desirable that the FB-NC microphone 520-1 be arranged between the eardrum 9 of the user and the driver 510. The shielding objects herein are passive sound insulation elements and correspond to the housing 501, the ear pad 502, and the user's head. As illustrated in FIG. 68, the FB-NC microphone 520-1 is provided on the wall portion 501*a* of the housing 501 on the inner space 30 side. Then, the FB-NC microphone 520-1 collects audio of the inner space 30 and generates an audio signal. The audio collected at this time contains noise after passive sound insulation by the passive sound insulation elements. The FB-NC microphone 520-1 corresponds to a first audio input unit, and the audio signal generated by the FB-NC microphone 520-1 can also be referred to as a first audio signal. The audio signal generated by the FB-NC microphone 520-1 is input to the FB filter and used to generate the noise cancellation signal.

The audio input unit 520-2 is a microphone that performs sound collection for FF-NC (that is, the FF-NC microphone). In addition, the FF-NC microphone 520-2 is arranged at a position where the distance from the eardrum 9 of the user is longer than the FB-NC microphone 520-1 in the state where the headphones 500 are worn by the user. More specifically, the FF-NC microphone 520-2 is arranged at a position where noise is collected without passing through shielding objects, that is, without being subjected to passive sound insulation in the state where the headphones 500 are worn by the user. As illustrated in FIG. 68, the FF-NC microphone 520-2 is provided on the wall portion 501*b* of the housing 501 on the outer space 31 side. Then, the FF-NC microphone 520-2 collects audio of the outer space 31 and generates an audio signal. The audio collected at this time contains noise that has arrived at the outer space 31. The FF microphone 520-2 corresponds to a second audio input unit, and the audio signal generated by the FF microphone 520-2 can also be referred to as a second audio signal. Here, the FF-NC microphone 520-2 may be exposed to the outer space 31 or is not necessarily exposed. For example, the FF-NC microphone 520-2 may be embedded in the housing 501 and may collect a wrap-around sound or a sound transmitted through a cover such as a cloth. The audio signal generated by the FF-NC microphone 520-2 is input to the FF filter and used to generate the noise cancellation signal.

Note that FIG. 68 illustrate an exterior configuration on the right ear side of the headphones 500, an exterior configuration on the left ear side is bilaterally symmetric with the exterior configuration on the right ear side. The headphones 500 may be configured to be separated and independent from each other between the right ear side and the left ear side, or may be integrally configured. In addition, the headphones 500 can have an arbitrary structure such as an overhead type, a neckband type, and an ear hook type.

The exterior configuration of the headphones 500 has been described above. Subsequently, the internal processing when headphones 500 operate alone will be described with reference to FIG. 68.

The lower part of FIG. 68 illustrates an outline of internal processing when the headphones 500 operate alone. The audio signal generated by the FB-NC microphone 520-1 is input to a FB filter 701. The FB filter 701 performs a noise cancellation process of an FB scheme using the FB-NC microphone 520-1 as a cancellation point based on the input audio signal and generates a noise cancellation signal. The generated noise cancellation signal is input to an adder 703. On the other hand, an audio signal generated by the FF-NC microphone 520-2 is input to a FF filter 702. The FF filter 702 performs a noise cancellation process of a FF scheme based on the input audio signal and generates a noise cancellation signal. The generated noise cancellation signal is input to an adder 703. The adder 703 synthesizes the noise cancellation signals input from the FB filter 701 and the FF filter 702, and outputs the synthesized signal to the driver 110. The driver 110 outputs audio based on the input synthesized signal. In this manner, the combination-type noise cancellation process is performed.

Detailed signal processing is the same as described above with reference to FIG. 27. Specifically, the FB filter 701 corresponds to the FB filter 385, and the FF filter 702 corresponds to the FF filter 387.

<3.3. Details of Noise Cancellation Process>

The user can additionally wear the headphones 500 while wearing the ear hole opening device 100. In this case, a noise canceling effect can be improved as compared with a case where either one of the ear hole opening device 100 or the headphones 500 is used alone. Hereinafter, the noise cancellation process when the ear hole opening device 100 and the headphones 500 are used in combination will be described with reference to FIGS. 69 to 74.

(1) First Combination Example

A first combination example is an example in which the ear hole opening device 100 and the headphones 500 perform noise cancellation processes independently of each other. This example will be described with reference to FIG. 69.

Figure 69:
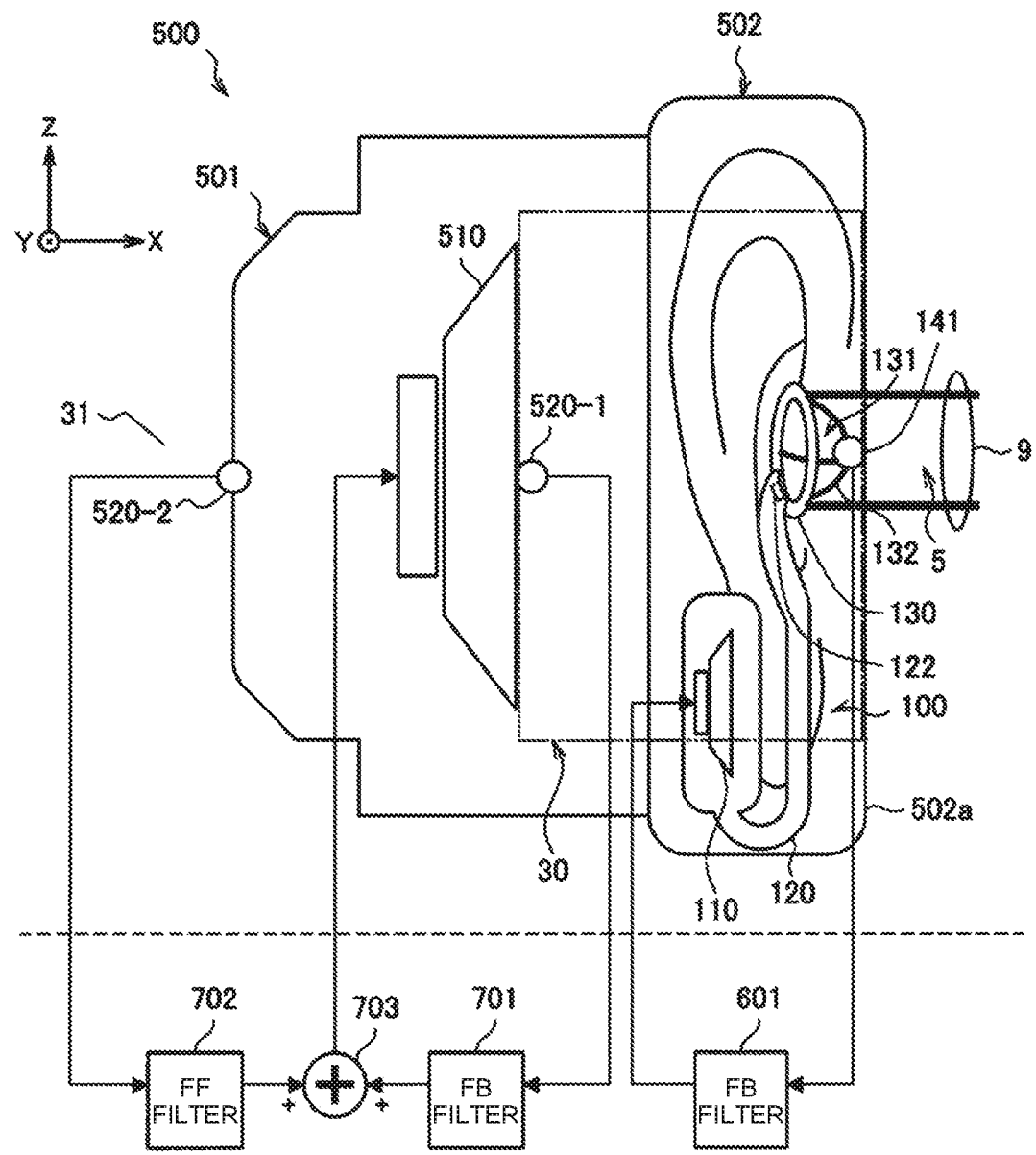
FIG. 69 is a diagram for describing a first combination example of the ear hole opening device and the headphones according to the embodiment.

FIG. 69 is a diagram for describing the first combination example of the ear hole opening device 100 and the headphones 500 according to the present embodiment. As illustrated in FIG. 69, the ear hole opening device 100 and the headphones 500 are worn in an overlapping manner. Specifically, the ear hole opening device 100 is worn to overlap the inner side (the user's ear side, that is, the X-axis positive direction) of the headphones 500 worn by the user. The headphones 500 are worn to overlap the outer side (the opposite side to the user's ear, that is, in the X-axis negative direction) of the ear hole opening device 100 worn by the user. The wearing of the headphones 500 and the ear hole opening device 100 in the overlapping manner indicates that at least the microphone 141 of the ear hole opening device 100 is included in the inner space 30 of the headphones 500. The inner space 30 of the headphones 500 may include the entire ear hole opening device 100 or only a part thereof.

Here, the ear hole opening device 100 and the headphones 500 do not communicate with each other in this example. That is, each of the noise cancellation processes described above with reference to FIGS. 66 and 68 is performed independently. In this case, noise that has not been canceled by the noise cancellation process described above with reference to FIG. 68 is canceled by the noise cancellation process described above with reference to FIG. 66. Therefore, the noise canceling effect can be improved as compared with a case where either one of the ear hole opening device 100 or the headphones 500 is used alone.

As described above, the noise canceling effect is improved even when the ear hole opening device 100 and the headphones 500 operate independently. However, the noise canceling effect can be further improved as the ear hole opening device 100 and the headphones 500 operate in cooperation. Hereinafter, a case where the ear hole opening device 100 and the headphones 500 operate in cooperation with each other will be described with reference to FIGS. 70 to 74.

(2) Second Combination Example

A second combination example is an example in which the headphones 500 perform the noise cancellation process of the FB scheme based on an audio signal received from the ear hole opening device 100. This example will be described with reference to FIG. 70.

Figure 70:
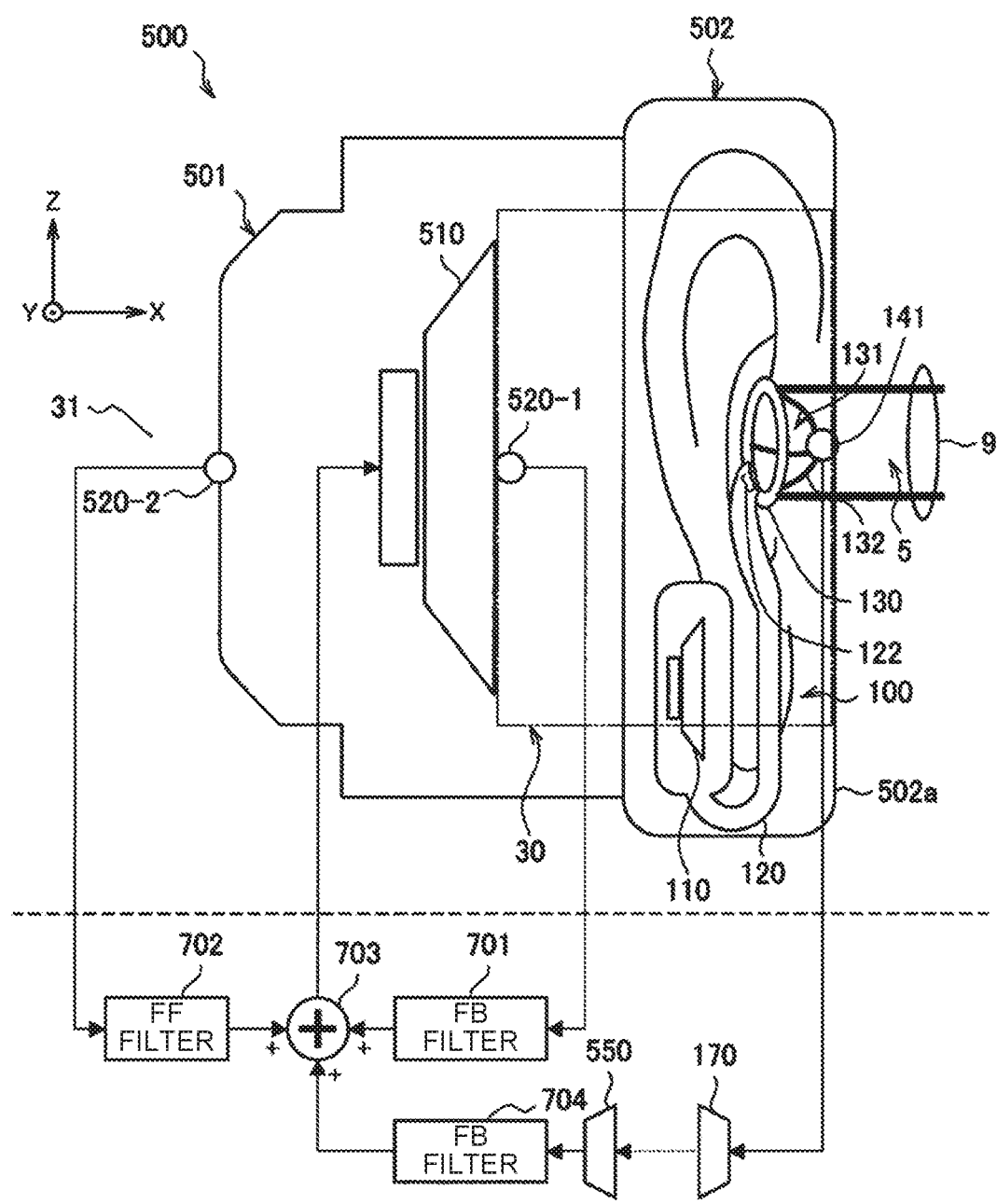
FIG. 70 is a diagram for describing a second combination example of the ear hole opening device and the headphones according to the embodiment.

FIG. 70 is a diagram for describing the second combination example of the ear hole opening device 100 and the headphones 500 according to the present embodiment. As illustrated in FIG. 70, the ear hole opening device 100 and the headphones 500 are worn in an overlapping manner. When worn in this manner, the wireless communication unit 170 of the ear hole opening device 100 and the wireless communication unit 550 of the headphones 500 perform wireless communication. Then, the ear hole opening device 100 and the headphones 500 cooperate to perform the noise cancellation process. Specifically, the audio signal generated by the microphone 141 is input to the wireless communication unit 170 as illustrated in FIG. 70. Then, the wireless communication unit 170 wirelessly transmits the audio signal generated by the microphone 141 to the headphones 500. The wireless communication unit 550 receives the audio signal wirelessly transmitted from the ear hole opening device 100. The wireless communication unit 550 outputs the received audio signal to a FB filter 704. The FB filter 704 performs the noise cancellation process of the FB scheme using the microphone 141 as a cancellation point based on the input audio signal, and generates a noise cancellation signal. The generated noise cancellation signal is input to an adder 703. The adder 703 synthesizes the noise cancellation signal input from the FB filter 704 in addition to the noise cancellation signals respectively input from the FB filter 701 and the FF filter 702, and outputs the synthesized signal to the driver 110. The driver 110 outputs audio based on the input synthesized signal.

Detailed signal processing is substantially the same as the first noise cancellation process described above with reference to FIG. 32. That is, the FF filter 702 corresponds to the FF filter 414, the FB filter 701 corresponds to the first FB filter 411, and the FB filter 704 corresponds to the second FB filter 412. However, this example is different from the first noise cancellation process described above with reference to FIG. 32 in terms that the internal models illustrated in the blocks 441, 442, 443, and 444 in FIG. 32 are not included.

Note that the noise cancellation process on the ear hole opening device 100 side is not illustrated in FIG. 70, but it is a matter of course that the noise cancellation process may also be performed on the ear hole opening device 100 side. For example, the ear hole opening device 100 generates a noise cancellation signal based on the audio signal generated by the microphone 141 and outputs the generated noise cancellation signal from the driver 110. The same applies to the subsequent combination examples.

In addition, the case where the ear hole opening device 100 transmits the audio signal generated by the microphone 141 to the headphones 500 has been described in the present embodiment, but the present technique is not limited to such an example. For example, another device may be interposed between the ear hole opening device 100 and the headphones 500. In addition, the headphones 500 may transmit the audio signal generated by the FB-NC microphone 520-1 and/or the FF-NC microphone 520-2 to the ear hole opening device 100. The same applies to the subsequent combination examples.

(3) Third Combination Example

A third combination example is an example in which the headphones 500 perform the noise cancellation process of the FB scheme in which an internal model is applied based on an audio signal received from the ear hole opening device 100. This example will be described with reference to FIG. 71.

Figure 71:
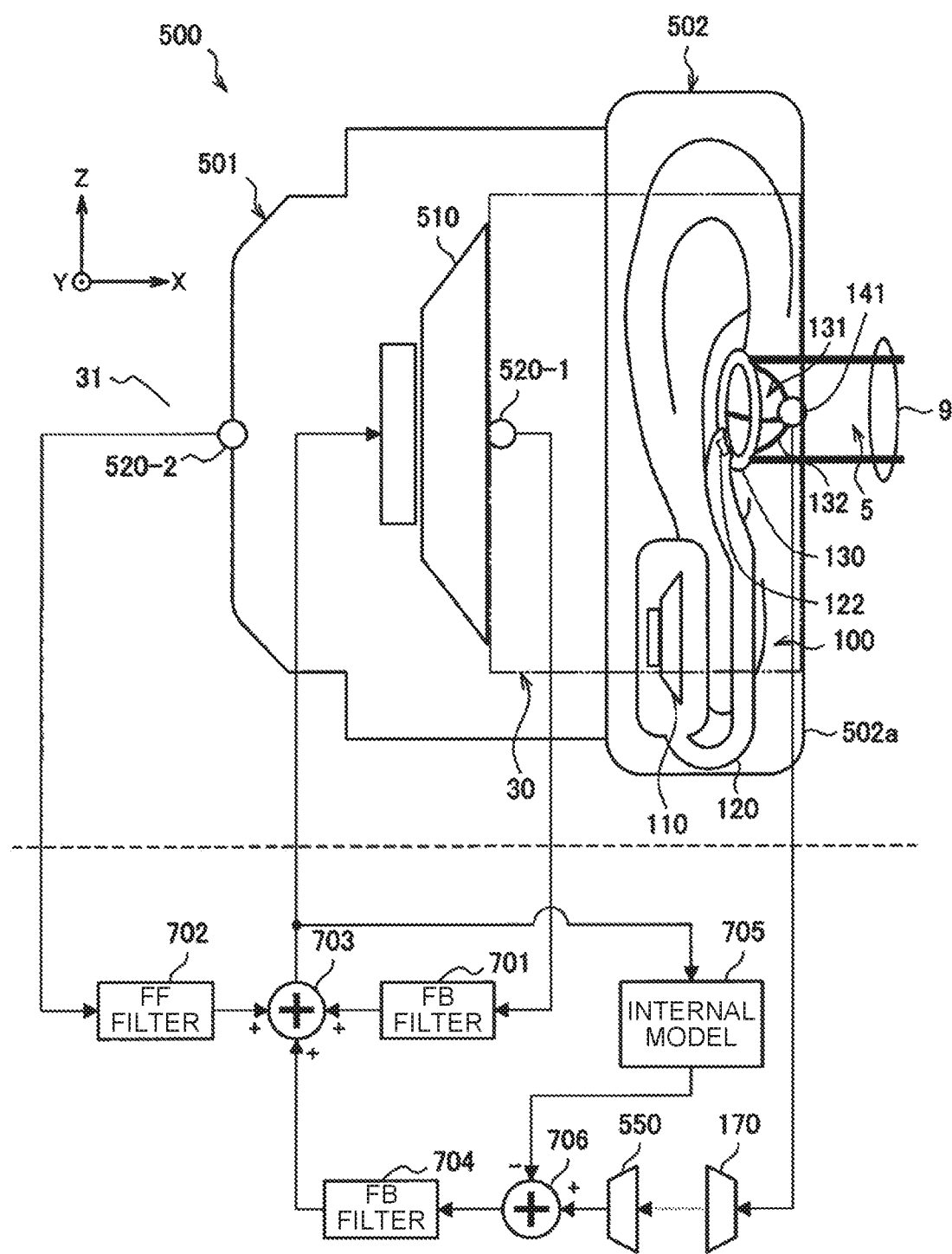
FIG. 71 is a diagram for describing a third combination example of the ear hole opening device and the headphones according to the embodiment.

FIG. 71 is a diagram for describing the third combination example of the ear hole opening device 100 and the headphones 500 according to the present embodiment. Processing blocks illustrated in FIG. 71 are obtained by adding an internal model 705 and an adder 706 to the processing blocks illustrated in FIG. 70. An output signal output from the adder 703 is input to the internal model 705. The internal model 705 has a characteristic that simulates the characteristic from the input of the output signal to the driver 510 to the generation of the audio signal by the microphone 141. The audio signal that has passed through the internal model 705 is input to the adder 706. The adder 706 subtracts the signal that has passed through the internal model 705 from the audio signal generated by the microphone 141 to perform synthesis. Then, the adder 706 outputs the synthesized signal to the FB filter 704.

Detailed signal processing is the same as the first noise cancellation process described above with reference to FIG. 32. That is, the FF filter 702 corresponds to the FF filter 414, the FB filter 701 corresponds to the first FB filter 411, and the FB filter 704 corresponds to the second FB filter 412. In addition, the internal model 705 corresponds to the blocks 441, 442, 443, and 444, and the adder 706 corresponds to the adder 432.

(4) Fourth Combination Example

A fourth combination example is an example in which the headphones 500 perform the noise cancellation process of the adaptive FF scheme based on an audio signal received from the ear hole opening device 100. This example will be described with reference to FIG. 72.

Figure 72:
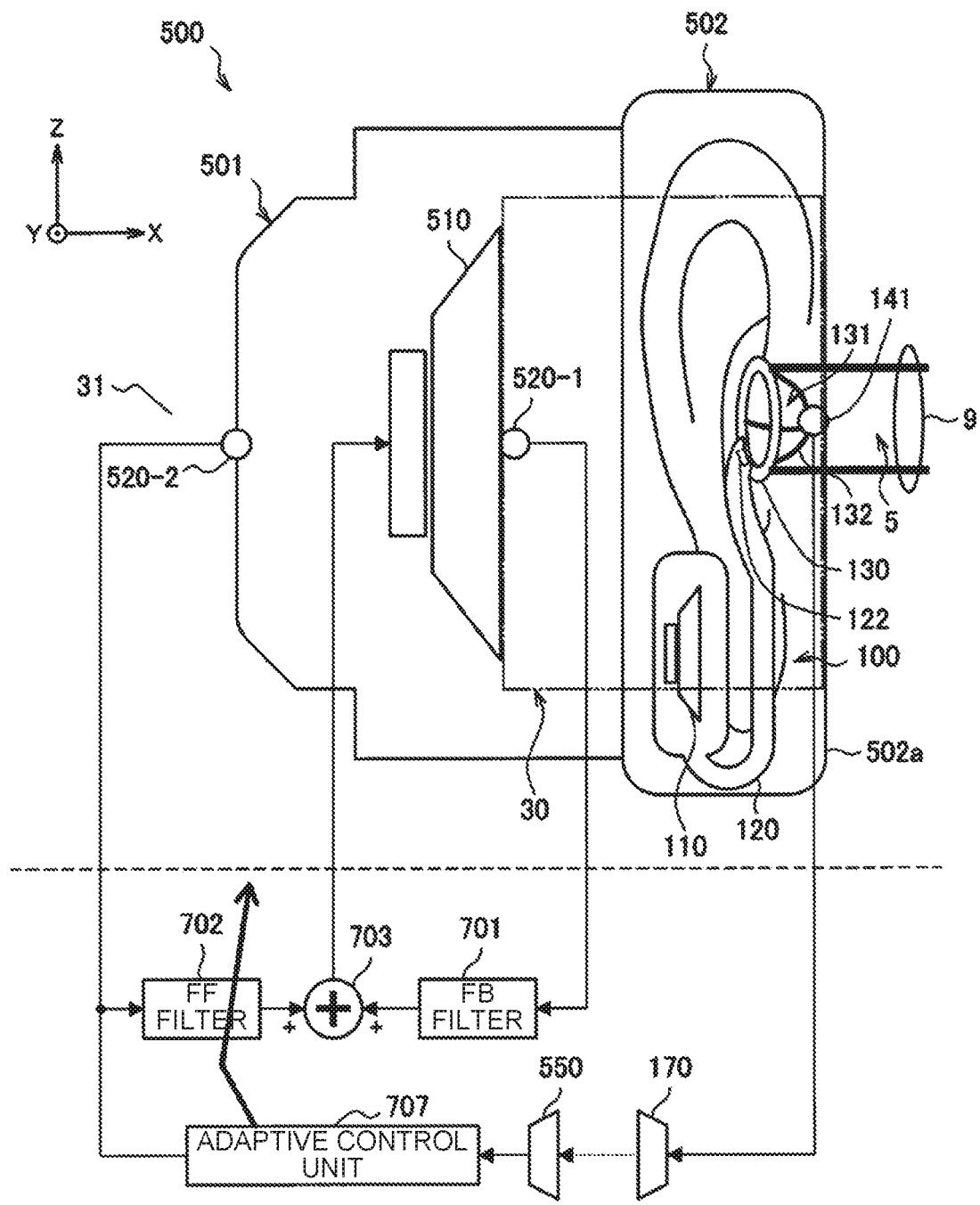
FIG. 72 is a diagram for describing a fourth combination example of the ear hole opening device and the headphones according to the embodiment.

FIG. 72 is a diagram for describing the fourth combination example of the ear hole opening device 100 and the headphones 500 according to the present embodiment. Processing blocks illustrated in FIG. 72 are obtained by adding an adaptive control unit 707 instead of the FB filter 704 in the processing blocks illustrated in FIG. 70. An audio signal generated based on audio collected by the FF-NC microphone 520-2 and the audio signal received by the wireless communication unit 550 are input to the adaptive control unit 707. The adaptive control unit 707 adaptively controls the characteristic of the FF filter 702 based on these audio signals. Under the adaptive control by the adaptive control unit 707, the FF filter 702 generates a noise cancellation signal by the noise cancellation process of the FF scheme based on the input audio signals. The noise cancellation signal generated by the FF filter 702 is synthesized with the noise cancellation signal generated by the FB filter 701 by the adder 703. The synthesized signal is output from the driver 510.

Detailed signal processing is the same as the second noise cancellation process described above with reference to FIG. 33. That is, the FF filter 702 corresponds to the FF filter 414, the FB filter 701 corresponds to the first FB filter 411, and the adaptive control unit 707 corresponds to the adaptive control unit 415.

(5) Fifth Combination Example

A fifth combination example is a combination of the third combination example and the fourth combination example. This example will be described with reference to FIG. 73.

Figure 73:
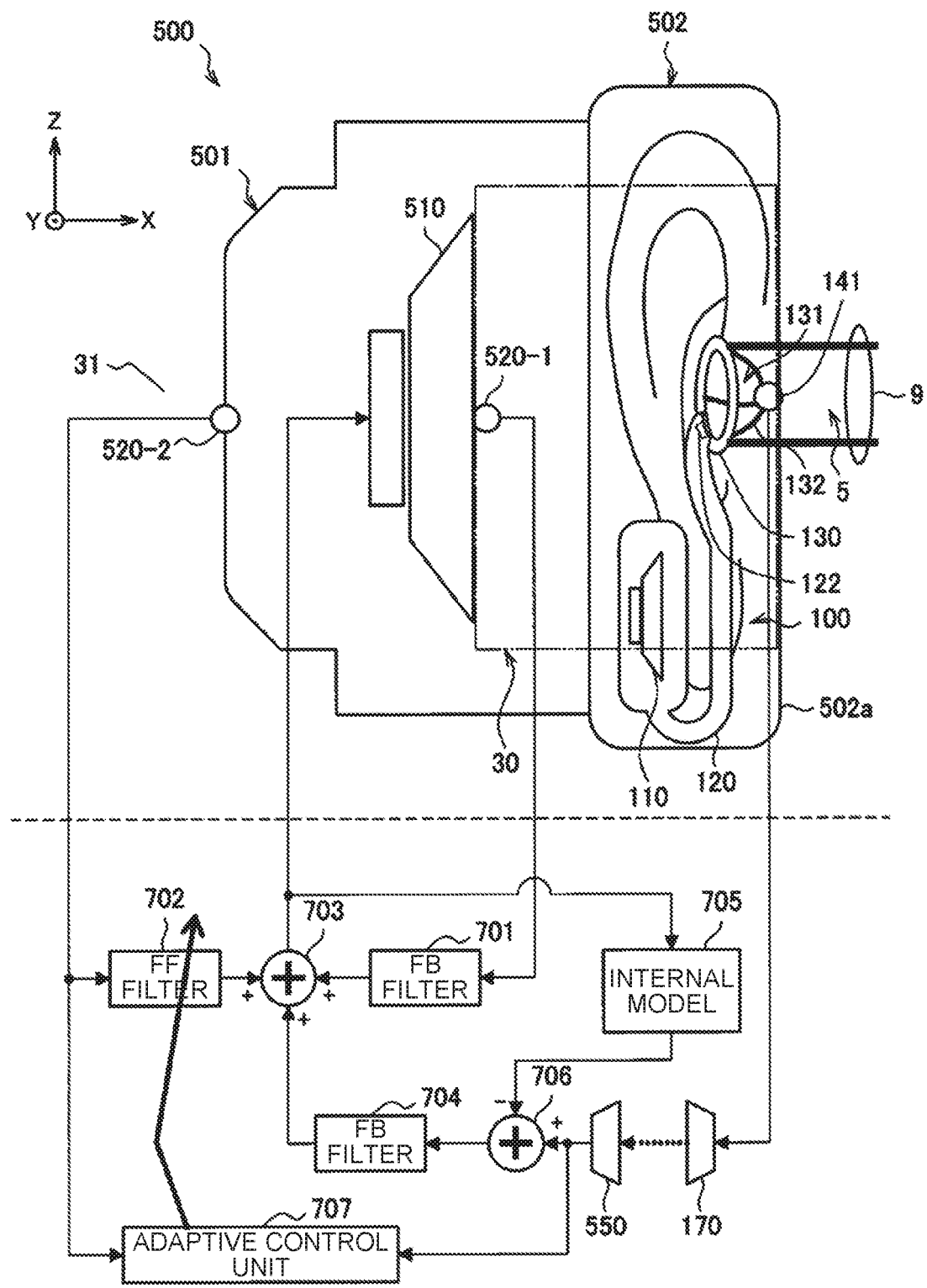
FIG. 73 is a diagram for describing a fifth combination example of the ear hole opening device and the headphones according to the embodiment.

FIG. 73 is a diagram for describing the fifth combination example of the ear hole opening device 100 and the headphones 500 according to the present embodiment. Processing blocks illustrated in FIG. 73 include the internal model 705 and the adder 706 illustrated in FIG. 71 and the adaptive control unit 707 illustrated in FIG. 72.

Detailed signal processing is the same as the third noise cancellation process described above with reference to FIG. 35. That is, the FF filter 702 corresponds to the FF filter 414, the FB filter 701 corresponds to the first FB filter 411, the FB filter 704 corresponds to the second FB filter 412, and the adaptive control unit 707 corresponds to the adaptive control unit 415. In addition, the internal model 705 corresponds to the blocks 441, 442, 443, and 444, and the adder 706 corresponds to the adder 432.

(6) Sixth Combination Example

A sixth combination example is an example in which a noise cancellation signal is output on the ear hole opening device 100 side in addition to the fifth combination example. This example will be described with reference to FIG. 74.

Figure 74:
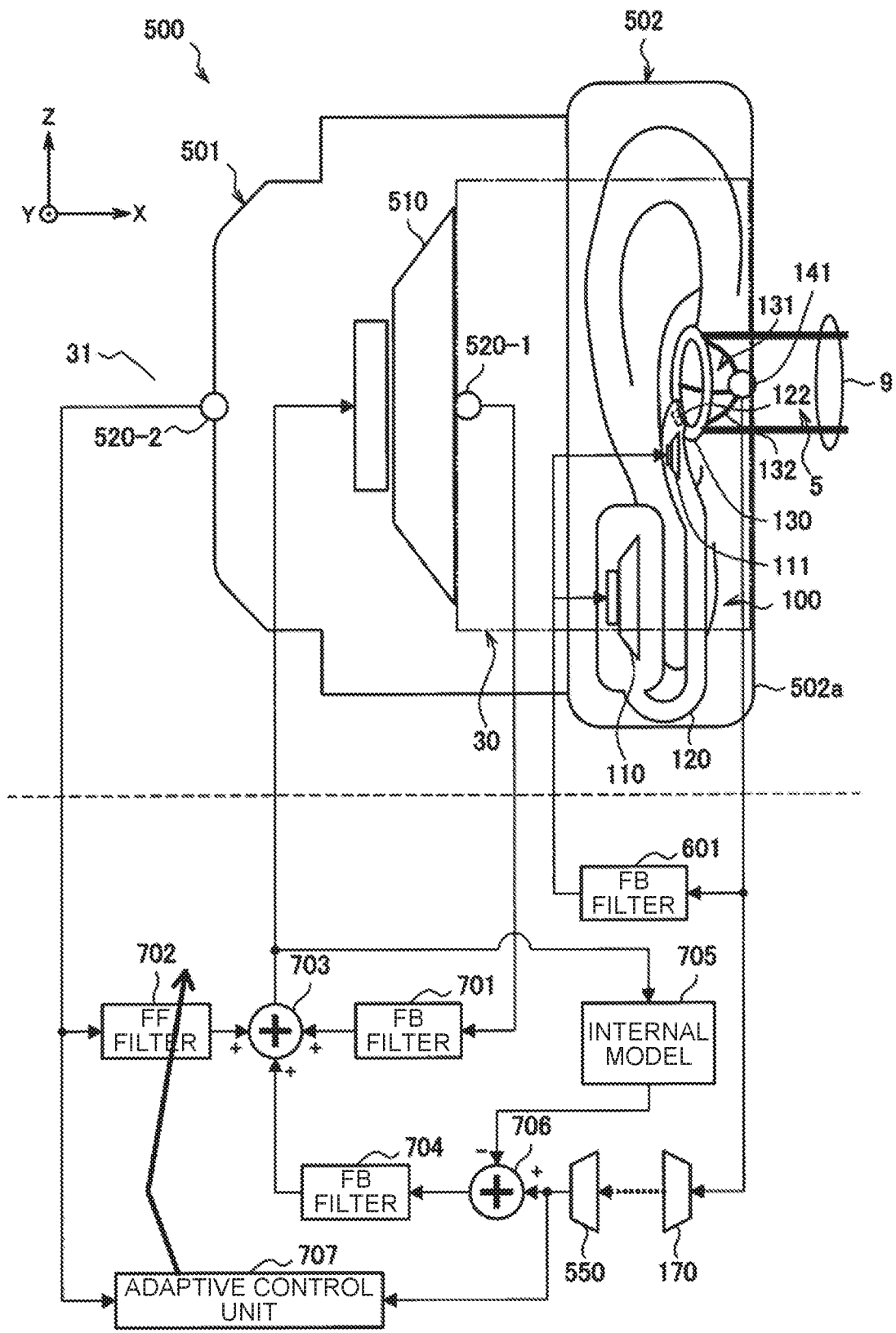
FIG. 74 is a diagram for describing a sixth combination example of the ear hole opening device and the headphones according to the embodiment.

FIG. 74 is a diagram for describing the sixth combination example of the ear hole opening device 100 and the headphones 500 according to the present embodiment. Processing blocks illustrated in FIG. 74 are obtained by adding the FB filter 601 to the processing blocks illustrated in FIG. 73. The operation of the FB filter 601 is the same as described above with reference to FIG. 66.

In this example, audio based on the noise cancellation signal is output from both the driver 110 and the driver 310. If considering that the ear hole opening device 100 can be always worn by the user, it is assumed that a diaphragm of the driver 110 is smaller than the driver 310. Therefore, the ear hole opening device 100 generates a noise cancellation signal for noise in a higher frequency range than a predetermined frequency, and outputs audio based on the noise cancellation signal. On the other hand, the headphones 500 generate a noise cancellation signal for noise in a lower frequency range than the predetermined frequency, and output audio based on the noise cancellation signal. For example, the ear hole opening device 100 targets a mid-high range, and the headphones 500 target a low range. Note that the bands targeted by both the ear hole opening device 100 and the headphones 500 may be duplicated. Due to such sharing, power consumptions of both the ear hole opening device 100 and the headphones 500 can be reduced.

Here, the audio output from the driver 110 is radiated in the vicinity of the ear hole via the sound guide unit 120 in the ear hole opening device 100. Therefore, a phase delay depending on the distance between the driver 110 and the microphone 141 can occur. Therefore, the ear hole opening device 100 may include, for example, a balanced armature type second audio output unit at a position close to the holding unit 130 in the sound guide unit 120. Then, the ear hole opening device 100 may output audio based on the noise cancellation signal from the second audio output unit. In this case, since the second audio output unit is closer to the microphone 141 than the driver 110, the phase delay depending on the distance decreases. Further, the second audio output unit is closer to the microphone 141 than the driver 310. Therefore, it is desirable that the second audio output unit output the audio based on the noise cancellation signal targeting the high range. As a result, the noise canceling performance with respect to the high frequency noise can be improved.

<7. Summary>

Heretofore, each combination example has been described. According to each of these combination examples, the same effect as the effect described in the second embodiment is achieved. Further, according to the present embodiment, the user does not prepare the headphones 300 having the ear canal microphone 320-3 described in the second embodiment but wears the headphones 500 to overlap the ear hole opening device 100, whereby the same effect can be easily obtained.

<3.4. Variations of Wireless Communication>

The ear hole opening device 100 and the headphones 500 can perform wireless communication by an arbitrary scheme. Here, as an example, wireless communication processing using optical communication will be described with reference to FIGS. 75 to 77. Thereafter, wireless communication processing using NFMI will be described with reference to FIG. 78. Note that it is assumed in the following description that the ear hole opening device 100 and the headphones 500 have active batteries and circuits, respectively. In addition, a description will be given on the assumption that wireless transmission is performed from the ear hole opening device 100 to the headphones 500.

(1) Case of Communication Using Light

Figure 75:
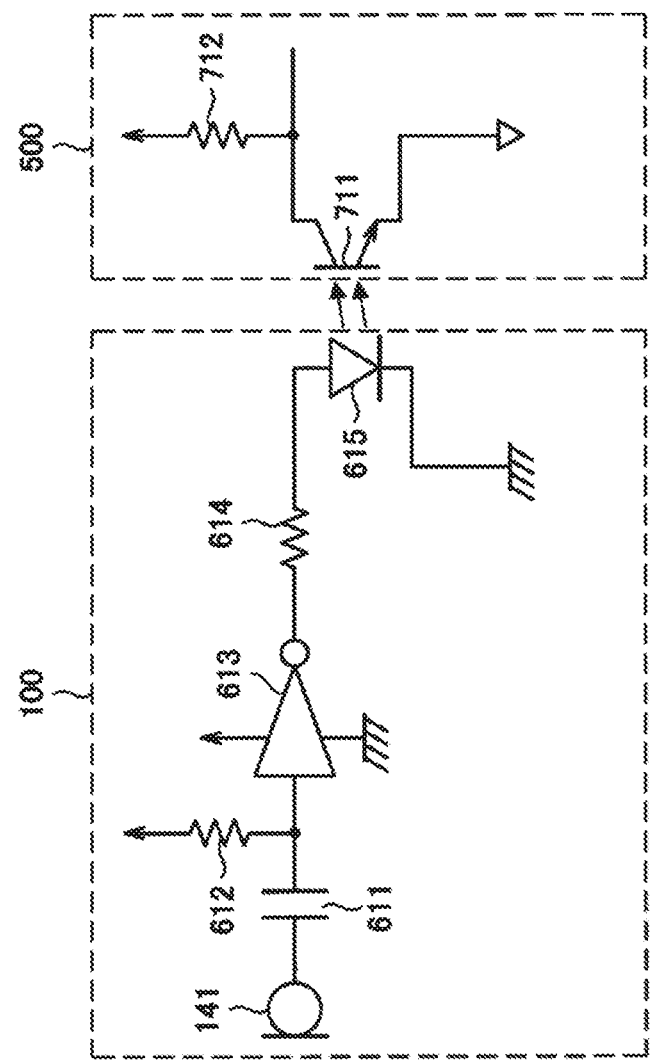
FIG. 75 is a diagram for describing an example of wireless communication processing using light between the ear hole opening device and headphones according to the embodiment.

FIG. 75 is a diagram for describing an example of wireless communication processing using light between the ear hole opening device 100 and the headphones 500 according to the present embodiment. In particular, FIG. 75 illustrates processing blocks for transmission in an analog system. First, processing of the ear hole opening device 100, which is a transmission side, will be described. An audio signal (analog signal) generated by the microphone 141 is input to an amplifier 613 via a capacitor 611 and a resistor 612. The audio signal is amplified by the amplifier 613 and radiated as light from an optical transmission unit 615 via a resistor 614. Next, processing of the headphones 500, which is a reception side, will be described. An optical reception unit 711 receives the light emitted from the optical transmission unit 615 and outputs a signal indicating the reception result. The signal indicating the reception result is input to a resistor 712. A voltage at the microphone 141 and a voltage generated at the resistor 712 have a proportional relationship. Therefore, the headphones 500 acquire the audio signal generated by the microphone 141 based on the voltage at the resistor 712.

Figure 76:
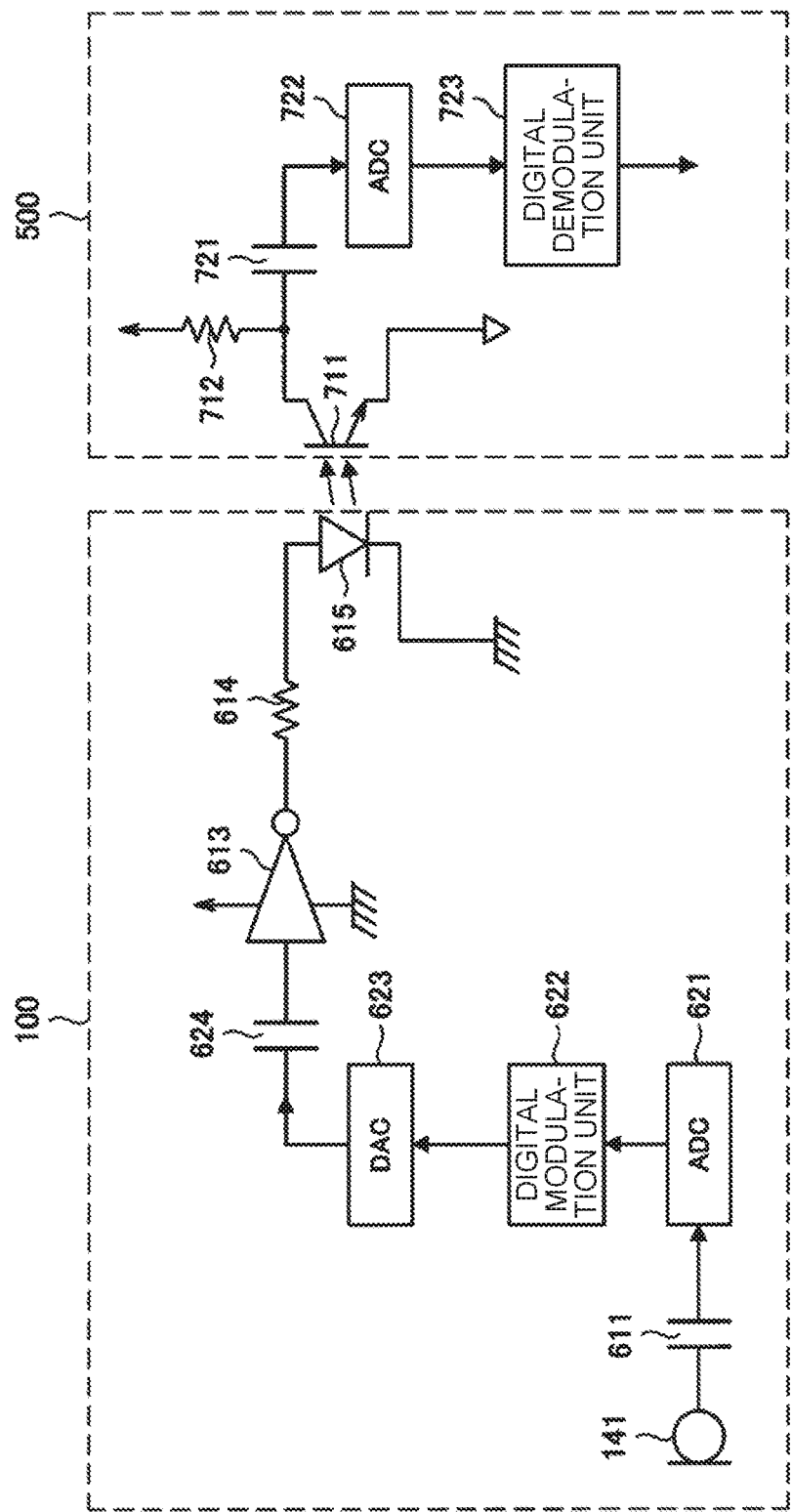
FIG. 76 is a diagram for describing an example of the wireless communication processing using light between the ear hole opening device and headphones according to the embodiment.

FIG. 76 is a diagram for describing an example of wireless communication processing using light between the ear hole opening device 100 and the headphones 500 according to the present embodiment. In particular, FIG. 76 illustrates processing blocks for transmission in a digital system. First, processing of the ear hole opening device 100, which is a transmission side, will be described. An audio signal (analog signal) generated by the microphone 141 is input to an ADC 621 via the capacitor 611. The audio signal is converted to a digital signal by the ADC 621, modulated by a digital modulation unit 622, and then converted to an analog signal by a DAC 623. Thereafter, the audio signal is emitted as light from the optical transmission unit 615 via the capacitor 624, the amplifier 613, and the resistor 614. Next, processing of the headphones 500, which is a reception side, will be described. An optical reception unit 711 receives the light emitted from the optical transmission unit 615 and outputs a signal indicating the reception result. A signal indicating the reception result is input to the ADC 722 via a capacitor 721 parallel to the resistor 712. The ADC 722 converts the input signal into a digital signal and outputs the digital signal to a digital demodulation unit 723. The digital demodulation unit 723 demodulates the input signal. In this manner, the headphones 500 acquire the audio signal generated by the microphone 141 as the digital signal.

Figure 77:
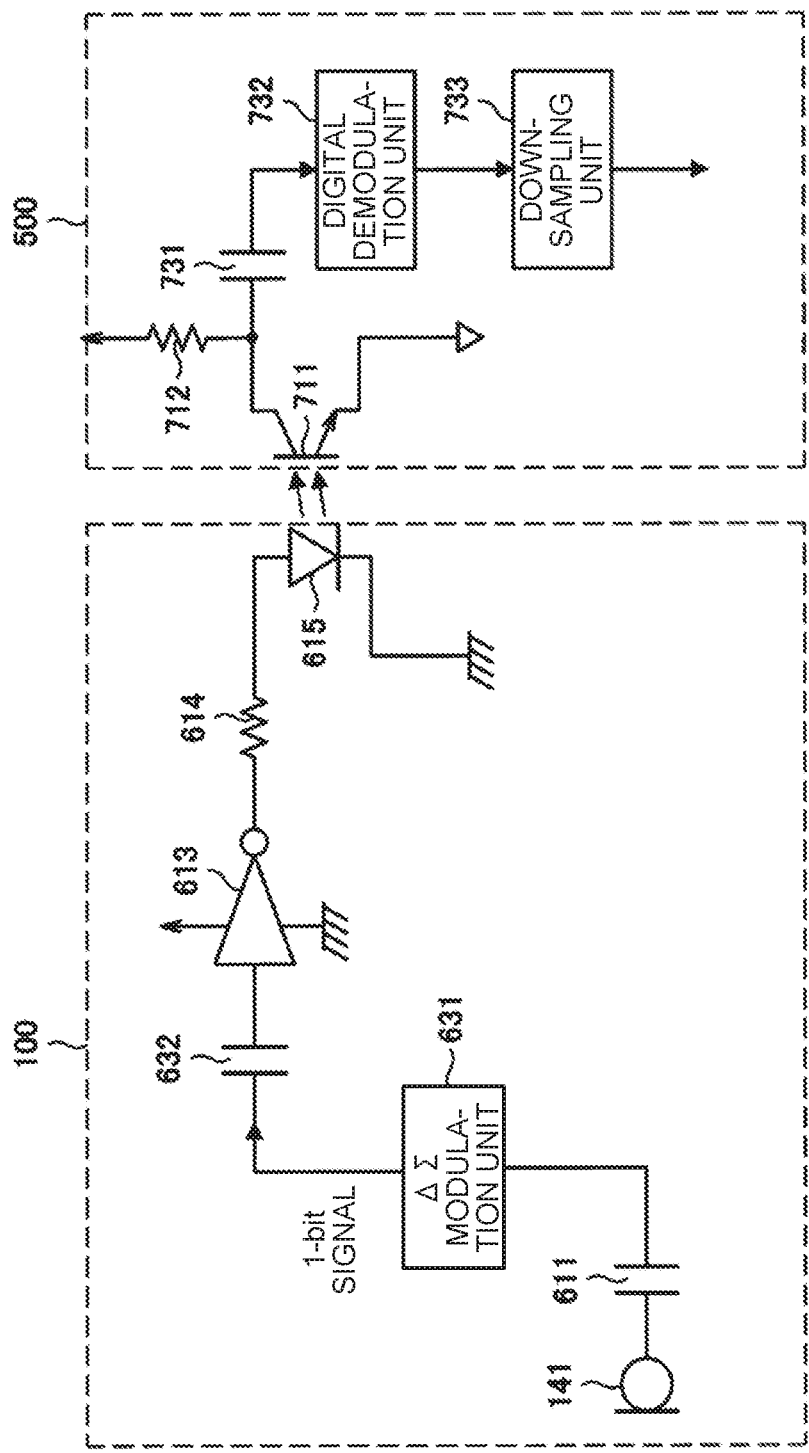
FIG. 77 is a diagram for describing an example of the wireless communication processing using light between the ear hole opening device and headphones according to the embodiment.

FIG. 77 is a diagram for describing an example of wireless communication processing using light between the ear hole opening device 100 and the headphones 500 according to the present embodiment. In particular, processing blocks using delta-sigma modulation are illustrated in FIG. 77. First, processing of the ear hole opening device 100, which is a transmission side, will be described. An audio signal (analog signal) generated by the microphone 141 is input to a delta-sigma modulation unit 631 via the capacitor 611, and delta-sigma modulation is applied. The delta-sigma modulation unit 631 converts the audio signal, which is originally the analog signal, into a 1-bit signal and outputs the converted signal. The signal output from the delta-sigma modulation unit 631 is radiated as light from the optical transmission unit 615 via the capacitor 632, the amplifier 613, and the resistor 614. Next, processing of the headphones 500, which is a reception side, will be described. An optical reception unit 711 receives the light emitted from the optical transmission unit 615 and outputs a signal indicating the reception result. The signal indicating the reception result passes through a capacitor 731 parallel to the resistor 712, is demodulated into a digital signal by the digital modulation unit 732, and is down-sampled by a down-sampling unit 733. In this manner, the headphones 500 acquire the audio signal generated by the microphone 141 as the digital signal. Since the delta-sigma modulation is used according to the wireless communication processing illustrated in FIG. 77, a calculation time required for modulation is little, and high-speed transmission at several MHz/bit is possible as compared with the wireless communication processing illustrated in FIG. 76. For this reason, the headphones 500 can receive the audio signal generated by the microphone 141 with an ultra-low delay and can use the received audio signal for the noise cancellation process.

(2) Case of Communication Using NFMI

Figure 78:
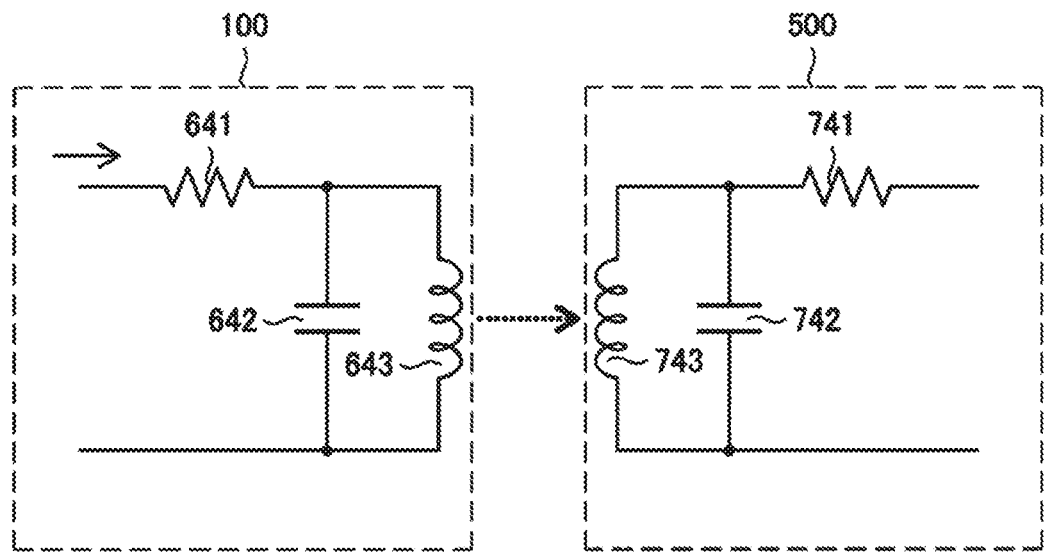
FIG. 78 is a diagram for describing an example of wireless communication processing using NFMI between the ear hole opening device and headphones according to the embodiment.

FIG. 78 is a diagram for describing an example of wireless communication processing using NFMI between the ear hole opening device 100 and headphones 500 according to the present embodiment. First, processing of the ear hole opening device 100, which is a transmission side, will be described. As illustrated in FIG. 78, the ear hole opening device 100 includes a resistor 641, a capacitor 642, and an inductor 643. An audio signal (analog signal) generated by the microphone 141 is input to the capacitor 642 and the inductor 643 after passing through the resistor 641. The inductor 643 generates magnetism corresponding to the input signal. Next, processing of the headphones 500, which is a reception side, will be described. As illustrated in FIG. 78, the headphones 500 include a resistor 741, a capacitor 742, and an inductor 743. The inductor 743 resonates with the magnetism generated by the inductor 643 and generates and outputs a signal similar to the signal that has been input to the inductor 643. In this manner, the headphones 500 acquire the audio signal generated by the microphone 141.

<3.5. Mutual Device Detection>

A user wears the headphones 500 in an overlapping manner in the state of wearing the ear hole opening device 100. What is considered as the motive thereof is that the user desires a stronger noise canceling effect than that in the case of using the ear hole opening device 100 alone.

Therefore, it is desirable that the noise cancellation process according to any of the first to sixth combination examples described above be started when detecting that the headphones 500 are worn outside the ear hole opening device 100. Therefore, the ear hole opening device 100 and the headphones 500 detect mutual devices in the case of being worn in the overlapping manner, and start the noise cancellation process. For example, if any one power is off, the power is turned on. In addition, wireless communication is started if the wireless communication has not been performed. That is, the ear hole opening device 100 starts transmitting the audio signal generated by the microphone 141 to the headphones 500, and the headphones 500 start receiving the audio signal from the ear hole opening device 100. As a result, the user can automatically enjoy the strong noise canceling effect simply by wearing the headphones 500 to overlap the ear hole opening device 100. Hereinafter, this point will be described in detail.

(1) Contactless Power Supply

The wearing of the headphones 500 on the outer side of the ear hole opening device 100 may be detected based on contactless power supply performed between the ear hole opening device 100 and the headphones 500. The contactless power supply may be performed from the headphones 500 to the ear hole opening device 100, or may be performed from the ear hole opening device 100 to the headphones 500. Hereinafter, these two systems will be described.

Contactless Power Supply from Headphones 500 to Ear Hole Opening Device 100

The power of the ear hole opening device 100 may be turned on when contactless power supply is performed from the headphones 500 in the power-off state. For example, when the contactless power supply is performed from the headphones 500, the operation control unit 153 is first activated. Next, the operation control unit 153 turns on the power of the ear hole opening device 100 using the battery power provided in the ear hole opening device 100. Thereafter, the operation control unit 153 causes the wireless communication unit 170 to start wireless communication. The wireless communication unit 170 starts transmitting the audio signal generated by the microphone 141 to the headphones 500.

The headphones 500 include a contactless power supply unit that performs contactless power supply to the ear hole opening device 100. The contactless power supply unit attempts contactless power supply to the ear hole opening device 100. The contactless power supply unit may attempt the contactless power supply with detection of wearing of the ear hole opening device 100 and the headphones 500 in an overlapping manner as a trigger, or may periodically attempt the contactless power supply without the trigger. When the contactless power supply unit has performed the contactless power supply to the ear hole opening device 100 (that is, when the contactless power supply has succeeded), the wireless communication unit 550 starts receiving the audio signal generated by the microphone 141 from the ear hole opening device 100.

Contactless Power Supply from Ear Hole Opening Device 100 to Headphones 500

The power of the headphones 500 may be turned on when contactless power supply is performed from the ear hole opening device 100 in the power-off state. For example, when the contactless power supply is performed from the ear hole opening device 100, the operation control unit 533 is first activated. Next, the operation control unit 533 turns on the power of the headphones 500 using the battery power provided in the headphones 500. Thereafter, the operation control unit 533 causes the sensor unit 540 to start wireless communication. For example, the wireless communication unit 550 starts receiving the audio signal generated by the microphone 141.

The ear hole opening device 100 includes a contactless power supply unit that performs contactless power supply to the headphones 500. The contactless power supply unit attempts contactless power supply to the headphones 500. The contactless power supply unit may attempt the contactless power supply with detection of wearing of the ear hole opening device 100 and the headphones 500 in an overlapping manner as a trigger, or may periodically attempt the contactless power supply without the trigger. When the contactless power supply unit has performed the contactless power supply to the headphones 500 (that is, when the contactless power supply has succeeded), the wireless communication unit 170 starts transmitting the audio signal generated by the microphone 141 to the headphones 500.

Example of Contactless Power Supply Using RFID Device

The contactless power supply described above can be performed by an RFID device. When a reader reads an RF tag, the RF tag is energized by a radio wave emitted from the reader. As a result, the side having the RF tag detects a device having the reader. Meanwhile, tag data stored in the RF tag is returned from the RF tag to the reader side with the energization of the RF tag as a trigger. As a result, the side having the reader detects a device having the RF tag. For the contactless power supply, an arbitrary scheme, such as an electromagnetic induction scheme and a magnetic field resonance scheme, can be adopted in addition to a radio wave reception scheme such as the RFID device. Hereinafter, a configuration in which the ear hole opening device 100 and the headphones 500 include the RFID device will be described with reference to FIG. 79.

Figure 79:
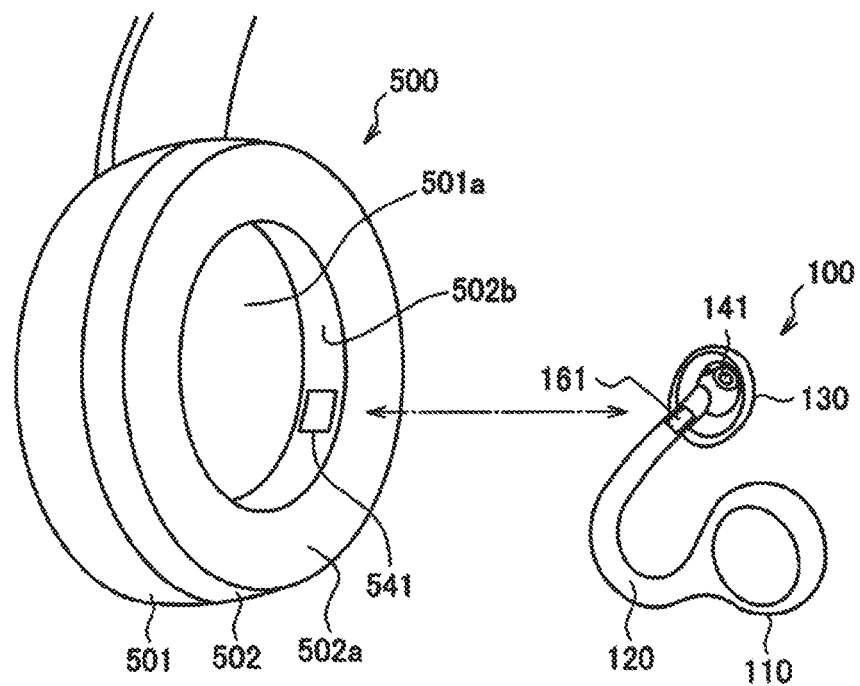
FIG. 79 is a view for describing mutual device detection using an RFID device performed by the ear hole opening device and the headphones according to the embodiment.

FIG. 79 is a view for describing mutual device detection using the RFID device performed by the ear hole opening device 100 and the headphones 500 according to the present embodiment. As illustrated in FIG. 79, the headphones 500 are provided with an RFID device 541 on a side wall 502*b* at the inner side of the contact surface 502*a* of the ear pad. In addition, the ear hole opening device 100 is provided with an RFID device 161 near the holding unit 130 of the sound guide unit 120. The contactless power supply from the headphones 500 to the ear hole opening device 100 is realized when the RFID device 541 is a reader and the RFID device 161 is an RF tag. On the other hand, the contactless power supply from the ear hole opening device 100 to the headphones 500 is realized when the RFID device 161 is a reader and the RFID device 541 is an RF tag. Each of the RFID device 541 and the RFID device 161 may include both the reader and the RF tag. When the ear hole opening device 100 and the headphones 500 are worn in an overlapping manner, the RFID device 541 and the RFID device 161 are close to each other. As a result, energization and reading are performed between the RF tag and the RF reader, and the mutual device detection is performed.

Hereinafter, an example of processing process when a noise cancellation process is started based on the contactless power supply from the headphones 500 to the ear hole opening device 100 will be described with reference to FIG. 80.

Figure 80:
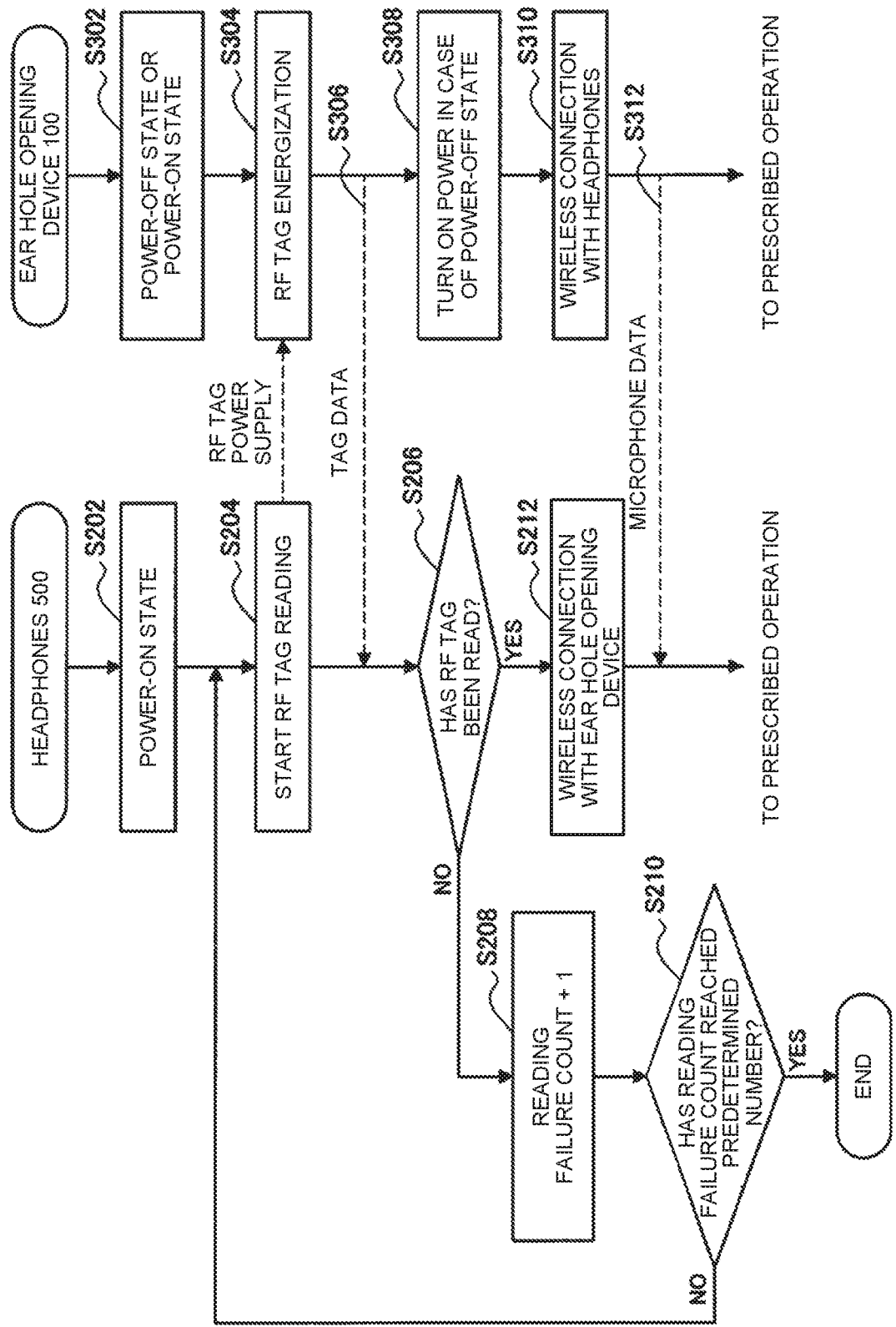
FIG. 80 is a sequence diagram illustrating an example of processing flow when a noise cancellation process according to the embodiment is started based on contactless power supply from the headphones to the ear hole opening device.

FIG. 80 is a sequence diagram illustrating an example of the processing flow when the noise cancellation process according to the present embodiment is started based on the contactless power supply from the headphones 500 to the ear hole opening device 100. As illustrated in FIG. 80, the ear hole opening device 100 and the headphones 500 are involved in this sequence. This sequence is a sequence when the ear hole opening device 100 has an RF tag and the headphones 500 have a reader.

It is assumed that the headphones 500 are in the power-on state at the start time (Step S202), and the ear hole opening device 100 is in either the power-off state or the power-on state (Step S302). The headphones 500 start reading the RF tag by the reader (Step S204). Power is supplied to the RF tag from the reader, and the RF tag of the ear hole opening device 100 is energized (Step S304), and tag data is returned from the RF tag to the reader side (Step S306).

The power of the ear hole opening device 100 is turned on in the power-off state with the energization of the RF tag as a trigger (Step S308). Thereafter, the ear hole opening device 100 is wirelessly connected to the headphones 500 (Step S310). Then, the ear hole opening device 100 transmits microphone data (that is, the audio signal generated by the microphone 141) to the headphones 500 (Step S312). Thereafter, the ear hole opening device 100 performs a prescribed operation relating to the noise cancellation process described above.

The headphones 500 determine whether the tag data from the RF tag has been read (Step S206). When it is determined that the tag data from the RF tag is not readable (Step S206/NO), the headphones 500 increment a reading failure count (Step S208). Next, the headphones 500 determine whether the reading failure count has reached a predetermined number (Step S210). When it is determined that the reading failure count has reached the predetermined number (Step S210/YES), the processing ends. On the other hand, when it is determined that the reading failure count has not reached the predetermined number (Step S210/NO), the processing returns to Step S204 again. In addition, when it is determined that the tag data from the RF tag has been read (Step S206/YES), the headphones 500 are wirelessly connected to the ear hole opening device 100 (Step S212). Then, the headphones 500 receive the microphone data from the ear hole opening device 100 (Step S312). Thereafter, the headphones 500 perform a prescribed operation relating to the noise cancellation process described above.

Next, an example of processing flow when the noise cancellation process is started based on the contactless power supply from the ear hole opening device 100 to the headphones 500 will be described with reference to FIG. 81.

Figure 81:
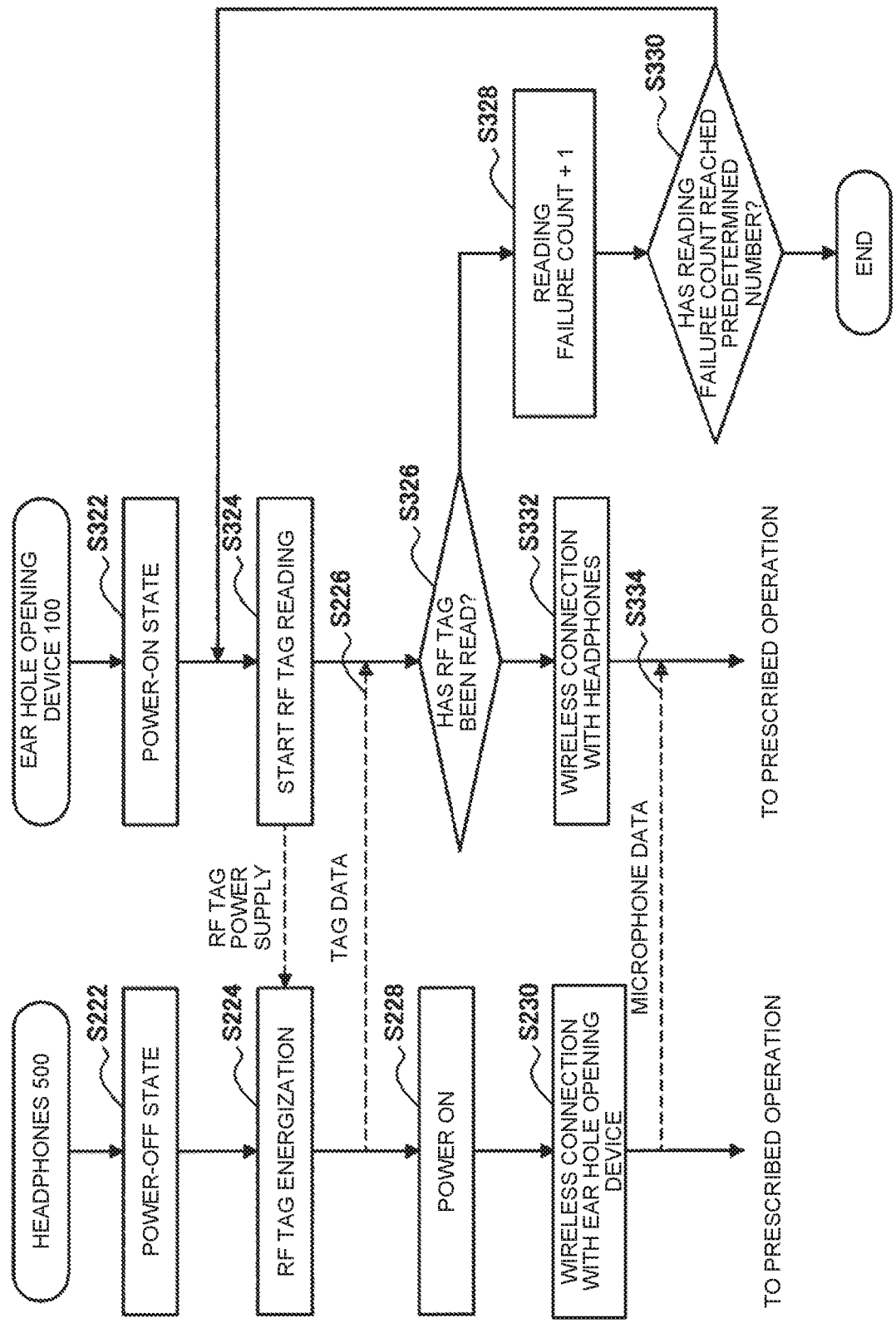
FIG. 81 is a sequence diagram illustrating an example of processing flow when the noise cancellation process according to the embodiment is started based on contactless power supply from the ear hole opening device to the headphones.

FIG. 81 is a sequence diagram illustrating an example of the processing flow when the noise cancellation process according to the present embodiment is started based on the contactless power supply from the ear hole opening device 100 to the headphones 500. As illustrated in FIG. 81, the ear hole opening device 100 and the headphones 500 are involved in this sequence. In this sequence, the ear hole opening device 100 has a reader, and the headphones 500 have an RF tag.

It is assumed that the headphones 500 are in the power-off state at the start time (Step S222), and the ear hole opening device 100 is in the power-on state (Step S322). The ear hole opening device 100 starts reading the RF tag by the reader (Step S324). Power is supplied to the RF tag from the reader, and the RF tag of the headphones 500 is energized (Step S224), and tag data is returned from the RF tag to the reader side (Step S226).

The ear hole opening device 100 determines whether the tag data from the RF tag has been read (Step S326). When it is determined that the tag data from the RF tag is not readable (Step S326/NO), the ear hole opening device 100 increments a reading failure count (Step S328). Next, the ear hole opening device 100 determines whether the reading failure count has reached a predetermined number (Step S330). When it is determined that the reading failure count has reached the predetermined number (Step S330/YES), the processing ends. On the other hand, when it is determined that the reading failure count has not reached the predetermined number (Step S330/NO), the processing returns to Step S324 again. In addition, when it is determined that the tag data from the RF tag has been read (Step S326/YES), the ear hole opening device 100 is wirelessly connected to the headphones 500 (Step S332), and microphone data (that is, the audio signal generated by the microphone 141) is transmitted to the headphones 500 (Step S334). Thereafter, the ear hole opening device 100 performs a prescribed operation relating to the noise cancellation process described above.

The power of the headphones 500 is turned on with the energization of the RF tag as a trigger (Step S228). Thereafter, the headphones 500 are wirelessly connected to the ear hole opening device 100 (Step S230). Then, the headphones 500 receive the microphone data (that is, the audio signal generated by the microphone 141) from the ear hole opening device 100 (Step S334). Thereafter, the headphones 500 perform a prescribed operation relating to the noise cancellation process described above.

(2) NFMI

The wearing of the headphones 500 on the outer side of the ear hole opening device 100 may be detected based on magnetic resonance performed between the ear hole opening device 100 and the headphones 500. When the ear hole opening devices 100 are worn on both left and right ears, the left and right ear hole opening devices 100 can transmit and receive a music signal and the like by NFMI. When the headphones 500 are worn to overlap the left and right ear hole opening devices 100, the headphones 500 may detect the communication between the left and right ear hole opening devices 100 by the NFMI and start the noise cancellation process. Hereinafter, this point will be described with reference to FIGS. 82 to 85.

FIGS. 82 to 85 are views for describing mutual device detection using NFMI performed by the ear hole opening devices 100 and the headphones 500 according to the present embodiment. In FIGS. 82 to 85, "A" is added to each end of reference signs of constituent elements of an ear hole opening device 100A, and "B" is added to each end of reference signs of constituent element of an ear hole opening device 100B. In addition, among constituent elements of the headphones 500, "A" is added to each end of reference signs of constituent element adjacent to the ear hole opening device 100A, and "B" is added to each end of reference signs of constituent element adjacent to the ear hole opening device 100B. The terminal device 800 is an arbitrary device such as a tablet terminal, a smartphone, and an agent device.

Figure 82:
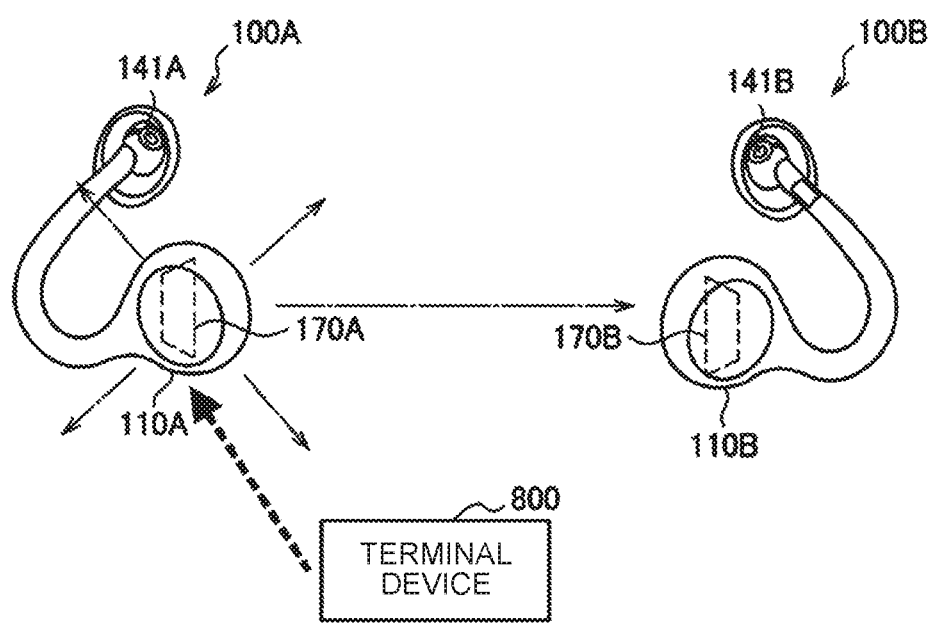
FIG. 82 is a view for describing the mutual device detection using NFMI performed by the ear hole opening devices and the headphones according to the embodiment.

As illustrated in FIG. 82, it is assumed that a user wears the ear hole opening device 100A in one ear and the ear hole opening device 100B in the other ear. The terminal device 800 transmits a music signal using an arbitrary communication scheme such as Bluetooth or Wi-Fi. A wireless communication unit 170A receives the music signal transmitted by the terminal device 800, and a driver 110A outputs music based on the received music signal. In addition, the wireless communication unit 170A transfers the music signal to the ear hole opening device 100B using NFMI. A wireless communication unit 170B receives the transferred music signal, and a driver 110B outputs music based on the received music signal.

Figure 83:
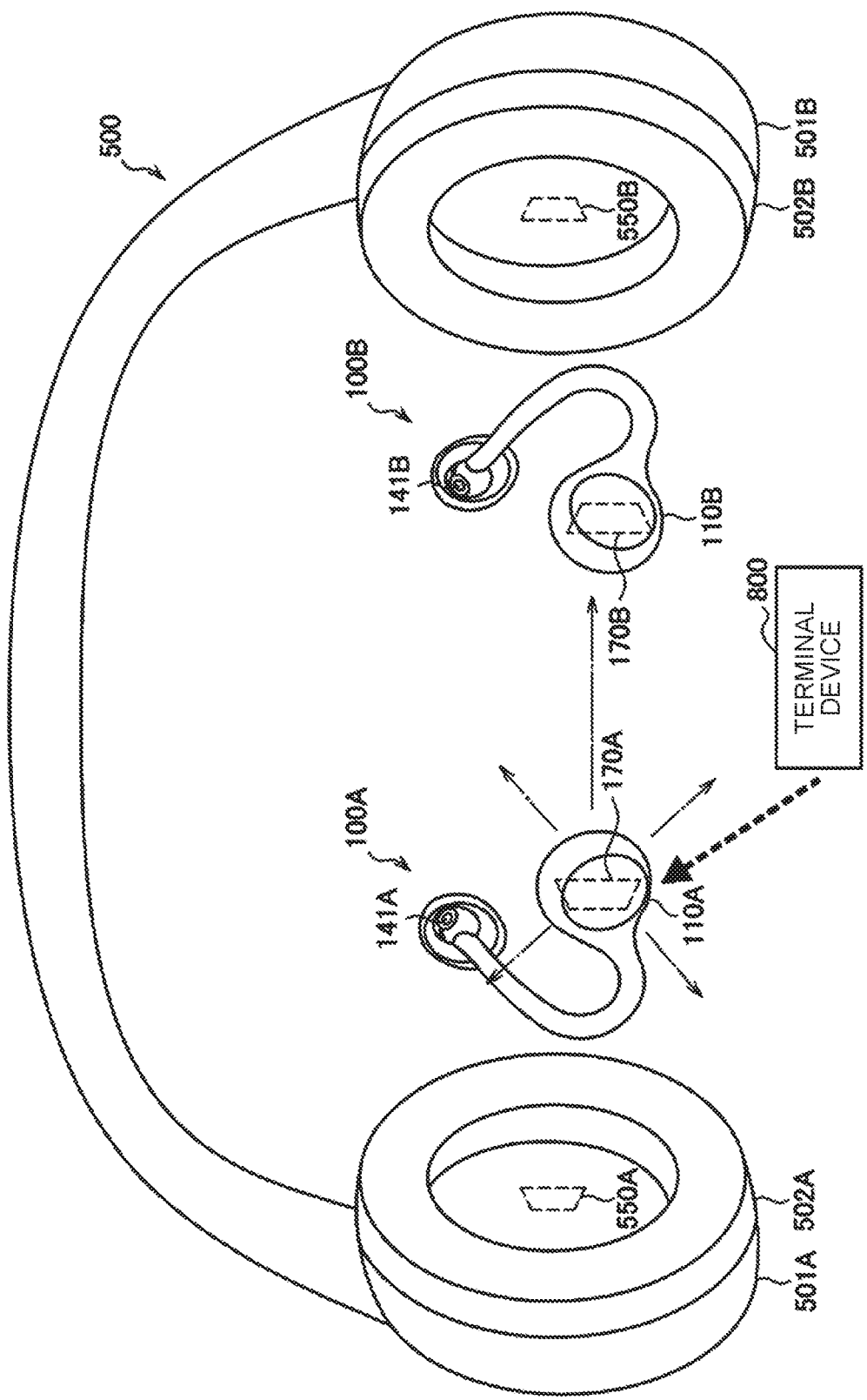
FIG. 83 is a view for describing the mutual device detection using NFMI performed by the ear hole opening devices and the headphones according to the embodiment.

Next, it is assumed that the user wears the headphones 500 to overlap the ear hole opening devices 100A and 100B as illustrated in FIG. 83. In this case, NFMI transceivers of wireless communication units 550A and 550B of the headphones 500 also resonate with the music signal transmitted from the ear hole opening device 100A to the ear hole opening device 100B using NFMI. The headphones 500 detect that the headphones 500 have been worn to overlap the ear hole opening devices 100A and 100B by such magnetic resonance. Similarly, the ear hole opening devices 100A and 100B also detect that the headphones 500 have been worn in the overlapping manner.

Figure 84:
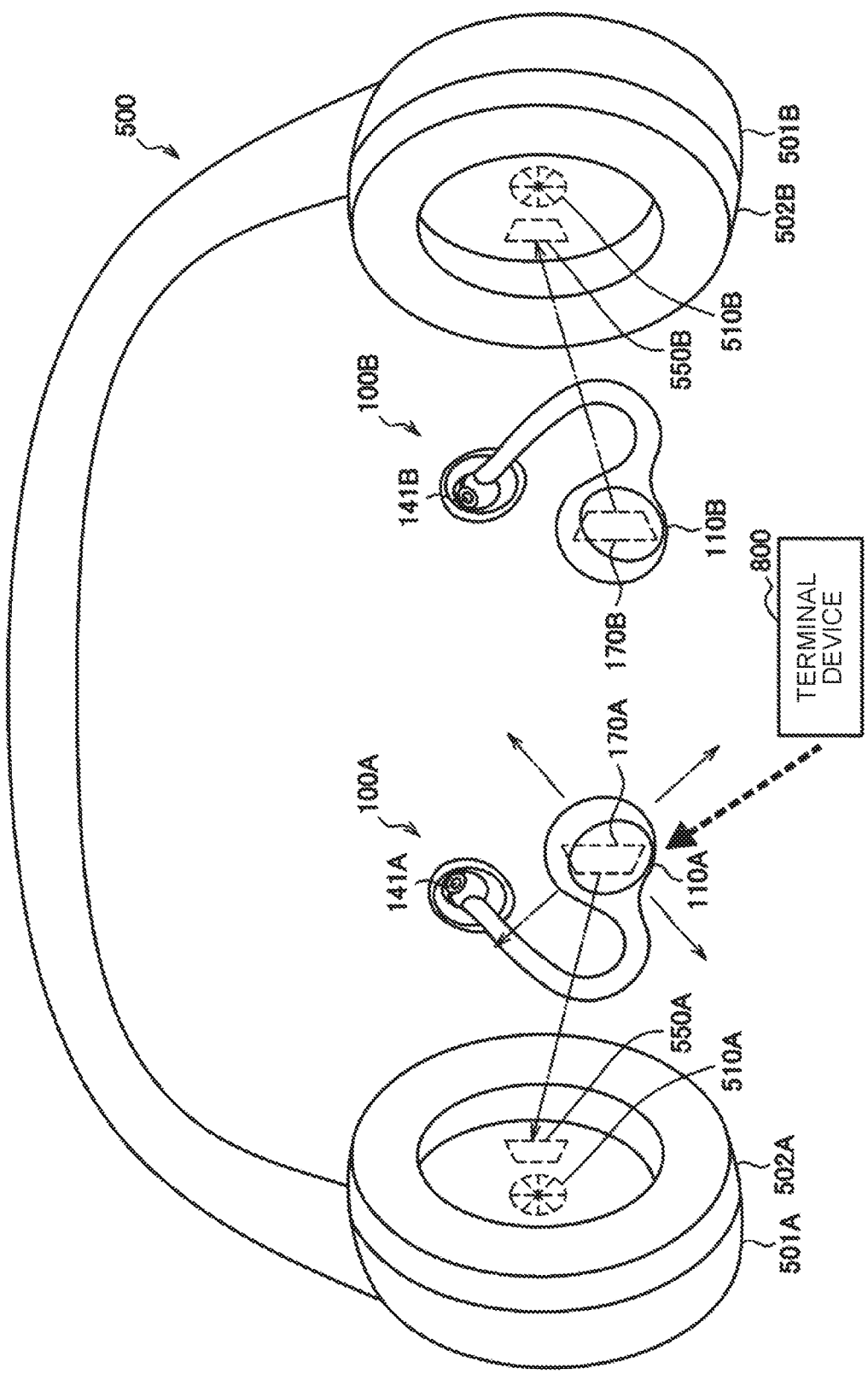
FIG. 84 is a view for describing the mutual device detection using NFMI performed by the ear hole opening devices and the headphones according to the embodiment.

Thereafter, the headphones 500 and the ear hole opening devices 100A and 100B start a noise cancellation process as illustrated in FIG. 84. Specifically, the ear hole opening device 100A transmits microphone data generated by a microphone 141A by the wireless communication unit 170A. For example, the wireless communication unit 170A stops transferring the music signal using NFMI and transmits microphone data using NFMI. The microphone data transmitted from the wireless communication unit 170A is received by the wireless communication unit 550A adjacent to the wireless communication unit 170A. The headphones 500 perform the noise cancellation process based on the received audio signal, and output a generated noise cancellation signal from a driver 510A. The same applies to the ear hole opening device 100B.

Figure 85:
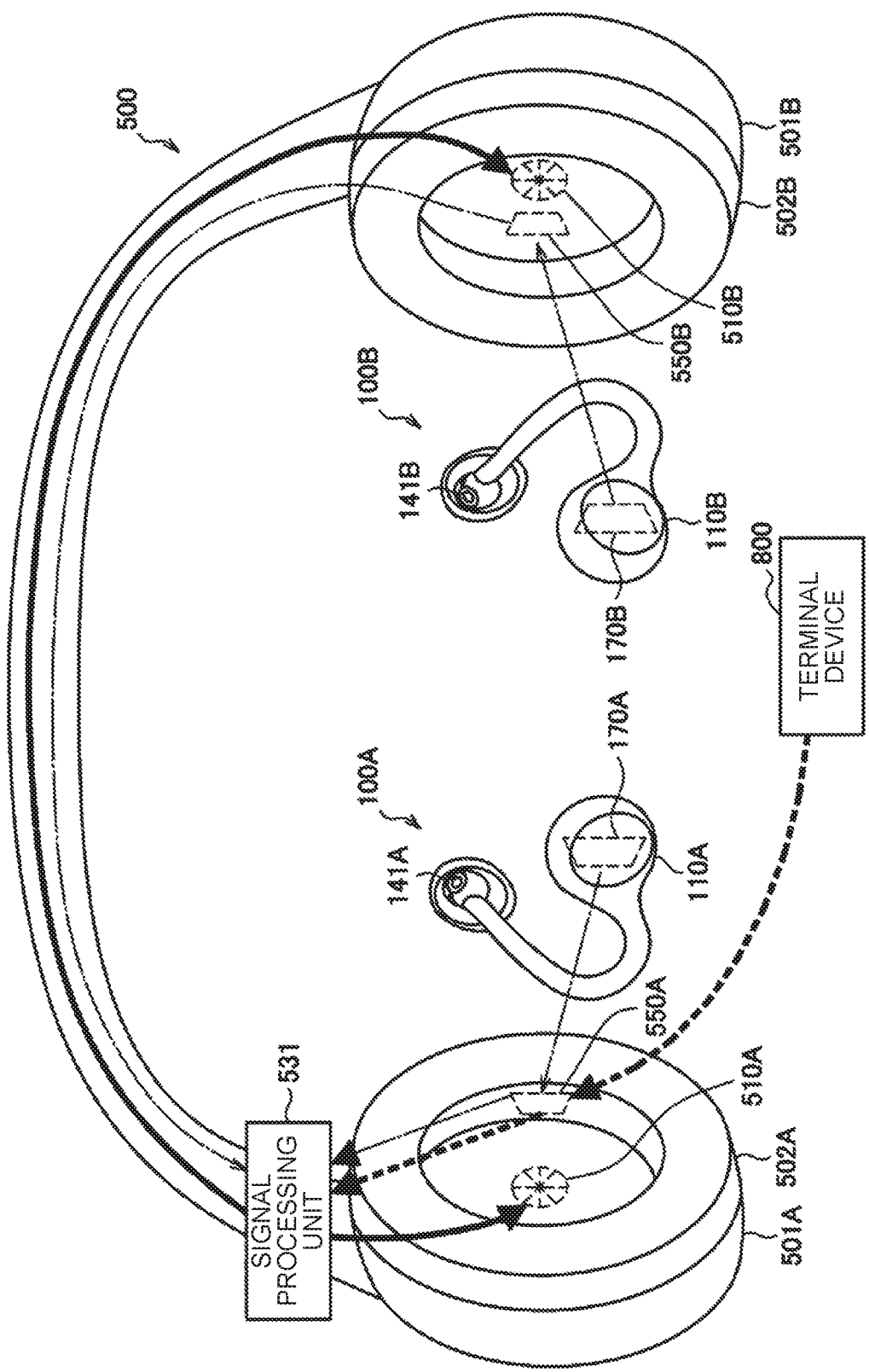
FIG. 85 is a view for describing the mutual device detection using NFMI performed by the ear hole opening devices and the headphones according to the embodiment.

As illustrated in FIG. 85, the headphones 500 may perform reception of a music signal and distribution of the music signal to the right and left. Specifically, first, the wireless communication unit 550A receives a music signal transmitted from the terminal device 800. The wireless communication unit 550A outputs the music signal received from terminal device 800 and microphone data received from the ear hole opening device 100A to the signal processing unit 531. In addition, the wireless communication unit 550B outputs the microphone data received from the ear hole opening device 100B to the signal processing unit 531. The signal processing unit 531 generates a noise cancellation signal based on the microphone data received from the ear hole opening devices 100A and 100B, and generates a synthesized signal by synthesizing the music signal with the generated noise cancellation signal. The synthesized signal is input to the driver 510A and a driver 510B, and is output as audio. With such processing, it is possible to realize seamless transition mainly for music reproduction without causing the user to feel uncomfortable due to interruption of the music reproduction before and after wearing the headphones 500.

Since NFMI does not particularly require pairing or the like, the above mutual device detection is possible. Of course, only paired devices may be subjected to the mutual device detection.

Hereinafter, an example of processing flow when the noise cancellation process is started based on the magnetic resonance among the ear hole opening devices 100 and the headphones 500 will be described with reference to FIG. 86.

Figure 86:
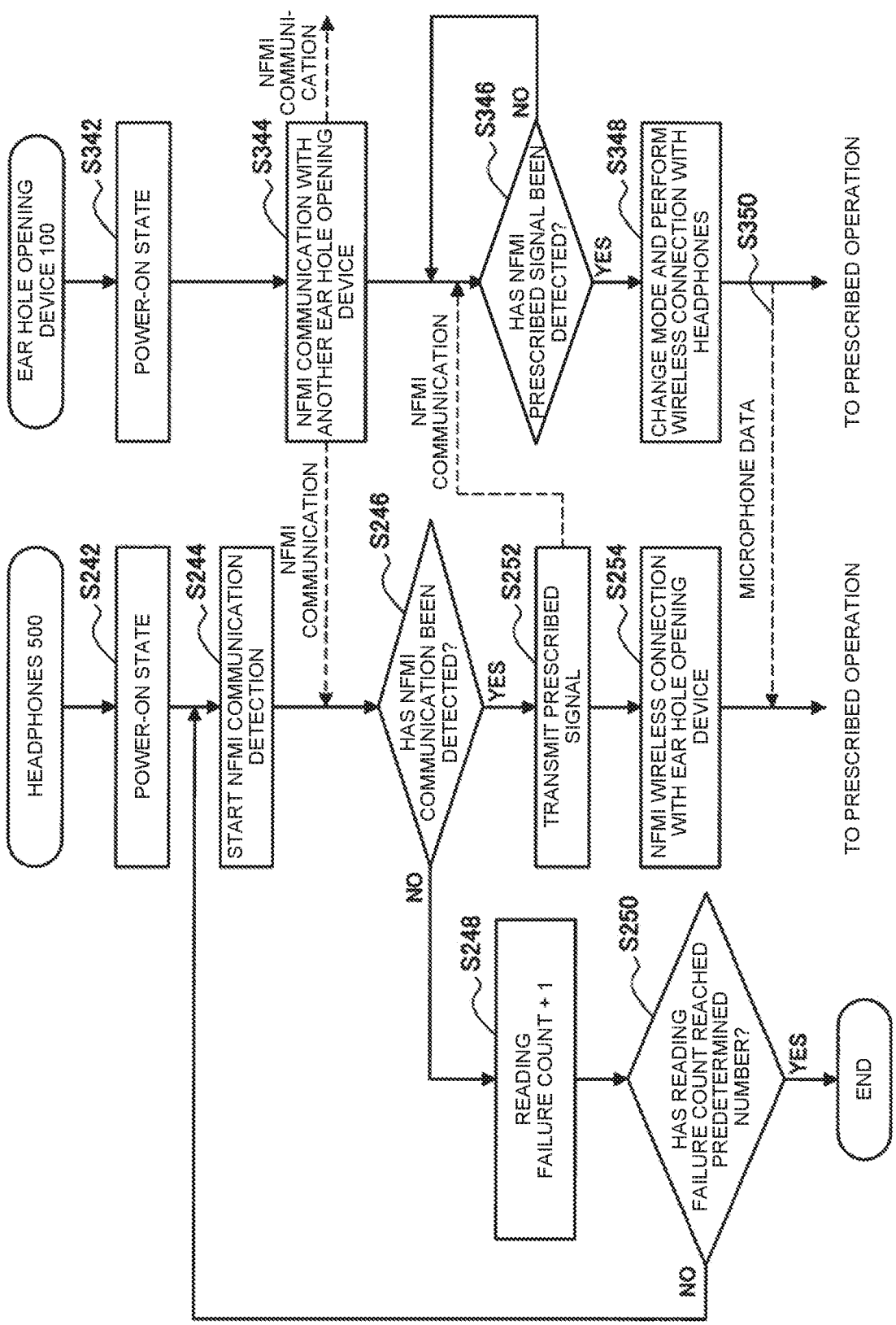
FIG. 86 is a sequence diagram illustrating an example of processing flow when the noise cancellation process according to the embodiment is started based on magnetic resonance among the ear hole opening devices and the headphones.

FIG. 86 is a sequence diagram illustrating an example of the processing flow when the noise cancellation process according to the present embodiment is started based on the magnetic resonance among the ear hole opening devices 100 and the headphones 500. As illustrated in FIG. 86, the ear hole opening device 100 and the headphones 500 are involved in this sequence.

At the start time, the headphones 500 are in the power-on state (Step S242). In addition, the ear hole opening device 100 is in the power-on state (Step S342), and performs NFMI communication with the other ear hole opening device 100 (Step S344).

The ear hole opening device 100 determines whether a prescribed signal transmitted by NFMI has been detected during the NFMI communication (Step S346). When it is determined that the prescribed signal transmitted by NFMI has not been detected (Step S346/NO), the processing returns to Step S346 again. On the other hand, when it is determined that the prescribed signal transmitted by NFMI has been detected (Step S346/YES), the ear hole opening device 100 changes an operation mode from an operation mode of performing NFMI communication with the other ear hole opening device 100 to an operation mode of performing NFMI communication with the headphones 500, and is wirelessly connected to the headphones 500 by NFMI (Step S348). Then, the ear hole opening device 100 transmits microphone data (that is, the audio signal generated by the microphone 141) to the headphones 500 (Step S350). Thereafter, the ear hole opening device 100 performs a prescribed operation relating to the noise cancellation process described above.

The headphones 500 start detecting NFMI communication (Step S244), and determine whether the NFMI communication has been detected (Step S246). When it is determined that the NFMI communication has not been detected (Step S246/NO), the headphones 500 increment a reading failure count (Step S248). Next, the headphones 500 determine whether the reading failure count has reached a predetermined number (Step S250). When it is determined that the reading failure count has reached the predetermined number (Step S250/YES), the processing ends. On the other hand, when it is determined that the reading failure count has not reached the predetermined number (Step S250/NO), the processing returns to Step S244 again. When it is determined that the FMI communication has been detected (Step S246/YES), the headphones 500 transmits the prescribed signal by NFMI (Step S252). Then, the headphones 500 are wirelessly connected to the ear hole opening device 100 by NFMI (Step S254), and receives the microphone data from the ear hole opening device 100 (Step S350). Thereafter, the headphones 500 perform a prescribed operation relating to the noise cancellation process described above.

(3) Audio

The wearing of the headphones 500 on the outer side of the ear hole opening device 100 may be detected based on collection of predetermined audio by the ear hole opening devices 100 or the headphones 500. This point will be described with reference to FIG. 87.

Figure 87:
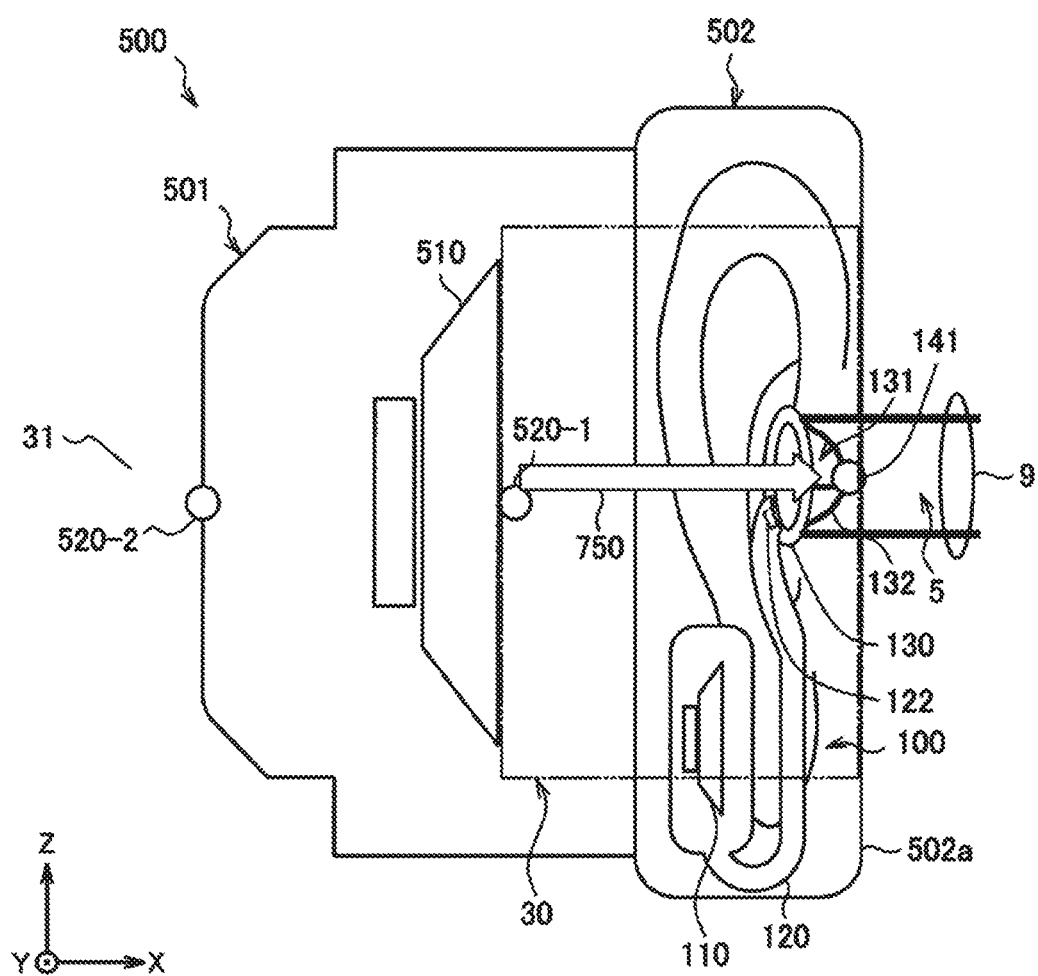
FIG. 87 is a diagram for describing mutual device detection using audio by the ear hole opening device and the headphones according to the embodiment.

FIG. 87 is a diagram for describing mutual device detection using audio by the ear hole opening device 100 and the headphones 500 according to the present embodiment. For example, the headphones 500 output predetermined audio when it is detected that the headphones 500 are worn by a user. The wearing/non-wearing by the user can be detected based on the deformation of the ear pad 502 detected by, for example, a pressure-sensitive sensor. When the predetermined audio is collected by the microphone 141, the ear hole opening device 100 detects that the headphones 500 are worn in an overlapping manner. The predetermined audio may be audio in an ultrasonic region above the audible band. In this case, the mutual device detection can be performed without causing discomfort to the user. In addition, the ear hole opening device 100 may output predetermined audio and the headphones 500 may collect the audio conversely to the example illustrated in FIG. 87.

(4) Magnetism of Driver

The wearing of the headphones 500 on the outer side of the ear hole opening device 100 may be detected based on detection of predetermined magnetism by the ear hole opening devices 100 or the headphones 500. This point will be described with reference to FIG. 88.

Figure 88:
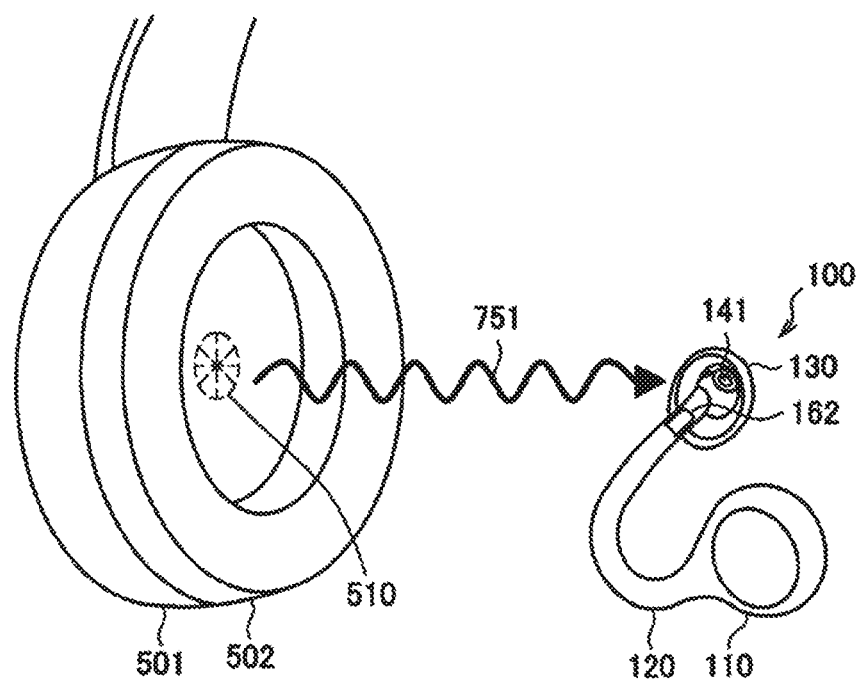
FIG. 88 is a diagram for describing mutual device detection using magnetism by the ear hole opening device and the headphones according to the embodiment.

FIG. 88 is a diagram for describing mutual device detection using magnetism by the ear hole opening device 100 and the headphones 500 according to the present embodiment. For example, the ear hole opening device 100 is provided with a magnetic sensor 162 near the holding unit 130 of the sound guide unit 120. The driver 510 of the headphones 500 includes a magnet and emits magnetism 751. Therefore, the ear hole opening device 100 detects that the headphones 500 are worn in an overlapping manner based on the detection of the magnetism 751 by the magnetic sensor 162. The headphones 500 may be provided with a magnetic sensor to detect magnetism from the driver 110 of the ear hole opening device 100 conversely to the example illustrated in FIG. 88.

<3.6. Summary>

The third embodiment has been described in detail above. As described above, the ear hole opening device 100 and the headphones 500 that are worn by the user in the overlapping manner can cooperate with each other by wireless communication according to the third embodiment. Specifically, the ear hole opening device 100 transmits the audio signal generated by the audio input unit 141 to the headphones 500. The headphones 500 perform the noise cancellation process based on the received audio signal. Since the headphones 500 can perform the noise cancellation process based on the sound collection result at the position close to the eardrum, high noise canceling performance can be realized.

4. Hardware Configuration Example

Figure 89:
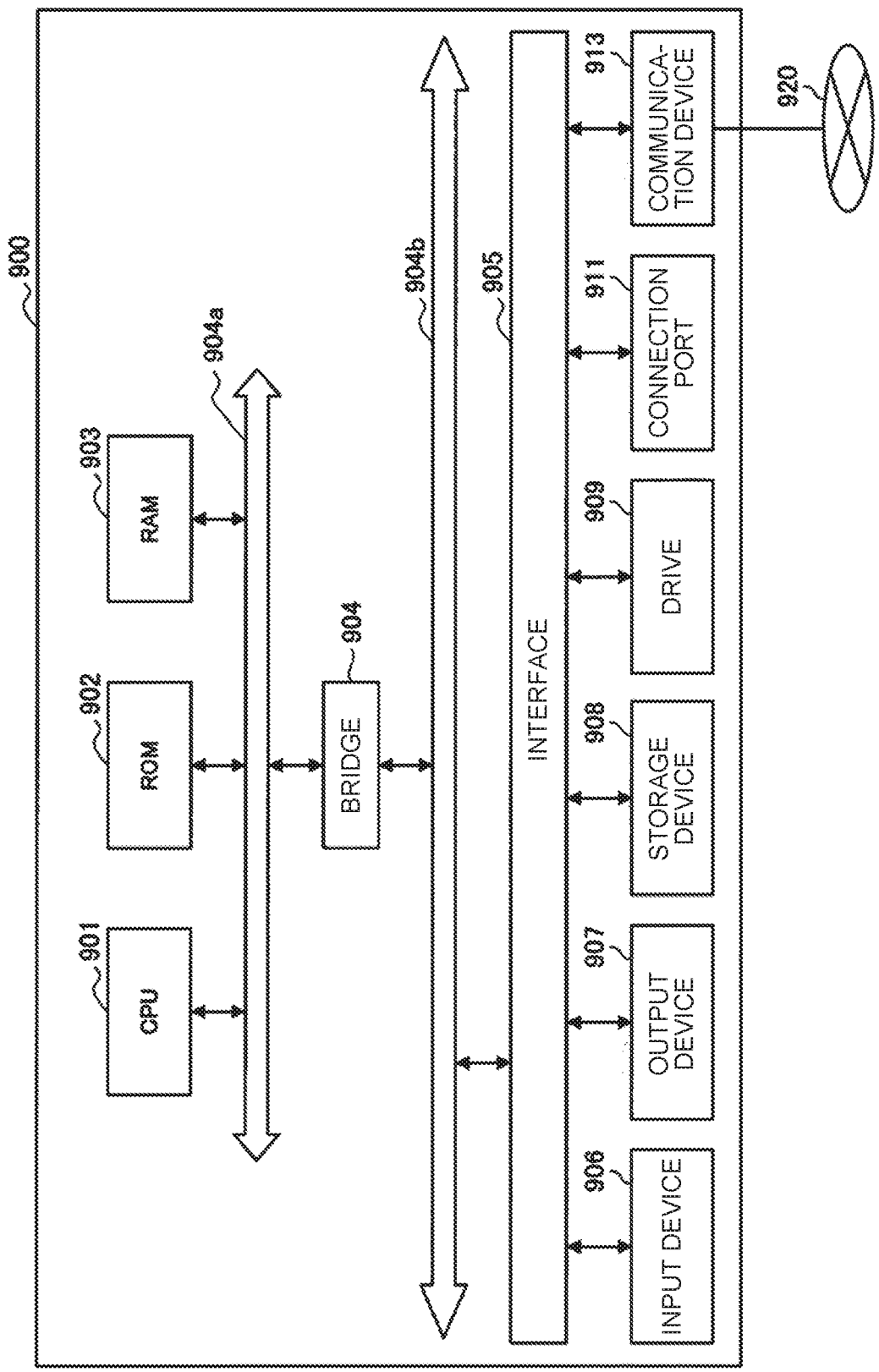
FIG. 89 is a block diagram illustrating an example of a hardware configuration of an information processing apparatus according to each embodiment.

Finally, a hardware configuration of an information processing apparatus according to each embodiment will be described with reference to FIG. 89. FIG. 89 is a block diagram illustrating an example of the hardware configuration of the information processing apparatus according to each embodiment. Note that an information processing apparatus 900 illustrated in FIG. 89 can realize, for example, the ear hole opening device 100 illustrated in FIG. 3, the headphones 300 illustrated in FIG. 31, the ear hole opening device 100 illustrated in FIG. 65, and the headphones 500 illustrated in FIG. 67. Information processing performed by the ear hole opening device 100, the headphones 300, or the headphones 500 according to the present embodiment is realized by cooperation between software and hardware to be described hereinafter.

As illustrated in FIG. 89, the information processing apparatus 900 includes a central processing unit (CPU) 901, a read-only memory (ROM) 902, a random-access memory (RAM) 903, and a host bus 904a. In addition, the information processing apparatus 900 includes a bridge 904, an external bus 904b, an interface 905, an input device 906, an output device 907, a storage device 908, a drive 909, a connection port 911, and a communication device 913. The information processing apparatus 900 may include an electric circuit and a processing circuit such as a DSP and an ASIC instead of or in addition to the CPU 901.

The CPU 901 functions as an arithmetic processing device and a control device, and controls the overall operations in the information processing apparatus 900 according to various programs. In addition, the CPU 901 may be a microprocessor. The ROM 902 stores programs to be used by the CPU 901, calculation parameters, and the like. The RAM 903 temporarily stores programs used in the execution of the CPU 901, parameters and the like that appropriately change during the execution. The CPU 901 can form, for example, the control unit 150 illustrated in FIG. 3, the control unit 330 illustrated in FIG. 31, the control unit 150 illustrated in FIG. 65, or the control unit 530 illustrated in FIG. 67.

The CPU 901, the ROM 902, and the RAM 903 are mutually connected by the host bus 904a including a CPU bus and the like. The host bus 904a is connected to the external bus 904b such as a peripheral component interconnect/interface (PCI) bus via the bridge 904. The host bus 904a, the bridge 904, and the external bus 904b are not necessarily configured to be separate from each other, and these functions may be implemented on one bus.

The input device 906 is realized by a device that can collect audio and generate an audio signal, for example, a microphone, an array microphone, or the like. In addition, the input device 906 includes a distance measurement sensor and a circuit that processes vibration information obtained by the distance measurement sensor, and is realized by a device that can acquire sound pressure information at a distant position. These input devices 906 can form, for example, the audio information acquisition unit 140 illustrated in FIG. 3, the audio input unit 320 illustrated in FIG. 31, the audio information acquisition unit 140 illustrated in FIG. 65, or the audio input unit 520 illustrated in FIG. 67.

In addition, the input device 906 can be formed using a device that detects various types of information. For example, the input device 906 can include various sensors such as an image sensor (for example, a camera), a depth sensor (for example, a stereo camera), an acceleration sensor, a gyro sensor, a magnetic sensor, a geomagnetic sensor, an optical sensor, a sound sensor, a distance sensor, and a force sensor. In addition, the input device 906 may acquire information on the information processing device 900 itself, such as an attitude and a movement speed of the information processing device 900 and information on the surrounding environment of the information processing apparatus 900 such as brightness and noise around the information processing device 900. In addition, the input device 906 may include a global navigation satellite system (GNSS) module that receives a GNSS signal from a GNSS satellite (for example, a global positioning system (GPS) signal from a GPS satellite) to measure position information including latitude, longitude, and altitude of a device. In addition, regarding the position information, the input device 906 may detect a position by transmission/reception with Wi-Fi (registered trademark), a mobile phone/PHS/smartphone, and the like or near field communication. These input devices 906 can form, for example, the sensor unit 370 illustrated in FIG. 31, the sensor unit 160 illustrated in FIG. 65, or the sensor unit 540 illustrated in FIG. 67.

The output device 907 is an audio output device that can output audio such as a speaker, a directional speaker, and a bone conduction speaker. The output device 907 can form, for example, the audio output unit 110 illustrated in FIG. 3, the audio output unit 310 illustrated in FIG. 31, the audio output unit 110 illustrated in FIG. 65, or the audio output unit 510 illustrated in FIG. 67.

The storage device 908 is a device for data storage which is formed as an example of a storage unit of the information processing apparatus 900. The storage device 908 is realized by, for example, a magnetic storage unit device such as an HDD, a semiconductor storage device, an optical storage device, a magneto-optical storage device, or the like. The storage device 908 may include a storage medium, a recording device that records data in the storage medium, a reading device that reads data from the storage medium, a deletion device that deletes data recorded in the storage medium, and the like. The storage device 908 stores programs to be executed by the CPU 901, various types of data, various types of data acquired from the outside, and the like.

The drive 909 is a reader/writer for a storage medium, and is built in or externally attached to the information processing apparatus 900. The drive 909 reads information recorded in an attached removable storage medium, such as a magnetic disk, an optical disk, a magneto-optical disk, or a semiconductor memory, and outputs the read information to the RAM 903. In addition, the drive 909 can also write information to the removable storage medium.

The connection port 911 is an interface to be connected to an external device, and is a connection port with the external device capable of data transmission, for example, by universal serial bus (USB) or the like.

The communication device 913 is, for example, a communication interface formed using a communication device or the like for connection to a network 920. The communication device 913 is, for example, a communication card or the like for wired or wireless local area network (LAN), long term evolution (LTE), Bluetooth (registered trademark), or wireless USB (WUSB). In addition, the communication device 913 may be a router for optical communication, a router for asymmetric digital subscriber line (ADSL), a modem for various communications, or the like. The communication device 913 can transmit and receive a signal and the like according to a predetermined protocol, for example, TCP/IP or the like with the Internet or another communication device. The communication device 913 can form, for example, the wireless communication unit 170 illustrated in FIG. 65 or the wireless communication unit 550 illustrated in FIG. 67.

The network 920 is a wired or wireless transmission path of information to be transmitted from a device connected to the network 920. For example, the network 920 may include a public line network such as the Internet, a telephone line network, and a satellite communication network, various local area networks (LAN) including Ethernet (registered trademark), a wide area network (WAN), and the like. In addition, the network 920 may include a dedicated line network such as an Internet protocol-virtual private network (IP-VPN).

The example of the hardware configuration capable of realizing the functions of the information processing apparatus 900 according to the present embodiment has been illustrated above. Each of the constituent elements described above may be realized using a general-purpose member, or may be realized by hardware dedicated for the function of each constituent element. Therefore, it is possible to change the hardware configuration to be used as appropriate according to a technical level at the time of implementing the present embodiment.

Note that a computer program configured to realize each function of the information processing apparatus 900 according to the present embodiment as described above can be created and mounted on a PC or the like. In addition, a computer-readable recording medium in which such a computer program is stored can be provided. The recording medium is, for example, a magnetic disk, an optical disk, a magneto-optical disk, a flash memory, or the like. In addition, the above computer program may be distributed via, for example, a network without using the recording medium.

5. Summary

The embodiments of the present disclosure have been described above with reference to FIGS. 1 to 89.

The ear hole opening device 100 according to the first embodiment opens the ear hole to the outside through the opening portion 131 while holding the audio information acquisition unit 140 acquiring the audio information in the space closer to the eardrum than the tragus using the holding unit 130 that abuts on the cavum concha or the inner wall of the ear canal. Then, the ear hole opening device 100 generates the noise cancellation signal based on the audio information acquired by the audio information acquisition unit 140. For example, the ear hole opening device 100 performs the noise cancellation process using the position of the audio information acquisition unit 140 or the eardrum position as the cancellation point. Since the position near the eardrum or the eardrum is the cancellation point, the high noise canceling performance can be realized.

The headphones 300 according to the second embodiment include the three microphones 320-1 to 320-3 that are arranged on one ear side of the user in the state of being worn by the user. Then, the headphones 300 perform the noise cancellation processes to generate the plurality of noise cancellation signals based on the three audio signals generated by the three microphones 320-1 to 320-3. Although the maximum number of microphones is two in the typical headphones equipped with the noise cancellation function, the headphones 300 have the three microphones. In particular, the ear canal microphone 320-3 is arranged near the entrance of the ear canal in the worn state. Therefore, the headphones 300 can perform the noise cancellation process based on appropriate information such as the audio signals generated by many microphones or the audio signal generated by microphone arranged near the entrance of the ear canal.

In addition, the headphones 300 according to the second embodiment include the housing 301, the ear pad 302, the ear canal microphone 320-3, and the driver 310. Then, the headphones 300 open the ear hole to the inner space of the headphones 300 through the opening portion 304 while holding the ear canal microphone 320-3 in the space closer to the eardrum side than the tragus by the holding unit 130 that abuts on the cavum concha or the inner wall of the ear canal in the worn state. With such a configuration, the ear canal microphone 320-3 is held in the space closer to the eardrum side than the tragus. Therefore, the headphones 300 can set the cancellation point of the noise cancellation process to be closer to the user's eardrum than the typical headphones having the combination-type noise cancellation function.

The ear hole opening device 100 according to the third embodiment wirelessly communicates with headphones 500 that are worn to overlap the outer side of the ear hole opening device 100 worn by the user. Similarly, the headphones 300 according to the third embodiment wirelessly communicate with the ear hole opening device 100 worn to overlap the inner side of the headphones 500 worn by the user. In this manner, the ear hole opening device 100 and the headphones 500, which are worn in the overlapping manner, can cooperate by wireless communication. Specifically, the ear hole opening device 100 transmits the audio signal generated by the audio input unit 141 to the headphones 500. The headphones 500 perform the noise cancellation process based on the received audio signal. Since the headphones 500 can perform the noise cancellation process based on the sound collection result at the position close to the eardrum, high noise canceling performance can be realized.

Although the preferred embodiments of the present disclosure have been described as above in detail with reference to the accompanying drawings, a technical scope of the present disclosure is not limited to such examples. It is apparent that a person who has ordinary knowledge in the technical field of the present disclosure can find various alterations and modifications within the scope of technical ideas described in the claims, and it should be understood that such alterations and modifications will naturally pertain to the technical scope of the present disclosure.

In addition, the processing described with reference to the flowcharts and sequence diagrams in the present specification are not necessarily executed in the illustrated order. Some processing steps may be executed in parallel. In addition, additional processing steps may be adopted, and some processing steps may be omitted.

In addition, the effects described in the present specification are merely illustrative or exemplary, and are not limited. That is, the technique according to the present disclosure can exhibit other effects apparent to those skilled in the art on the basis of the description of the present specification, in addition to or instead of the above-described effects.

Note that the following configurations also belong to the technical scope of the present disclosure.

(1)

An audio processing device comprising:

an audio information acquisition unit that acquires audio information;

a holding unit that abuts on a cavum concha or an inner wall of an ear canal and holds the audio information acquisition unit in a space closer to an eardrum side than a tragus, in a state of being worn by a user;

an opening portion that opens an ear hole to an outside; and a signal processing unit that generates a noise cancellation signal based on the audio information acquired by the audio information acquisition unit.

(2)

The audio processing device according to (1), wherein the holding unit holds the audio information acquisition unit in a space up to 15 mm away from a boundary between the cavum concha and the ear canal to the eardrum side or in a space up to 15 mm away from the boundary between the cavum concha and the ear canal on an opposite side of the eardrum.

(3)

The audio processing device according to (1) or (2), further comprising an audio output unit that outputs audio based on an output signal generated based on the noise cancellation signal, wherein the holding unit maintains a relative positional relationship between the audio information acquisition unit and an output hole of the audio output from the audio output unit.

(4)

The audio processing device according to any one of (1) to (3), wherein the holding unit holds the audio information acquisition unit at a position where the inner wall of the ear canal is not present on a straight line between the audio information acquisition unit and the eardrum.

(5)

The audio processing device according to any one of (1) to (4), wherein the audio information acquisition unit acquires vibration information of the ear canal or the eardrum, and acquires sound pressure information of a cancellation point based on the acquired vibration information.

(6)

The audio processing device according to (5), wherein the cancellation point is one point of the eardrum.

(7)

The audio processing device according to (5) or (6), wherein the audio information acquisition unit estimates the sound pressure information of the cancellation point based on the vibration information of two or more points on the inner wall of the ear canal.

(8)

The audio processing device according to any one of (5) to (7), wherein the audio information acquisition unit transmits a transmission wave, acquires a reflection wave which is the reflected transmission wave, and acquires the vibration information indicating displacement or a speed at a reflection point.

(9)

The audio processing device according to (8), wherein the audio information acquisition unit estimates the sound pressure information of the cancellation point based on information indicating a three-dimensional shape of the ear canal.

(10)

The audio processing device according to (9), wherein the audio information acquisition unit acquires the information indicating the three-dimensional shape of the ear canal by scanning the ear canal while changing a transmission direction of the transmission wave.

(11)

The audio processing device according to (10), further comprising an authentication unit that authenticates the user based on the information indicating the three-dimensional shape of the ear canal.

(12)

The audio processing device according to any one of (5) to (11), further comprising an audio output unit that outputs audio based on an output signal generated based on the noise cancellation signal, wherein the signal processing unit adjusts a sound quality of the output signal based on information indicating a three-dimensional shape of the ear canal.

(13)

The audio processing device according to any one of (5) to (12), further comprising an operation control unit that determines whether the audio processing device is worn by the user based on the audio information, and controls an operation of the audio processing device based on a determination result.

(14)

The audio processing device according to any one of (1) to (12), wherein the signal processing unit extracts the user's own voice based on the audio information acquired by each of a pair of the audio information acquisition units for both ears, and synthesizes the extracted user's voice with the noise cancellation signal.

(15)

The audio processing device according to (13), further comprising another audio information acquisition unit configured to collect the user's own voice, wherein the signal processing unit extracts the user's own voice additionally based on the audio information acquired by the other audio information acquisition unit.

(16)

An audio processing method comprising:

acquiring audio information using an audio information acquisition device that abuts on a cavum concha or an inner wall of an ear canal and is held in a space closer to an eardrum side than a tragus while opening an ear hole to an outside in a state of being worn by a user; and generating a noise cancellation signal based on the acquired audio information.

REFERENCE SIGNS LIST

1 EAR
2 PINNA
3 CRUS OF HELIX
4 CAVUM CONCHA
5 EAR CANAL
6 TRAGUS
7 INTERTRAGIC NOTCH
8 ANTITRAGUS
9 EARDRUM
11 FIRST CURVE
12 SECOND CURVE
19 BOUNDARY BETWEEN CAVUM CONCHA AND EAR CANAL
30 INNER SPACE
31 OUTER SPACE
100 EAR HOLE OPENING DEVICE
110 AUDIO OUTPUT UNIT, DRIVER
120 SOUND GUIDE UNIT
121 ONE END
122 OTHER END
123 PINCH PORTION
130 HOLDING UNIT
131 OPENING PORTION
132 SUPPORT MEMBER
140 AUDIO INFORMATION ACQUISITION UNIT
141 AUDIO INPUT UNIT, MICROPHONE
142 EARDRUM SOUND PRESSURE ACQUISITION UNIT
150 CONTROL UNIT
151 SIGNAL PROCESSING UNIT
153 OPERATION CONTROL UNIT
155 AUTHENTICATION UNIT
157 COMMUNICATION CONTROL UNIT
160 SENSOR UNIT
161 RFID DEVICE
162 MAGNETIC SENSOR
170 WIRELESS COMMUNICATION UNIT
300 HEADPHONES
301 HOUSING
302 EAR PAD
303 HOLDING UNIT
304 OPENING PORTION
305 FIRST SUPPORT MEMBER
306 SECOND SUPPORT MEMBER

307 LINK
310 AUDIO OUTPUT UNIT, DRIVER
320 AUDIO INPUT UNIT, MICROPHONE
330 CONTROL UNIT
331 SIGNAL PROCESSING UNIT
333 OPERATION CONTROL UNIT
340 WIRED CONNECTION UNIT
341 WINDING UNIT
342 RECESS
350 LINK
351 JOINT PORTION
352 RESTRAINING MEMBER
353 SLIDING MEMBER
354 RAIL
360 ATTITUDE CONTROL DEVICE
361 OPERATING BODY
362 LINK
363 JOINT PORTION
370 SENSOR UNIT
500 HEADPHONES
501 HOUSING
502 EAR PAD
510 AUDIO OUTPUT UNIT, DRIVER
520 AUDIO INPUT UNIT, MICROPHONE
530 CONTROL UNIT
531 SIGNAL PROCESSING UNIT
533 OPERATION CONTROL UNIT
535 COMMUNICATION CONTROL UNIT
540 SENSOR UNIT
541 RFID DEVICE
550 WIRELESS COMMUNICATION UNIT
800 TERMINAL DEVICE

The invention claimed is:

1. An audio processing device, comprising:
a first audio information acquisition unit configured to:
  acquire first audio information; and
  transmit a transmission wave to one of an ear canal or an eardrum, wherein
    the first audio information includes a distance between the first audio information acquisition unit and a reflection point, and
    the reflection point is a point at which the transmission wave is reflected in one of the ear canal or the eardrum;
a holding unit configured to:
  hold the first audio information acquisition unit in a space closer to the eardrum than a tragus;
  hold the first audio information acquisition unit in a wearable state; and
  abut one of a cavum concha or an inner wall of the ear canal;
an opening portion configured to open an ear hole to an outside;
a signal processing unit configured to generate a noise cancellation signal based on the first audio information; and
an operation control unit configured to:
  determine whether the audio processing device is worn by a user based on the distance between the first audio information acquisition unit and the reflection point; and
  control an operation of the audio processing device based on the determination.

2. The audio processing device according to claim 1, wherein the holding unit holds the audio information acquisition unit in a space up to 15 mm away from a boundary between the cavum concha and the ear canal to the eardrum side or in a space up to 15 mm away from the boundary between the cavum concha and the ear canal on an opposite side of the eardrum.

3. The audio processing device according to claim 1, further comprising
an audio output unit that outputs audio based on an output signal generated based on the noise cancellation signal,
wherein the holding unit maintains a relative positional relationship between the audio information acquisition unit and an output hole of the audio output from the audio output unit.

4. The audio processing device according to claim 1, wherein the holding unit holds the audio information acquisition unit at a position where the inner wall of the ear canal is not present on a straight line between the audio information acquisition unit and the eardrum.

5. The audio processing device according to claim 1, wherein the first audio information acquisition unit is further configured to:
  acquire vibration information of one of the ear canal or the eardrum; and
  acquire sound pressure information of a cancellation point based on the acquired vibration information.

6. The audio processing device according to claim 5, wherein the cancellation point is one point of the eardrum.

7. The audio processing device according to claim 5, wherein the audio information acquisition unit estimates the sound pressure information of the cancellation point based on the vibration information of two or more points on the inner wall of the ear canal.

8. The audio processing device according to claim 5, wherein the audio information acquisition unit acquires a reflection wave which is the reflected transmission wave, and acquires the vibration information indicating displacement or a speed at the reflection point.

9. The audio processing device according to claim 8, wherein the audio information acquisition unit estimates the sound pressure information of the cancellation point based on information indicating a three-dimensional shape of the ear canal.

10. The audio processing device according to claim 9, wherein the audio information acquisition unit acquires the information indicating the three-dimensional shape of the ear canal by scanning the ear canal while changing a transmission direction of the transmission wave.

11. The audio processing device according to claim 10, further comprising an authentication unit that authenticates the user based on the information indicating the three-dimensional shape of the ear canal.

12. The audio processing device according to claim 5, further comprising
an audio output unit that outputs audio based on an output signal generated based on the noise cancellation signal,
wherein the signal processing unit adjusts a sound quality of the output signal based on information indicating a three-dimensional shape of the ear canal.

13. The audio processing device according to claim 1, wherein the signal processing unit is further configured to:
  extract a voice of the user based on the first audio information acquired by the first audio information acquisition unit corresponding to each ear of the user, and
  synthesize the extracted voice with the noise cancellation signal.

14. The audio processing device according to claim 1, further comprising a second audio information acquisition unit configured to collect second audio information that includes a voice of the user, wherein
the signal processing unit is further configured to extract the voice of the user based on the second audio information collected by the second audio information acquisition unit.

\* \* \* \* \*